(12) United States Patent
Lee et al.

(10) Patent No.: US 12,157,888 B2
(45) Date of Patent: Dec. 3, 2024

(54) MODULATING THE CELLULAR STRESS RESPONSE

(71) Applicant: The General Hospital Corporation, Boston, MA (US)

(72) Inventors: Jeannie T. Lee, Boston, MA (US); Athanasios Zovoilis, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 17/411,313

(22) Filed: Aug. 25, 2021

(65) Prior Publication Data

US 2022/0049255 A1 Feb. 17, 2022

Related U.S. Application Data

(62) Division of application No. 16/308,638, filed as application No. PCT/US2017/036829 on Jun. 9, 2017, now Pat. No. 11,130,951.

(60) Provisional application No. 62/433,770, filed on Dec. 13, 2016, provisional application No. 62/408,639, filed on Oct. 14, 2016, provisional application No. 62/347,737, filed on Jun. 9, 2016.

(51) Int. Cl.
*C12N 15/113* (2010.01)
*A61P 35/00* (2006.01)

(52) U.S. Cl.
CPC ............ *C12N 15/113* (2013.01); *A61P 35/00* (2018.01); *C12N 2310/11* (2013.01); *C12N 2310/113* (2013.01); *C12N 2310/314* (2013.01); *C12N 2310/3145* (2013.01); *C12N 2310/321* (2013.01); *C12N 2310/3231* (2013.01); *C12N 2310/3233* (2013.01); *C12N 2310/341* (2013.01)

(58) Field of Classification Search
None
See application file for complete search history.

(56) References Cited

U.S. PATENT DOCUMENTS

| | | | |
|---|---|---|---|
| 9,328,346 | B2 | 5/2016 | Lee et al. |
| 2005/0119217 | A1 | 6/2005 | LaCasse et al. |
| 2005/0186589 | A1 | 8/2005 | Kowalik et al. |
| 2013/0131142 | A1 | 5/2013 | Libertine et al. |
| 2013/0197207 | A1 | 8/2013 | Ambati |
| 2014/0178309 | A1* | 6/2014 | Ambati .......... A61P 27/02 435/375 |

FOREIGN PATENT DOCUMENTS

| WO | WO 2006/060308 | 6/2006 |
|---|---|---|
| WO | WO 2016/030501 | 3/2016 |

OTHER PUBLICATIONS

Allen et al., "The SINE-encoded mouse B2 RNA represses mRNA transcription in response to heat shock," Nat Struct Mol Biol, 2004,11: 816-821.
Bachvarova, "Small B2 RNAs in mouse oocytes, embryos, and somatic tissues," Developmental Biology, 1988, 130: 513-523.
Basenko et al., "Genome-wide redistribution of H3K27me3 is linked to genotoxic stress and defective growth," PNAS, 2015, 112: E6339-6348.
Bourque et al., "Evolution of the mammalian transcription factor binding repertoire via transposable elements," Genome Res, 2008, 18: 1752-1762.
Brown, et al., "Activator-dependent regulation of transcriptional pausing on nucleosomal templates," Genes Dev, 1996, 10: 1479-1490.
Chircop and Speidel, "Cellular stress responses in cancer and cancer therapy," Frontiers in Oncology, 2014, 4: 304.
Cifuentes-Rojas et al., "Regulatory interactions between RNA and polycomb repressive complex 2," Mol Cell, 2014, 55: 171-185.
Daniels and Deininger, "Repeat sequence families derived from mammalian tRNA genes," Nature, 1985, 317: 819-822.
Davidovich et al., "Promiscuous RNA binding by Polycomb repressive complex 2," Nat Struct Mol Biol, 2013, 20: 1250-1257.
Davidovich et al., "Toward a consensus on the binding specificity and promiscuity of PRC2 for RNA," Mol Cell, 2015, 57: 552-558.
De Koning et al., "Repetitive elements may comprise over two-thirds of the human genome," PLoS Genet, 2011, 7: e1002384.
De Nadal et al., "Controlling gene expression in response to stress," Nature Reviews Genetics, 2011, 12: 833-845.
Down and Hubbard, "Computational detection and location of transcription start sites in mammalian genomic DNA," Genome Res, 2002, 12: 458-461.
Espinoza et al., "B2 RNA binds directly to RNA polymerase II to repress transcript synthesis," Nat Struct Mol Biol, 2004, 11: 822-829.
Espinoza et al., "Characterization of the structure, function, and mechanism of B2 RNA, an ncRNA repressor of RNA polymerase II transcription," RNA, 2007, 13: 583-596.
Ferrigno et al., "Transposable B2 SINE elements can provide mobile RNA polymerase II promoters," Nature Genetics, 2001, 28: 77-81.
Fornace et al., "Induction of B2 RNA polymerase III transcription by heat shock: enrichment for heat shock induced sequences in rodent cells by hybridization subtraction," Nucleic Acids Res, 1986, 14: 5793-5811.
Gall, "Chromosome structure and the C-value paradox," J Cell Biol, 1981, 91: 3s-14s.
International Search Report and Written Opinion in International Application No. PCT/US2017/036829, mailed on Sep. 28, 2017, 18 pages.
Kaczkowski et al., "Transcriptome Analysis of Recurrently Deregulated Genes across Multiple Cancers Identifies New Pan-Cancer Biomarkers," Cancer Research, 2016, 76, 216-226.
Kaneko et al., "DICER1 deficit induces Alu RNA toxicity in age-related macular degeneration," Nature, 2011, 471: 325-330.

(Continued)

*Primary Examiner* — Sean McGarry
(74) *Attorney, Agent, or Firm* — Fish & Richardson P.C.

(57) ABSTRACT

Methods of using B2 or Alu nucleic acids, or antisense oligonucleotides that modulate the EZH2/B2 or EZH2/Alu interaction and have the capacity to alter cleavage of B2 and Alu RNA, for increasing or decreasing cell and organismal viability.

20 Claims, 42 Drawing Sheets

Specification includes a Sequence Listing.

(56) References Cited

OTHER PUBLICATIONS

Kaneko et al., "PRC2 binds active promoters and contacts nascent RNAs in embryonic stem cells," Nat Struct Mol Biol, 2013, 20: 1258-1264.
Kapranov et al., "Genome-wide transcription and the implications for genomic organization," Nature Reviews Genetics, 2007, 8: 413-423.
Kleinmanns and Schubert, "Polycomb and Trithorax group protein-mediated control of stress responses in plants," Biological Chemistry, 2014, 395: 1291-1300.
Kramerov and Vassetzky, "SINEs," WIREs RNA, 2011, 2: 772-786.
Kramerov et al., "The sequences homologous to major interspersed repeats B1 and B2 of mouse genome are present in mRNA and small cytoplasmic poly(A) + RNA," Nucleic Acids Res, 1982, 10: 7477-7491.
Krayev et al., "Ubiquitous transposon-like repeats B1 and B2 of the mouse genome: B2 sequencing," Nucleic Acids Res, 1982, 10: 7461-7475.
Kung et al., "Locus-specific targeting to the X chromosome revealed by the RNA interactome of CTCF," Mol Cell, 2015, 57: 361-375.
Kwak et al., "Precise maps of RNA polymerase reveal how promoters direct initiation and pausing," Science, Feb. 2013, 339: 950-953.
Lawrence et al., "Analysis of repetitive sequence elements containing tRNA-like sequences," Nucleic Acids Res, 1985, 13: 4239-4252.
Lee and Bartolomei, X-Inactivation, Imprinting, and Long Noncoding RNAs in Health and Disease, Cell, 2013, 152: 1308-1323.
Li and Durbin, "Fast and accurate long-read alignment with Burrows-Wheeler transform," Bioinformatics, 2010, 26: 589-595.
Li et al., "Enhancers as non-coding RNA transcription units: recent insights and future perspectives," Nature Reviews Genetics, 2016, 17: 207-223.
Li et al., "Physiological stresses increase mouse short interspersed element (SINE) RNA expression in vivo," Gene, 1999, 239: 367-372.
Lowe and Haussler, "29 mammalian genomes reveal novel exaptations of mobile elements for likely regulatory functions in the human genome," PLoS One, 2012, 7: e43128.
Lunyak et al., "Developmentally regulated activation of a SINE B2 repeat as a domain boundary in organogenesis," Science, 2007, 317: 248-251.
Margueron and Reinberg, "The Polycomb complex PRC2 and its mark in life," Nature, 2011, 469: 343-349.
Mirsky and Ris, "The desoxyribonucleic acid content of animal cells and its evolutionary significance," J Gen Physiol, 1951, 34: 451-462.
Moolhuijzen et al., "The transcript repeat element: the human Alu sequence as a component of gene networks influencing cancer," Functional & Integrative Genomics, 2010, 10: 307-319.
Pandey et al., "Kcnq1ot1 Antisense Noncoding RNA Mediates Lineage-Specific Transcriptional Silencing through Chromatin-Level Regulation," Molecular Cell, 2008, 32: 232-246.
Ponicsan et al., "Genomic gems: SINE RNAs regulate mRNA production," Curr Opin Genet Dev, 2010, 20: 149-155.
Ponicsan et al., "Repression of RNA Polymerase II Transcription by B2 RNA Depends on a Specific Pattern of Structural Regions in the RNA," Noncoding RNA, 2015, 1: 4-16.
Quinlan and Hall, "BEDTools: a flexible suite of utilities for comparing genomic features," Bioinformatics, 2010, 26: 841-842.
Rinn and Chang, "Genome regulation by long noncoding RNAs," Annu Rev Biochem, 2012, 81: 145-166.
Robinson et al., "Integrative genomics viewer," Nat Biotechnol, 2011, 29: 24-26.
Siebold et al., "Polycomb Repressive Complex 2 and Trithorax modulate *Drosophila* longevity and stress resistance," PNAS, 2010, 107: 169-174.
Simon et al., "High-resolution Xist binding maps reveal two-step spreading during X-chromosome inactivation," Nature, 2013, 504: 465-469.
Singh et al., "Expression of enhanced levels of small RNA polymerase III transcripts encoded by the B2 repeats in simian virus 40-transformed mouse cells," Nature, 1985, 314: 553-556.
Tarallo et al., "DICER1 loss and Alu RNA induce age-related macular degeneration via the NLRP3 inflammasome and MyD88," Cell, 2012, 149: 847-859.
Tay et al., "The multilayered complexity of ceRNA crosstalk and competition," Nature, 2014, 505: 344-352.
The ENCODE Project Consortium, "Identification and analysis of functional elements in 1% of the human genome by the ENCODE pilot project," Nature, 2007, 447: 799-816.
Thomas, "The genetic organization of chromosomes," Annu Rev Genet, 1971, 5: 237-256.
Trapnell et al., "TopHat: discovering splice junctions with RNA-Seq," Bioinformatics, 2009, 25: 1105-1111.
Treangen and Salzberg, "Repetitive DNA and next-generation sequencing: computational challenges and solutions," Nature Reviews Genetics, 2012, 13: 36-46.
Xu et al., "Spatial clustering for identification of ChIP-enriched regions (SICER) to map regions of histone methylation patterns in embryonic stem cells," Methods Mol Biol, 2014, 1150: 97-111.
Yakovchuk et al., "B2 RNA and Alu RNA repress transcription by disrupting contacts between RNA polymerase II and promoter DNA within assembled complexes," PNAS, 2009, 106: 5569-5574.
Zhao et al., "Genome-wide identification of polycomb-associated RNAs by RIP-seq," Mol Cell, 2010, 40: 939-953.
Zhao et al., "Polycomb proteins targeted by a short repeat RNA to the mouse X chromosome," Science, 2008, 322: 750-756.

\* cited by examiner

B2 sub-families consensus sequences

POL-III start →

```
B3       GGGGCTGGAGAGATGGCTCAGCGGTTAAGAGCACT-KGCTGCTCTTSCAGAGGA
B2_Mm1a  GGGGCTGGTGAGATGGCTCAGTGGGTAAGAGCACCGACTGCTCTTCCGAAGGT
B2_Mm1t  GGGGCTGGTGAGATGGCTCAGTGGGTAAGAGCACCGACTGCTCTTCCGAAGGT
B2_Mm2   GGGGCTGGAGAGATGGCTCAGCGGTTAAGAGCACT-GACTGCTCTTCCAGAGGT
                                   Box A
```

```
CCCGGGTTCGGTTCCCAGCACCCACATGGCGGCTCACAACCGTCTGTAACTCCAGTTCCAGG
CCGGAGTTCAAATCCCAGCAACCACATGGTGGCTCACAACCATCCGTAAC-----------G
CCGGAGTTCAAATCCCAGCAACCACATGGTGGCTCACAACCATCCGTAAC-----------G
CCTGAGTTCAATTCCCAGCAACCACATGGTGGCTCACAACCATCTGTAAT-----------G
         Box B                                      Position 98
```

```
GGATCCGACGCCCTCTTCTGGCCTCCGCGGGCACCGCAT
AGATCTGACTCCCTCTTCTGGAGTGTCTGAAGACAGC--
AGATCTGACGCCCTCTTCTGGTGTGTCTGAAGACAGC--
GGATCTGATGCCCTCTTCTGGTGTGTCTGAAGACAGC--
```

*FIG. 2A*

| | B2 | B2+GST | B2+EED | B2+EZH2 |
|---|---|---|---|---|
| $k_{obs}$ (min$^{-1}$) | $2 \times 10^{-5}$ | $6 \times 10^{-4}$ | 0.008 | 0.029 |
| Rate relative to no protein | 1 | 30 | 400 | 1400 |
| HALF-LIFE | B2 | B2+GST | B2+EED | B2+EZH2 |
| Minutes | 34657.359 | 1155.2453 | 86.6433976 | 24.755256 |
| Hours | 577.62265 | 19.2540883 | 1.44405663 | 0.4125876 |
| Days | 24.0676104 | 0.80225368 | 0.06016903 | 0.0171912 |

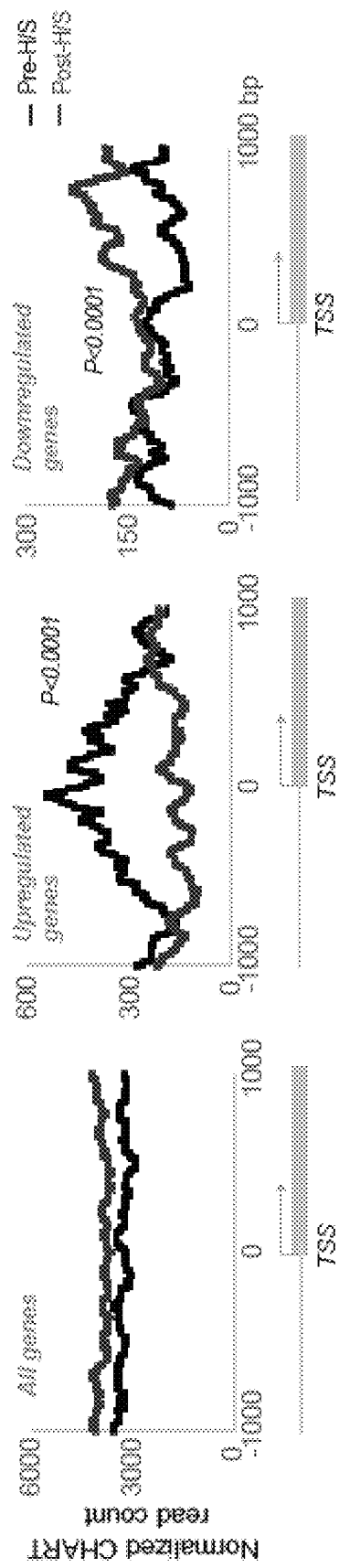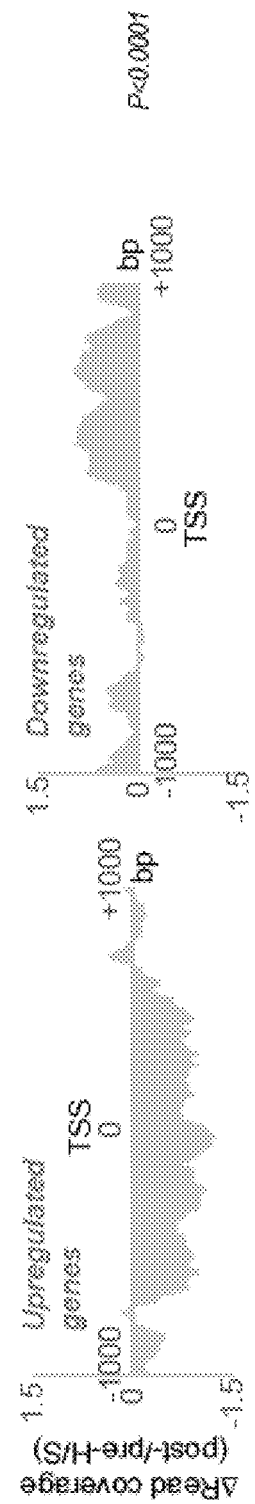
FIG. 4F
FIG. 4G

FIG. 6A
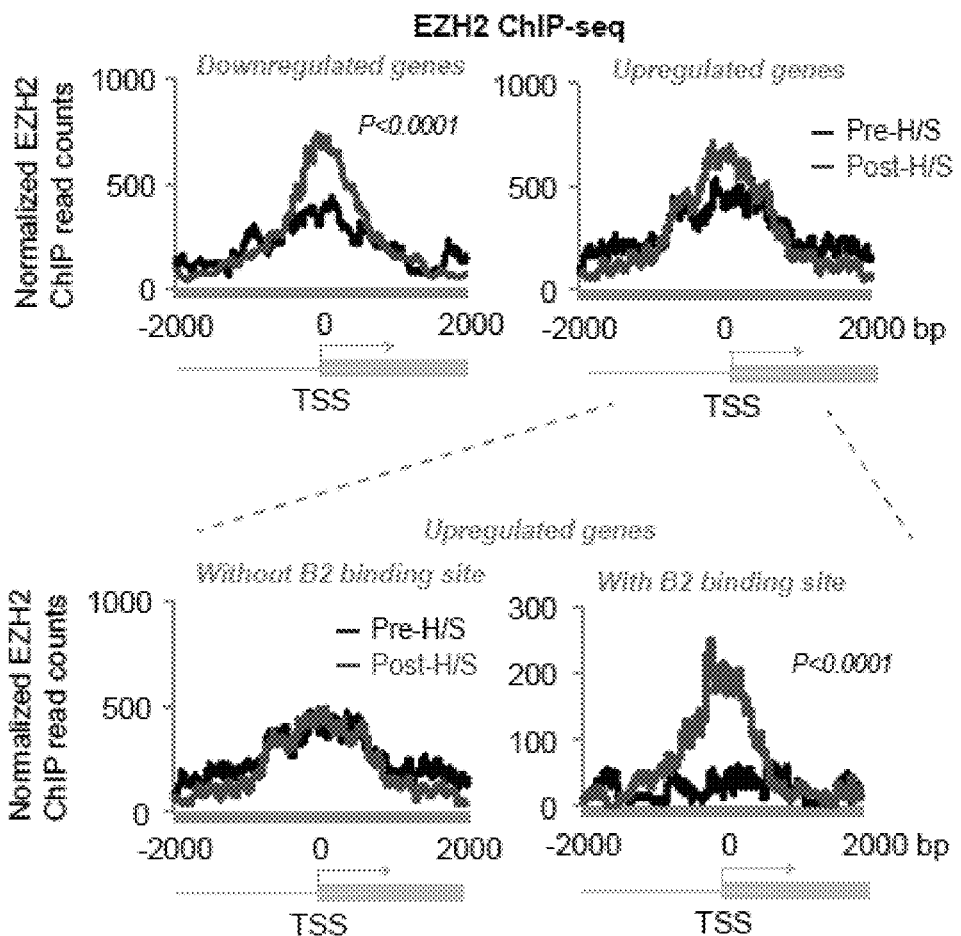
FIG. 6B
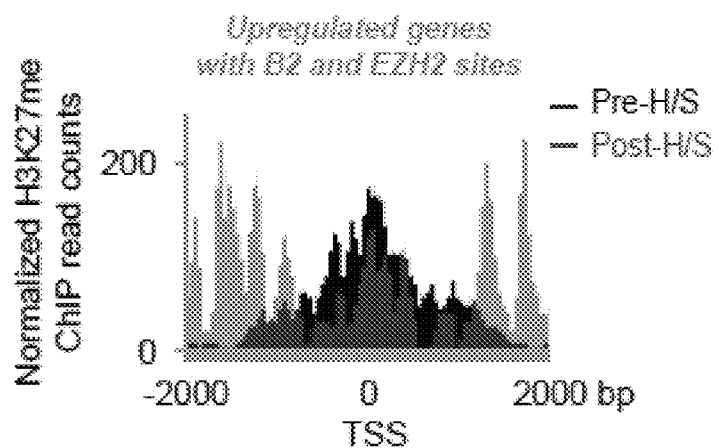
FIG. 6C

| Name | Sequence | SEQ ID |
|---|---|---|
| Alu | AAAAAAAA---------------------- | SEQ ID NO: 1 |
| AlU_rb | AAAAAAAAAAAAAAAA-------------- | SEQ ID NO: 2 |
| Alu1_OG | AAAAAAAAAAAA------------------ | SEQ ID NO: 3 |
| Alu1_TS | AAAAAAAAAAAAAAA--------------- | SEQ ID NO: 4 |
| Alu2_OG | AAAAAAA----------------------- | SEQ ID NO: 5 |
| Alu2_TS | AAAAAAAAAAAAAAA--------------- | SEQ ID NO: 6 |
| Alu3_TS | AAAAAAGTCTGAAAAAGGAAGA-------- | SEQ ID NO: 7 |
| AluJb | AA---------------------------- | SEQ ID NO: 8 |
| AluJo | AAAAAAAAAAAAAAAAA------------- | SEQ ID NO: 9 |
| AluJr | AAAAAAAAAAAAAAAA-------------- | SEQ ID NO: 10 |
| AluJr4 | AAAAAAAAAAAAAAAAA------------- | SEQ ID NO: 11 |
| AluJ_Mim | AAAAAAAAAAAAA----------------- | SEQ ID NO: 12 |
| AluMacYa3 | AAAAAAAAAAAAAAAA-------------- | SEQ ID NO: 13 |
| AluMacYb2 | AAAAAAAAAAAAAAA--------------- | SEQ ID NO: 14 |
| AluMacYb4 | AAAAAAAAAAAAAAA--------------- | SEQ ID NO: 15 |
| AluSc | AA---------------------------- | SEQ ID NO: 16 |
| AluSc5 | AAAAAAAAAAAAAAAAA------------- | SEQ ID NO: 17 |
| AluSc8 | AAAAAAAAAAAAAAAA-------------- | SEQ ID NO: 18 |
| AluSg | AA---------------------------- | SEQ ID NO: 19 |
| AluSg1 | AA---------------------------- | SEQ ID NO: 20 |
| AluSg4 | AAAAAAAAAAAAAAAAA------------- | SEQ ID NO: 21 |
| AluSg7 | AAAAAAAAAAAAAAAAAA------------ | SEQ ID NO: 22 |
| AluSp | AAAAAAAAAAAAAAA--------------- | SEQ ID NO: 23 |
| AluSq | AA---------------------------- | SEQ ID NO: 24 |
| AluSq10 | AAAAAAAAAAAAA----------------- | SEQ ID NO: 25 |
| AluSq2 | AAAAAAAAAAAAAAAA-------------- | SEQ ID NO: 26 |
| AluSq4 | AAAAAAAAAAAAAAAAA------------- | SEQ ID NO: 27 |
| AluSx | AAAAAAAAAAAAAA---------------- | SEQ ID NO: 28 |
| AluSx1 | AAAAAAAAAAAAAAAA-A------------ | SEQ ID NO: 29 |
| AluSx3 | AAAAAAAAAAAAAAAAAA------------ | SEQ ID NO: 30 |
| AluSx4 | AAAAAAAAAAAAAAAAAA------------ | SEQ ID NO: 31 |

FIG. 11, Cont'd

| | | | | | | | | | | | | | | | | |
|---|---|---|---|---|---|---|---|---|---|---|---|---|---|---|---|---|
| AluSz | - | - | - | - | - | - | - | - | - | - | - | - | - | - | - | - SEQ ID NO: 32 |
| AluSz6 | A | A | A | A | A | A | A | A | A | A | A | A | A | A | A | - SEQ ID NO: 33 |
| AluY | - | - | - | - | - | - | - | - | - | - | - | - | - | - | - | - SEQ ID NO: 34 |
| AluYa1 | - | - | - | - | - | - | - | - | - | - | - | - | - | - | - | - SEQ ID NO: 35 |
| AluYa4 | - | - | - | - | - | - | - | - | - | - | - | - | - | - | - | - SEQ ID NO: 36 |
| AluYa5 | - | - | - | - | - | - | - | - | - | - | - | - | - | - | - | - SEQ ID NO: 37 |
| AluYa8 | - | - | - | - | - | - | - | - | - | - | - | - | - | - | - | - SEQ ID NO: 38 |
| AluYb3a1 | - | - | - | - | - | - | - | - | - | - | - | - | - | - | - | - SEQ ID NO: 39 |
| AluYb3a2 | - | - | - | - | - | - | - | - | - | - | - | - | - | - | - | - SEQ ID NO: 40 |
| AluYb8 | - | - | - | - | - | - | - | - | - | - | - | - | - | - | - | - SEQ ID NO: 41 |
| AluYb9 | - | - | - | - | - | - | - | - | - | - | - | - | - | - | - | - SEQ ID NO: 42 |
| AluYbc3a | - | - | - | - | - | - | - | - | - | - | - | - | - | - | - | - SEQ ID NO: 43 |
| AluYc1 | - | - | - | - | - | - | - | - | - | - | - | - | - | - | - | - SEQ ID NO: 44 |
| AluYc2 | - | - | - | - | - | - | - | - | - | - | - | - | - | - | - | - SEQ ID NO: 45 |
| AluYc5 | A | A | A | A | A | A | A | A | A | A | A | A | A | A | A | - SEQ ID NO: 46 |
| AluYd2 | - | - | - | - | - | - | - | - | - | - | - | - | - | - | - | - SEQ ID NO: 47 |
| AluYd3 | - | - | - | - | - | - | - | - | - | - | - | - | - | - | - | - SEQ ID NO: 48 |
| AluYd3a1 | - | - | - | - | - | - | - | - | - | - | - | - | - | - | - | - SEQ ID NO: 49 |
| AluYd3a1_gib | - | - | - | - | - | - | - | - | - | - | - | - | - | - | - | - SEQ ID NO: 50 |
| AluYd8 | - | - | - | - | - | - | - | - | - | - | - | - | - | - | - | - SEQ ID NO: 51 |
| AluYe2 | - | - | - | - | - | - | - | - | - | - | - | - | - | - | - | - SEQ ID NO: 52 |
| AluYe5 | - | - | - | - | - | - | - | - | - | - | - | - | - | - | - | - SEQ ID NO: 53 |
| AluYf1 | - | - | - | - | - | - | - | - | - | - | - | - | - | - | - | - SEQ ID NO: 54 |
| AluYf2 | - | - | - | - | - | - | - | - | - | - | - | - | - | - | - | - SEQ ID NO: 55 |
| AluYf5 | A | A | A | A | A | A | A | A | A | A | A | A | A | A | A | A SEQ ID NO: 56 |
| AluYg6 | - | - | - | - | - | - | - | - | - | - | - | - | - | - | - | - SEQ ID NO: 57 |
| AluYh9 | - | - | - | - | - | - | - | - | - | - | - | - | - | - | - | - SEQ ID NO: 58 |
| AluYi6 | - | - | - | - | - | - | - | - | - | - | - | - | - | - | - | - SEQ ID NO: 59 |
| AluYk11 | A | A | A | A | A | A | A | A | A | A | A | A | A | A | A | - SEQ ID NO: 60 |
| AluYk12 | - | - | - | - | - | - | - | - | - | - | - | - | - | - | - | - SEQ ID NO: 61 |
| AluYk13 | A | A | A | A | A | A | A | A | A | A | A | A | A | A | A | A SEQ ID NO: 62 |

FIG. 11, Cont'd

MODULATING THE CELLULAR STRESS RESPONSE

CLAIM OF PRIORITY

This application is a divisional of U.S. patent application Ser. No. 16/308,638, filed Dec. 10, 2018, which is a § 371 national stage application of International Application No. PCT/US2017/036829, filed on Jun. 9, 2017, which claims the benefit of U.S. Provisional Patent Application Serial Nos. 62/433,770, filed on Dec. 13, 2016; 62/408,639, filed on Oct. 14, 2016; and 62/347,737, filed on Jun. 9, 2016. The entire contents of the foregoing are hereby incorporated by reference.

FEDERALLY SPONSORED RESEARCH OR DEVELOPMENT

This invention was made with Government support under Grant Nos. R01-GM090278 awarded by the National Institutes of Health and Zo 287/4-1 awarded by the German Research Foundation. The Government has certain rights in the invention.

SEQUENCE LISTING

The instant application contains a Sequence Listing which has been submitted electronically in ASCII format and is hereby incorporated by reference in its entirety. Said ASCII copy, created on Aug. 20, 2021, is named Sequence_Listing.txt and is 30,950 bytes in size.

TECHNICAL FIELD

Described herein are methods of using Alu or B2 nucleic acids, or antisense oligonucleotides that modulate the EZH2/B2 or EZH2/ALU interaction and have the capacity to alter cleavage of B2/ALU and its expression levels, for increasing or decreasing whole-organism or cell health, proliferation potential, functionality and viability, such as during various types of environmental stress (thermal (e.g., heat or cold), radiation, chemical, or hypoxic stress), inflammation, infection, and cancer.

BACKGROUND

Environmental stress is an everyday reality for all organisms. A rapid and effective response is essential for survival in the face of acute stress, such as those resulting from exposure to extreme temperatures (cold, heat), chemical toxin, radiation, and infection. Activation of the so-called stress response genes protects cells from conditions that would normally be lethal, and a failure to mount an effective or controlled stress response can lead to a variety of diseases, including cancer and autoimmunity. Cancer therapeutic agents often target components of the stress/heat shock response pathway to overcome unchecked growth of cancer cells, but cancer cells frequently respond by mutating these stress-control genes (Chircop and Speidel, 2014). A better understanding of how the stress response is controlled would therefore be beneficial towards human health.

SUMMARY

More than 98% of the mammalian genome is noncoding and interspersed transposable elements account for ~50% of noncoding space. Because of their repetitive nature and relative lack of conservation, these elements have been termed "junk DNA". As demonstrated herein, an interaction between the Polycomb protein, EZH2, and RNA made from B2 SINE retrotransposons controls the stress response. Using the heat shock model, the present results show that B2 RNA binds stress genes and suppresses their transcription before stress. Upon stress, EZH2 is recruited and triggers cleavage of B2 RNA. B2 degradation in turn upregulates stress genes. Evidence indicates that B2 RNA operates as "speed bumps" to slow progression of RNA polymerase and stress rapidly releases the brakes on transcription. Thus, the present inventors have attributed a new function to EZH2 that is independent of its histone methyltransferase activity and revealed that EZH2 and B2 together control the activation of a large network of stress-response genes. In humans, the B2 element is known as ALU. As shown herein, ALUs are also subject to cleavage.

Thus, provided herein are methods for of modulating health, proliferation potential, functionality or viability of a cell or tissue, comprising contacting the cell with an antisense oligonucleotide (ASO) comprising at least one locked nucleotide that binds to an Alu or B2 RNA and alters levels of the Alu or B2 RNA, by promoting or blocking cleavage of the B2/Alu RNA. As used herein, functionality means the typical physiological function of the cell, e.g., a pancreatic beta cell that is alive but not producing insulin is viable but not functional. Neural or muscle cells with an ion channel disorder are still viable but cannot transmit or receive the message, thus they are not functional.

In some embodiments, the cell is in a subject who suffers from an inflammatory or autoimmune disorder affecting the cell.

In some embodiments, the cell is in a subject who suffers from a degenerative disorder affecting the cell.

In some embodiments, the degenerative disorder is macular degeneration.

Also provided herein are methods for enhancing health or viability of a cell, comprising contacting the cell with an antisense oligonucleotide (ASO) comprising at least one locked nucleotide that binds to an Alu or B2 RNA and promotes cleavage of the Alu or B2 RNA, preferably wherein the ASO is an siRNA, shRNA or comprises at least one locked nucleotide, e.g., is a gapmer or mixmer.

In some embodiments, the cell is in a subject who suffers from an environmental stress.

In some embodiments, the environmental stress is infection, thermal (e.g., heat or cold), radiation, or chemical exposure or hypoxic stress.

Also provided herein are methods for promoting or inhibiting proliferation of a cell, comprising contacting the cell with an antisense oligonucleotide (ASO) that binds to an Alu or B2 RNA and reduces binding of EZH2 to the Alu or B2 RNA and inhibits or promotes cleavage of the Alu or B2 RNA.

Further provided herein are methods for promoting or inhibiting apoptosis in a cell, comprising contacting the cell with an antisense oligonucleotide (ASO) that binds to an Alu or B2 RNA and reduces binding of EZH2 to the Alu or B2 RNA and inhibits or promotes cleavage of the Alu or B2 RNA.

In some embodiments, proliferation is inhibited, or apoptosis is promoted, and the cell is a cancer cell. In some embodiments, the cancer cell is in a subject who has cancer; optionally, the ASO is administered locally to the cancer in the subject.

In some embodiments, the ASO is selected from the group consisting of peptide nucleic acids, N3',P5'-phosphoramidates, morpholino phosphoroamidates, 2'-O-methoxyethyl nucleic acids, or ribonucleic acids delivered through an RNA degradation protective carrier.

Also provided herein are compositions comprising a plurality of isolated antisense oligonucleotides (ASOs), preferably each comprising at least one locked nucleotide, that target a plurality of different Alu or B2 sequences and mediate or promote cleavage of the sequences, and a pharmaceutically acceptable carrier.

Also provided herein are compositions for use in a method of promoting viability of a cell, preferably a cell in a living subject, comprising a plurality of isolated antisense oligonucleotides (ASOs), preferably each comprising at least one locked nucleotide, that target a plurality of different Alu or B2 sequences and mediate or promote cleavage of the sequences, and a pharmaceutically acceptable carrier In some embodiments, the subject suffers from an autoimmune disorder or a degenerative disorder.

Additionally, provided herein are compositions comprising a plurality of antisense oligonucleotides that target a plurality of different Alu or B2 sequences and inhibit cleavage of the sequences, and a pharmaceutically acceptable carrier.

In some embodiments, the ASO is selected from the group consisting of peptide nucleic acids, N3',P5'-phosphoramidates, morpholino phosphoroamidates, 2'-O-methoxyethyl nucleic acids, and ribonucleic acids delivered through an RNA degradation protective carrier.

Further provided herein are compositions for use in a method of decreasing viability of a cell, comprising a plurality of antisense oligonucleotides that target a plurality of different Alu or B2 sequences and inhibit cleavage of the sequences, and a pharmaceutically acceptable carrier.

In some embodiments, the cell is a cancer cell in a subject.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control. Other features and advantages of the invention will be apparent from the following detailed description and figures, and from the claims.

Figure 1A:
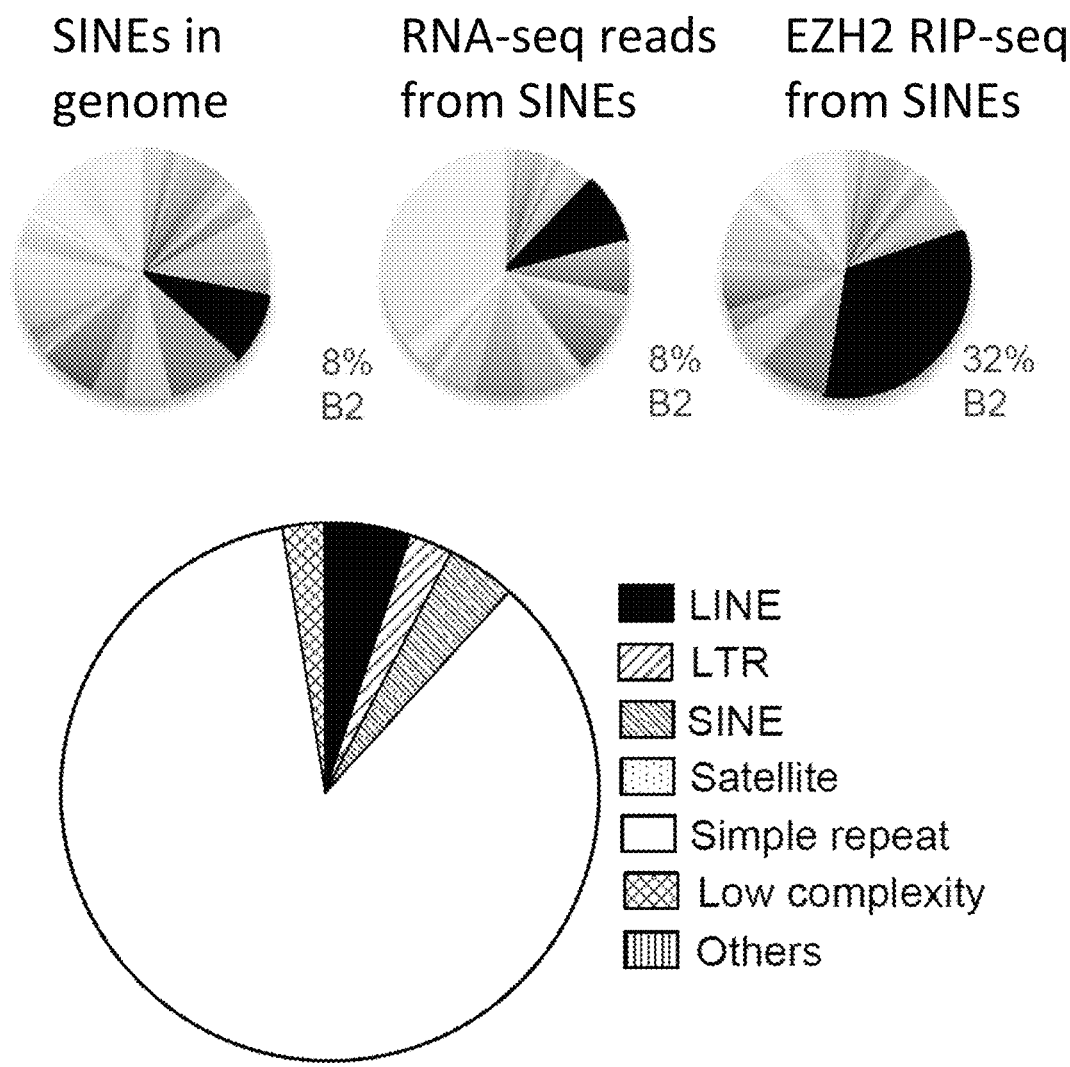
FIGS. 1A-F. B2 RNA associates with PRC2 and can be detected as multiple shorter species in vivo.
Figure 1B:
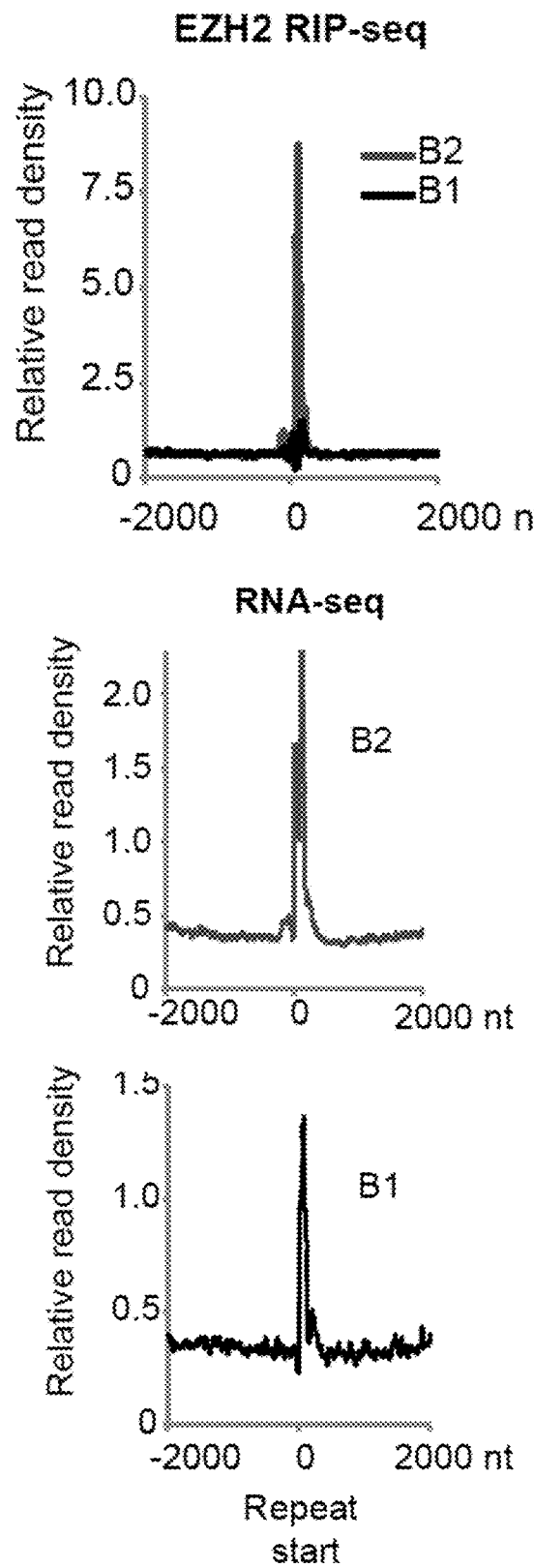

A) Relative B2 representation (red pie slice) among SINEs in the mouse genome, among the female ES cell transcriptome (RNA-seq), and among the EZH2 interactome (RIP-seq), as indicated. Right pie chart is reproduced from (Zhao et al., 2010) and depicts relative representation of SINEs among all reads in the PRC2 interactome.

B) Top panel: Distribution of EZH2 RIP-seq reads around the start site (+/−2000 bp) of two classes of SINE elements, B2 and B1. Repeats of each class have been collapsed into a metagene with a common start site. B2 RNA is enriched but B1 is not, in spite of their relatively equal expression levels in ES cells, as shown by RNA-seq (bottom two panels).

C) Distribution of EZH2 RIP-seq reads within the B2 element. Upper panel: Distribution of reads across a metagene profile inclusive of all B2 elements aligned to their start from nucleotides 1-201 (x-axis/absolute distance in nucleotides from repeat start is maintained in the metagene). Lower panel: Alignment of EZH2 RIP-seq reads within the B2 metagene. Sharp discontinuities implie existence of different B2 subfragments.

D) Distribution of short RNA-seq reads within the B2 element (upper panel) and alignment of these reads within the B2 metagene between nt 1-201 (lower panel).

E) Top panel: Map, structure, and critical domain of B2 RNA as determined previously (Espinoza et al., 2007); SEQ ID NO:73. Bottom panel: 5' ends of the short RNA-seq reads are plotted along the B2 locus (x-axis). Red X's (Top panel) and asterisks (Bottom panel) mark sites of discontinuity, as observed by the short RNA-seq analysis.

F) Top left: Binding isotherms of EZH2 generated from data obtained from double-filter binding experiments. Top right: Table of $K_d$ and $R^2$ values for EZH2-B2 RNA interactions. Bottom: Filter binding assay performed as previously described (Cifuentes-Rojas et al., 2014) for B2 RNA and EZH2. RepA I-IV and RepA I-II were used as positive controls and MBP and P4P6 as negative controls. Error bars within binding curves and standard deviations (SD) within the table represent three independent experiments. U, unbound; B, bound.

FIGS. 2A-K. EZH2 triggers cleavage of B2 RNA in vitro.

A) B2 sub-family consensus sequences of the 5' end, inclusive of the TSS, Box A and B motifs, and the major site of discontinuity at position 98 for B3 (SEQ ID NO:65), B2_Mm1a (SEQ ID NO:66), B2_Mm1t (SEQ ID NO:67), and M2_Mm2 (SEQ ID NO:68).

B) Incubation of in vitro-transcribed B2 RNA (200 nM) with purified recombinant EZH2 (25 nM) results in B2 cleavage and loss in vitro after 13 hours at 22° C. in vitro. Arrowhead, full-length B2 RNA. Asterisks, cleaved B2 fragments.

C) Incubation with 25 nM purified control proteins, GST and EED, does not result in significant cutting after 13 hours at 22° C. in vitro. Arrowhead, full-length B2 RNA. Asterisks, cleaved B2 fragments.

D) Cleaved RNA fragments (asterisks) are purified, adapter ligated, reverse-transcribed, and subjected to deep sequencing. Start coordinates for the sequenced reads are mapped along the x-axis. Arrowhead, full-length B2 RNA.

E) Incubation of in vitro-transcribed RNAs (100 nM) with purified recombinant EZH2 (50 nM) results in cleavage only of B2 RNA. RNAs were mixed with EZH2 and incubated at 37° C. or 4° C. for 30 min. B2 was also incubated with FLAG peptide (50 nM) at 37° C. as control.

F) Kinetic analysis of B2 cleavage in the presence of EZH2 protein. 25 nM EZH2 was incubated with 200 nM B2 RNA at 37° C. for 0-100 minutes and the products were run on a 6% TBE-Urea-PAGE. Arrowhead, full-length B2 RNA. Asterisks, cleaved B2 fragments.

G) Fraction of full-length B2 RNA at each time point from panel E (arrow) was plotted as a function of time. Cleavage rate constants were then determined by a linear fit using the differential form of the rate equation for an irreversible, first-order reaction. The slope is the observed cleavage rate constant ($k_{obs}$). $R^2$ values indicate that data points have an excellent fit to the curve. Two independent experiments have been used for this plotting.

H) Table of calculated ob $k_{obs}$ and RNA half-lives for B2 in the presence of various test proteins.

I) Rate of B2 cleavage depends on the concentration of EZH2 protein. 50 nM B2 RNA is incubated with increasing concentrations of EZH2 for 20 minutes at 37° C. in vitro. The products were then run on a 6% TBE-Urea PAGE. Arrowhead, full-length B2 RNA. Asterisks, cleaved B2 fragments.

J) Kinetic analysis showing that the rate of B2 cleavage depends on the concentration of EZH2. 200 nM B2 RNA is incubated with increasing EZH2 concentrations (25-500 nM) at 37° C. and the amount of remaining full-length B2 RNA is plotted as a function of time. Cleavage rate constants were then determined by a linear fit using the differential form of the rate equation for an irreversible, first-order reaction. The slope approximated observed rate constant ($k_{obs}$). $R^2$ values indicate that datapoints have an excellent fit to the curve. Two independent experiments have been used for this plotting.

K) $k_{obs}$ values from panel I are plotted as a function of EZH2 concentration. High $R^2$ values indicate that data points have an excellent fit to the curve.

FIGS. 3A-D. Heat shock destabilizes B2 RNA in vivo.

A) Full-length B2 RNA was pre-incubated with 25 nM EZH2 for 7 h at 37° C. The RNA was then gel purified and either the whole B2 or the subfragments were then transfected into NIH/3T3 cells and cells were grown at 37° C. Mock represents transfection without any RNA. Photographs were taken after 3 days.

B) NIH/3T3 cells transfected with either synthesized full-length B2 RNA or a synthesized B2 fragment starting at position 99. Cells were then allowed to recover for 2-5 days. Cell were photographed (left panels) and counted (right panels) at days 2 and 5.

C) Diagram of the heat shock response. Hundreds of genes are increased in expression ("upregulated"), and others are decreased in expression ("downregulated"). B2 expression increases within 15 minutes of heat shock.

D) Short RNA-seq of NIH/3T3 cells before and after heat shock (45° C. for 15 minutes). Two biological replicates yielded similar results. 5' ends of short RNA-seq reads are mapped to the B2 transcript and the relative number of 5' ends is plotted on the y-axis. The 5' end counts are normalized to the number of full length B2 RNAs to account for any possible changes in the general B2 levels during heat shock (KS test; P<0.0001).

FIGS. 4A-G. CHART-seq analysis: B2 RNA binds heat shock responsive genes in vivo.

A) For CHART-seq analysis, a cocktail of 17-base B2 capture probes is designed to span nt 87-103 and overlap the major cut site. Thus, the cocktail should only pull down chromatin regions associated with full-length B2 RNA. The cocktail contains a pool of oligos that would capture SNP variants for the vast majority of B2 elements.

B) Genome-wide peak annotation analysis (Galaxy) of the distribution of B2 CHART peaks with reference to UCSC RefSeq genes.

C) Pie charts (PAVIS) showing relative distributions of B2 CHART hits genome-wide with reference to different mm9 RefSeq gene features. A comparison of the relative genomic representation for each feature is shown in the bottom pie chart. Satellites represent 0.1% of the total and in this resolution are not visible.

D) An exon/intron 1-focused metagene analysis of B2 CHART reads shows a significant decrease of B2 binding within intron 1 after heat shock (KS test, P<0.0001).

E) IGV screenshots of B2 binding patterns for two H/S-upregulated and two H/S-downregulated genes, along with RNA-seq data. Pre- and post-H/S profiles are shown. Paired data are shown at the same scale (numbers in brackets, right) for comparison.

F) B2 binding across TSS-centered metagene profiles+/−1000 bp of flanking sequence. Pre- and post-H/S traces are shown for all genes, upregulated genes (Table 1), and downregulated genes (Table 2), as indicated. Analysis from two biological replicates corresponds to an FDR<0.05 estimation of noise to input signal, and an E-value of 1000. Statistical significance (P) of the difference between pre- and post-H/S read counts is determined by KS test (P<0.0001).

G) Relative change in B2 binding after H/S. Relative change is indicated by the ratio of post- to pre-H/S CHART reads as described in methods. Positive and negative values represent an increase and decrease in B2 binding after heat shock, respectively. The metagene profiles are centered on the TSS of up- and down-regulated genes, as indicated (KS test, P<0.0001) for the read distribution changes between up- and down-regulated genes).

FIGS. 5A-F. Loss of B2 binding induces H/S-responsive genes.

A) Metagene analysis of changes in POL-II-S2P binding (ChIP-seq) at H/S-upregulated and -downregulated genes. Analysis corresponds two biological replicates and an FDR<0.05 estimation of noise to input signal. Statistical significance (P) between pre- and post-H/S read counts is determined by KS test (P<0.0001).

B) Metagene analysis of changes in POL-II-S2P binding at Type I (B2 binding in pre-H/S) and Type II (B2 binding in post-H/S) genes. Analysis performed as in (A) (KS test, P<0.0001).

C) Metagene analysis showing relative changes in POL-II-S2P binding after H/S for Types I and II genes. Relative change is indicated by the ratio of post- to pre-H/S ChIP coverage. Positive and negative values represent an increase and decrease in POL-II-S2P density, respectively (KS test (P<0.0001) for the read distribution changes between Type I and Type II genes).

D) Cleavage of B2 RNA induced by B2-specific LNA. NIH/3T3 cells are transfected with B2 or Scr LNAs and short RNA-seq analysis is performed after 24 hours. 5' ends of short RNA-seq reads are mapped to the B2 transcript and the relative number of 5' ends is plotted on the y-axis (KS test, P<0.0001)

E) ChIP-seq analysis indicates that B2 LNA recapitulates increased POL-II-S2P density across H/S-upregulated genes without application of heat shock (KS test, P<0.0001).

F) Metagene analysis of RNA-seq data demonstrates that B2 LNA treatment also recapitulates increased expression of H/S-upregulated genes in the absence of H/S (KS test, P<0.0001).

FIGS. 6A-J. EZH2 is recruited to B2 target genes to direct H/S activation.

A) Metagene analysis of changes in EZH2 binding (ChIP-seq) at H/S-upregulated and -downregulated genes. Analysis corresponds to two biological replicates (FDR<0.05 for sample signal to input noise) and P<0.0001 (KS test) between pre- and post-H/S read count distribution of downregulated genes only.

B) EZH2 is recruited to H/S-responsive genes with a B2-binding site. Metagene analysis of changes in EZH2 binding (ChIP-seq) at H/S-upregulated with or without B2 binding sites (Type I versus Type II). P<0.0001 (KS test) for upregulated genes with B2 binding site.

C) H3K27me3 coverage is not increased at the TSS after EZH2 recruitment to H/S-upregulated genes. The metagene analysis is performed on the subclass of H/S-upregulated genes with B2 and EZH2 binding sites (either before or after H/S) (Difference not statistically significant, KS test).

D) Metagene analysis showing relative changes in H3K27me3 coverage after H/S for the subclass of upregulated genes shown in (C). Relative change is indicated by the ratio of post- to pre-H/S ChIP coverage. Positive and negative values represent an increase and decrease in H3K27me3 coverage, respectively.

E) Meta-site analysis centered on the EZH2 binding site shows B2 binds in pre-H/S cells where EZH2 is gained after H/S. x=0 corresponds to EZH2 peaks start of post-H/S cells.

F) Meta-site analysis centered on the B2 binding site shows that EZH2 binds where B2 is lost during H/S. x=0 corresponds to B2 peaks of pre-H/S cells.

G) Anti-correlation of B2 and EZH2 binding viewed in a metagene plot. Relative changes in either B2 or EZH2 coverage at upregulated genes are shown after H/S. Relative change is indicated by the ratio of post- to pre-H/S coverage. Positive and negative values represent an increase and decrease in density, respectively.

H) Linear anti-correlation between B2 coverage and EZH2 density. Change in B2 density (x-axis) plotted as a function of change in EZH2 density (y-axis). R=−0.7, P<0.05.

I) Depleting EZH2 reduces processing of B2 RNA. NIH/3T3 cells are transfected with EZH2 or Scr LNAs and short RNA-seq analysis is performed after 24 hours. 5' ends of short RNA-seq reads are mapped to the B2 transcript and the relative number of 5' ends is plotted on the y-axis (P<0.0001, KS test).

J) EZH2 is required for the heat shock response. Metagene analysis of RNA-seq data demonstrates that EZH2 depletion reduces expression of H/S-upregulated genes (P<0.0001, KS test for pre-post-HS distributions).

Figure 7A:
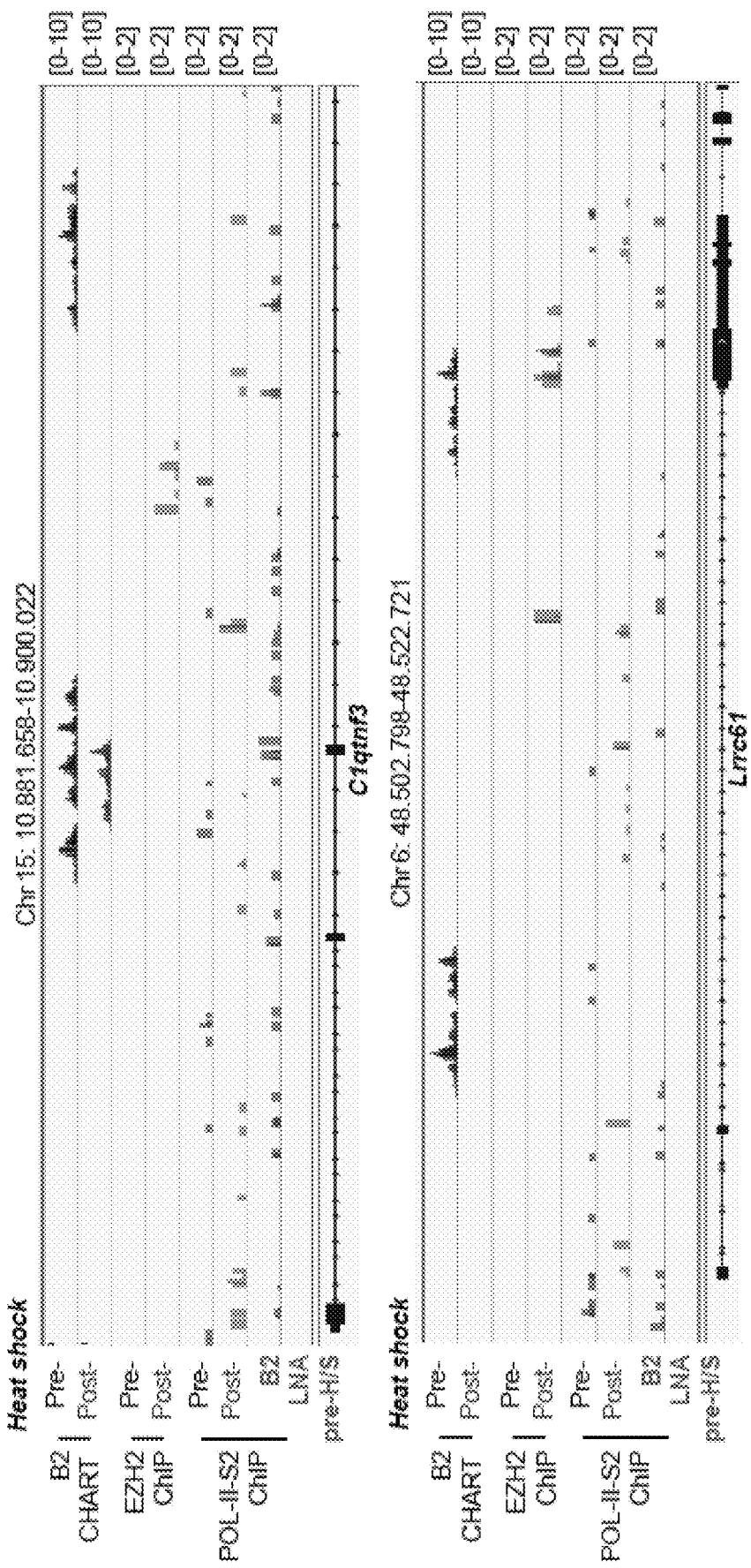
Figure 7B:
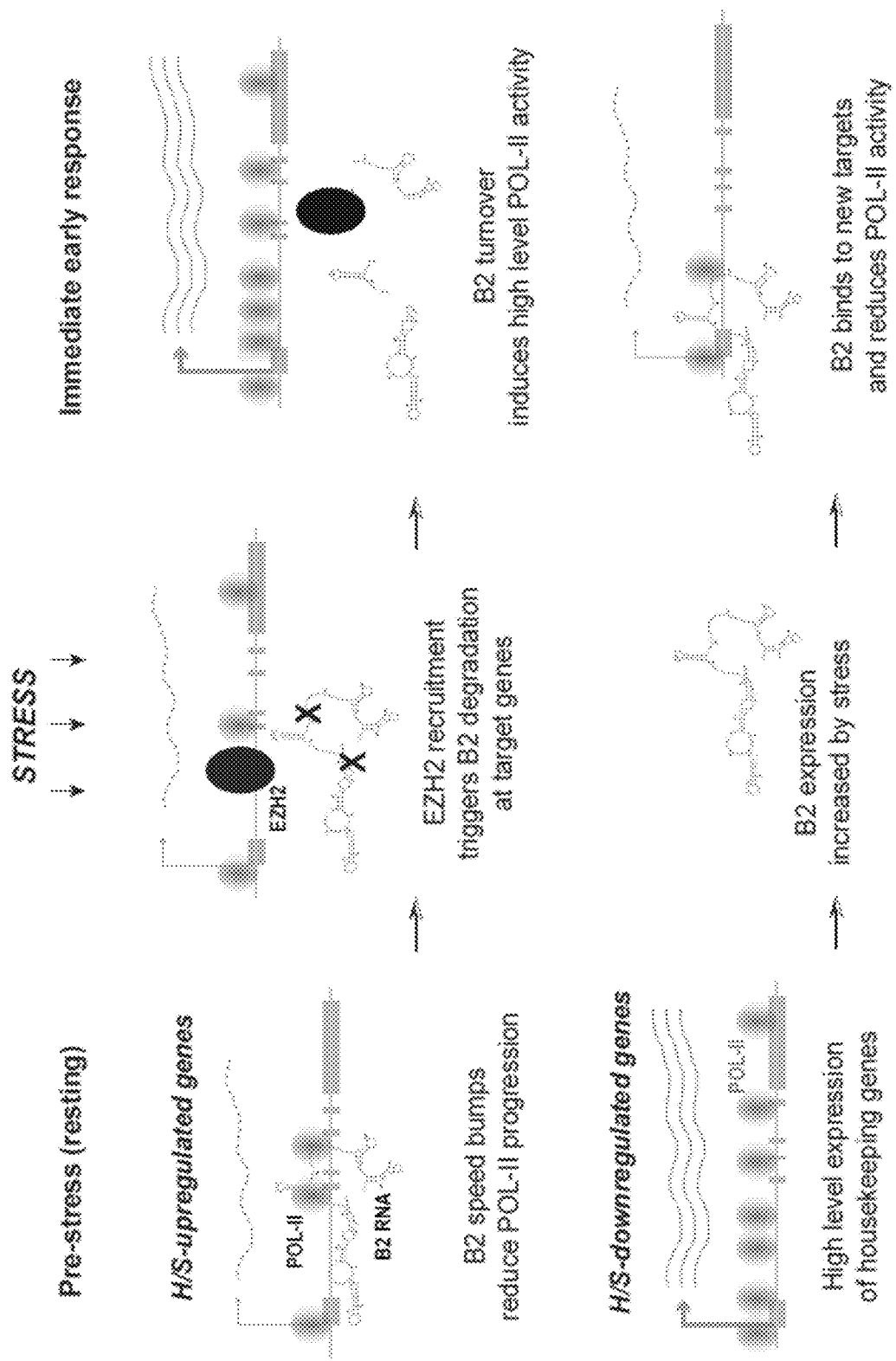

FIGS. 7A-B. The Speed Bump Model of B2/EZH2-mediated gene control.

A) Compilation of data from FIGS. 4-6: IGV screenshots showing alignments of binding patterns for B2 RNA, EZH2, and POL-II-S2P to specific genes.

B) The Speed Bump Model. Upper panels: In resting cells, B2 RNA binds H/S-responsive genes and reduces their expression by establishing "speed bumps" for POL-II progression. Upon stress (e.g., heat shock), PRC2 is recruited to H/S-responsive genes and triggers B2 degradation. The speed bumps are removed and POL-II elongates at faster speed, thereby resulting in transcriptional upregulation. Bottom panels: B2 also regulates housekeeping genes that undergo transcriptional downregulation upon H/S. H/S results in B2 upregulation. These newly transcribed B2 RNA binds new target genes and reduces POL-II activity, thereby reducing expression of housekeeping genes. Both transcriptional initiation and elongation may be affected. The speed bump mechanism enables a rapid and specific response to cellular stress. All changes are observed within 15 minutes of heat shock.

Figure 8:
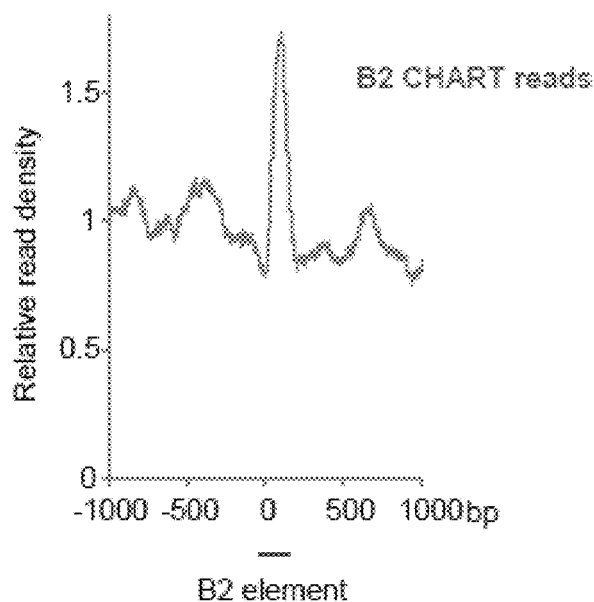

FIG. 8. Correlation between biological replicates of the B2 CHART-seq experiment.

Metagene plot of B2 CHART read density at B2 elements, the site of nascent transcription. As expected, B2 RNA is enriched at the site of transcription. These loci served as positive control and are excluded from further analysis.

Figure 9:
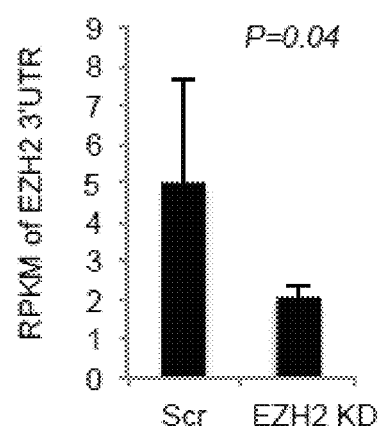

FIG. 9. Correlation between biological replicates of RNA-seq data after EZH2 knockdown.

Significant EZH2 knockdown by LNA transfection. P=0.04, as determined by t-test.

Figure 10A:
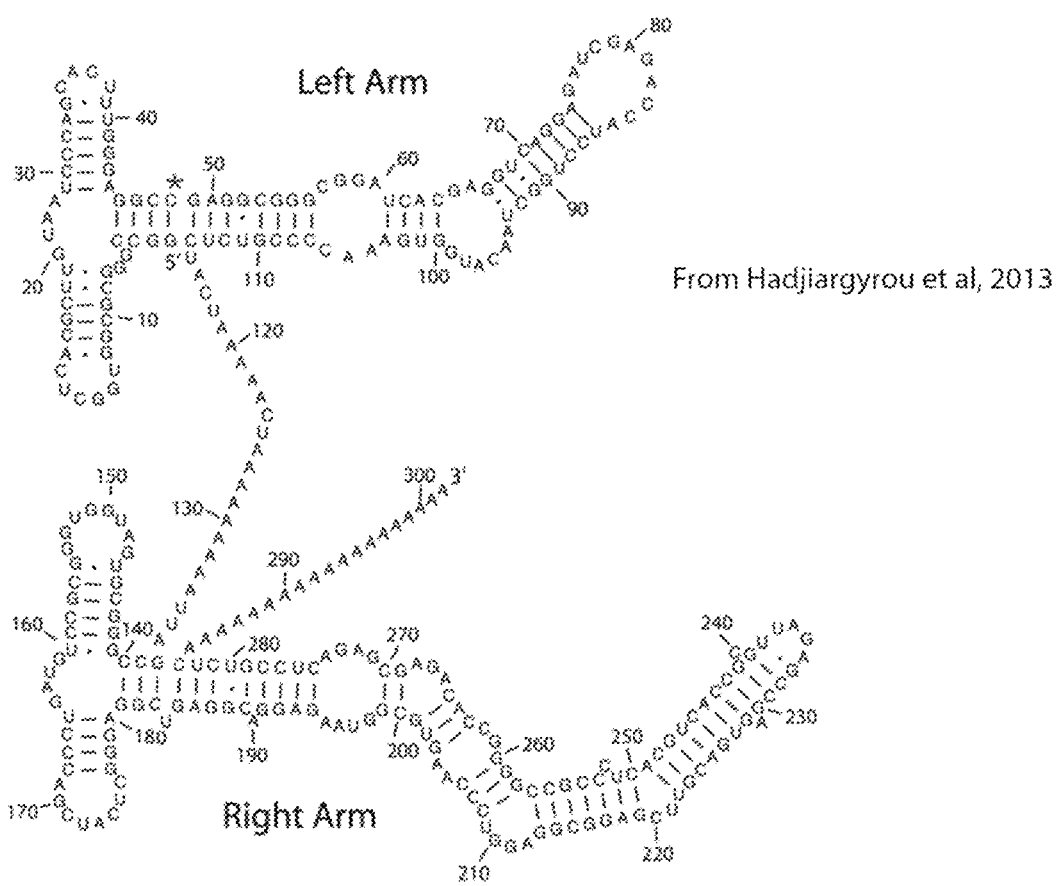
Figure 10B:
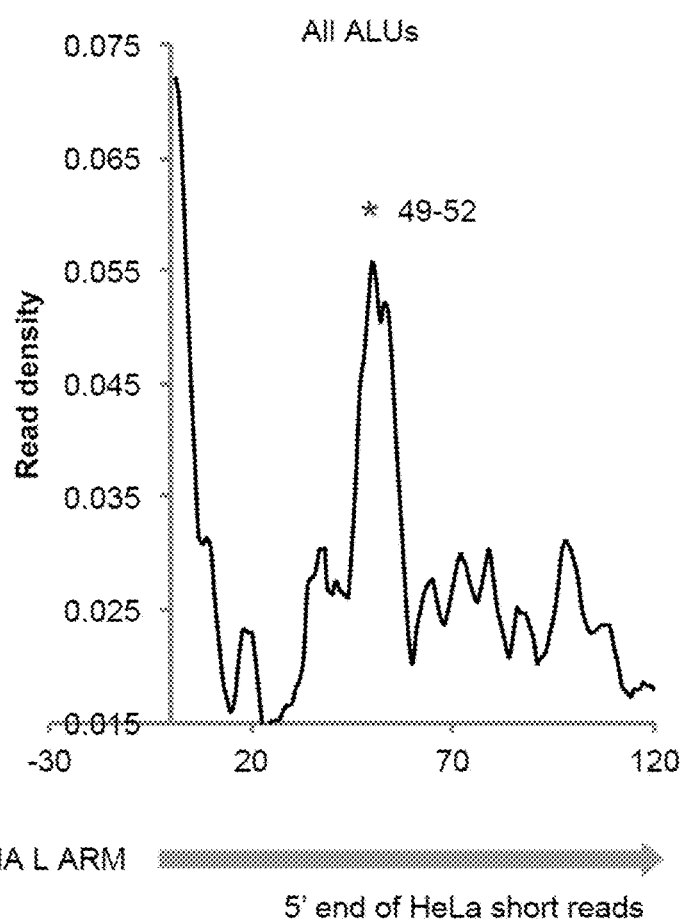
Figure 10C:
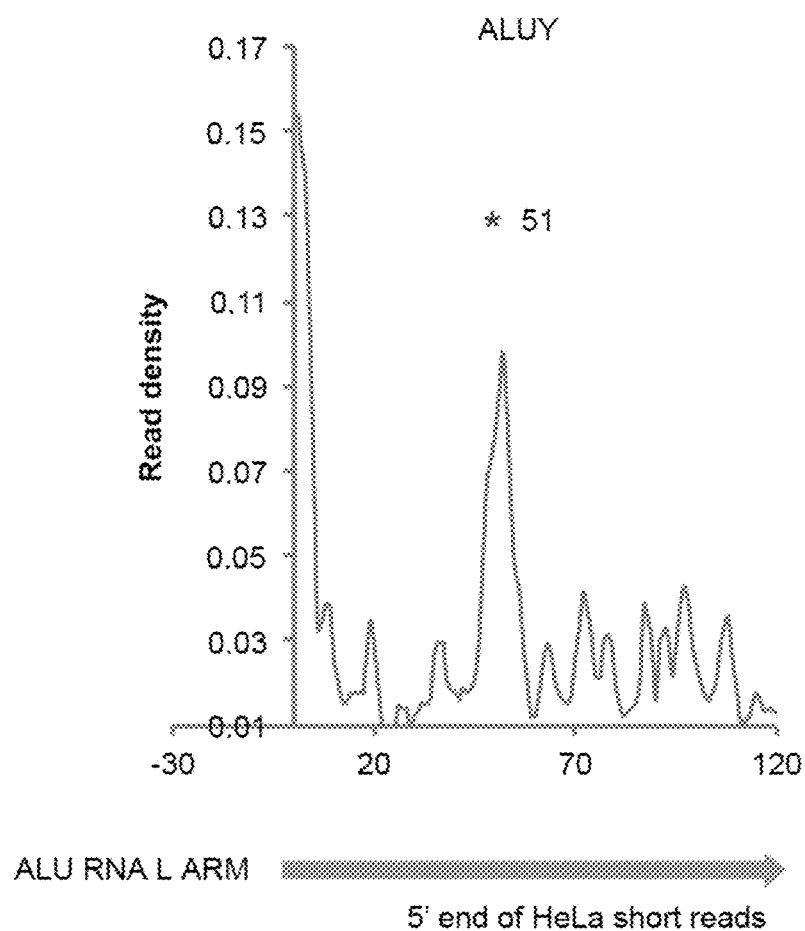

FIGS. 10A-C. Human Alu are the equivalent of mouse B2, and are also cleaved.

A) Human Alu consensus sequence (SEQ ID NO:1) and secondary structure adapted from Hadjiargyrou and Delihas, Int J Mol Sci. 14(7):13307-28 (2013). Alu sequence consists of a sequence dimer, of which the monomers constitute its left and right arms, respectively. The asterisk indicates the Alu cut point in vivo as defined in FIG. 10B below.

Figure 11:
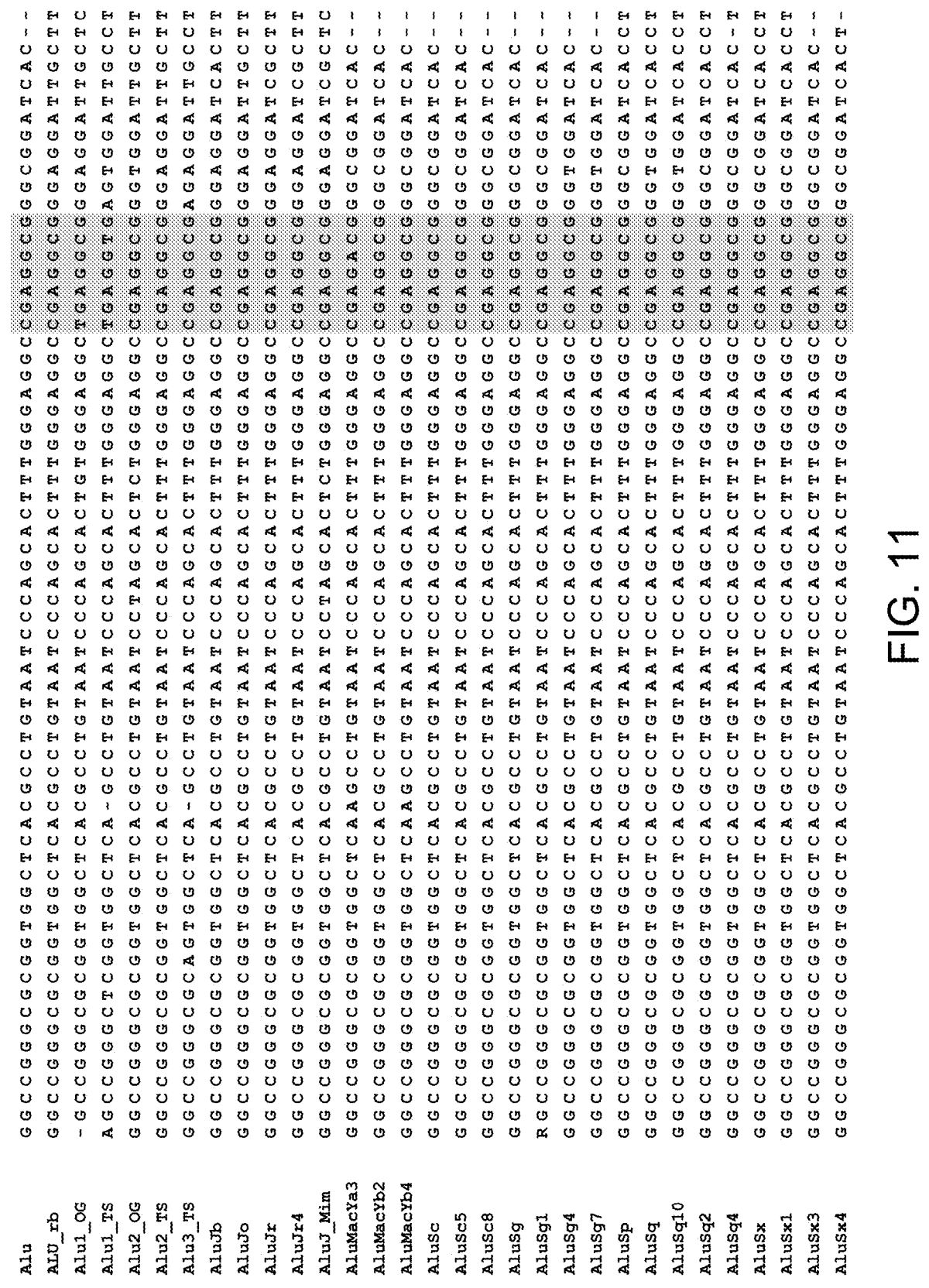
Figure 11:
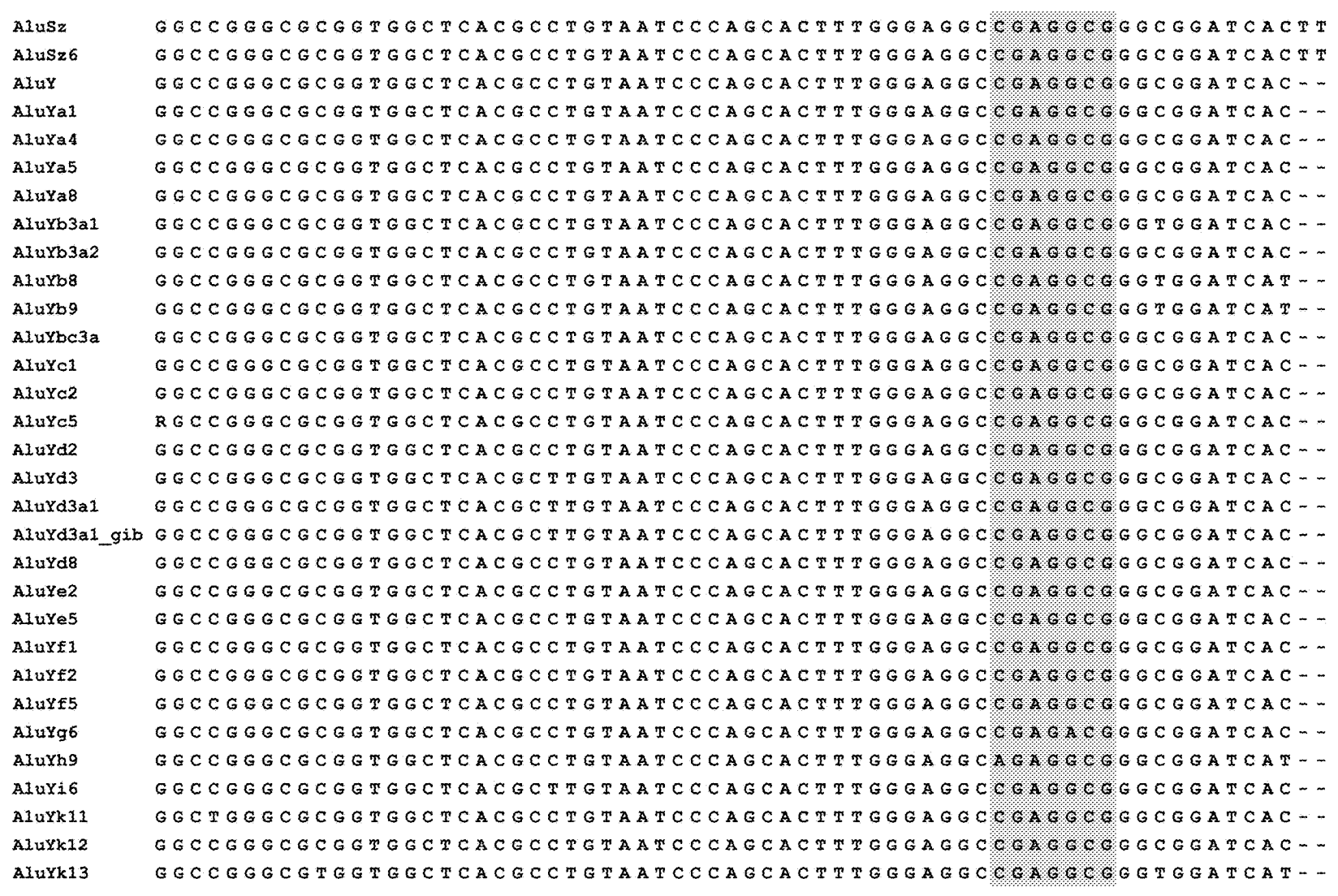
Figure 11:
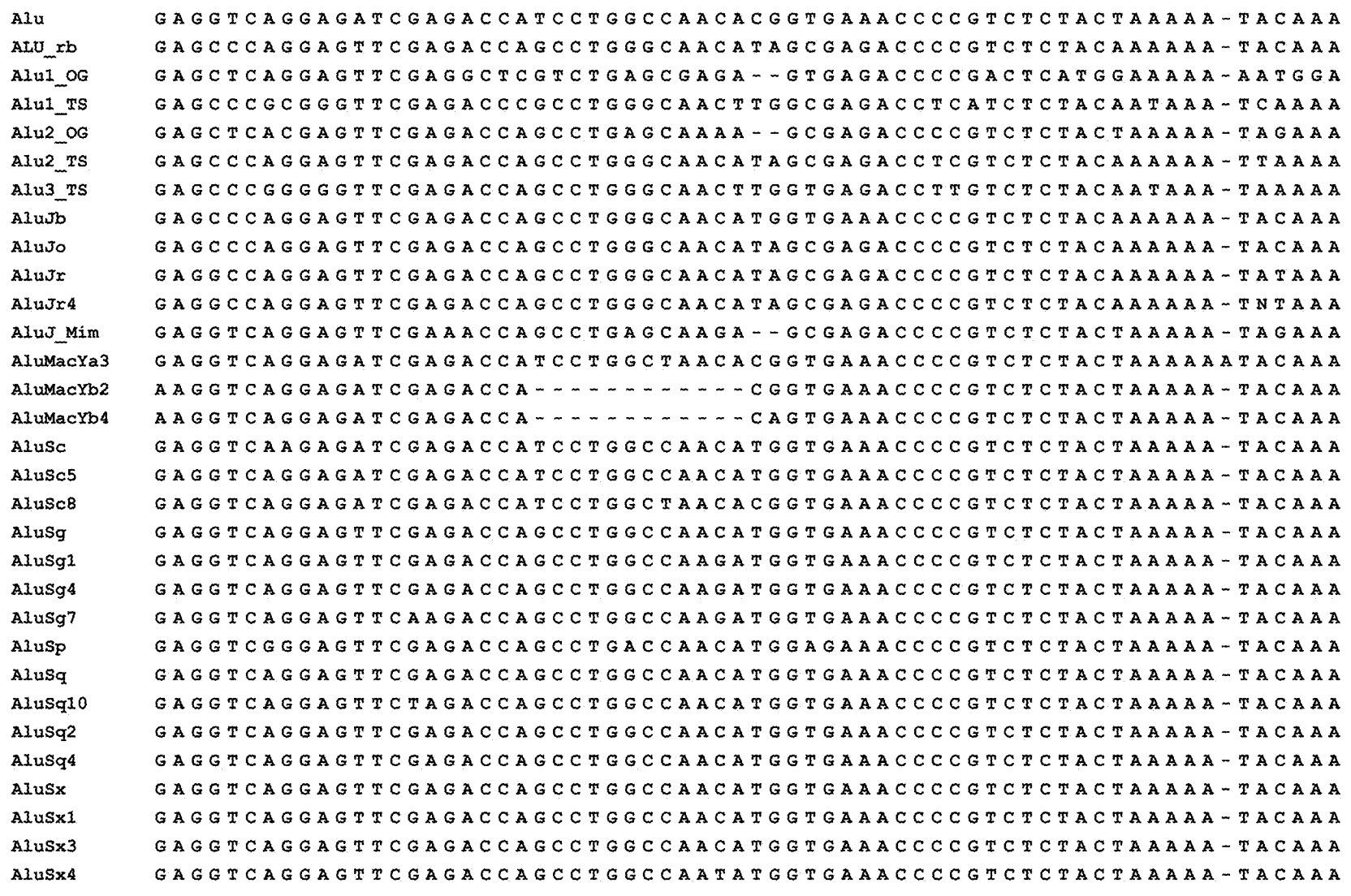
Figure 11:
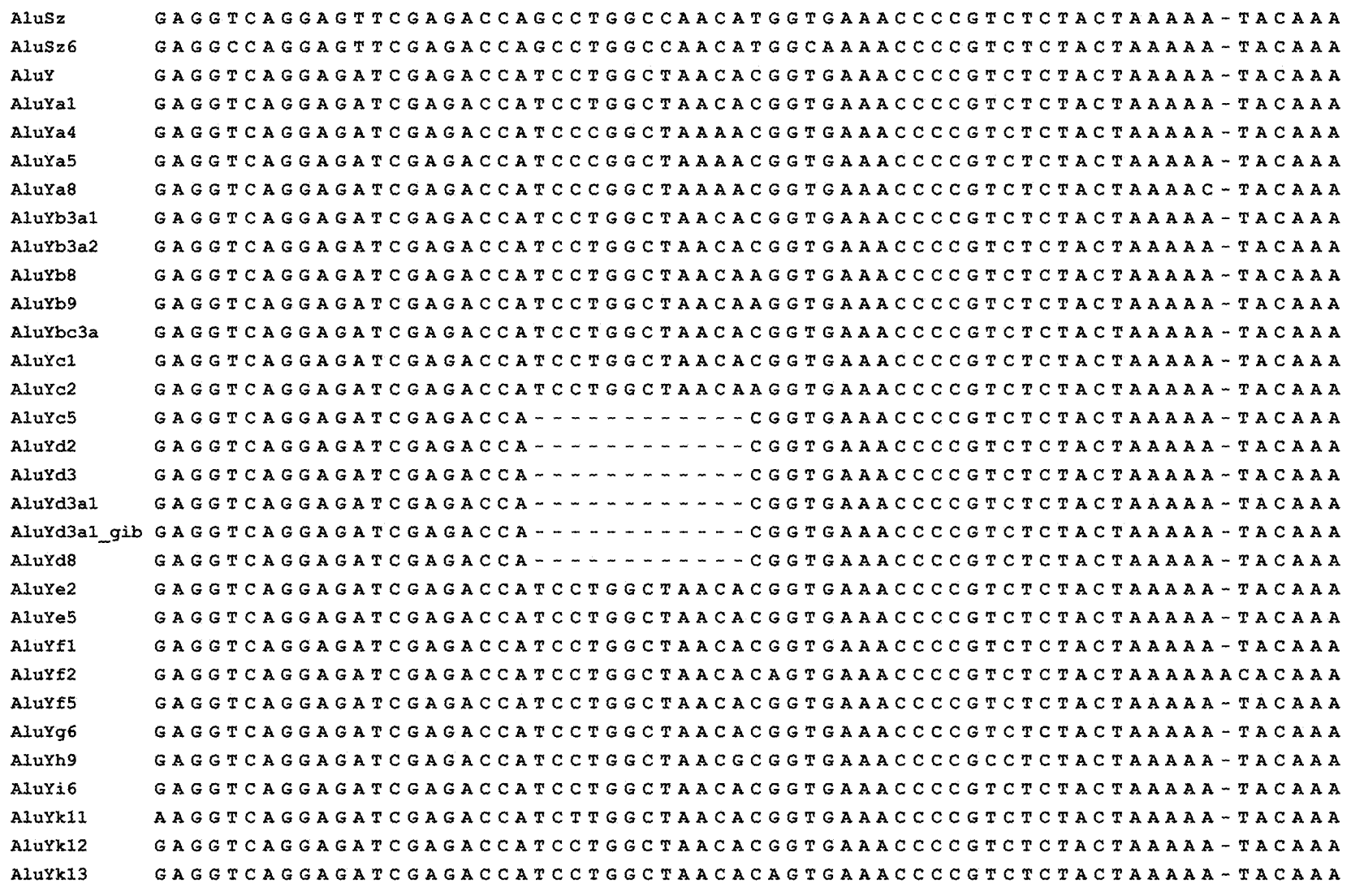
Figure 11:
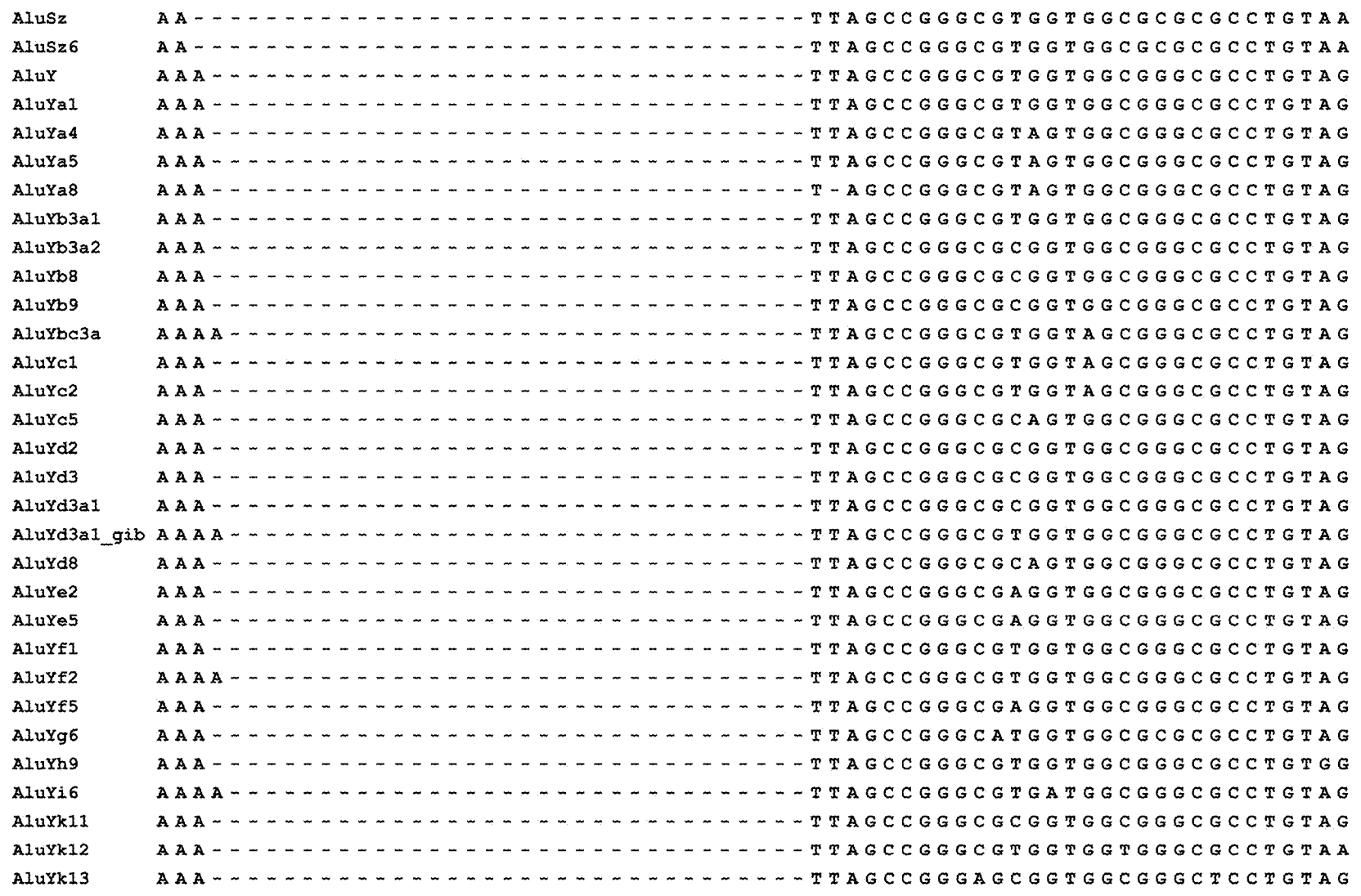
Figure 11:
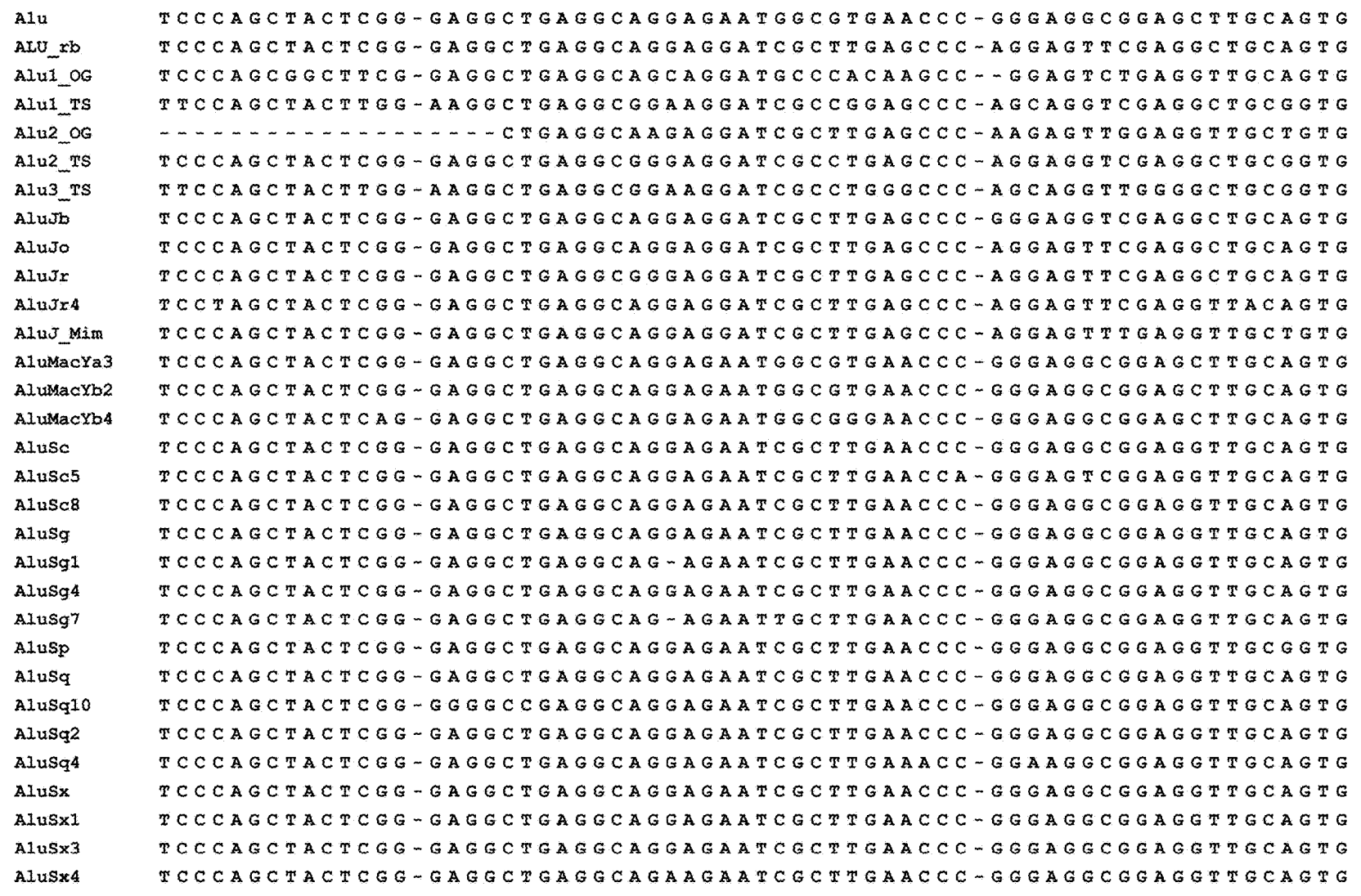
Figure 11:
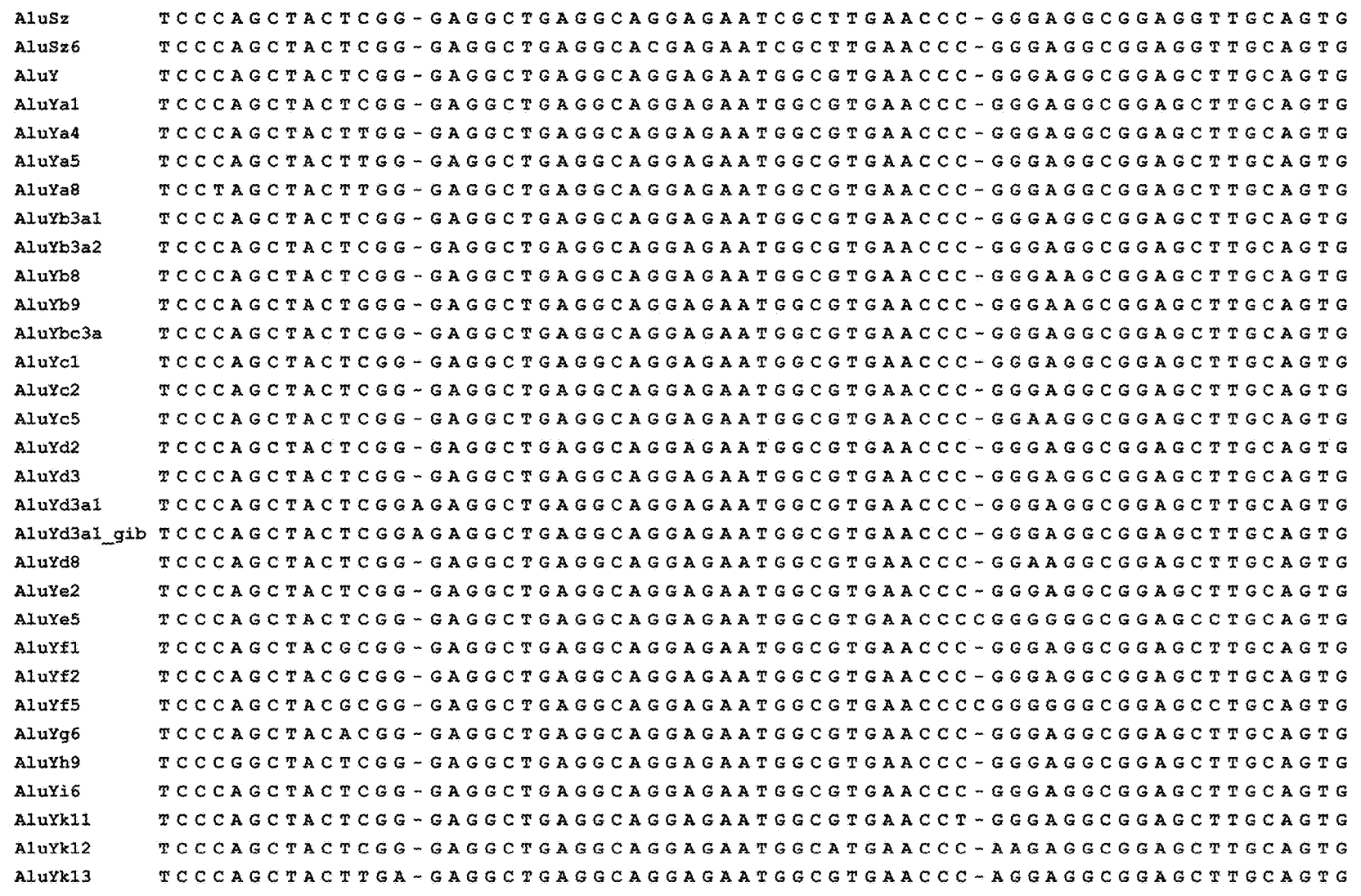
Figure 11:
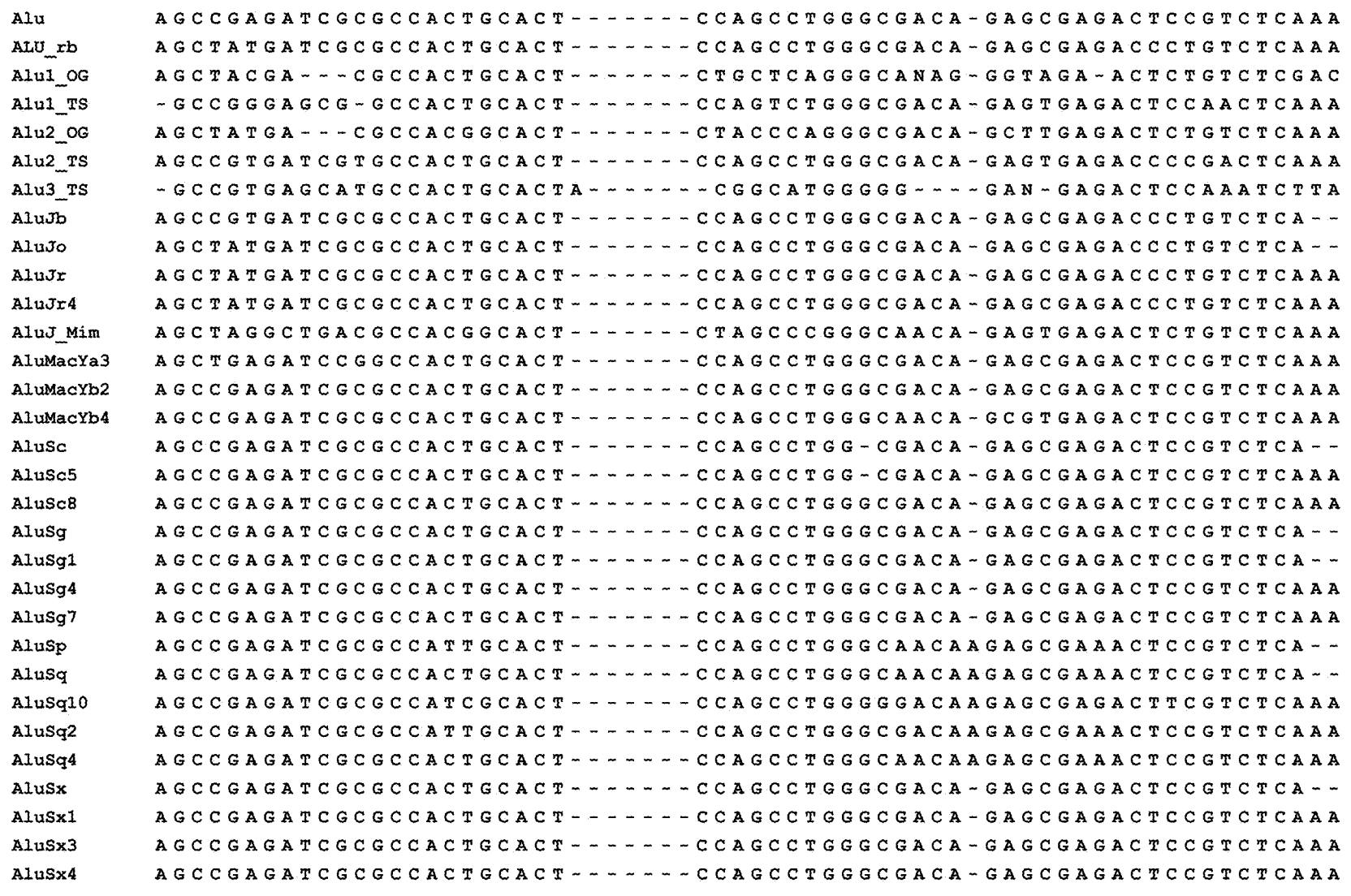
Figure 11:
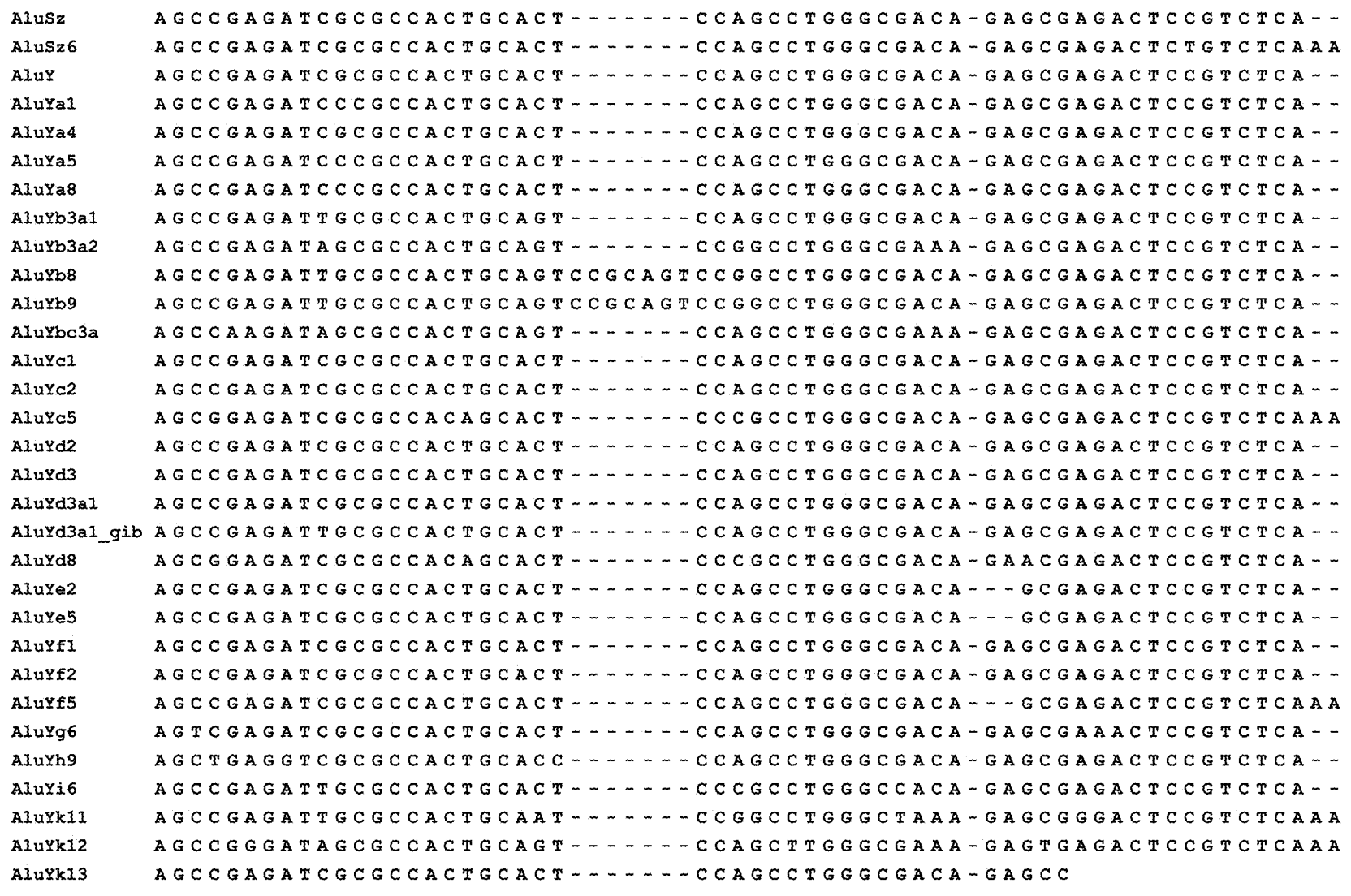

B) Alu's are cut at a position within the position range 49-52 from the start of the Alu SINE genomic elements. The graph shows 5' ends of short RNA-seq reads mapped against mm9 genomic Alu elements creating the transcript metagene of the Alu elements. The metagene x axis is constructed by aligning the 5' end start points of all Alu RNAs as defined in UCSC repeat masker as of September 2016. The x axis position numbers represent absolute distance in nucleotides from the Alu start site (i.e. position 1 in the metagene corresponds to the start site of each Alu genomic element from which the Alu RNA transcript metagene is constructed). The relative number of short RNA 5' ends is plotted on the y-axis. Because, as shown in Table 3, various Alu elements present variations from the consensus sequence showed in FIG. 10A, the cut position varies accordingly based on various insertions and deletions of each Alu that constitutes this metagene (i.e. cut position of different Alu sabfamilies relative to the Alu start site is heterogenous based on these variations creating the compound metagene profile of this figure). These variations and the respective cut range (highlighted in gray), are shown in FIG. 11. Mapping is focused on only the first Alu Arm (left) to prevent cross mapping because of sequence similarity between the two Alu sequence dimers.

C) For a specific Alu class, AluY, the cut is at position 51. This is presented as an example of the cut point within an Alu subfamily.

FIG. 11. Table of sequences for human Alu family members and their respective cut sites. Each row represents the sequence of an Alu family aligned with each other based on Vassetzky amd Kramerov, Nucleic Acids Res. 41(Database issue):D83-9 (2013). The cut region is highlighted in grey. These sequences represent the consensus sequences of all human Alu subfamilies.

DETAILED DESCRIPTION

For more than half a century, genome size has been known to correlate poorly with organism size and developmental complexity (Gall, 1981; Mirsky, 1951; Thomas, 1971). Many flowering plants and amphibians, for example, have genome sizes (or C-value) that are 10- to 100-times larger than those of mammals. This so-called "C-value paradox" was thought to be solved by the discovery that only 1-2% of mammalian genomes have protein-coding potential. The rest of the genome consists largely of repetitive DNA, with satellite DNA, retrotransposable elements, and DNA transposons accounting for ~50% of noncoding sequences (de Koning et al., 2011). For much of the past few decades, these poorly conserved elements have been considered "junk DNA", believed to be remnants of evolution and genetic parasites that proliferate without constraint of purifying selection (Kramerov and Vassetzky, 2011). Emerging studies, however, have been hinting at possible functions for these noncoding sequences (Bourque et al., 2008; Lowe and Haussler, 2012; Lunyak et al., 2007; Ponicsan et al., 2010). It is now known through ENCODE that >80% of the noncoding genome is transcribed during development (Consortium et al., 2007). A growing number of the resulting long noncoding RNAs (lncRNA)—particularly the unique ones—now appear to have important cellular roles, including during X-chromosome inactivation, genomic imprinting, and cancer progression (Kapranov et al., 2007; Lee and Bartolomei, 2013; Li et al., 2016; Rinn and Chang, 2012; Tay et al., 2014).

Nevertheless, functions for repetitive elements remain largely a mystery. One class of repeat elements, however, has garnered some attention in recent years. The B2 element belongs to a family of short intersperse nuclear element (SINE), is present in 100,000 copies, and is transcribed by RNA polymerase III into a 180- to 200-base lncRNA (Kramerov et al., 1982; Kramerov and Vassetzky, 2011) with a 5' tRNA-like sequence and A-rich 3' end (Daniels and Deininger, 1985; Krayev et al., 1982; Lawrence et al., 1985). B2 expression changes significantly during development (Bachvarova, 1988) and its expression is highly induced by specific cellular stresses and disease states, such as viral infection (Singh et al., 1985), age-related macular degeneration (Kaneko et al., 2011; Tarallo et al., 2012), and various cancers (Kaczkowski et al., 2016; Kramerov et al., 1982; Moolhuijzen et al., 2010). The functional and mechanistic relationships between B2 and these various disease states are not currently known. Notably, B2 RNA has been shown to play a role in heat shock (Fornace and Mitchell, 1986; Li et al., 1999), during which B2 RNA is assembled into the pre-initiation complex of RNA polymerase II (POL-II) (Espinoza et al., 2004) and becomes inhibitory to transcription in vitro (Allen et al., 2004). Transcription of the B2 element has also been implicated in formation of a boundary between heterochromatin and euchromatin (Lunyak et al., 2007). The B2 DNA element can also lend its promoter activity to mammalian genes (Ferrigno et al., 2001). Thus, in the mammalian noncoding genome, the B2 repeat currently stands out as one element that is likely to be much more than junk.

With this in mind, we became intrigued by a set of data involving the RNA-binding activity of an epigenetic complex known as Polycomb repressive complex 2 (PRC2) (Zhao et al., 2010). PRC2 is a histone methyltransferase complex consisting of four core subunits, EED, RBBP4/7, SUZ12, and the catalytic subunit EZH2, that together mediate the trimethylation of histone H3 at lysine 27 (H3K27me3) and help to establish repressive chromatin (Margueron and Reinberg, 2011). By RNA immunoprecipitation with deep sequencing (RIP-seq), previous work in mouse cells revealed an RNA interactome of >9,000 unique transcripts (Zhao et al., 2010). While the raison d'etre for the large RNA interactome is under intensive investigation (Cifuentes-Rojas et al., 2014; Davidovich et al., 2015; Davidovich et al., 2013; Kaneko et al., 2013), it is clear that interacting transcripts can target PRC2 in cis to repress gene expression (Pandey et al., 2008; Zhao et al., 2010; Zhao et al., 2008). Further examination of PRC2-RNA interactions has also shown that PRC2 binding can be found at active genes (Davidovich et al., 2013; Kaneko et al., 2013), implying that PRC2 may not solely be involved in gene repression.

The PRC2 RIP-seq analysis also identified RNAs made from repetitive elements (Zhao et al., 2010). However, because repeats pose technical challenges for sequence alignment during analysis of next-generation sequencing data (Treangen and Salzberg, 2012), the repeat fraction had been unexamined despite the fact that such transcripts were present in large numbers. Described herein is an exploration of PRC2's interaction with repetitive RNAs. These findings integrate two previously unconnected networks—Polycomb and junk RNA—in the cellular response to stress and demonstrate the importance of a B2-specific RNA cleavage event. Herein, data show that EZH2 and a B2 transcript made from "junk" DNA play a central role (FIG. 7B). Intriguingly, the key triggering event is B2 RNA elimination. Without wishing to be bound by theory, it is proposed that B2 RNA act as transcriptional "speed bumps" for POL-II. B2 RNA binds broadly in intronic regions, sometimes to one intron, sometimes to two or more (FIG. 4B-E, 7A). The present data suggest that, in resting cells, B2 binding to gene bodies reduces the elongation rate of POL-II and thereby controls the rate at which target genes are expressed in the unstressed state.

Figure 5A:
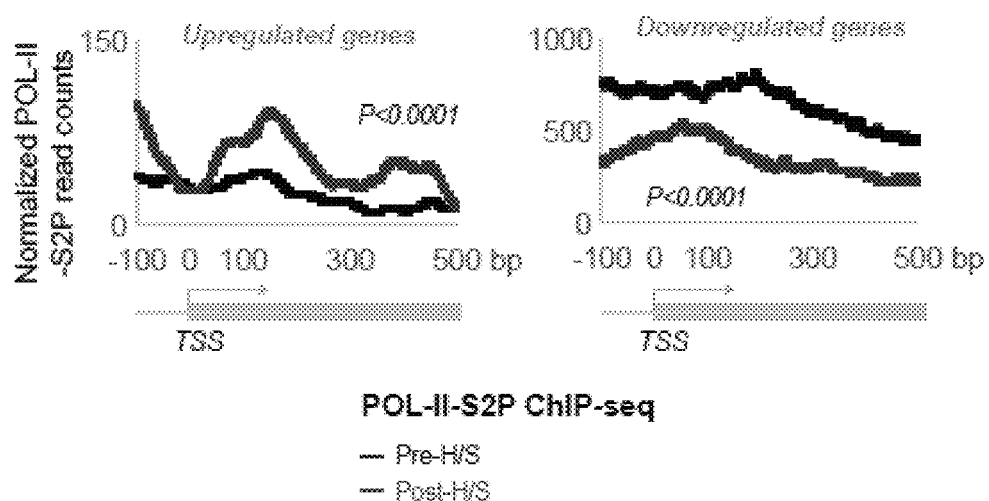
Figure 5B:
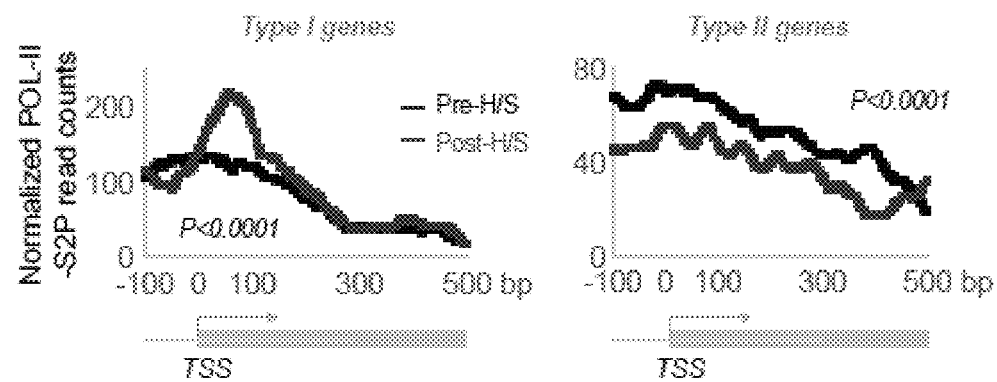
Figure 5C:
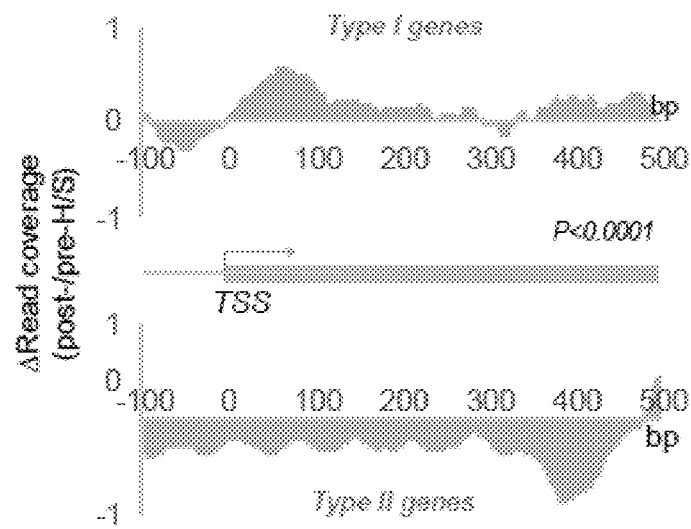
Figure 5D:
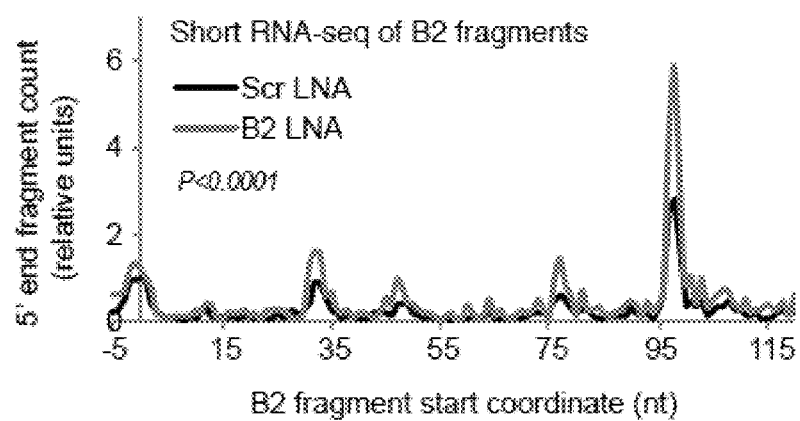
Figure 5E:
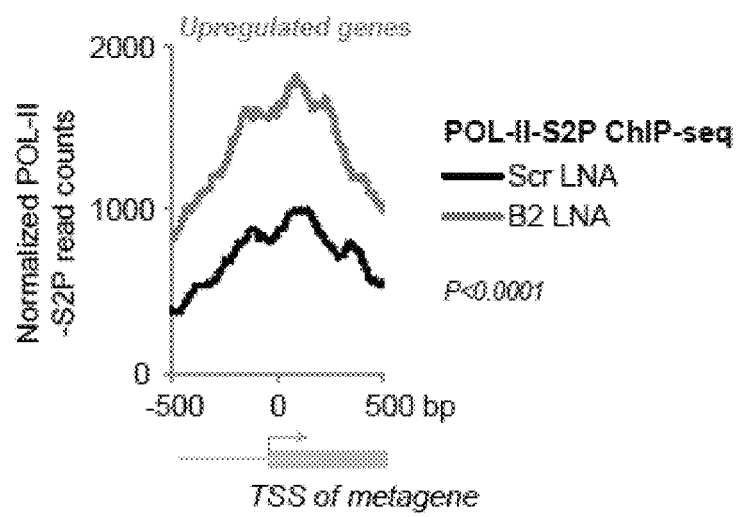
Figure 5F:
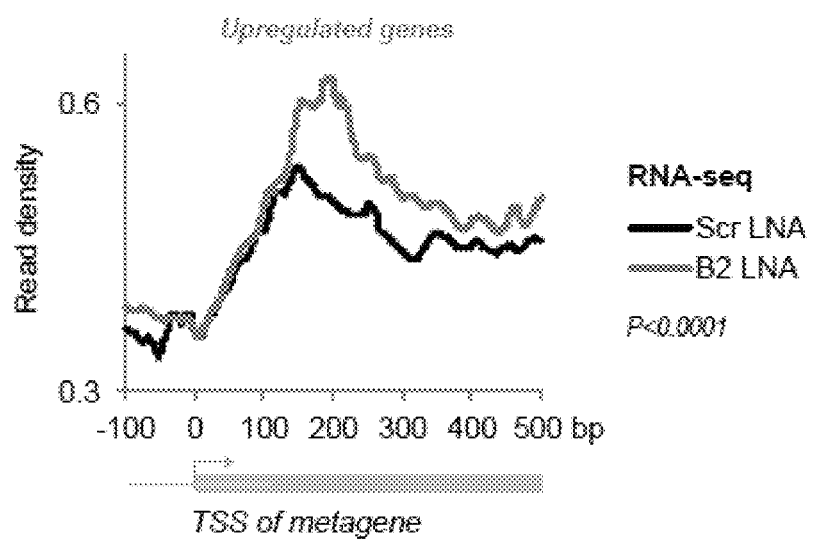

Upon stress, EZH2 is rapidly recruited to H/S-responsive genes (within 15 minutes). A significant consequence is a degradation of B2 RNA involving endonucleolytic cleavages at multiple positions (e.g., nt 98, 77, 33) both in vitro and in vivo (FIG. 1E, 2D, 3D, 61). Cleavage of B2 RNA is sufficient to induce H/S-responsive genes (FIG. 5E, F, 7A). Notably, cut B2 fragments have dramatically reduced affinities for EZH2 ($\Delta K_d$ from 423 nM to >3000 nM; FIG. 1F). Without wishing to be bound by theory, it is suggested that the cleavage event results in disintegration and release of B2 RNA from target genes. B2 degradation at target genes removes the POL-II speed bumps, enabling a larger percent of elongating POL-II to reach the 3' termini of target genes. Previous studies had shown transcriptional pausing downstream of H/S-responsive promoters (Brown et al., 1996; Kwak et al., 2013). Speculatively, some pause sites may correspond to sites of B2 binding. A B2 speed bump mechanism would enable a swift cellular response to stress, as EZH2 recruitment and B2 cleavage occur rapidly—within minutes of the stimulus in vivo.

Figure 3A:
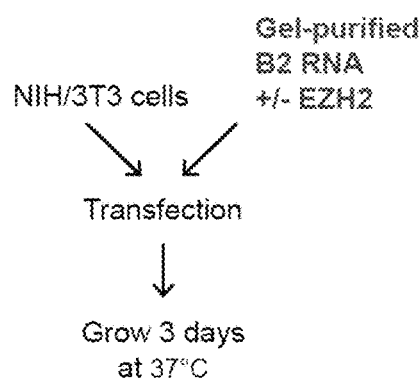
Figure 3A:
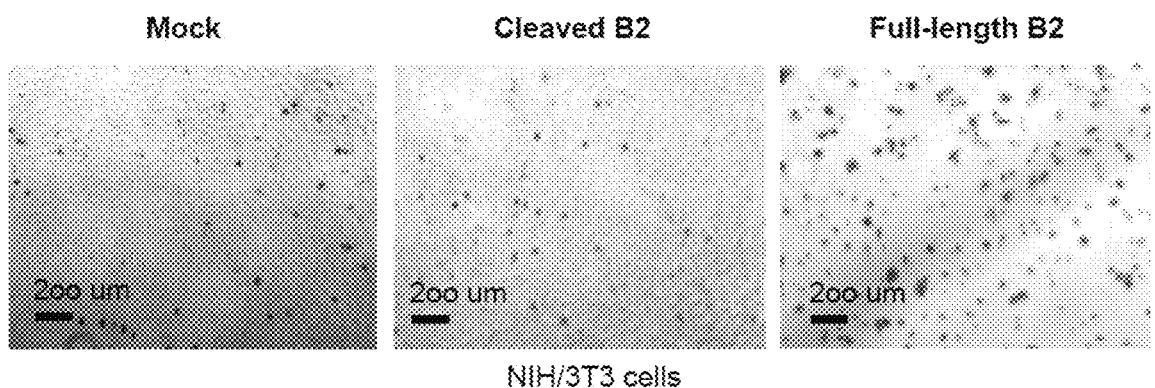
Figure 3B:
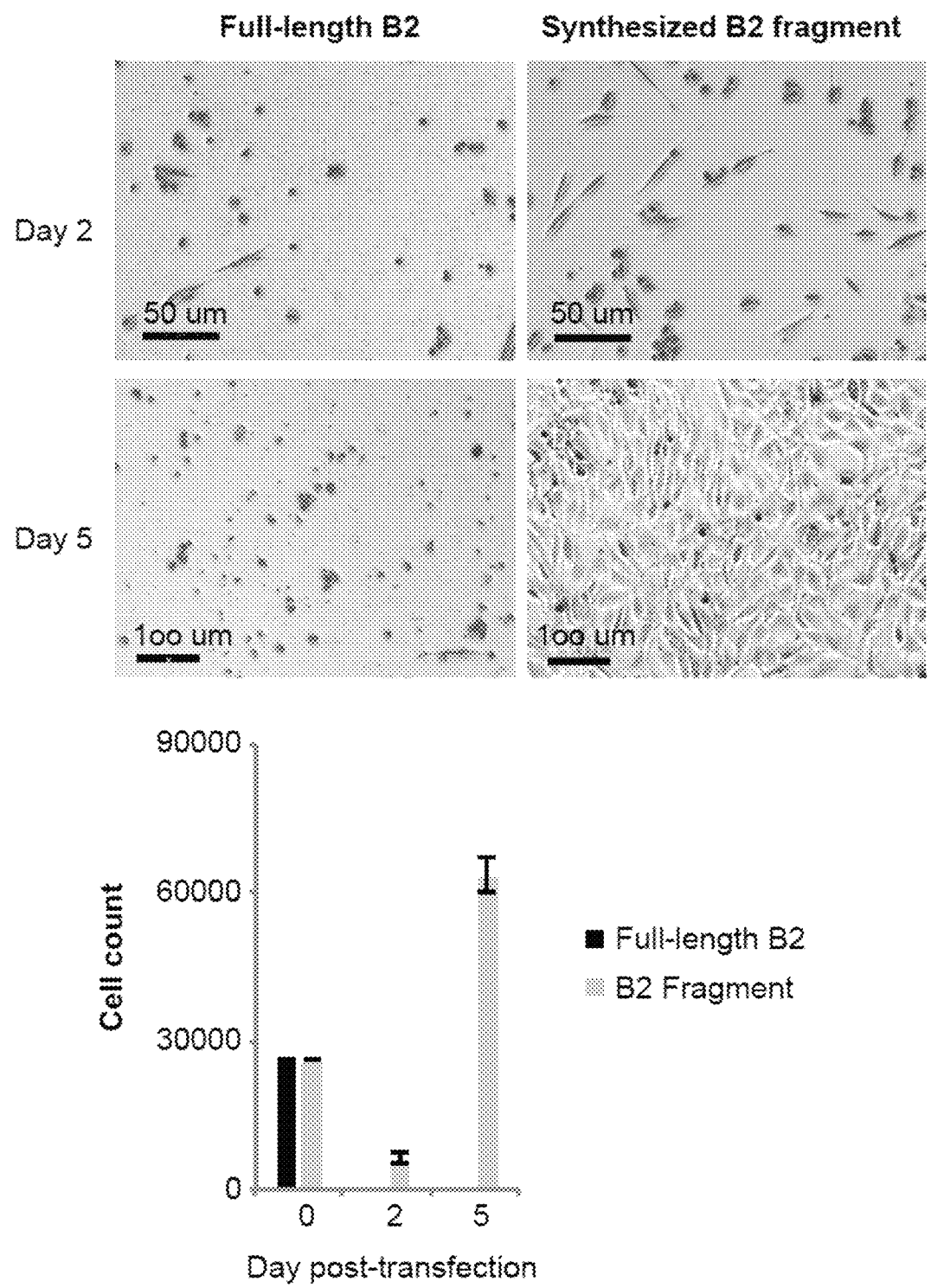
Figure 3C:
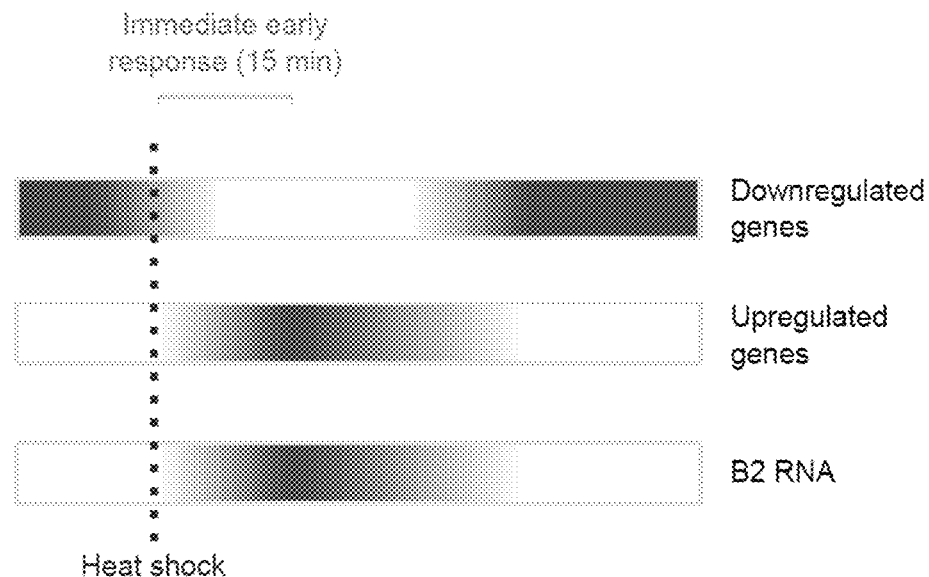

The present study ascribes a specific new function to EZH2 that is independent of its well-known histone methyltransferase activity. Although this work was conducted in mammalian cells, EZH2 may also function during stress in flies, plants, and fungi, (Basenko et al., 2015; Kleinmanns and Schubert, 2014; Siebold et al., 2010). The present work also provides an explanation for the paradoxical observation that EZH2 and its associated RNAs can be found at both active and inactive genes (Davidovich et al., 2013; Kaneko et al., 2013; Zhao et al., 2010). Whereas the H3K27me3 mark is a critical part of EZH2-mediated gene silencing (Margueron and Reinberg, 2011), gene activation by the EZH2-B2 interaction does not depend on H3K27 trimethylation (FIG. 6C,D). Rather activation depends on contact-dependent B2 elimination. Thus, frequent mutation of EZH2 (Margueron and Reinberg, 2011) and misexpression of Alu/B2 elements (Chircop and Speidel, 2014; Kaczkowski et al., 2016; Kramerov et al., 1982; Moolhuijzen et al., 2010) in cancer cells may in part be explained by the critical roles played by EZH2 and B2 during the stress response. Finally, it should be noted that heat shock normally leads to two distinct responses—transcriptional upregulation of stress response genes (Table 1) and transcriptional downregulation of housekeeping genes, among others (Table 2). The EZH2-B2 dynamic relates primarily to the former set of genes. B2 plays an equally important role for the latter (FIG. 3C, 7B). Repression of a large number of genes that are non-essential to stress is an adaptation to conserve cellular resources. Existing studies have demonstrated a role for B2 RNA in repression of two housekeeping genes, including ActinB and Hk2 (Allen et al., 2004; Espinoza et al., 2004; Fornace and Mitchell, 1986; Li et al., 1999). The B2 CHART-seq data now provide a genomic view for this second arm of the heat shock response and reveal that a large number of genes are targeted by B2 RNA immediately after heat shock (FIG. 4F,G; Tables S2,S4,S7), concurrently with the increase in B2 expression (Allen et al., 2004; Fornace and Mitchell, 1986). Because EZH2 is not recruited to the downregulated gene set, B2 RNA is spared the degradation. Previous studies convincingly showed that incorporated B2 can act in vitro by blocking formation of the POL-II pre-initiation complex at promoters. The present findings suggest that B2 may suppress both transcriptional initiation and elongation in vivo. Notably, the present study explains how H/S-upregulated genes can be immune to increased B2 expression immediately following heat shock, as indeed the recruitment of EZH2 ensures B2 degradation at H/S-upregulated genes. In conclusion, the present results have shown that a specific interaction between EZH2 and B2 "junk RNA" triggers the heat shock response via an RNA elimination event.

Methods of Modulating the Mammalian Stress Response

The present results demonstrate that EZH2 interaction with B2 SINE retrotransposons triggers PRC2-mediated cleavage of the B2 elements (consensus sequences are shown in FIG. 2A; the ASOs targeting B2 included a mixture of 5'-GTTACGGATGGTTGTG-3' (SEQ ID NO:63) and 5'-TGTAGCTGTCTTCAG-3' (SEQ ID NO:64) LNAs, e.g., the +in front of the base depicts an LNA nt: 5-G+TTA+CGG+ATGG+TTG+TG-3 (SEQ ID NO:69) and 5-TG+T+AGC+TGTC+TTC+AG-3' (SEQ ID NO:70)), inducing the heat shock response in mammalian cells. Antisense oligonucleotides that modulate the EZH2/B2 interaction have the capacity to alter cleavage of B2. Non-cleaving antisense oligos (ASOs) that prevent or decrease binding of EZH2 to B2 without increasing cleavage of B2 can increase levels of intact B2, resulting in cell death. Such pro-apoptotic ASOs would be useful, e.g., in conditions associated with unwanted cellular proliferation, such as cancer. These ASOs include peptide nucleic acids, N3',P5'-phosphoramidates, morpholino phosphoroamidates, 2'-O-methoxyethyl nucleic acids, and ribonucleic acids delivered through an RNA degradation protective carrier (e.g., using the the HiPerfect reagent from Qiagen; see, e.g., Zovoilis et al., EMBO J. 2011 Sep. 23; 30(20):4299-308). This includes sequences that have both continuing stretches of the modification or clusters of modified nucleotides separated by not modified ones.

In contrast, ASOs such as Locked Nucleic Acids (LNAs, ribonucleotides containing a "lock" or methylene bridge that connects the 2'-oxygen of ribose with the 4'-carbon), that increase cleavage of B2 elements (e.g., by RNAseH) would increase cell viability, useful in conditions associated with cell death such as autoimmune diseases, degenerative diseases, and ischemic injury. Cyclohexenyl nucleic acids can also be used. See, e.g., Kurreck et al., Nucleic Acids Res. 30(9): 1911-1918 (2002). Also as shown herein, the introduction of B2 RNA into a cell, e.g., a cancer cell, induces cell death. Thus the present methods can include administration of an Alu or B2 RNA, or a DNA encoding an Alu or B2 RNA, or a fragment thereof (RNA or DNA), to induce cell death.

Human Alu Repeats

Repetitive DNA elements account for at least about 20% of the human genome, and have been classified into four principal families of interspersed repeats; Alu, Line 1, MIR and MaLR (Schmid, Prog. Nucleic Acid Res. Mol. Biol., 53:283-319 (1996)). The rodent B2 family of repetitive sequence elements corresponds to the human Alu sequence family (see, e.g., Clawson et al., Cell Growth and Diff 7(5):635-646 (1996)); thus, in the methods described herein, Alu sequences can be used as a target for modulating the stress response in humans. The Alu sequences are typically about 280-300 nucleotides in length, and account for about 11% of the human genome (Lander et al., Nature, 409, 860-921 (2001); Deininger et al., Genome Biol. 2011; 12(12): 236). Exemplary consensus sequences of human Alu repeats can be found in FIG. 11; see also FIG. 1 of Weisenberger et al., Nucleic Acids Research 33(21):6823-36 (2005); in FIG. 1 of Luo et al., Biomed Res Int. 2014:784706 (2014); and in Hambor et al., Molecular and Cellular Biology, 13(11): 7056-7070 (1993).

Antisense Oligonucleotides (ASOs)

In some embodiments, the ASOs used in the present methods are 10 to 50, 10 to 20, 10 to 25, 13 to 50, or 13 to 30 nucleotides in length. One having ordinary skill in the art will appreciate that this embodies ASOs having complementary portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. In some embodiments, the ASOs are 15 nucleotides in length. In some embodiments, the ASOs are 12 or 13 to 20, 25, or 30 nucleotides in length. One having ordinary skill in the art will appreciate that this embodies ASOs having complementary portions of 12, 13, 14, 15, 16, 17, 18, 19, 20, 21, 22, 23, 24, 25, 26, 27, 28, 29 or 30 nucleotides in length, or any range therewithin (complementary portions refers to those portions of the ASOs that are complementary to the target sequence). (As used herein, the "target sequence" or "target RNA" means B2 RNA, or Alu RNA in humans, or other equivalent sequences in other organisms).

The ASOs useful in the present methods are sufficiently complementary to the target RNA, i.e., hybridize sufficiently well and with sufficient specificity, to give the desired effect. "Complementary" refers to the capacity for pairing, through hydrogen bonding, between two sequences comprising naturally or non-naturally occurring bases or analogs thereof. For example, if a base at one position of an ASO is capable of hydrogen bonding with a base at the corresponding position of a RNA, then the bases are considered to be complementary to each other at that position. 100% complementarity is preferred but not required.

Routine methods can be used to design an ASO that binds to the target sequence with sufficient specificity. In some embodiments, the methods include using bioinformatics methods known in the art to identify regions of secondary structure, e.g., one, two, or more stem-loop structures, or pseudoknots, and selecting those regions to target with an ASO. For example, "gene walk" methods can be used to optimize the inhibitory activity of the nucleic acid; for example, a series of oligonucleotides of 10-30 nucleotides spanning the length of a target RNA can be prepared, followed by testing for activity. Optionally, gaps, e.g., of 5-10 nucleotides or more, can be left between the target sequences to reduce the number of oligonucleotides synthesized and tested. GC content is preferably between about 30-60%. Contiguous runs of three or more Gs or Cs should be avoided where possible (for example, it may not be possible with very short (e.g., about 9-10 nt) oligonucleotides).

In some embodiments, the ASO molecules can be designed to target a specific region of the RNA sequence. For example, a specific functional region can be targeted, e.g., a region comprising a known RNA localization motif (i.e., a region in which EZH2 binds to the target nucleic acid, e.g., the region between position 70 and 160 at the sequences of the B2 mm1a sequence of FIG. 2A). Alternatively, or in addition, highly conserved regions can be targeted, e.g., regions identified by aligning sequences from disparate species such as primate (e.g., human) and rodent (e.g., mouse) and looking for regions with high degrees of identity. Percent identity can be determined routinely using basic local alignment search tools (BLAST programs) (Altschul et al., J. Mol. Biol., 1990, 215, 403-410; Zhang and Madden, Genome Res., 1997, 7, 649-656), e.g., using the default parameters.

Once one or more target regions, segments or sites have been identified, e.g., within a sequence known in the art or provided herein, ASO compounds are chosen that are sufficiently complementary to the target, i.e., that hybridize sufficiently well and with sufficient specificity (i.e., do not substantially bind to other non-target RNAs), to give the desired effect.

In the context of this invention, hybridization means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as used herein, refers to the capacity for precise pairing between two nucleotides. For example, if a nucleotide at a certain position of an oligonucleotide is capable of hydrogen bonding with a nucleotide at the same position of a RNA molecule, then the ASO and the RNA are considered to be complementary to each other at that position. The ASOs and the RNA are complementary to each other when a sufficient number of corresponding positions in each molecule are occupied by nucleotides which can hydrogen bond with each other. Thus, "specifically hybridisable" and "complementary" are terms which are used to indicate a sufficient degree of complementarity or precise pairing such that stable and specific binding occurs between the ASO and the RNA target. For example, if a base at one position of an ASO is capable of hydrogen bonding with a base at the corresponding position of a RNA, then the bases are considered to be complementary to each other at that position. 100% complementarity is not required.

As noted above, a complementary nucleic acid sequence need not be 100% complementary to that of its target nucleic acid to be specifically hybridisable. A complementary nucleic acid sequence for purposes of the present methods is specifically hybridisable when binding of the sequence to the target RNA molecule interferes with the normal function of the target RNA to cause a loss of activity, and there is a sufficient degree of complementarity to avoid non-specific binding of the sequence to non-target RNA sequences under conditions in which specific binding is desired, e.g., under physiological conditions in the case of in vivo assays or therapeutic treatment, and in the case of in vitro assays, under conditions in which the assays are performed under suitable conditions of stringency. For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., *Molecular Cloning: A Laboratory Manual*, Cold Spring Harbor Laboratory Press, New York.

In general, the ASOs useful in the methods described herein have at least 80% sequence complementarity to a target region within the target nucleic acid, e.g., 90%, 95%, or 100% sequence complementarity to the target region within an RNA. For example, an antisense compound in which 18 of 20 nucleobases of the antisense oligonucleotide are complementary, and would therefore specifically hybridize, to a target region would represent 90 percent complementarity. Percent complementarity of an ASO with a region of a target nucleic acid can be determined routinely using basic local alignment search tools (BLAST programs) (Altschul et al., J. Mol. Biol., 1990, 215, 403-410; Zhang and Madden, Genome Res., 1997, 7, 649-656). ASOs that hybridize to an RNA can be identified through routine experimentation. In general, the ASOs must retain specificity for their target, i.e., must not directly bind to, or directly significantly affect levels or expression levels of, transcripts other than the intended target.

For further disclosure regarding ASOs, please see US2010/0317718 (antisense oligos); US2009/0181914 and US2010/0234451 (LNAs); and WO2010/129746 and WO2010/040112 (ASOs), as well as WO 2012/065143, WO 2012/087983, and WO 2014/025887 (ASOs targeting non-coding RNAs/supRNAs), all of which are incorporated herein by reference in their entirety.

In some embodiments, the ASOs used in the methods described herein are modified, e.g., comprise one or more modified bonds or bases. A number of modified bases include phosphorothioate, methylphosphonate, peptide nucleic acids, or locked nucleic acid (LNA) molecules. Some ASOs are fully modified, while others are chimeric and contain two or more chemically distinct regions, each made up of at least one nucleotide. These ASOs typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric ASOs of the invention may be formed as composite structures of two or more types of oligonucleotides, modified oligonucleotides, oligonucleosides and/or oligonucleotide mimetics as described above. Such compounds have also been referred to in the art as hybrids or gapmers (e.g., wherein a central block of DNA monomers is flanked by 2'-O modified ribonucleotides or other artificially modified ribonucleotide monomers such as bridged nucleic acids (BNAs), e.g., LNA/DNA/LNA or BNA/DNA/DNA gapmers, usually wherein the central block of deoxynucleotide monomers is sufficiently long to induce RNase H cleavage) or mixmers, i.e., LNAs containing a limited number of modified ribonucleotide or nucleotide monomers, e.g., LNA monomers, in combination with other types of monomers, typically DNA. See Wahlestedt et al., Proc. Natl Acad. Sci. USA, 97, 5633-5638 (2000). Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In some embodiments, the ASO comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target.

A number of nucleotide and nucleoside modifications have been shown to make the ASO into which they are incorporated more resistant to nuclease digestion than the native oligodeoxynucleotide; these modified oligos survive intact for a longer time than unmodified ASOs. Specific examples of modified ASOs include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are ASOs with phosphorothioate backbones and those with heteroatom backbones, particularly CH2-NH—O—CH2, CH, ~N(CH3)~O~CH2 (known as a methylene(methylimino) or MMI backbone], CH2-O—N(CH3)-CH2, CH2-N(CH3)-N(CH3)-CH2 and O—N(CH3)-CH2-CH2 backbones, wherein the native phosphodiester backbone is represented as O—P—O—CH); amide backbones (see De Mesmaeker et al. Ace. Chem. Res. 1995, 28:366-374); morpholino backbone structures (see Summerton and Weller, U.S. Pat. No. 5,034,506); peptide nucleic acid (PNA) backbone (wherein the phosphodiester backbone of the ASO is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050.

Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991.

Cyclohexenyl nucleic acid ASO mimetics are described in Wang et al., J. Am. Chem. Soc., 2000, 122, 8595-8602.

Modified ASO backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315; 5,185,444; 5,214,134; 5,216,141; 5,235,033; 5,264, 562; 5, 264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

One or more substituted sugar moieties can also be included, e.g., one of the following at the 2' position: OH, SH, SCH3, F, OCN, OCH3 OCH3, OCH3 O(CH2)n CH3, O(CH2)n NH2 or O(CH2)n CH3 where n is from 1 to about 10; Ci to C10 lower alkyl, alkoxyalkoxy, substituted lower alkyl, alkaryl or aralkyl; Cl; Br; CN; CF3; OCF3; O-, S-, or N-alkyl; O-, S-, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an ASO; or a group for improving the pharmacodynamic properties of an ASO and other substituents having similar properties. A preferred modification includes 2'-methoxyethoxy [2'-O-CH$_2$CH$_2$OCH$_3$, also known as 2'-O-(2-methoxyethyl)] (Martin et al, Hely. Chim. Acta, 1995, 78, 486). Other preferred modifications include 2'-methoxy (2'-O—CH3), 2'-propoxy (2'-OCH$_2$ CH$_2$CH$_3$) and 2'-fluoro (2'-F). Similar modifications may also be made at other positions on the ASO, particularly the 3' position of the sugar on the 3' terminal nucleotide and the 5' position of 5' terminal nucleotide. ASOs may also have sugar mimetics such as cyclobutyls in place of the pentofuranosyl group.

ASOs can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. Kornberg, A., DNA Replication, W. H. Freeman & Co., San Francisco, 1980, pp 75-77; Gebeyehu, G., et al. Nucl. Acids Res. 1987, 15:4513). A "universal" base known in the art, e.g., inosine, can also be included. 5-Me-C substitutions have been shown to increase nucleic acid duplex stability by 0.6-1.2<0>C. (Sanghvi, Y. S., in Crooke, S. T. and Lebleu, B., eds., Antisense Research and Applications, CRC Press, Boca Raton, 1993, pp. 276-278) and are presently preferred base substitutions.

It is not necessary for all positions in a given ASO to be uniformly modified, and in fact more than one of the aforementioned modifications may be incorporated in a single ASO or even at within a single nucleoside within an ASO.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an ASO mimetic that has been shown to have excellent hybridization properties, is referred to as a peptide nucleic acid (PNA). In PNA compounds, the sugar-backbone of an ASO is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen et al, Science, 1991, 254, 1497-1500. ASOs can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in 'The Concise Encyclopedia of Polymer Science And Engineering', pages 858-859, Kroschwitz, J.I., ed. John Wiley & Sons, 1990, those disclosed by Englisch et al., Angewandle Chemie, International Edition', 1991, 30, page 613, and those disclosed by Sanghvi, Y. S., Chapter 15, Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2<0>C (Sanghvi, Y.S., Crooke, S. T. and Lebleu, B., eds, 'Antisense Research and Applications', CRC Press, Boca Raton, 1993, pp. 276-278) and are presently preferred base substitutions, even more particularly when combined with 2'-O-methoxyethyl sugar modifications. Modified nucleobases are described in US patent nos. 3,687,808, as well as U.S. Pat. Nos. 4,845,205; 5,130, 302; 5,134,066; 5,175, 273; 5, 367,066; 5,432,272; 5,457, 187; 5,459,255; 5,484,908; 5,502,177; 5,525,711; 5,552, 540; 5,587,469; 5,596,091; 5,614,617; 5,750,692, and 5,681,941, each of which is herein incorporated by reference.

In some embodiments, the ASOs are chemically linked to one or more moieties or conjugates that enhance the activity, cellular distribution, or cellular uptake of the ASO. Such moieties comprise but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al, Ann. N. Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., dihexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylaminocarbonyl-t oxycholesterol moiety (Crooke et al., J. Pharmacol. Exp. Ther., 1996, 277, 923-937). See also U.S. Pat. Nos. 4,828,979; 4,948,882; 5,218,105; 5,525,465; 5,541,313; 5,545,730; 5,552, 538; 5,578,717; 5,580,731; 5,580,731; 5,591,584; 5,109,124; 5,118,802; 5,138,045; 5,414,077; 5,486, 603; 5,512,439; 5,578,718; 5,608,046; 4,587,044; 4,605,735; 4,667,025; 4,762, 779; 4,789,737; 4,824,941; 4,835,263; 4,876,335; 4,904,582; 4,958,013; 5,082, 830; 5,112,963; 5,214,136; 5,082,830; 5,112,963; 5,214,136; 5, 245,022; 5,254,469; 5,258,506; 5,262,536; 5,272,250; 5,292,873; 5,317,098; 5,371,241, 5,391, 723; 5,416,203, 5,451,463; 5,510,475; 5,512,667; 5,514,785; 5, 565,552;

5,567,810; 5,574,142; 5,585,481; 5,587,371; 5,595,726; 5,597,696; 5,599,923; 5,599, 928 and 5,688,941, each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Because of the heterogeneity in human Alu sequences across the genome, the use of pools of ASOs that target multiple families may be desired. In some embodiments, ASOs comprising the following sequences are used: 5-GGCCGAGGCGGGCGG-3 (SEQ ID NO:71) and 5-TTTGGGAGGCCGAGG-3 (SEQ ID NO:72).

siRNA/shRNA

In some embodiments, the ASOs used in the present methods are interfering RNAs, including but not limited to a small interfering RNAs ("siRNAs") or a small hairpin RNAs ("shRNAs"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

In some embodiments, the interfering RNA coding region encodes a self-complementary RNA molecule having a sense region, an antisense region and a loop region. Such an RNA molecule when expressed desirably forms a "hairpin" structure, and is referred to herein as an "shRNA." The loop region is generally between about 2 and about 10 nucleotides in length. In some embodiments, the loop region is from about 6 to about 9 nucleotides in length. In some embodiments, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. For details, see Brummelkamp et al., Science 296:550-553, (2002); Lee et al, Nature Biotechnol., 20, 500-505, (2002); Miyagishi and Taira, Nature Biotechnol 20:497-500, (2002); Paddison et al. Genes & Dev. 16:948-958, (2002); Paul, Nature Biotechnol, 20, 505-508, (2002); Sui, Proc. Natl. Acad. Sd. USA, 99(6), 5515-5520, (2002); Yu et al. Proc NatlAcadSci USA 99:6047-6052, (2002).

The target RNA cleavage reaction guided by siRNAs is highly sequence specific. In general, siRNA containing a nucleotide sequences identical to a portion of the target nucleic acid are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. In general the siRNAs must retain specificity for their target, i.e., must not directly bind to, or directly significantly affect expression levels of, transcripts other than the intended target.

Because of the heterogeneity in human Alu sequences across the genome, the use of pools of siRNAs that target multiple families may be desired.

Locked Nucleic Acids (LNAs)

In some embodiments, the modified ASOs used in the methods described herein comprise locked nucleic acid (LNA) molecules, e.g., including [alpha]-L-LNAs. LNAs comprise ribonucleic acid analogues wherein the ribose ring is "locked" by a methylene bridge between the 2'-oxgygen and the 4'-carbon—i.e., ASOs containing at least one LNA monomer, that is, one 2'-0,4'-C-methylene-fl-D-ribofuranosyl nucleotide. LNA bases form standard Watson-Crick base pairs but the locked configuration increases the rate and stability of the basepairing reaction (Jensen et al., Oligonucleotides, 14, 130-146 (2004)). LNAs also have increased affinity to base pair with RNA as compared to DNA and initiate cleavage by RNAse H. These properties render LNAs especially useful as probes for fluorescence in situ hybridization (FISH) and comparative genomic hybridization, as knockdown tools for miRNAs, and as antisense oligonucleotides to target mRNAs or other RNAs, e.g., RNAs as described herein. See, e.g., Kurreck et al., Nucleic Acids Res. 30(9): 1911-1918 (2002).

The LNA molecules can include molecules comprising 10-30, e.g., 12-24, e.g., 12, 13, 14, 15, 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the RNA. The LNA molecules can be chemically synthesized using methods known in the art.

The LNA molecules can be designed using any method known in the art; a number of algorithms are known, and are commercially available (e.g., on the internet, for example at exiqon.com). See, e.g., You et al., Nuc. Acids. Res. 34:e60 (2006); McTigue et al., Biochemistry 43:5388-405 (2004); and Levin et al., Nuc. Acids. Res. 34:e142 (2006). For example, "gene walk" methods, similar to those used to design antisense oligos, can be used to optimize the inhibitory activity of the LNA; for example, a series of ASOs of 10-30 nucleotides spanning the length of a target RNA can be prepared, followed by testing for activity. Optionally, gaps, e.g., of 5-10 nucleotides or more, can be left between the LNAs to reduce the number of ASOs synthesized and tested. GC content is preferably between about 30-60%. General guidelines for designing LNAs are known in the art; for example, LNA sequences will bind very tightly to other LNA sequences, so it is preferable to avoid significant complementarity within an LNA. Contiguous runs of more than four LNA residues, should be avoided where possible (for example, it may not be possible with very short (e.g., about 9-10 nt) ASOs). In some embodiments, the LNAs are xylo-LNAs. For additional information regarding LNAs see U.S. Pat. Nos. 6,268,490; 6,734,291; 6,770,748; 6,794,499; 7,034,133; 7,053,207; 7,060,809; 7,084,125; and 7,572,582; and U.S. Pre-Grant Pub. Nos. 20100267018; 20100261175; and 20100035968; Koshkin et al. Tetrahedron 54, 3607-3630 (1998); Obika et al. Tetrahedron Lett. 39, 5401-5404 (1998); Jepsen et al., Oligonucleotides 14:130-146 (2004); Kauppinen et al., Drug Disc. Today 2(3):287-290 (2005); and Ponting et al., Cell 136(4):629-641 (2009), and references cited therein.

Because of the heterogeneity in human Alu sequences across the genome, the use of pools of LNAs that target multiple families may be desired.

Making and Using ASOs

Nucleic acid sequences used to practice this invention can be made using methods known in the art, e.g., synthesized in vitro by well-known chemical synthesis techniques, as described in, e.g., Adams (1983) J. Am. Chem. Soc. 105: 661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook et al., Molecular Cloning; A Laboratory Manual 3d ed. (2001); Current Protocols in Molecular Biology, Ausubel et al., eds. (John Wiley & Sons, Inc., New York 2010); Kriegler, Gene Transfer and Expression: A Laboratory Manual (1990); Laboratory Techniques In Biochemistry And Molecular Biology: Hybridization With Nucleic Acid Probes, Part I. Theory and Nucleic Acid Preparation, Tijssen, ed. Elsevier, N.Y. (1993).

Alu/B2 Nucleic Acids

The methods described herein can also include the use of Alu or B2 nucleic acids to induce cell death in a cell, e.g., for the treatment of disorders associated with abnormal apoptotic or differentiative processes. The Alu or B2 nucleic acids can be, e.g., Alu or B2 RNA comprising a full length Alu or B2 sequence, or a fragment thereof that induces cell death. Methods for identifying fragments that induce cell death are known in the art and described herein, see, e.g., Example 3 herein. The methods can include incubating a sample of test cells, e.g., cancer cells, in the presence of a candidate fragment and a control fragment (e.g., of the same length and modifications but having a scrambled sequence), and selecting those fragments that induce cell death under conditions in which the control fragment does not induce cell death.

The Alu or B2 nucleic acids can be administered to the cells as RNA, e.g., naked RNA or RNA encapsulated in a carrier, e.g., a liposomal carrier. Alternatively, an expression construct encoding the Alu or B2 nucleic acid or fragment thereof can be administered.

Expression Constructs

Expression constructs encoding an Alu or B2 nucleic acid or fragment thereof can be administered in any effective carrier, e.g., any formulation or composition capable of effectively delivering the component gene to cells in vivo. Approaches include insertion of the gene in viral vectors, including recombinant retroviruses, adenovirus, adeno-associated virus, lentivirus, and herpes simplex virus-1, or recombinant bacterial or eukaryotic plasmids. Viral vectors transfect cells directly; plasmid DNA can be delivered naked or with the help of, for example, cationic liposomes (lipofectamine) or derivatized (e.g., antibody conjugated), polylysine conjugates, gramacidin S, artificial viral envelopes or other such intracellular carriers, as well as direct injection of the gene construct or $CaPO_4$ precipitation carried out in vivo. A preferred approach for in vivo introduction of nucleic acid into a cell is by use of a viral vector containing nucleic acid, e.g., a cDNA. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, Blood 76:271 (1990)). A replication defective retrovirus can be packaged into virions, which can be used to infect a target cell through the use of a helper virus by standard techniques. Protocols for producing recombinant retroviruses and for infecting cells in vitro or in vivo with such viruses can be found in Ausubel, et al., eds., Current Protocols in Molecular Biology, Greene Publishing Associates, (1989), Sections 9.10-9.14, and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include ΨCrip, ΨCre, Ψ2 and ΨAm. Retroviruses have been used to introduce a variety of genes into many different cell types, including epithelial cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150:4104-4115; U.S. Pat. Nos. 4,868,116; 4,980,286; PCT Application WO 89/07136; PCT Application WO 89/02468; PCT Application WO 89/05345; and PCT Application WO 92/07573).

Another viral gene delivery system useful in the present methods utilizes adenovirus-derived vectors. The genome of an adenovirus can be manipulated, such that it encodes and expresses a gene product of interest but is inactivated in terms of its ability to replicate in a normal lytic viral life cycle. See, for example, Berkner et al., BioTechniques 6:616 (1988); Rosenfeld et al., Science 252:431-434 (1991); and Rosenfeld et al., Cell 68:143-155 (1992). Suitable adenoviral vectors derived from the adenovirus strain Ad type 5 dl324 or other strains of adenovirus (e.g., Ad2, Ad3, or Ad7 etc.) are known to those skilled in the art. Recombinant adenoviruses can be advantageous in certain circumstances, in that they are not capable of infecting non-dividing cells and can be used to infect a wide variety of cell types, including epithelial cells (Rosenfeld et al., (1992) supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ, where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham, J. Virol. 57:267 (1986).

Yet another viral vector system useful for delivery of nucleic acids is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al., Curr. Topics in Micro. and Immunol. 158:97-129 (1992). It is also one of the few viruses that may integrate its DNA into non-dividing cells, and exhibits a high frequency of stable integration (see for example Flotte et al., Am. J. Respir. Cell. Mol. Biol. 7:349-356 (1992); Samulski et al., J. Virol. 63:3822-3828 (1989); and McLaughlin et al., J. Virol. 62:1963-1973 (1989). Vectors containing as little as 300 base pairs of AAV can be packaged and can integrate. Space for exogenous DNA is limited to about 4.5 kb. An AAV vector such as that described in Tratschin et al., Mol. Cell. Biol. 5:3251-3260 (1985) can be used to introduce DNA into cells. A variety of nucleic acids have been introduced into different cell types using AAV vectors (see for example Hermonat et al., Proc. Natl. Acad. Sci. USA 81:6466-6470 (1984); Tratschin et al., Mol. Cell. Biol. 4:2072-2081 (1985); Wondisford et al., Mol. Endocrinol. 2:32-39 (1988); Tratschin et al., J. Virol. 51:611-619 (1984); and Flotte et al., J. Biol. Chem. 268:3781-3790 (1993).

In some embodiments, Alu or B2 nucleic acid or fragments thereof, or nucleic acids encoding an Alu or B2 nucleic acid or fragments thereof, are entrapped in liposomes bearing positive charges on their surface (e.g., lipofectins), which can be tagged with antibodies against cell surface antigens of the target cancer cells.

In clinical settings, the nucleic acids can be introduced into a subject by any of a number of methods, each of which is familiar in the art. For instance, a pharmaceutical preparation can be introduced systemically, e.g., by intravenous injection, and specific transduction of the protein in the target cells will occur predominantly from specificity of transfection, provided by the gene delivery vehicle, cell-type or tissue-type expression due to the transcriptional regulatory sequences controlling expression of the receptor gene, or a combination thereof. In other embodiments, initial delivery of the nucleic acids is more limited, with introduction into the subject being quite localized. For example, the nucleic acids can be introduced by catheter (see U.S. Pat. No. 5,328,470) or by stereotactic injection (e.g., Chen et al., PNAS USA 91: 3054-3057 (1994)). In some embodiments, the nucleic acids are administered during or after surgical resection of a tumor; in some embodiments, a controlled-release hydrogel comprising the nucleic acids is administered at the conclusion of resection before closure to provide a steady dose of the nucleic acids over time.

A pharmaceutical preparation of the nucleic acids can consist essentially of the gene delivery system (e.g., viral vector(s)) in an acceptable diluent, or can comprise a slow release matrix in which the gene delivery vehicle is embedded. Alternatively, where the complete gene delivery system can be produced intact from recombinant cells, e.g., retroviral vectors, the pharmaceutical preparation can comprise one or more cells, which produce the gene delivery system.

Treating Cellular Differentiative Disorders

As noted above, the methods described herein can also include the use of Alu or B2 nucleic acids or fragments thereof to induce cell death in a cell, e.g., for the treatment of disorders associated with abnormal apoptotic or differentiative processes, e.g., cellular proliferative disorders or cellular differentiative disorders, e.g., cancer, e.g., by producing an active or passive immunity. Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair. The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the disease is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

Additional examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) *Crit Rev. in Oncol./Hemotol.* 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Other examples of proliferative and/or differentiative disorders include skin disorders. The skin disorder may involve the aberrant activity of a cell or a group of cells or layers in the dermal, epidermal, or hypodermal layer, or an abnormality in the dermal-epidermal junction. For example, the skin disorder may involve aberrant activity of keratinocytes (e.g., hyperproliferative basal and immediately suprabasal keratinocytes), melanocytes, Langerhans cells, Merkel cells, immune cell, and other cells found in one or more of the epidermal layers, e.g., the stratum basale (stratum germinativum), stratum spinosum, stratum granulosum, stratum lucidum or stratum corneum. In other embodiments, the disorder may involve aberrant activity of a dermal cell, e.g., a dermal endothelial, fibroblast, immune cell (e.g., mast cell or macrophage) found in a dermal layer, e.g., the papillary layer or the reticular layer. Examples of skin disorders include psoriasis, psoriatic arthritis, dermatitis (eczema), e.g., exfoliative dermatitis or atopic dermatitis, pityriasis rubra pilaris, pityriasis rosacea, parapsoriasis, pityriasis lichenoiders, lichen planus, lichen nitidus, ichthyosiform dermatosis, keratodermas, dermatosis, alopecia areata, pyoderma gangrenosum, vitiligo, pemphigoid (e.g., ocular cicatricial pemphigoid or bullous pemphigoid), urticaria, prokeratosis, rheumatoid arthritis that involves hyperproliferation and inflammation of epithelial-related cells lining the joint capsule; dermatitises such as seborrheic dermatitis and solar dermatitis; keratoses such as seborrheic keratosis, senile keratosis, actinic keratosis. photo-induced keratosis, and keratosis follicularis; acne vulgaris; keloids and prophylaxis against keloid formation; nevi; warts including verruca, condyloma or condyloma acuminatum, and human papilloma viral (HPV) infections such as venereal warts; leukoplakia; lichen planus; and keratitis. The skin disorder can be dermatitis, e.g., atopic dermatitis or allergic dermatitis, or psoriasis.

In some embodiments, the disorder is psoriasis. The term "psoriasis" is intended to have its medical meaning, namely, a disease which afflicts primarily the skin and produces raised, thickened, scaling, nonscarring lesions. The lesions are usually sharply demarcated erythematous papules covered with overlapping shiny scales. The scales are typically silvery or slightly opalescent. Involvement of the nails frequently occurs resulting in pitting, separation of the nail, thickening and discoloration. Psoriasis is sometimes associated with arthritis, and it may be crippling. Hyperproliferation of keratinocytes is a key feature of psoriatic epidermal hyperplasia along with epidermal inflammation and reduced differentiation of keratinocytes. Multiple mechanisms have been invoked to explain the keratinocyte hyperproliferation that characterizes psoriasis. Disordered cellular immunity has also been implicated in the pathogenesis of psoriasis. Examples of psoriatic disorders include chronic stationary psoriasis, psoriasis vulgaris, eruptive (gluttate) psoriasis, psoriatic erythroderma, generalized pustular psoriasis (Von Zumbusch), annular pustular psoriasis, and localized pustular psoriasis.

Pharmaceutical Compositions

The methods described herein can include the administration of pharmaceutical compositions and formulations comprising an Alu or B2 RNA, a DNA encoding an Alu or B2 RNA, or an ASO that targets Alu or B2 RNA.

In some embodiments, the compositions are formulated with a pharmaceutically acceptable carrier. The pharmaceutical compositions and formulations can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration of pharmaceuticals are well described in the scientific and patent literature, see, e.g., Remington: The Science and Practice of Pharmacy, 21st ed., 2005.

The ASOs can be administered alone or as a component of a pharmaceutical formulation (composition). The compounds may be formulated for administration, in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the compositions of the invention include those suitable for intradermal, inhalation, oral/nasal, topical, parenteral, rectal, and/or intravaginal administration. The formulations may conveniently be presented in unit dosage form and may be prepared by any methods well known in the art of pharmacy. The amount of active ingredient (e.g., nucleic acid sequences of this invention) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect, e.g., an antigen specific T cell or humoral response.

Pharmaceutical formulations can be prepared according to any method known to the art for the manufacture of pharmaceuticals. Such drugs can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., nucleic acid sequences of the invention) in admixture with excipients suitable for the manufacture of aqueous suspensions, e.g., for aqueous intradermal injections. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

In some embodiments, oil-based pharmaceuticals are used for administration of nucleic acid sequences of the invention. Oil-based suspensions can be formulated by suspending an active agent in a vegetable oil, such as *arachis* oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102.

Pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent. In alternative embodiments, these injectable oil-in-water emulsions of the invention comprise a paraffin oil, a sorbitan monooleate, an ethoxylated sorbitan monooleate and/or an ethoxylated sorbitan trioleate.

The pharmaceutical compounds can also be administered by in intranasal, intraocular and intravaginal routes including suppositories, insufflation, powders and aerosol formulations (for examples of steroid inhalants, see e.g., Rohatagi (1995) J. Clin. Pharmacol. 35:1187-1193; Tjwa (1995) Ann. Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In some embodiments, the pharmaceutical compounds can be delivered transdermally, by a topical route, formulated as applicator sticks, solutions, suspensions, emulsions, gels, creams, ointments, pastes, jellies, paints, powders, and aerosols. In some embodiments, the pharmaceutical compounds can also be delivered as microspheres for slow release in the body. For example, microspheres can be administered via intradermal injection of drug which slowly release subcutaneously; see Rao (1995) J. Biomater Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In some embodiments, the pharmaceutical compounds can be parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

In some embodiments, the pharmaceutical compounds and formulations can be lyophilized. Stable lyophilized formulations comprising an ASO can be made by lyophilizing a solution comprising a pharmaceutical of the invention and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. 20040028670.

The compositions and formulations can be delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587. As used in the present invention, the term "liposome" means a vesicle composed of amphiphilic lipids arranged in a bilayer or bilayers. Liposomes are unilamellar or multilamellar vesicles that have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes can also include "sterically stabilized" liposomes, i.e., liposomes comprising one or more specialized lipids. When incorporated into liposomes, these specialized lipids result in liposomes with enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The formulations of the invention can be administered for prophylactic and/or therapeutic treatments. In some embodiments, for therapeutic applications, compositions are administered to a subject who is need of reduced triglyceride levels, or who is at risk of or has a disorder described herein, in an amount sufficient to cure, alleviate or partially arrest the clinical manifestations of the disorder or its complications; this can be called a therapeutically effective amount. For example, in some embodiments, pharmaceutical compositions of the invention are administered in an amount sufficient to decrease serum levels of triglycerides in the subject. The amount of pharmaceutical composition adequate to accomplish this is a therapeutically effective dose. The dosage schedule and amounts effective for this use, i.e., the dosing regimen, will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; *Remington: The Science and Practice of Pharmacy*, 21st ed., 2005). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on for example: the dosage and frequency as required and tolerated by the patient, the degree and amount of therapeutic effect generated after each administration (e.g., effect on tumor size or growth), and the like. The formulations should provide a sufficient quantity of active agent to effectively treat, prevent or ameliorate conditions, diseases or symptoms.

In alternative embodiments, pharmaceutical formulations for oral administration are in a daily amount of between about 1 to 100 or more mg per kilogram of body weight per day. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as Remington: The Science and Practice of Pharmacy, 21st ed., 2005.

In some embodiments, the methods described herein can include co-administration with other drugs or pharmaceuticals, e.g., compositions for providing cholesterol homeostasis. For example, the ASOs can be co-administered with drugs for treating or reducing risk of a disorder described herein.

EXAMPLES

The invention is further described in the following examples, which do not limit the scope of the invention described in the claims.
Experimental Procedures
The following materials and methods were used in the Examples below.

Cell culture and transfections. NIH/3T3 cells were cultured in DMEM+Glutamax (Life Technologies) supplemented with 10% fetal bovine serum and 1% Penicillin/Streptomycin. Before heat shock stimulus cells were trypsinized and resuspended in 5 ml complete medium in a 15 ml falcon tube. Subsequently, cells were either placed in 37° C. (control cells, pre-H/S condition) or in 45° C. (treated cells, post-H/S condition) for 15 min. Time points mentioned throughout this work have as a starting point the moment of the start of the heat shock stimulus. After the end of this 15 minute period, cells were centrifuged shortly (2 min) and cell pellets were directly resuspended into Trizol (Thermofischer) for the RNA-seq analysis or fixated with 1% formaldehyde for the ChIP-seq and CHART-seq analysis. For LNA transfections against B2 RNA we used the HiPerfect transfection reagent (Qiagen) and the sequence of the LNAs used were as follows: LNA11: 5'-GTTACG-GATGGTTGTG-3' and LNA12: 5'-TGTAGCTGTCTTCAG-3'. The scramble LNA sequence was 5'-CACGTCTATACACCAC-3'. In detail, the LNAs were diluted to 100 uM and incubated with 1.35 ul of the transfection reagent in a final volume of 10 ul for 15-20 min at room temperature (RT). Subsequently the transfection mix was transferred to 2 ml of recently trypsinized cells in full culture medium containing $5\times10^5$ cells (final LNA concentration 500 nM). A fluorophore conjugated LNA was also transfected to test transfection efficiency. Subsequently cells were plated and incubated at 37° C. for 24 hours before testing. In the meanwhile, after 1 h from plating, a subset of cells was subjected to FACS analysis and transfection rate was estimated to 90% of live cells. For LNA transfections against Ezh2 we used the following LNA ASO sequence: 5'-TTCTTCTTCTGTGCAG-3'. Transfections were performed with HiPerfect as mentioned above but for a final LNA concentration of 25 nM. For RNA transfections of the B2 RNA and its fragments we used the TransMessenger Transfection Reagent (Qiagen). In brief, 16 pmol of RNA in Buffer EC was incubated for 5 min at RT with 2 ul enhancer, and subsequently 8 ul transfection reagent was added to a total reaction of 100 ul and incubated for 10 min at RT before addition to recently trypsinized cells in culture medium without serum. $2,6\times10^4$ transfected cells were plated and incubated at 37° C. for 30 min before adding an equal volume of complete medium (with serum). After 2 hours, a subset of these cells were washed with PBS twice and RNA was extracted using Trizol and analyzed with qPCR against B2 RNA to confirm B2 overexpression. After 6 hours from plating the medium was changed to complete medium and cells were counted during the subsequent days using a Nexcelom Cellometer.

RNA in vitro transcription and RNA-protein incubations. RNAs were transcribed in vitro and Ezh2, Eed and GST proteins were purified as described previously (32) with the following modifications: For RNA in vitro transcription we used the AmpliScribe T7 High Yield Transcription Kit (Epicentre) applying a 3 h incubation at 42° C. and using a template resulting to the following B2 RNA sequence:
5'-GGGGCTGGTGAGATGGCTCAGTGGGTAA GAGCACCCGACTGCTCTTCCGA AGGTCCGGAGTT-CAAATCCCAGCAACCACATGGTGGCTCACAAC-CATCCG TAACGAGATCTGACTCCCTCTTCTG-GAGTGTCTGAAGACAGCTACAGTGT ACTTACATATAATAAATAAATAAATCTT-TAAAAAAAAAA-3'.

For smaller B2 RNA fragments the respective templates were constructed based on the above sequence and the nt numbering mentioned in the text. In detail, domain I RNA was from +lnt to +72 nt, domain RNA from +lnt to +105 nt, and domain III from +99 to +140 nt. The quality of the transcribed RNA was tested running a 6% UREA PAGE gel as well as through small RNA-seq library construction and next generation sequencing (see below). RNAs were purified using the ZymoResearch RNA clean kit. Incubations, unless mentioned differently in the text were performed with 200 nM in-vitro-transcribed B2 RNA folded with 300 mM NaCl and supplemented with TAP buffer (final reaction concentrations: 5 nM Tris pH 7.9, 0.5 mM MgCl2, 0.02 mM EDTA, 0.01% NP40, 1% glycerol, 0.2 mM DTT). For RNA folding the RNA was incubated for 1 min at 50° C. and cooled down with a rate of 1° C./10 sec. Cleavage time-courses were quantified using ImageJ (NIH). The fraction of full-Length B2 RNA present at each time point was measured and this data was fit using Kaleidagraph (Synergy) using the differential form of the rate equation for an irreversible, first-order reaction.

Double-Filter Binding Assays. Binding reactions were assembled with 1 µl of 1,000 cpm/µl (0.1 nM final concentration) folded RNA and purified protein at the shown concentrations in binding buffer (50 mM Tris-HCl [pH 8.0], 100 mM NaCl, 5 mM MgCl2, 10 µg/ml BSA, 0.05% NP40, 1 mM DTT, 20 U RNaseOUT [Invitrogen], and 5% glycerol) in 30 µl. A total of 50 ng/µl yeast tRNA (Ambion catalog number AM7119) was used as a nonspecific competitor. After 30 min at 30° C., the reactions were filtered through nitrocellulose (PROTRAN, Schleicher & Schuell) and Hybond-N+(GE Healthcare) membranes using a Minifold I system (Whatman), washed with 600 µl washing buffer (50 mM Tris-HCl [pH 8.0], 100 mM NaCl, 1.5 mM MgCl2, 0.05% NP40, 1 mM DTT), dried, exposed to a phosphor screen, and scanned after 2 hr in a Typhoon Trio (GE Healthcare Life Sciences). Data were quantified by Quantity One and normalized as previously described (Cifuentes-Rojas et al., 2014). Equilibrium dissociation constants, Kd, were obtained by fitting the binding data to a one-site binding model by nonlinear regression using Graphpad Prism.

CHART and ChIP analyses. At least two biological replicates were analyzed for CHART and ChIP experiments. The B2 CHART was modified from the original CHART protocols (33). In detail, 12 millions cells were crosslinked with 1% formaldehyde for 10 min at room temperature. Crosslinking was then quenched with 0.125 M glycine for 5 min and washed with PBS 3 times. Snap freezing cells could be stored at −80° C. Crosslinked cells were re-suspended in 2 ml of sucrose buffer (0.3 M sucrose, 1% Triton-X-100, 10 mM HEPES pH 7.5, 100 mM KOAc, 0.1 mM EGTA), dounced 20 times with a tight pestle, and kept on ice for 10 min. The following steps were using polystyrene tubes, glass pipettes, and DNA LoBind microtubes (Eppendorf) to avoid cell clumps sticking onto the walls of tubes or pipettes. Nuclei were collected by centrifugation at 1,500 g for 10 min on top of a cushion of 5 ml glycerol buffer (25% glycerol, 10 mM HEPES pH7.5, 1 mM EDTA, 0.1 mM EGTA, 100 mM KOAc). Nuclei were further crosslinked with 3% formaldehyde for 30 min at room temperature. After washing three times with ice-cold PBS, nuclei were extracted once with 50 mM HEPES pH7.5, 250 mM NaCl, 0.1 mM EGTA, 0.5% N-lauroylsarcosine, 0.1% sodium deoxycholate, 5 mM DTT, 100 U/ml SUPERasIN (Invitrogen) for 10 min on ice, and centrifuged at 400 g for 5 min at 4° C. Nuclei were resuspended in 1.2 ml of sonication buffer (50 mM HEPES pH 7.5, 75 mM NaCl, 0.1 mM EGTA, 0.5% N-lauroylsarcosine, 0.1% sodium deoxycholate, 5 mM DTT, 10 U/ml SUPERasIN, and sonicated in microtubes using Covaris E220 sonicator at 10% duty cycle, 200 bursts per cycle, 105 peak intensity power for 5 min. The major size of chromatin fragments was around 3-4 kb. Fragmented chromatin was subjected to hybridization immediately. Hybridization, washing and elution were performed as follows. In brief, beads were blocked with 500 ng/ul yeast total RNA, and 1 mg/ml BSA for 1 hr at 37° C., and respuspended in 1× hybridization buffer. 360 µl of 2× hybridization buffer (750 mM NaCl, 1% SDS, 50 mM Tris pH 7.0, 1 mM EDTA, 15% Formamide, 1 mM DTT, PMSF, protease inhibitor, and 100 U/ml Superase-in) was added into 180 µl lysates, and then this 1× hybridization lysate was precleaned by 60 µl of blocked beads at room temperature for 1 hr. After removal of the beads, B2 probes (labeled with 3' biotin-TEG, 18 pmol) for B2 RNA were added into the 1× hybridization lysate and incubate at room temperature for overnight. Given the variability of the different B2 repeats, we used a pool of probes that correspond to the majority of the sequence variations within the target region presented at FIG. 4a. As control we used also a negative probe that does not show any sequence similarity to the used probes with he following sequence: 5-GCACGTCTATACACCACT-3'. 120 ul of blocked beads were added into lysates and incubated at RT for two hours. Beads:biotin-probes:RNA:chromatin adducts were captured by magnets, washed once with 1× hybridization buffer at 37° C. for 30 min, washed four times at 37° C. for 5 min with SDS wash buffer (2×SSC, 1% SDS, 1 mM DTT, 1 mM PMSF), and then washed once for 5 min at room temperature with 0.1% NP40 buffer (150 mM NaCl, 50 mM Tris pH8.0, 3 mM MgCl2, 10 mM DTT, 0.1% NP40). DNA was then eluted in 100 µl twice for 20 min in 100 µl of 0.1% NP40 buffer with 200 U/ml RNase H (NEB) at room temperature and purified further using phenol-chloroform extraction. Before ChIP analysis, 3 millions cells were crosslinked as above and sheared chromatin was prepared using the ChIP-IT Express kit (Active motif) in a 135 ul volume using the following conditions in a Covaris E220 sonicator: 2% duty cycle, 200 bursts per cycle, 105 peak intensity power for 5 min. Chromatin immunoprecipitations were performed in 100 ul reaction volumes using the same kit as with chromatin shearing and the following antibodies for 14 h incubation times: Ezh2 (D2C9, 5246S Cell signaling technology), H3K27me3 (39155, active motif), RNA pol II phospho S2 (from the ab103968 panel, abcam), RNA pol II phospho S5 (from the ab103968 panel, abcam), Hsf1P (ADI-SPA-901-D, Enzo life sciences). Eluted DNA was further purified with phenol-chloroform.

Library construction for RNA sequencing. RNA used for short RNA-seq and RNA-seq libraries was prepared as follows: Total RNA from cells was extracted using Trizol and 4 ug of total RNA was subjected to ribosomal RNA depletion using the ribominus V2 kit (Life technologies). Incubation of the RNA with the probe was done for 40 min instead of 20 min. RNA depleted RNA was separated into two fractions of short (<200) and longer RNAs using the mirVana separation kit (Life technologies) with the following modifications: After addition of the lysis/binding buffer and the miRNA homogenate additive solution, 100% EtOH at 1/3 of the volume was added and the mix was passed through the filter to bind long RNAs. The flow through was collected and 100% EtOH at 2/3 of the flow through volume was added and passed through a new filter column to bind short RNAs. Elution of the long and short RNAs from each column respectively was done per manufacturer instructions. Eluted RNAs were concentrated in both cases using the RNeasy MinElute Spin Columns (Qiagen) and tested for its size and quality using an Agilent Bioanalyzer RNA kit. For short RNA library construction, ribo-depleted short RNAs were subjected to PNK phosphorylation for 1 h at 37 C. Subsequently we used the NEBnext small RNA library construction kit (NEB) with the following modifications: Incubation of the 3'adaptor was performed for 2 h, and the libraries at the end were not subjected to double size selection with the Ampure beads but with 1,2× size selection. For sequencing of the in vitro B2 fragments no ribosomal depletion was applied For the longer RNAs we used the NEBNext Ultra directional RNA library kit (NEB) with an RNA fragmentation of 10 min at 95 C and with the following modifications: First strand synthesis at 42 C was done for 50 min and the End Prep of cDNA library was followed by an Ampure Beads selection of 1,8× and ligation of the adapters using the 5× quick ligation buffer and Quick T4 DNA ligase (NEB) for 30 min. Incubation with the USER enzyme was done before the PCR amplification for 30 min, followed by a double size selection of 0.5×-1×, while the final library was size selected using Ampure beads at a 1× sample-beads ratio. Libraries were evaluated using the Bioanalyser high sensitivity DNA kit (Agilent) and quantitated using the qPCR KAPPA kit (Kappa).

Library construction for ChIP and CHART sequencing. Purified DNA was subjected to further fragmentation in a Covaris E220 sonicator using 10% duty cycle, 200 bursts per cycle, 175 peak intensity power for 5 min in 125 ul. Subsequently, we used the NEBNext ChIP-seq library Prep Master MIX set (NEB) with the following modifications: For ChIP-seq the EndRepair of ChIP DNA was performed only for 15 min in a 10.5 ul total volume (using 1ul buffer and 0.5 ul enzyme) followed by no cleanup but dA-Tailing in a reaction scaled to 100 ul for 15 min. Subsequently we performed double size selection 0.2×-2.5× before adaptor (0.3 uM) ligation for 30 min and USER enzyme incubation for another 30 min. Ligation reaction was cleaned using1.4 sample-bead ratio and the final library was size selected and clean with Ampure beads twice using 1× and 0.5×-0.9× ratios. In addition, the PCR reaction had an extension time of 1min and 30 sec. For CHART-seq the end repair was scaled to 150 ul, while the dA-tailing was performed at 25.5 ul total volume. After adaptor ligation it was size selected with 0.6×-1.2× bead-sample ratio, while after the PCR it was cleaned twice with 1× and 0.9× Ampure beads and quantified using the qPCR KAPPA kit.

Bioinformatics analysis. Raw RIP-seq, CHART-seq and ChIP-seq reads and the respective sequenced input reads were mapped using bwa.0.5.5 (Li and Durbin, 2010) (default parameters). Using in home scripts and bedtools (Quinlan and Hall, 2010) the resulting sam files were converted to bed files and enriched genomics regions against the input were filtered using SICER (Xu et al., 2014) with a window and gap parameter of 300 and an FDR 0.05. Subsequently, CHART-seq reads of the B2 probe were filtered further based on distribution of reads captured by the negative CHART probe. Metagene profiles were constructed using the Babraham NGS analysis suite Seqmonk (www.bioinformatics.babraham.ac.uk/projects_seqmonk/) employing normalized cumulative distributions filtered in case of CHART-reads against the positions of B2 elements (3 KB radius). Normalization was performed based on the total number of mapped reads. Seqmonk genome browser was used for visualization using RefSeq and RepeatMasker annotations for mRNAs and B2 SINE elements, respectively. Peak annotation was done using Galaxy (Afgan et al., 2016) and PAVIS (Huang et al., 2013).

Short RNA reads were trimmed from adapters in both ends using cutadapt (doi.org/10.14806/ej.17.1.200) for the following adapter sequences: AAGATCG-GAAGAGCACACGTCT. Subsequently reads were mapped using bwa and converted to bed files with bedtools. Then, using in home transcripts 5' ends coordinates of the reads were extracted and plotted against a metagene representing the absolute distance between start of B2 repeats and downstream sequences. Reads distributions and alignments were performed using seqmonk. Raw RNA-seq reads were trimmed using cutadapt for the following adapter sequences: AAGATCGGAAGAGCACACGTCT and AGATCG-GAAGAGCGTCGTGTAGGGAAAGAGTGT for read 1 and read 2, respectively. Subsequently they were mapped against mm9 reference transcriptome using tophat (Trapnell et al., 2009) with the following parameters: bowtie1-r-100-N 20—read-gap-length 10—segment-mismatches 3—read-edit-dist 20. Subsequently, differential expression was performed using Seqmonk's intensify difference function for a p value less than 0.05. Metagene profiles were plotted with Seqmonk using the relative read density function. Transcriptional start site was defined using the TSS Eponine track from Seqmonk (Down and Hubbard, 2002). Area coverage was calculated (CoveragePostH/S−CoveragePreH/S)/((CoveragePostH/S+CoveragePreH/S)/2). Genome browser screenshots were derived using the IGV viewer (Robinson et al., 2011). For the statistical analysis of the read distributions we applied the Kolmogorov-Smirnov test, using Prism6 (Graphpad). Datasets for short-RNA-seq, RNA-seq, ChIP-seq and CHART-seq have been deposited in GEO (GSE82255).

Example 1. B2 RNA Associates with PRC2 and Exists as Short Fragments In Vivo

Previous RIP-seq analysis for the EZH2 subunit of PRC2 showed that reads derived from repetitive sequences comprised ~20% of total reads—a not so insignificant fraction (Zhao et al., 2010)(FIG. 1A, right pie chart). We asked whether any family of repeat RNAs might be enriched relative to its representation in the transcriptome of female mouse embryonic stem (ES) cells, the cell type in which the RIP-seq analysis was performed. While most repeats were not enriched, we noted that SINEs accounted for ~4% of all repetitive reads in the RIP-seq datasets and, within this family of repeats, the B2 element was enriched 4-fold above its representation in the female ES transcriptome (32% versus 8%; FIG. 1A) or the nuclear ES transcriptome (32% versus 12%, data from (Kung et al., 2015)). B2 RNA was highly enriched in RIP-seq reads relative to B1, another type of SINE repeat, in spite of the fact that the RNAs have similar expression profiles in the mouse genome (FIG. 1B, bottom panels)(Hasties, 1989). PRC2 therefore seems to have a preference for binding B2 RNA.

Figure 1C:
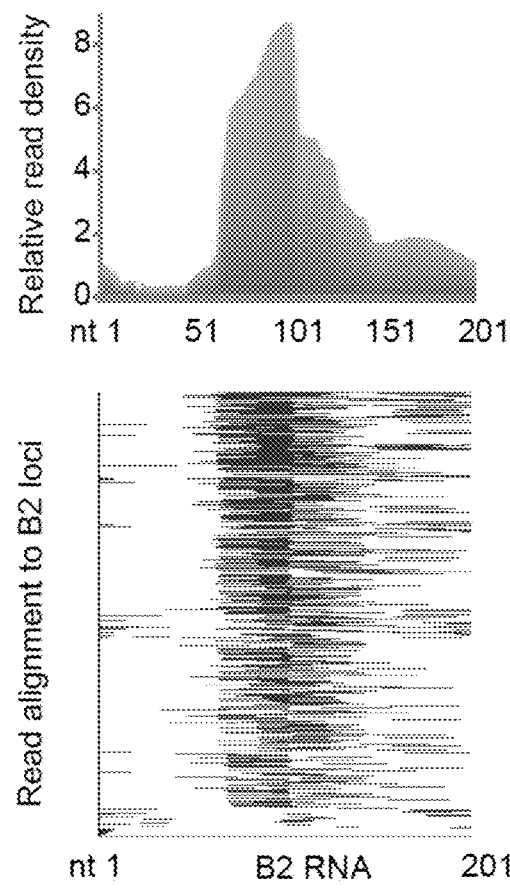
Figure 1D:
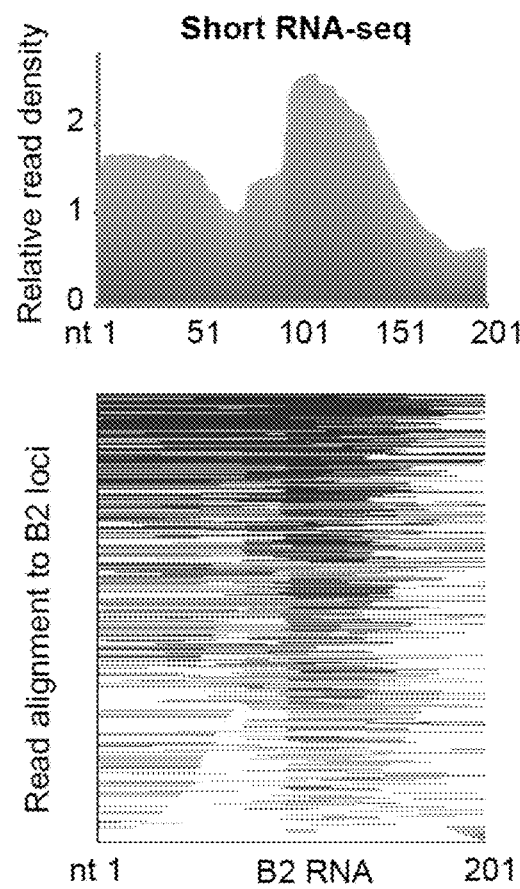

Examination of read distributions within the B2 element revealed an intriguing non-uniform pattern. Instead of the expected homogeneous distribution across the ~200-nucleotide (nt) B2 element, we observed at least two subpopulations, with a sharp discontinuity of reads at ~nt 98 (FIG. 1C). This pattern suggested that, apart from the full-length RNA, B2 may also exist as subfragments. The process of generating the RIP-seq libraries could have introduced biases in RNA fragmentation or cloning, however. Furthermore, only 36 bases could be sequenced by the older HiSeq2000 machine (Zhao et al., 2010). To rule out the possibility that the non-uniform RNA distributions arose from technical biases, we developed a short RNA-seq protocol that excludes an RNA fragmentation step and enriches for native transcripts in the 40- to 200-nt size range (see Experimental Procedures). Short RNA-seq of female mouse embryonic stem (ES) cells confirmed a discontinuity at nt 98 (FIG. 1D).

The discontinuity was interesting, as it occurred within the 51-nt critical region of B2 (nt 81-131; shaded region, FIG. 1E) previously shown by deletional analysis to be necessary and sufficient to stably bind an RNA docking site in POL-II in order to prevent formation of the pre-initiation complex (Espinoza et al., 2007; Ponicsan et al., 2015; Yakovchuk et al., 2009). To map the precise location of the break, we aligned 5' ends of reads from the short RNA-seq library to the B2 consensus sequence and observed a strong peak at position 98 (FIG. 1E, "X"), with additional but smaller peaks at positions 77, 49, and 33. Thus, shorter forms of B2 RNA can indeed be detected in vivo.

To determine whether EZH2 binds B2 RNAs directly, we produced affinity-purified, recombinant EZH2 in baculovirus-infected insect cells and performed filter-binding assays with in vitro-transcribed B2 RNA. The results demonstrated that the full-length (180 nt) B2 RNA interacted with EZH2 and it did so with a dissociation constant (Ka) of 422.6±63 nM (FIG. 1F). It has an affinity that is similar to that of a similar-sized positive control, RepA I-II—a 210-nt shortened form of Xist RepA containing four of eight repeats (Cifuentes-Rojas et al. and FIG. 1F). This affinity was much greater than that for the negative control P4P6 RNA, a 154-nt transcript from Tetrahymena ($K_d$>3000 nM) and also for the 300-nt MBP RNA from *E. coli*. Truncating B2 RNA also resulted in extremely low affinities for EZH2, with various domains—DI [nt 1-72], DI+D2 [nt 1-105], and DIII [nt 99-140]—all demonstrating Ka of >3000 nM. These data demonstrate that B2 RNA directly interacts with EZH2 in vitro and confirm the binding interaction observed by RIP-seq in vivo.

Example 2. B2 RNA is Cleaved and Degraded in the Presence of EZH2

Figure 1E:
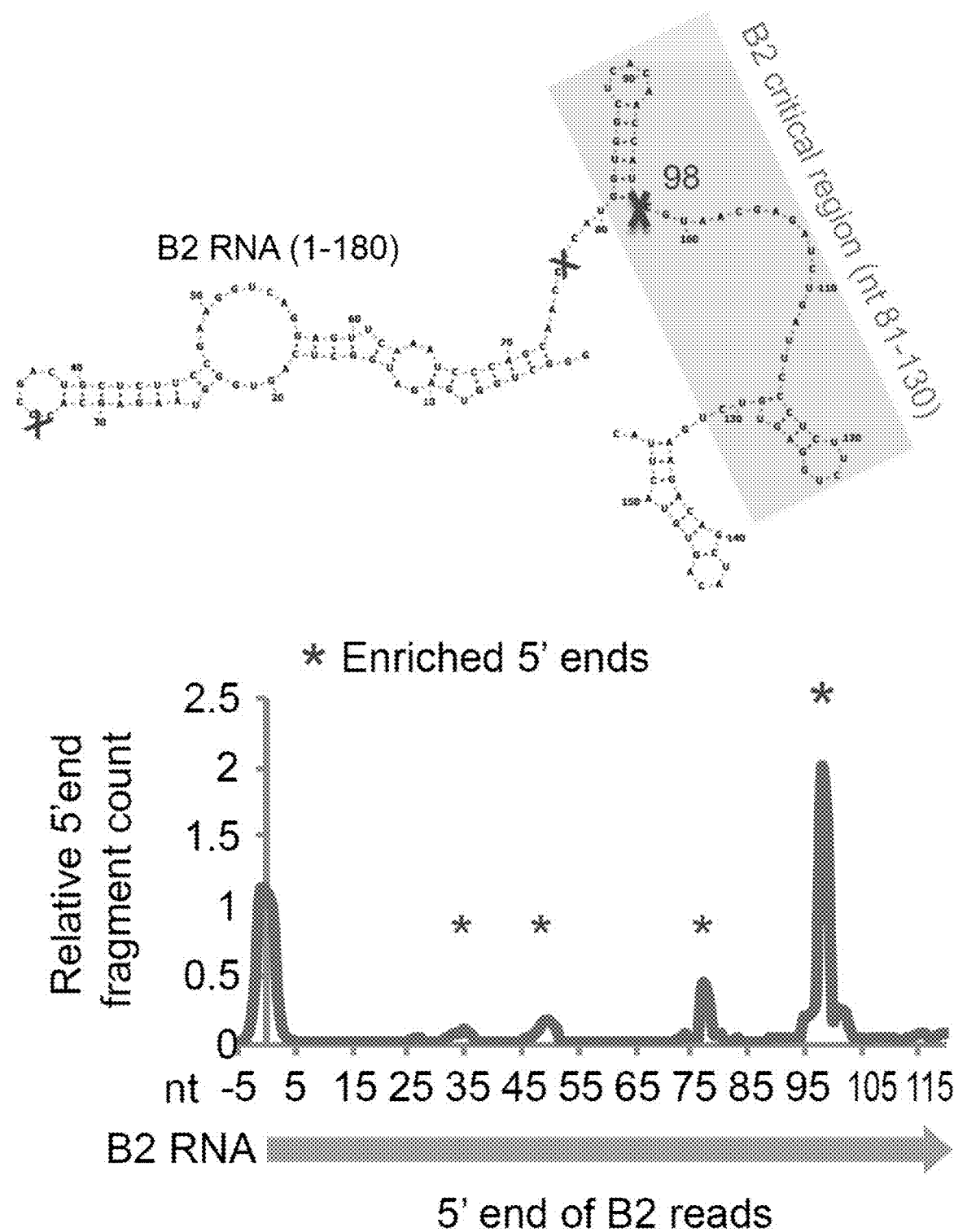
Figure 1F:
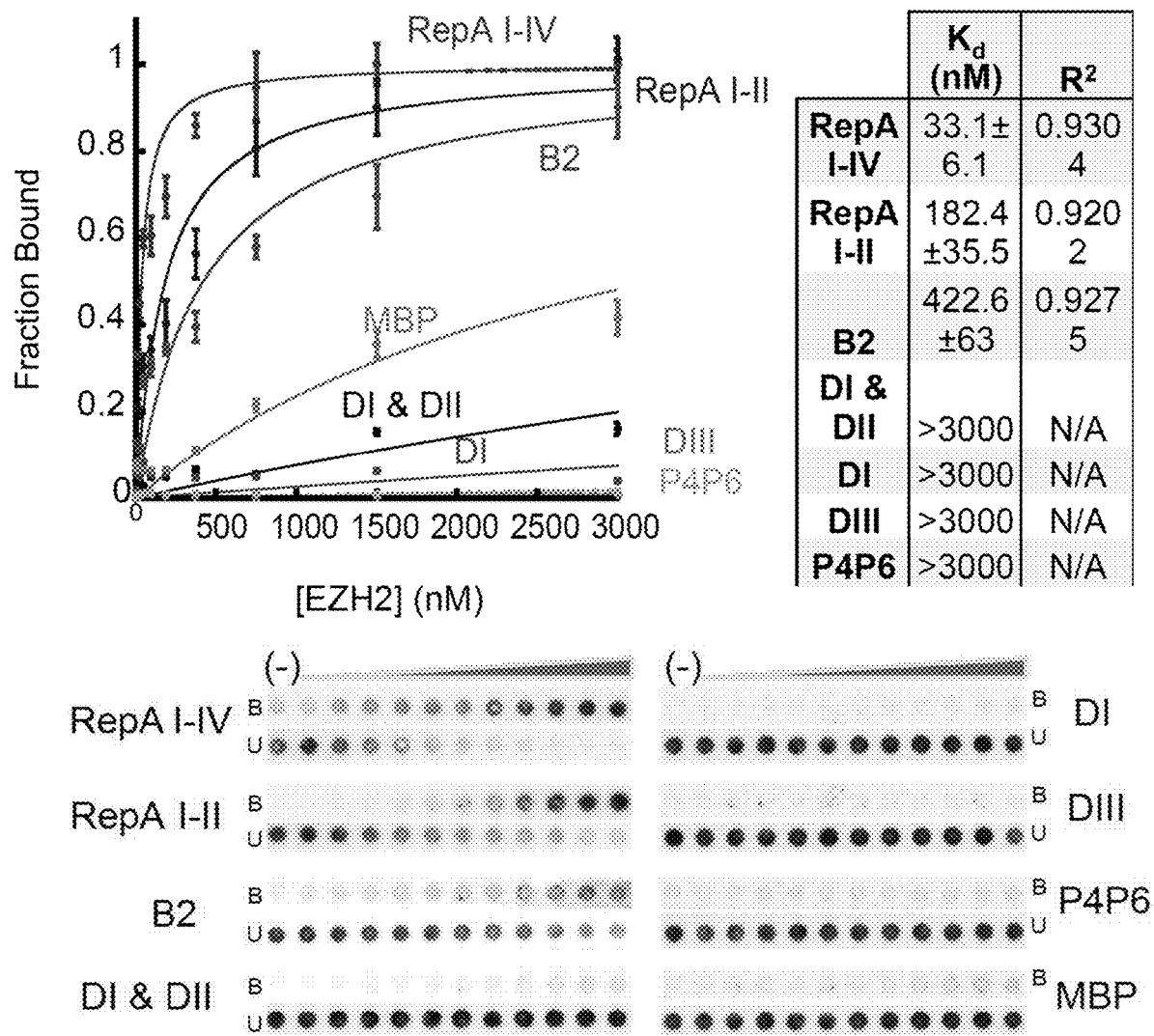
Figure 2B:
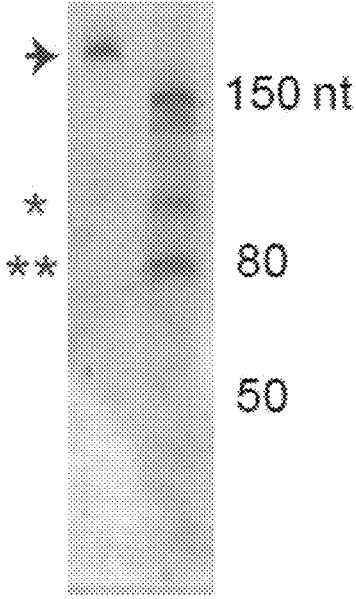
Figure 2C:
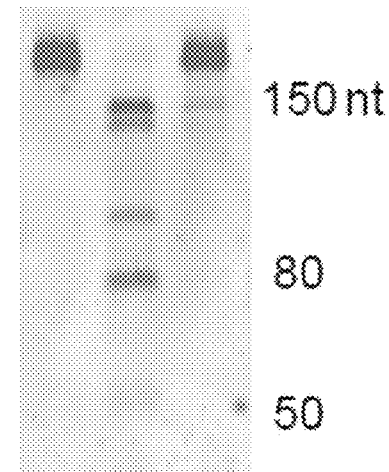
Figure 2D:
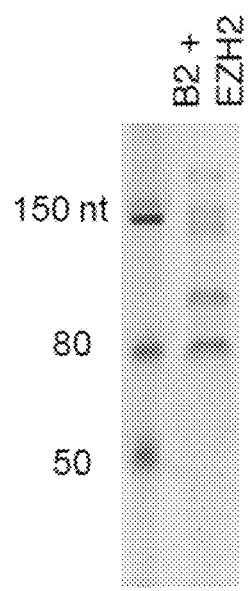
Figure 2D:
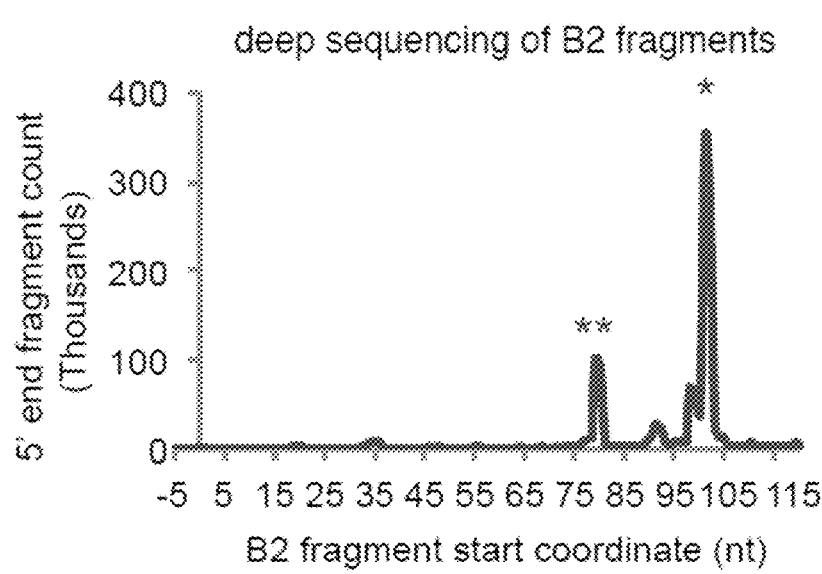
Figure 2E:
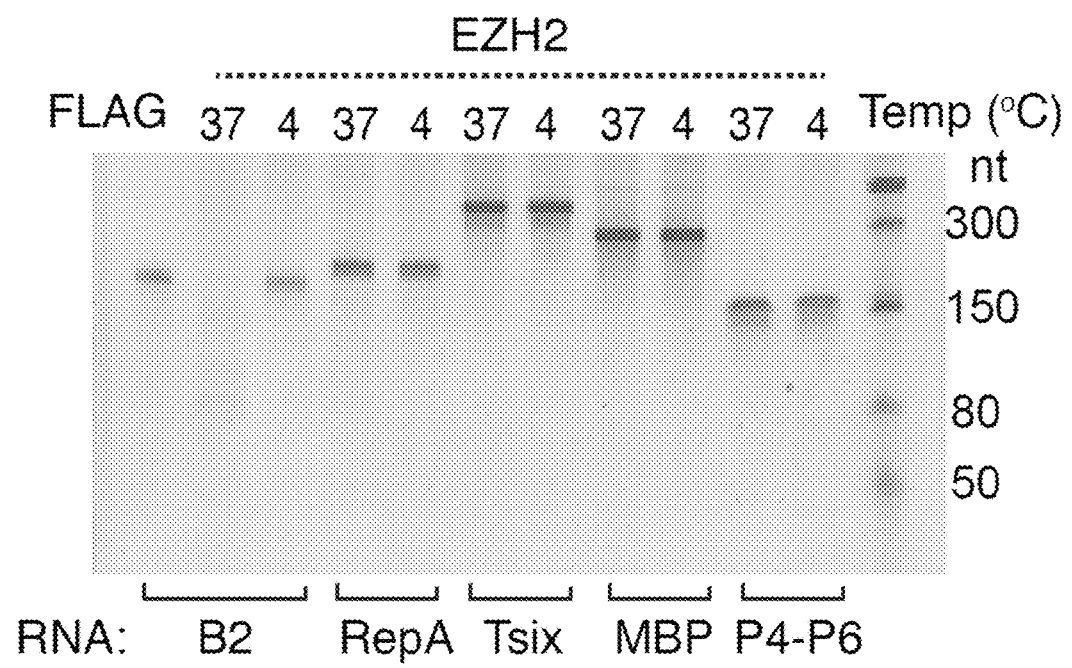

In principle, the discontinuity at position 98 could be due to an internal transcription start site or to an RNA processing event. Examination of the B2 sequence revealed internal Box A and Box B sites characteristic of RNA POL-III promoters and did not suggest additional transcription start sites around position 98 (FIG. 2A). Additionally, analysis of conventional and short RNA-seq data did not suggest a splice junction at position 98 or any other site of discontinuity. We therefore suspected a specific endonucleolytic event and set out to test this idea in vitro. Intriguingly, whereas incubation of 200 nM in-vitro-transcribed B2 RNA folded in 300 nM NaCl and supplemented with TAP100 buffer (incubation final concentrations: 5 nM Tris pH 7.9, 0.5 mM MgCl2, 0.02 mM EDTA, 0.01% NP40, 1% glycerol, 0.2 mM DTT) did not reveal any instability, addition of 25 nM purified recombinant PRC2 resulted in RNA fragmentation to sizes similar to those observed in vivo (FIG. 2B). This endonucleolytic event was recapitulated by addition of the EZH2 subunit alone, and was not observed with GST protein or with another PRC2 subunit, EED (FIG. 2C). We then performed deep sequencing of these RNA fragments to identify the exact cleavage sites. Several cleavage sites were observed, including a major one at position 98 and minor ones at positions 77 and 33 (FIG. 2D)—corresponding to the sharp discontinuities uncovered by EZH2 RIP-seq and the short RNA-seq analysis (FIG. 1C-E). Thus, the in vivo activity can be recapitulated in vitro using purified RNA and protein components (FIG. 2E). Collectively, these data demonstrate that full-length B2 RNA is subject to endonucleolytic cleavage at position 98, with minor cut sites at positions 77 and 33.

Figure 2F:
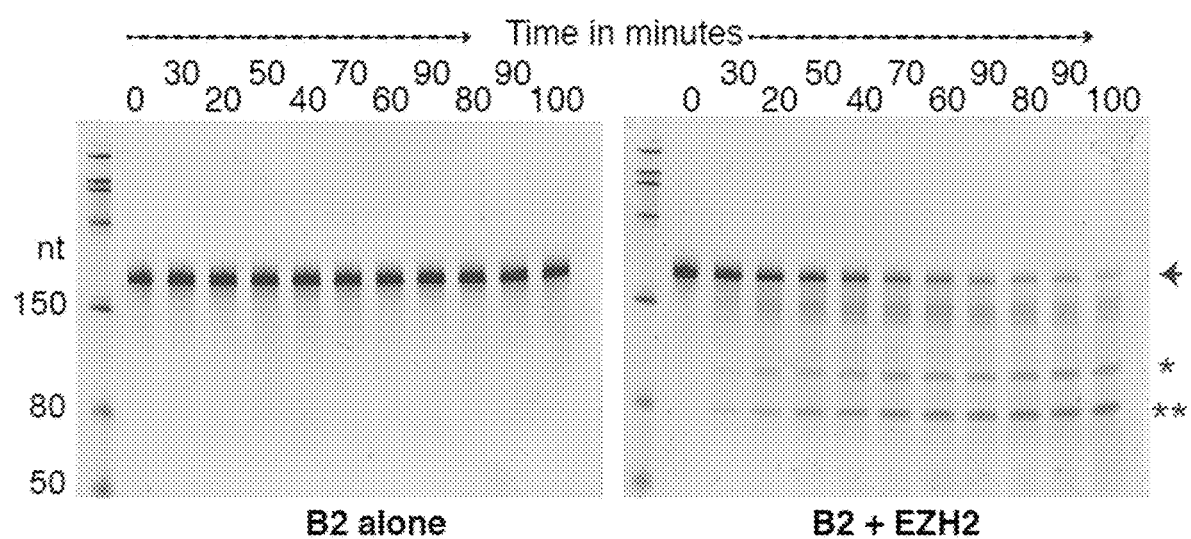
Figures 2G, 2H:
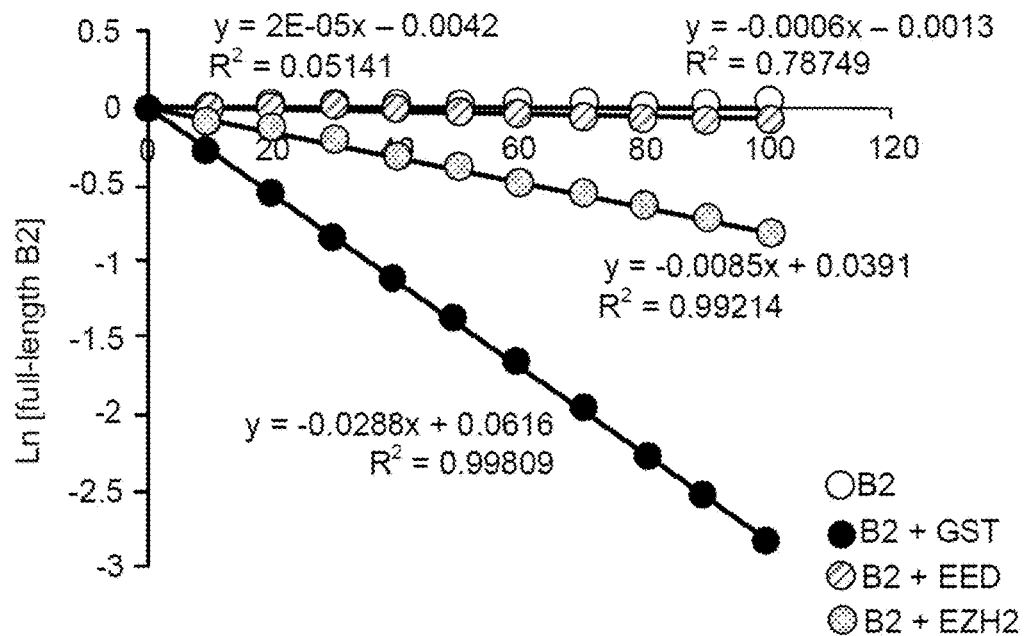
Figure 2I:
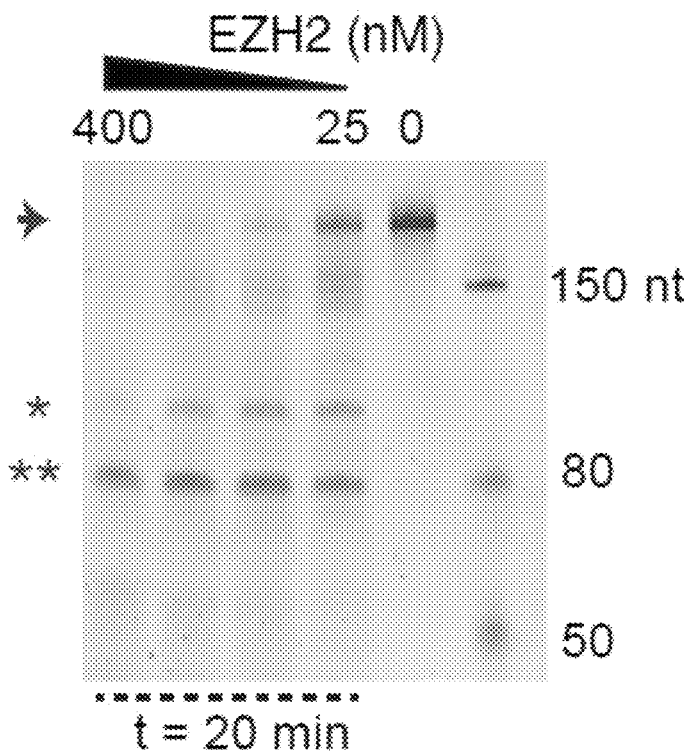

We next studied the in vitro kinetics of B2 RNA processing. In the presence of 25 nM EZH2, cleaved RNA accumulates over time between 0-100 minutes (FIG. 2F). To better understand the enhancement of B2 cleavage by EZH2, we plotted the amount of remaining full-length B2 RNA as a function of time (FIG. 2G). Cleavage rate constants were then determined by a linear fit using the differential form of the rate equation for an irreversible, first-order reaction (FIG. 2H). With either GST or no protein, we observed a low rate of turnover ($k_{obs}=2\times10^{-5}$ min$^{-1}$ and $6\times10^4$ min$^{-1}$, respectively). The presence of EED mildly enhanced B2 cleavage at a modest rate of $8\times10^{-3}$ min$^{-1}$. On the other hand, the presence of EZH2 resulted in a 1,400-fold rate increase to a $k_{obs}$ of 0.029 (FIG. 2G)($R^2$>0.99, indicating that the datapoints have an excellent fit to the curve). Without EZH2, full-length B2 has an extrapolated half-life of 24 days in vitro. In the presence of EZH2, its half-life was reduced to 24 minutes (FIG. 2I). Thus, the ribonucleolytic cleavages within B2 are accelerated considerably by contact with PRC2.

Figure 2J:
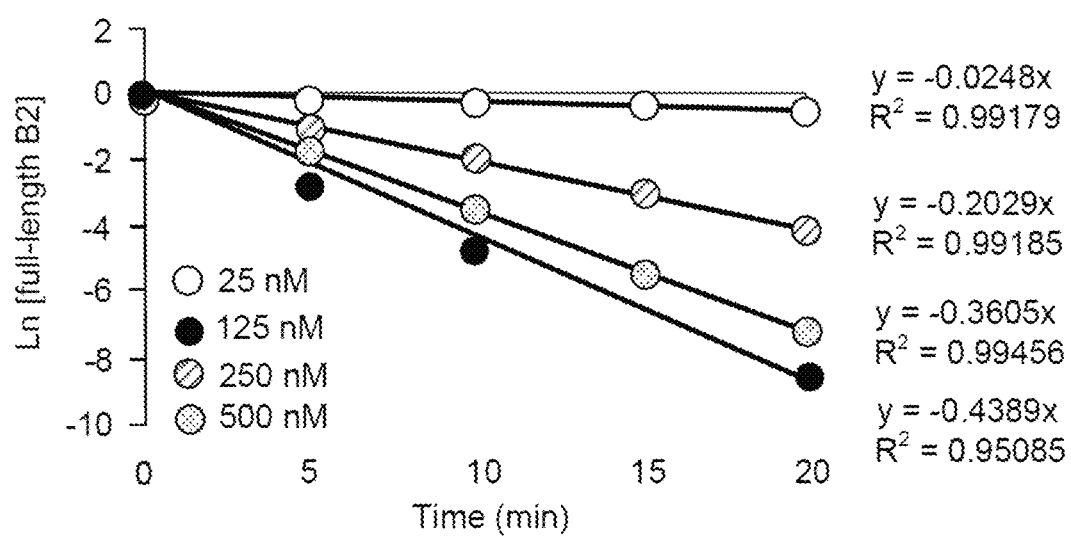
Figure 2K:
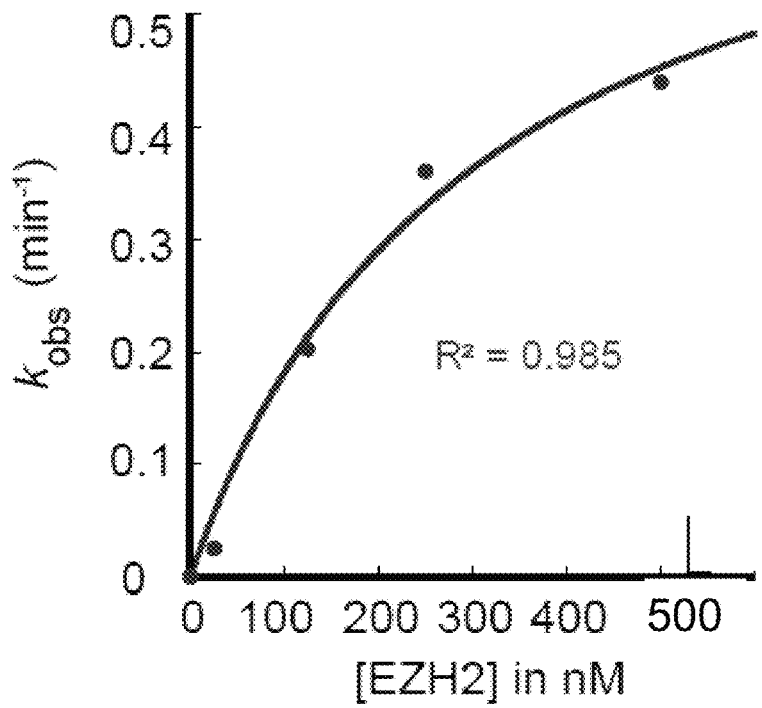

The rate of cleavage also depended on EZH2 concentration. In the presence of 50 nM B2 RNA, increasingly higher processing rates were observed as the concentration of EZH2 was increased from 25 to 400 during a constant 20-minute incubation (FIG. 2H). Cleavage rate constants were again determined by fitting the data to a single-exponential function (FIG. 2J). At 25 nM EZH2, the observed rate constant, $k_{obs}$, was 0.0248/min in the presence of 200 nM B2 RNA; at 125 nM EZH2, the $k_{obs}$ was 0.2029/min; at 250 nM, the $k_{obs}$ increased further to 0.3605/min; and at 500 nM EZH2, the $k_{obs}$ still increased further to 0.4389 without reaching saturation (FIG. 2J-K). Taken together, the present data demonstrate that B2 RNA associates with PRC2 and induces a process that destabilizes B2 RNA, resulting in its cleavage into multiple fragments. These events occur both in vitro and in vivo.

Example 3. B2 RNA Induces Cell Death; Heat Shock Induces B2 Cleavage In Vivo

We asked whether degradation of B2 RNA is biologically relevant. First, we interrogated the consequences of introducing excess B2 RNA into NIH/3T3 cells, the cell line used previously to study B2 effects (Allen et al., 2004). Surprisingly, transfecting purified full-length B2 RNA into the cells resulted in marked cell death within 2 days of treatment (FIG. 3A). Culturing out to 3 days did not lead to cellular recovery. However, when B2 RNA was pre-incubated with EZH2 to induce cutting, cytotoxicity was reduced and cells grew to confluence within 3 days (FIG. 3A). We then repeated this analysis using a synthesized and purified truncated B2 fragment (nt 99-140), rather than one cut from full-length B2. Similar results were obtained: Starting with a transfection of 30,000 cells, full-length B2 RNA killed all cells within 2 days with no recovery after 5 days, whereas transfection of synthesized truncated B2 showed reduced cytotoxicity at 2 days and full recovery at 5 days (FIG. 3B). These data demonstrate that B2 RNA has biological activity in vivo and that cutting B2 RNA neutralizes that activity.

We set out to determine the nature of that activity. B2 RNA has been shown to block POL-II transcription during the heat shock response (Allen et al., 2004; Espinoza et al., 2004; Fornace and Mitchell, 1986; Li et al., 1999). Heat shock is a type of stress that puts cells at risk, and a rapid response is essential for survival (Chircop and Speidel, 2014). One immediate response is transcriptional downregulation of a large number of cellular genes—an adaptation to suppress expression of unnecessary genes. An equally critical immediate response is transcriptional upregulation of so-called "immediate early genes". These genes are upregulated within the first 15 minutes after heat shock and encode proteins that buffer against cellular damage, such as those that assist in repair of damaged structures (FIG. 3C)(de Nadal et al., 2011). These proteins include transcription factors, epigenetic complexes, and chaperones that aid in refolding or elimination of damaged proteins. During the immediate early period, the B2 element is known to also increase in expression (Allen et al., 2004; Fornace and Mitchell, 1986).

Figure 3D:
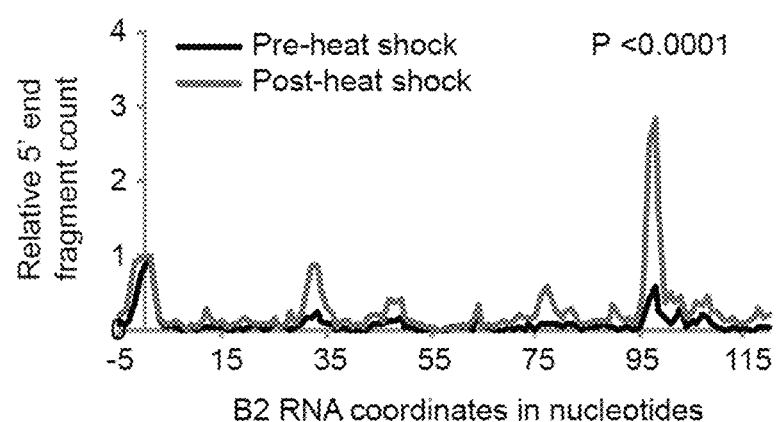

To determine whether B2 RNA stability bears connection to heat shock, we examined the integrity of B2 RNA after 15 minutes of heat shock (45° C.) in NIH/3T3 cells. We performed short RNA-sequencing and compared the number of cut B2 fragments before and after heat shock. As B2 RNA levels also rose after heat shock (FIG. 3C), we normalized the number of cut sites to total B2 RNA levels in order to exclude increased B2 expression as a confounding factor. Intriguingly, a major increase in cutting was observed at position 98 after 15 minutes of heat shock, as well as at positions 77 and 33 (FIG. 3D). The difference in cutting before and after heat shock was highly significant (Kolmogorov-Smirnov [KS] test; P<0.0001). We conclude that B2 RNA has biological activity and temperature stress induces turnover of B2 RNA in vivo.

Example 4. B2 RNA Binds to Heat Shock-Responsive Genes

To understand the mechanism of action, we mapped genomic binding sites for B2 RNA using "capture hybridization analysis of RNA targets" with deep sequencing [CHART-seq (Simon, 2013; Simon et al., 2013)]. For capture probes, we designed complementary oligonucleotides to B2 RNA to pull down chromatin regions associated with B2 RNA. These 17-base capture probes spanned nt 87-103 of B2 RNA and overlapped the major cut site (FIG. 4A), thereby enabling us to specifically identify target sites bound by intact B2 RNA. Given variability of the B2 sequence, we designed a probe cocktail that would capture SNP variants for the vast majority of B2's in NIH/3T3 cells. CHART reads were then normalized to input DNA and to CHART reads obtained by a scrambled capture probe. Peaks were called using SICER (Xu et al., 2014) to identify statistically significant B2 targets sites throughout the genome (FDR<0.05). CHART-seq was conducted on pre- and post-heat shock cells (pre-H/S and post-H/S, respectively), and biological replicates showed highly similar results (FIG. 8).

Figure 4A:
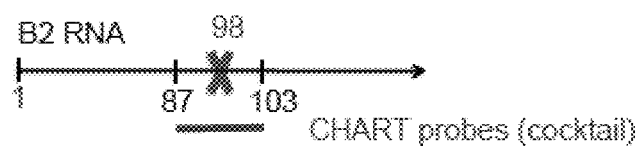
Figure 4B:
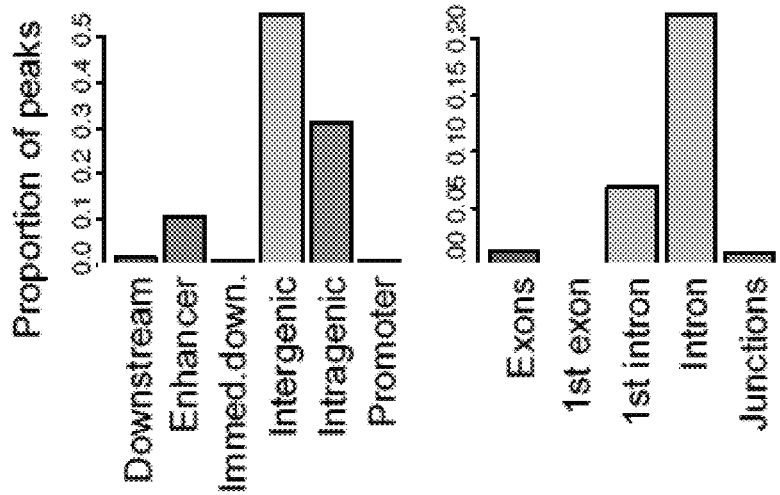
Figure 4C:
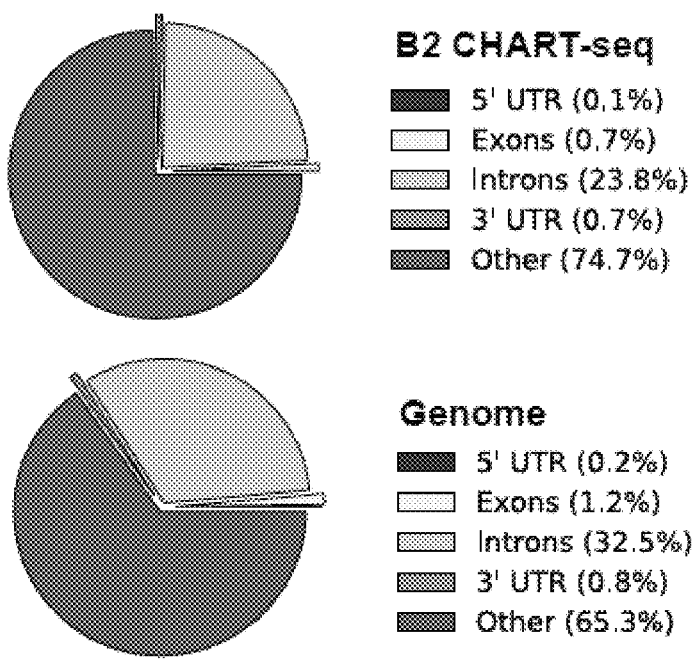
Figure 4D:
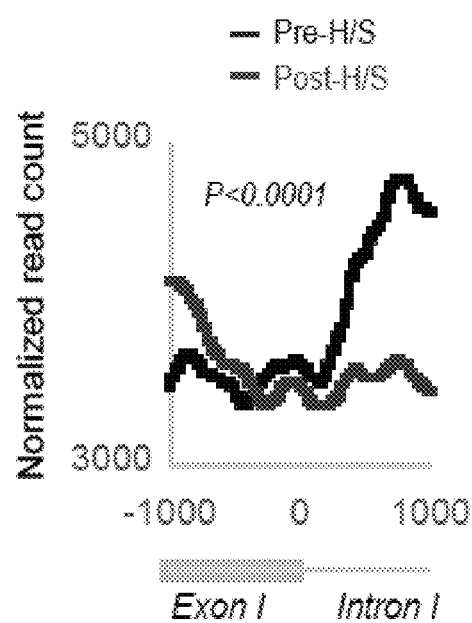
Figure 4E:
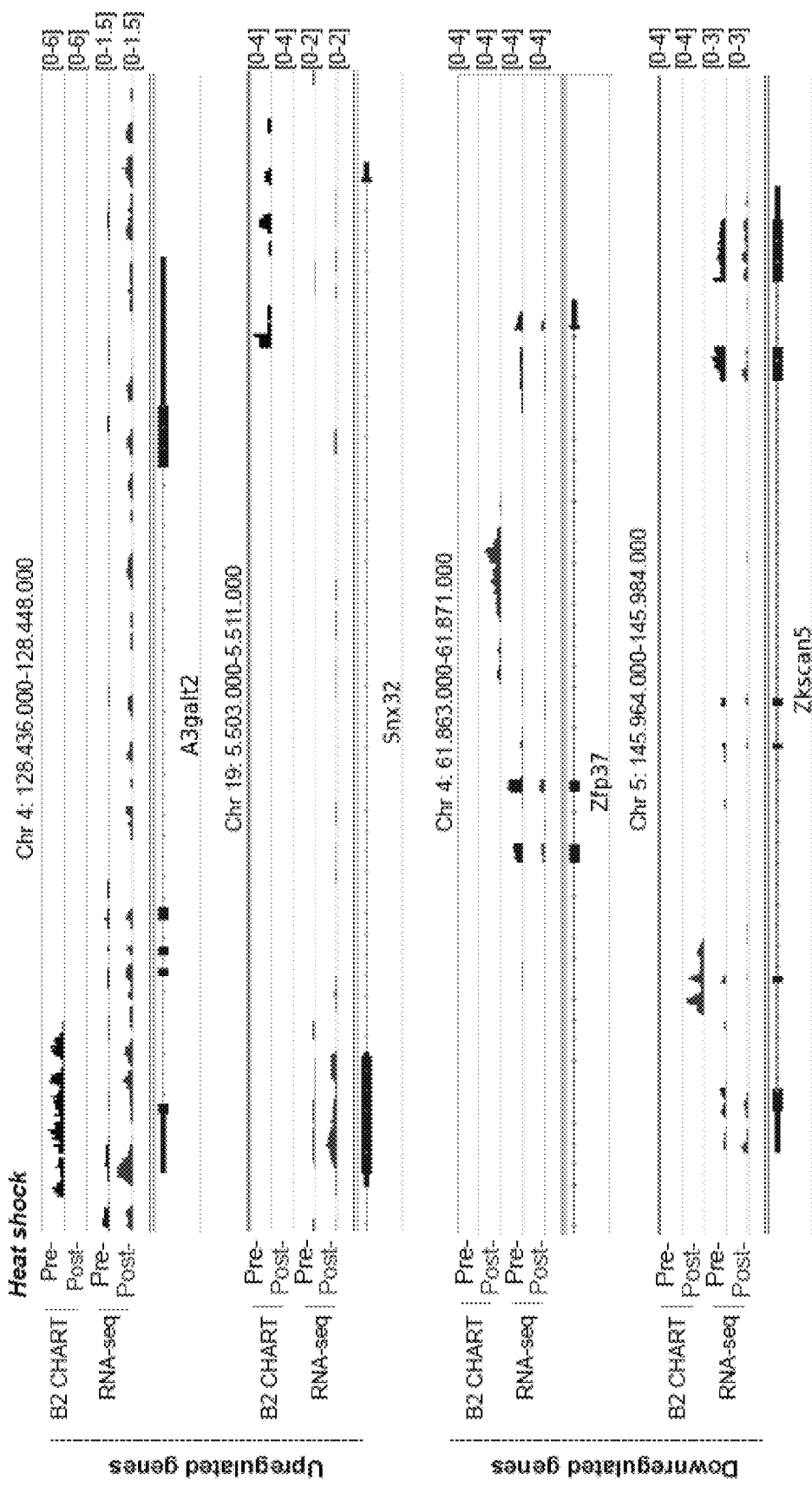

Among 83,928 significant peaks altogether, 39,330 corresponded to nascent transcription from genomic B2 elements and served as positive controls (FIG. 8). Because the goal was to identify B2 target sites, peaks localizing within +/−3 kb of a B2 element (the average size of captured fragments) were excluded from further analysis. We examined the remaining 44,598 B2 RNA target sites. In pre-H/S cells, we observed 18,964 such sites. After only 15 minutes of heat shock, the number of B2 target sites nearly doubled to 31,368. Interestingly, target sites were largely non-overlapping between the two conditions. Among 18,964 pre-H/S sites, 13,230 were present only before heat shock (mentioned as "Type I" sites. Reciprocally, among 31,368 post-H/S sites, 25,634 were observed only after H/S ("Type II" sites). A minority (5,734) occurred in both pre- and post-H/S cells ("Type III" sites). We then characterized the target sites and found that the vast majority of B2 binding sites were in intergenic space and introns (FIG. 4B,C; pre-H/S shock shown), especially the first intron (FIG. 4B), and this was true for all three types of B2-binding targets (Tables S3-S5). With regards to the $1^{st}$ intron, the peaks often occurred at the $1^{st}$ exon-intron boundary and generally within 1,000 bp of the transcription start site (TSS), as shown by both a metagene analysis (FIG. 4D; KS test, P<0.0001) and by examination of specific genic loci (FIG. 4E). It should be emphasized, however, that B2 binding sites could occur anywhere within the gene body, that the binding sites tend to be broad and frequently spanned adjacent introns (FIG. 4E,S3), appearing different from the discrete peaks typified by transcription factors.

To determine how B2 binding affects gene expression, we performed RNA-seq analysis of NIH/3T3 cells before and after 15 minutes of heat shock and compared the results to B2 CHART-seq profiles. We observed that 1,587 genes were upregulated ($log_2$ fold-change≥0.5; Table 1) and 1,413 genes were downregulated ($log_2$ fold-change≤0.5; Table 2) by heat shock. Biological replicates were highly correlated and showed similar results (Pearson's R=0.9). Intriguingly, H/S-upregulated genes were enriched in the Type I subclass of B2 targets—i.e., they were bound by B2 RNA prior to heat shock, and were released from binding following heat shock. In contrast, H/S-downregulated genes were enriched in the Type II subclass—i.e., they were free of B2 binding prior to heat shock, but became B2 targets after heat shock. These trends are illustrated by specific examples (FIG. 4E). For instance, at two H/S-upregulated genes, A3galt2 and Snx32, B2 binding was observed in the resting state when the genes were expressed at low levels, but was lost after 15 minutes of heat shock after which the genes were upregulated. On the other hand, at two H/S-downregulated genes, Zfp37 and Zkscan5, B2 binding was not apparent before H/S, but became significant after H/S.

Metagene analysis confirmed these trends on a genome-wide scale (FIG. 4F,G). At 15 minutes post-H/S, the vast majority of genes displayed no changes in B2 localization ("all genes"). By contrast, H/S-upregulated genes (Table 1) showed a significant loss of B2 binding, and H/S-downregulated genes (Table 2) showed a significant increase in B2 binding. Together, these data demonstrate that B2 RNA targets specific genomic regions and that the binding pattern is rapidly and dramatically altered by heat shock. The changes are measurable within 15 minutes. We conclude that B2 RNA targets heat shock-responsive genes and its binding is anti-correlated with H/S gene expression across the genome.

Example 5. Cleavage of B2 RNA Induces Heat Shock-Responsive Genes

In light of the anti-correlation between B2 binding and target gene activity, the cleavability of B2 RNA raised a fascinating possibility: That B2 RNA might normally suppress POL-II activity, and that stress would trigger B2 turnover in order to lift the block to POL-II activity. To investigate this hypothesis, we performed ChIP-seq for the Serine-2 phosphorylated form of RNA POL-II (POL-II-S2P) to examine the density of elongating RNA polymerase across H/S-responsive genes (FIG. 5). As expected, genes upregulated by H/S (Table 1) showed increased POL-II density within 15 minutes of H/S, whereas genes downregulated by H/S (Table 2) showed decreased POL-II density (FIG. 5A, KS test, P<0.0001). We then examined the subset of genes that bind B2 only before H/S (Type I). Indeed, among the Type I genes, the H/S stimulus resulted in a significant spike in POL-II density (KS test; P<0.0001) (FIG. 5B,C), coinciding with the loss of the B2 binding (FIG. 4E,F). Conversely, among genes that bind B2 only after H/S (Type II), the H/S stimulus led to a significant decrease in POL-II density (KS test; P<0.0001) (FIG. 5B, C), coinciding with the gain of B2 binding within the same timeframe (FIG. 4E). Thus, POL-II activity is reduced where B2 binding appears, and POL-II activity increases where B2 binding is lost.

These data suggested that B2 binding is central to control of H/S genes. If so, turnover of B2 alone might be sufficient to induce transcriptional release. To de-couple B2 turnover from heat shock, we designed a B2-specific antisense oligonucleotide (ASO) using locked nucleic acid chemistry (LNA) to cleave B2 RNA. After 24 hours of transfection into NIH/3T3 cells (without heat shock), we observed significantly elevated cutting of B2 fragments relative to that seen in a scrambled (Scr) LNA-treated sample (FIG. 5D, KS test; P<0.0001). B2 LNA treatment recapitulated the increase in POL-II density across H/S-responsive genes, again without the heat shock stimulus (FIG. 5E, KS test; P<0.0001). Concurrently, RNA-seq analysis showed activation of H/S-responsive genes (FIG. 5F, KS test; P<0.0001). Biological replicates for RNA-seq and POL-II-S2P ChIP-seq showed excellent reproducibility. We conclude that increased POL-II density and gene expression can be uncoupled from the heat shock stimulus by ectopically inducing B2 degradation. Thus, B2 cleavage is central to the H/S response.

Figure 6D:
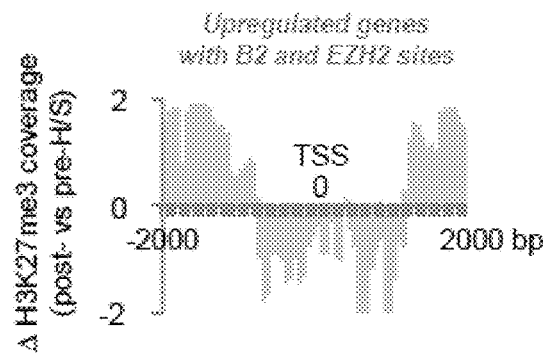

Example 6. EZH2 is Recruited to B2 Target Sites to Promote the Heat Shock Response We were initially led to consider the role B2 RNA after noting its enriched representation in the EZH2 RIP-seq data (FIG. 1). We subsequently discovered that contact with EZH2 resulted in cleavage of B2 RNA in vitro (FIG. 2) and that cut forms of B2 RNA have dramatically reduced affinity for EZH2 (FIG. 1F). Together, these findings suggested that contact with EZH2 might destabilize B2 RNA and thereby release POL-II from suppression at H/S genes. To test this possibility, we performed EZH2 ChIP-seq in NIH/3T3 cells before and after heat shock and called statistically significant peaks of EZH2 enrichment using SICER (FDR<0.05), with biological replicates showing similar results. Consistent with EZH2's repressive role for transcription, we observed an enrichment for EZH2 at the TSS of H/S-downregulated genes (FIG. 6A). Unexpectedly, EZH2 also appeared to be slightly increased at H/S-upregulated genes, though this small increase was not statistically significant. However, the difference became pronounced and significant when analysis was focused on the subpopulation of H/S-upregulated genes bound by B2 (in the pre-H/S state) (FIG. 6B, KS test; P<0.0001). Those without a B2 site did not show increased EZH2 binding. Therefore, genes induced by heat shock paradoxically gained EZH2 coverage during activation. This finding implied that EZH2 is recruited to genes repressed by B2 RNA. Recruitment of EZH2 was not accompanied by an increase in trimethylation of H3K27, however (FIG. 6C). Rather, there was a decrease in H3K27me3 over the TSS after heat shock (FIG. 6D), consistent with their transcriptional upregulation.

Figure 6E:
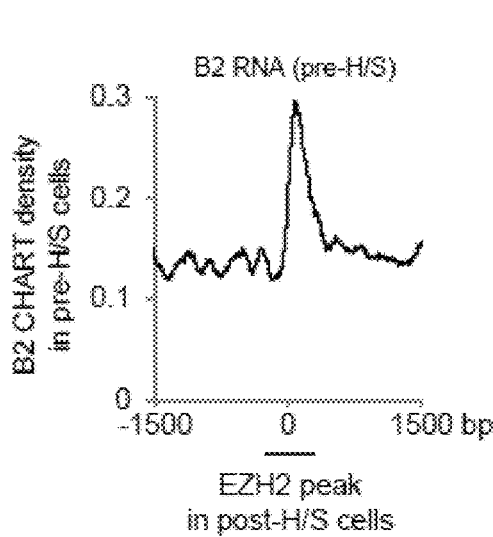
Figure 6F:
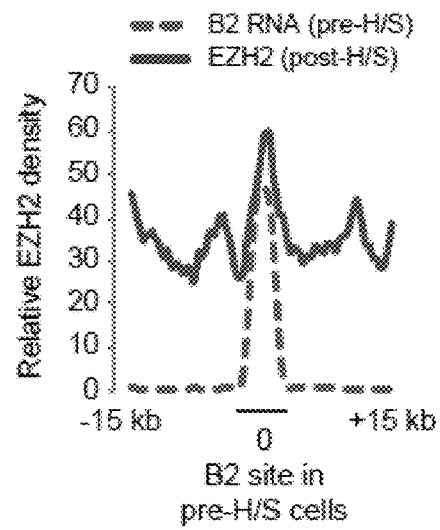
Figure 6G:
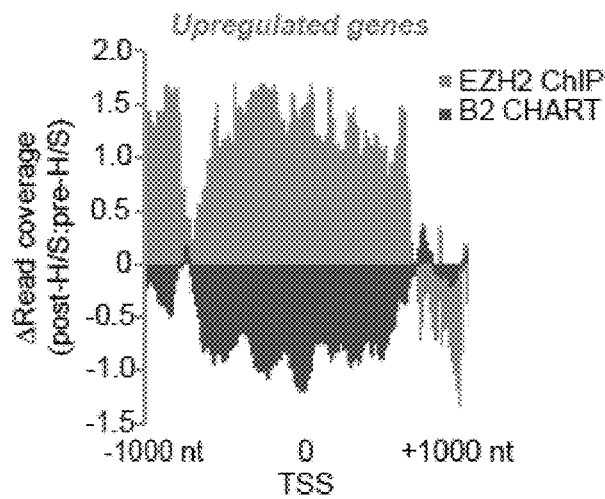
Figure 6H:
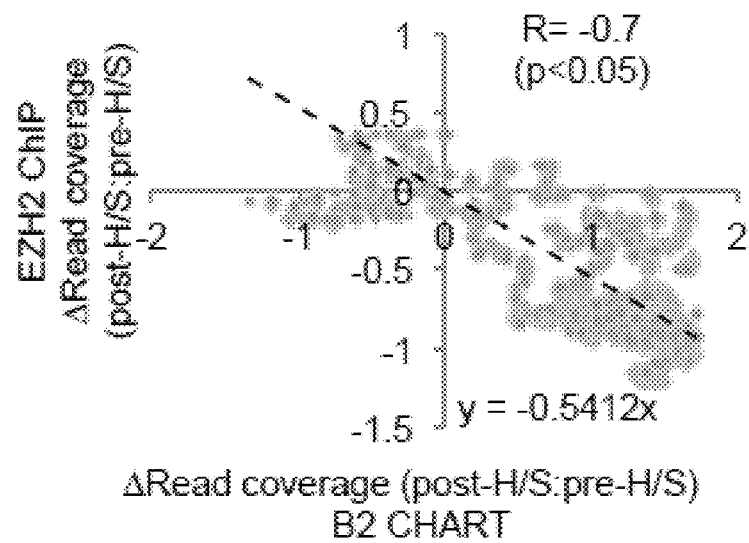
Figure 6I:
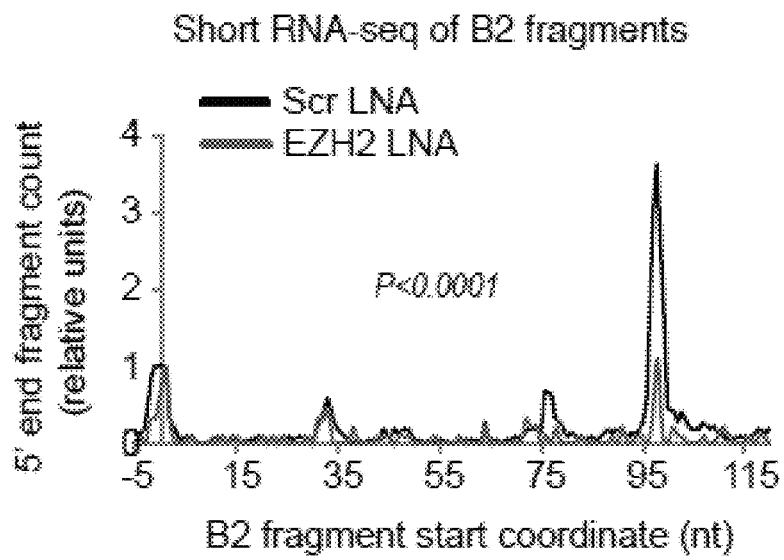
Figure 6J:
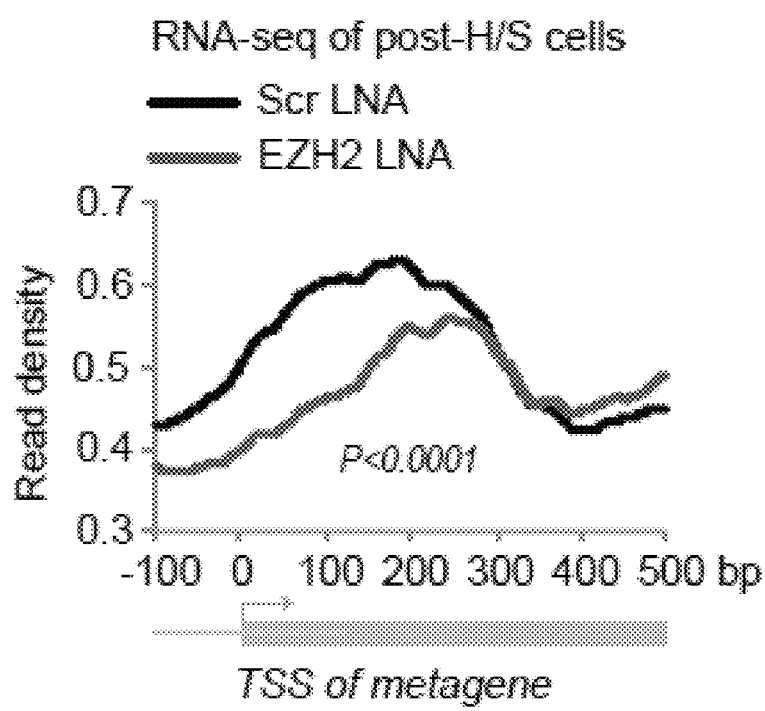

Thus, during heat shock, EZH2 is recruited to inducible genes for a purpose other than H3K27 trimethylation. Because the paradoxical association between EZH2 density and gene expression was most remarkable for genic targets of B2 RNA (FIG. 6B) and in light of EZH2's effect on B2 RNA in vitro, we suspected that recruited EZH2 may serve to destabilize B2 RNA in order to activate target genes. Indeed, "meta-site" analysis from an EZH2-centric view (x=0 at EZH2 site) revealed that, after introduction of stress, EZH2 was attracted to sites where B2 was bound (FIG. 6E). In the converse analysis, a B2-centric view (x=0 at B2 sites) revealed the same finding—a gain of EZH2 binding where B2 binding was lost (FIG. 6F). This conclusion was supported by a very strong anti-correlation between change in B2 binding density and change in EZH2 coverage (FIG. 6G,H). Collectively, these data lend credence to the hypothesis that, in resting cells, B2 RNA is bound to H/S-inducible genes and a stressful stimulus triggers recruitment of EZH2, which in turn destabilizes B2 RNA for the activation of H/S genes.

Thus, EZH2 appears to play an equally important role in the heat shock response. We asked whether perturbing EZH2 affects B2 processing and gene induction in vivo. Administering ASOs specific for EZH2 to NIH/3T3 cells led to a significant knockdown (KD) of EZH2 (FIG. 9). Short RNA-seq analysis showed that this effect was accompanied by significantly decreased B2 cleavage at positions 98 and 77 (FIG. 6I, KS test; P<0.0001). Depleting EZH2 also led to a blunted activation of H/S-responsive genes in two biological replicates (FIG. 6J, KS test; P<0.0001). These experiments thereby demonstrate that EZH2 is indeed a crucial factor in the induction of H/S-responsive genes.

The dynamic interplay between B2 RNA, EZH2, and POL-II activity can be appreciated by examination of specific H/S-inducible loci (FIG. 7A). For example, in resting cells, the gene for Cl tumor necrosis factor-related protein, C1qtnf3, was transcribed at low levels, as reflected by a low POL-II-S2P coverage (0.257) and a low RNA-seq value (FPKM=0.009). During rest, B2 RNA was bound at high levels and EZH2 binding was not detectable. Upon heat shock, EZH2 rapidly appeared within intron 3 at the same time that B2 binding decreased in introns 2 and 3. Concurrently, we observed increased POL-II-S2P coverage within the gene body (FPKM=0.308) and a 2.4-fold upregulation of CI qtnf3 transcription (FPKM=0.022). [N.B: The H/S genes respond in a graded rather than all-or-none manner (Brown et al., 1996; Chircop and Speidel, 2014; Kwak et al., 2013)]. Similarly, at another H/S-activated gene, Lrrc61, B2 binding disappeared when EZH2 binding appeared after heat shock, at which time POL-II-S2P coverage increased 2-fold (FPKM=0.093 to 0.192). All of these events were measurable within 15 minutes of heat shock. Ectopically cleaving B2 RNA (using B2 LNAs) recapitulated the H/S response in the absence of stimulus (FIG. 5E, 7A). For C1qtnf3, B2 LNA treatment resulted in a ~2-fold increase of POL-II-S2P coverage (FPKM=0.481) and a 3-fold increase in RNA levels (FPKM=0.027) relative to baseline. For Lrrc61, there was a 2.3-fold increase of POL-II-S2 coverage (FPKM=0.213) and a 1.36-fold increase in transcription (FPKM=0.420) relative to baseline. We conclude that EZH2 and B2 play pivotal roles during the stress response, and that contact-induced B2 elimination is the key trigger for gene activation.

TABLE 1

List of heat shock-upregulated genes shown by RNA-seq analysis.
Column A: Heat shock-upregulated gene shown by RNA-seq analysis of NIH/3T3 cells.
Column B: Log2 fold-change of the gene in post-H/S cells relative to pre-H/S state.

| gene | log2(fold_change) | gene | log2(fold_change) | gene | log2(fold_change) |
| --- | --- | --- | --- | --- | --- |
| Pla2g4b | 16.3925 | Gimap9 | 2.97228 | Cecr6 | 2.56515 |
| H2-L | 10.2141 | Prr18 | 2.94858 | Rps15a-ps4 | 2.54353 |
| Rbm14-rbm4 | 9.70033 | Col8a2 | 2.93686 | Lyl1 | 2.53327 |
| Btg3 | 7.92603 | Slc10a1 | 2.90647 | Gm10069 | 2.51012 |
| Snora64 | 4.4165 | Esr1 | 2.89912 | 5730480H06Rik | 2.50066 |
| Ccin | 4.38112 | Mfsd7c | 2.89912 | Il10 | 2.50066 |
| Xrra1 | 4.10699 | Muc1 | 2.89912 | Lrrc4b | 2.50066 |
| H1fx | 4.06394 | Zfp72 | 2.89912 | Mmp24 | 2.50066 |
| Mc1r | 3.80096 | Cmah | 2.84826 | Snora44 | 2.50066 |
| 9630028B13Rik | 3.72776 | Cr2 | 2.8482 | Tnfrsf13c | 2.50066 |
| Dusp18 | 3.68517 | Klhl41 | 2.8482 | Sap25 | 2.49155 |

TABLE 1-continued

List of heat shock-upregulated genes shown by RNA-seq analysis.
Column A: Heat shock-upregulated gene shown by RNA-seq analysis of NIH/3T3 cells.
Column B: Log2 fold-change of the gene in post-H/S cells relative to pre-H/S state.

| gene | log2(fold_change) | gene | log2(fold_change) | gene | log2(fold_change) |
|---|---|---|---|---|---|
| Ctxn1 | 3.62625 | Hspa1b | 2.82076 | 2810442I21Rik | 2.48463 |
| Ism2 | 3.59641 | Stxbp2 | 2.79653 | 4930565N06Rik | 2.46801 |
| Ipcef1 | 3.56099 | Efnb3 | 2.78526 | Col6a5 | 2.463 |
| C1rb | 3.53327 | Actl7b | 2.75266 | Il1f9 | 2.463 |
| Cyb561 | 3.50066 | Snord15b | 2.74752 | Ppfibp2 | 2.4581 |
| Camk4 | 3.49282 | Gm17801 | 2.74178 | 1700020D05Rik | 2.45648 |
| Gpr1 | 3.46731 | Gzmm | 2.74178 | Aldh1a3 | 2.43316 |
| Doc2b | 3.40167 | Il17rb | 2.74178 | Gnat1 | 2.43316 |
| Gpr3 | 3.39892 | Tmem132b | 2.74178 | Nek10 | 2.43316 |
| Pacsin1 | 3.2119 | Hebp2 | 2.72196 | Wnt6 | 2.43316 |
| Rsph6a | 3.19737 | Xntrpc | 2.68679 | Rplp2-ps1 | 2.42774 |
| A530013C23Rik | 3.15779 | BC055111 | 2.68487 | Jam2 | 2.37402 |
| Socs1 | 3.12905 | Btbd18 | 2.68487 | Olfr90 | 2.37402 |
| Gm15107 | 3.12894 | Fam219aos | 2.68487 | Gdap1 | 2.36384 |
| Unc13d | 3.12894 | Fzd9 | 2.68487 | Gpr82 | 2.36362 |
| Zfp296 | 3.10073 | Itga7 | 2.68487 | Snora17 | 2.33896 |
| 1700001L05Rik | 3.09658 | Nwd1 | 2.68487 | BC064078 | 2.33762 |
| Upk1a | 3.08563 | 1700113A16Rik | 2.63311 | Gm16287 | 2.33762 |
| BC065397 | 3.08515 | 4930558J18Rik | 2.62688 | Tas1r1 | 2.33762 |
| Jazf1 | 3.06248 | Opn3 | 2.62688 | Rnf43 | 2.32635 |
| Ddn | 3.04796 | Wdr96 | 2.62688 | Plxnc1 | 2.31983 |
| Sh2d2a | 3.0438 | Gm10390 | 2.60575 | Best1 | 2.29297 |
| Bcl2l14 | 3.04098 | Cxcl5 | 2.57392 | Klhl40 | 2.29166 |
| Brsk2 | 2.98871 | Rbpjl | 2.57344 | Reep6 | 2.28961 |
| 6330403K07Rik | 2.28945 | A3galt2 | 2.05897 | Wdr95 | 1.93686 |
| Dqx1 | 2.28945 | Mip | 2.04852 | Dpf3 | 1.93548 |
| Gca | 2.28945 | Bhlhe41 | 2.04593 | Snora21 | 1.91886 |
| Gper1 | 2.28945 | Trim72 | 2.04571 | Pstpip1 | 1.91647 |
| Jpx | 2.28945 | Igtp | 2.04536 | Sfrp5 | 1.9157 |
| Trpt1 | 2.2764 | Star | 2.0433 | Actr3b | 1.90441 |
| Sox15 | 2.25076 | Fut2 | 2.0423 | Hpgds | 1.90441 |
| Wdr78 | 2.24895 | Plekha6 | 2.04223 | Slfn8 | 1.90335 |
| Msh4 | 2.24419 | B430319G15Rik | 2.04192 | Hsph1 | 1.89988 |
| Gm16702 | 2.23912 | Gm3219 | 2.04192 | Pdzd2 | 1.89678 |
| Gbp3 | 2.23509 | Kcnab3 | 2.04192 | Mpeg1 | 1.87887 |
| H2-Q1 | 2.21109 | Pmel | 2.04192 | Dnajb1 | 1.87558 |
| Cplx3 | 2.211 | Tnni2 | 2.04192 | Rhpn2 | 1.87141 |
| E130310I04Rik | 2.211 | Gpr39 | 2.04098 | Mgat4a | 1.86854 |
| Gnb3 | 2.211 | Zpbp | 2.04098 | Ccdc166 | 1.84845 |
| Homer2 | 2.211 | Oas1b | 2.04097 | Slc1a2 | 1.84845 |
| Nipal4 | 2.211 | Opn1sw | 2.02673 | AI182371 | 1.84832 |
| Serpina6 | 2.211 | Fam221a | 2.01216 | 1700112E06Rik | 1.8482 |
| Spata21 | 2.211 | Fam83e | 2.01138 | 1810010H24Rik | 1.8482 |
| Tas1r3 | 2.211 | B3galt4 | 2.0113 | B3gnt6 | 1.8482 |
| Tppp | 2.211 | Snora26 | 2.00473 | Coro2b | 1.8482 |
| Prickle3 | 2.20323 | Kbtbd8 | 2.00401 | Elfn1 | 1.8482 |
| Adam1a | 2.17995 | Zfp783 | 2.00084 | Gm3558 | 1.8482 |
| Il18bp | 2.17376 | Gdf9 | 1.99587 | Hsf5 | 1.8482 |
| Ifitm5 | 2.16195 | Gm12504 | 1.99377 | Kcng4 | 1.8482 |
| Dnah7b | 2.15111 | Raver2 | 1.99377 | Myrf | 1.8482 |
| Stac3 | 2.15111 | Klrg2 | 1.98508 | Smim18 | 1.84815 |
| Gm15760 | 2.15011 | Nfe2l3 | 1.97729 | Gm10941 | 1.8477 |
| Snora24 | 2.14432 | Masp2 | 1.95104 | Phlda1 | 1.83422 |
| Snora78 | 2.13742 | Fcgbp | 1.94831 | Gm15545 | 1.83411 |
| Gdpd1 | 2.12849 | Gm6537 | 1.94831 | 4933413J09Rik | 1.82881 |
| Plcd4 | 2.11267 | Gm6578 | 1.94831 | Arhgef15 | 1.82881 |
| Vmn1r58 | 2.11637 | Med12l | 1.94831 | Cntn6 | 1.82881 |
| Gm9159 | 2.10744 | Serpinb1b | 1.94831 | Olfr1189 | 1.82881 |
| Ccdc106 | 2.10658 | Tmem82 | 1.94831 | Rprl2 | 1.82509 |
| Cers1 | 2.09773 | Xylb | 1.94831 | Cep97 | 1.81814 |
| Znf41-ps | 2.09439 | Hsf4 | 1.94331 | Ddx60 | 1.81715 |
| Cd68 | 2.09373 | Slc6a20b | 1.94114 | LOC101669761 | 1.81715 |
| Scn8a | 2.09301 | Kcnk7 | 1.9395 | Klhdc9 | 1.81396 |
| Vaultrc5 | 2.08566 | Nacad | 1.93879 | 1700022I11Rik | 1.80786 |
| Gt(ROSA)26Sor | 2.07448 | Ccpg1os | 1.93686 | Ttn | 1.80658 |
| Tha1 | 2.0712 | Kcnh3 | 1.93686 | Elmo3 | 1.80537 |
| Rxfp3 | 1.79653 | B3gnt5 | 1.685 | Atp1a2 | 1.57835 |
| Nipal1 | 1.79613 | Glyctk | 1.68497 | Baiap2l1 | 1.57245 |
| Mina | 1.79225 | Mboat1 | 1.68487 | D3Ertd751e | 1.57011 |
| Tnfsf13 | 1.78146 | Nodal | 1.68487 | Prdm9 | 1.5668 |
| Rassf4 | 1.77813 | Sh2d5 | 1.68487 | Itih4 | 1.56527 |
| Rdh9 | 1.77813 | Myh7b | 1.68431 | 1700034J05Rik | 1.5652 |
| Tlr1 | 1.77397 | Dclre1c | 1.67736 | Raver1-fdx1l | 1.56387 |
| Ccdc28a | 1.76904 | Wnt2 | 1.67199 | Tcf7 | 1.55402 |

TABLE 1-continued

List of heat shock-upregulated genes shown by RNA-seq analysis.
Column A: Heat shock-upregulated gene shown by RNA-seq analysis of NIH/3T3 cells.
Column B: Log2 fold-change of the gene in post-H/S cells relative to pre-H/S state.

| gene | log2(fold_change) | gene | log2(fold_change) | gene | log2(fold_change) |
|---|---|---|---|---|---|
| Ccdc64b | 1.76504 | Gm16386 | 1.67005 | Samd10 | 1.55366 |
| Pde8b | 1.7648 | Lyn | 1.66592 | Celf3 | 1.55217 |
| 1110046J04Rik | 1.75266 | Phkg1 | 1.6648 | Rel | 1.55198 |
| Cyp27b1 | 1.75266 | Igfals | 1.66368 | Slc10a6 | 1.54397 |
| Evpl | 1.75266 | 2310014L17Rik | 1.6616 | Bend4 | 1.5425 |
| Gm3230 | 1.75266 | Nudt15 | 1.65918 | Glp2r | 1.54222 |
| LOC102633315 | 1.75266 | Pde1b | 1.65858 | Sptbn4 | 1.54168 |
| Ppef1 | 1.75266 | Pycard | 1.64266 | Rxfp4 | 1.54144 |
| Csdc2 | 1.74675 | Serpina3h | 1.63923 | Snhg10 | 1.54144 |
| 4930404N11Rik | 1.74216 | Nfam1 | 1.62808 | Txlnb | 1.54144 |
| Gm11128 | 1.74178 | Ptpro | 1.62749 | Hid1 | 1.53588 |
| Lamc2 | 1.74178 | Serpina1a | 1.62696 | Csf1r | 1.53327 |
| Lct | 1.74178 | Bspry | 1.62688 | Avpr2 | 1.53196 |
| Ptgs2os | 1.74178 | Crabp2 | 1.62688 | Qrfp | 1.52681 |
| Slc5a5 | 1.74178 | Gm20756 | 1.62688 | Gpd1 | 1.52636 |
| Shank2 | 1.73997 | Hcn3 | 1.62688 | A330035P11Rik | 1.51543 |
| Gm13483 | 1.7356 | Ptprcap | 1.62688 | Slc35g1 | 1.51543 |
| Gpr61 | 1.72476 | Rnf208 | 1.62688 | Hspb6 | 1.50826 |
| Prph | 1.72265 | Smok4a | 1.62688 | Ppfia3 | 1.50177 |
| Pet117 | 1.72082 | Unc13c | 1.62688 | G530011O06Rik | 1.50141 |
| Sema7a | 1.7193 | 2900060B14Rik | 1.6267 | Papln | 1.50105 |
| 1700003F12Rik | 1.71621 | Spta1 | 1.61997 | Fmo5 | 1.50092 |
| Tmem117 | 1.71621 | Afap1l1 | 1.61903 | Nr1h3 | 1.50072 |
| Mtfr2 | 1.71536 | Cldn3 | 1.61903 | Ace2 | 1.50069 |
| Nkpd1 | 1.7136 | Nat8 | 1.61903 | 1700123M08Rik | 1.50066 |
| Loxl2 | 1.69758 | Cul9 | 1.6178 | 4930592I03Rik | 1.50066 |
| Immp2l | 1.69379 | Dusp4 | 1.61584 | 6330403A02Rik | 1.50066 |
| Gng3 | 1.6927 | Fcgr4 | 1.61584 | A930007I19Rik | 1.50066 |
| Snora7a | 1.68565 | Gpr160 | 1.61512 | Apol11b | 1.50066 |
| Liph | 1.68547 | Hspa1a | 1.61007 | Arhgef33 | 1.50066 |
| 4931403G20Rik | 1.68527 | Tnfrsf21 | 1.59665 | Atcay | 1.50066 |
| Fam180a | 1.68515 | E330033B04Rik | 1.59361 | Ccdc121 | 1.50066 |
| Gabre | 1.68515 | Zfp619 | 1.5887 | Cldn22 | 1.50066 |
| Gm5464 | 1.68515 | Fbxl22 | 1.58506 | Dpep2 | 1.50066 |
| Gm4532 | 1.50066 | Kndc1 | 1.42298 | Zbtb46 | 1.33407 |
| Gm7444 | 1.50066 | D630041G03Rik | 1.42212 | Ugt1a7c | 1.33286 |
| Kbtbd11 | 1.50066 | Lgals4 | 1.41708 | Artn | 1.33251 |
| Klhl30 | 1.50066 | Slc16a11 | 1.41091 | Gdpd5 | 1.33179 |
| Nat8l | 1.50066 | Gpr179 | 1.41042 | Cd4 | 1.33151 |
| Pih1d2 | 1.50066 | Ranbp3l | 1.40929 | Ptplad2 | 1.33151 |
| Prss27 | 1.50066 | Amd2 | 1.40852 | Wnt2b | 1.32923 |
| Prss8 | 1.50066 | Pex1 | 1.40713 | Hmga1-rs1 | 1.32721 |
| Rsg1 | 1.50066 | Plin4 | 1.40601 | F2rl3 | 1.3266 |
| Snora52 | 1.50066 | Fbxo2 | 1.40581 | Slc7a14 | 1.32262 |
| Srrm3 | 1.50066 | Trp53cor1 | 1.40434 | 4933421O10Rik | 1.322 |
| Infrsf11a | 1.50066 | Pde7b | 1.39892 | Gadd45b | 1.32079 |
| Zfp941 | 1.50066 | Cntf | 1.39812 | 4930562C15Rik | 1.31983 |
| Dlk2 | 1.49872 | AK010878 | 1.39473 | Map3k19 | 1.31983 |
| Dmtn | 1.49855 | Trim68 | 1.39431 | Map4k1 | 1.31983 |
| Gm19705 | 1.49424 | Htr2a | 1.39336 | 2700054A10Rik | 1.31827 |
| Hoxc6 | 1.48708 | Efcab4b | 1.39168 | Ttc38 | 1.31684 |
| Col23a1 | 1.48359 | Slc16a4 | 1.3892 | BC068281 | 1.31495 |
| Vipr1 | 1.48359 | Snord22 | 1.38615 | Dlgap2 | 1.31421 |
| Gimap1 | 1.47889 | Dph7 | 1.38372 | Rhof | 1.29987 |
| Tmc4 | 1.47717 | 2210039B01Rik | 1.38093 | Snora74a | 1.29838 |
| Rdh12 | 1.4742 | Gpr62 | 1.38093 | Plekhg6 | 1.2981 |
| Adcy7 | 1.47092 | Slc23a1 | 1.38093 | A930024E05Rik | 1.29391 |
| Ulk3 | 1.46879 | Dper1 | 1.37458 | AI317395 | 1.29391 |
| Lag3 | 1.46553 | Ttll13 | 1.37458 | Eva1a | 1.29391 |
| 1700007J10Rik | 1.46387 | Tctex1d4 | 1.37126 | Snora28 | 1.29376 |
| Kctd12b | 1.463 | Ccdc107 | 1.36936 | 5031414D18Rik | 1.29297 |
| Olfr1314 | 1.463 | Ism1 | 1.36865 | Ntrk3 | 1.28949 |
| Slc25a18 | 1.463 | Adam30 | 1.36334 | Adamtsl1 | 1.28945 |
| Zfp773 | 1.463 | Tatdn3 | 1.35879 | Esam | 1.28945 |
| Pianp | 1.45782 | D130040H23Rik | 1.35337 | Rltpr | 1.28945 |
| Msrb2 | 1.45731 | Snora43 | 1.35152 | Tmem240 | 1.28945 |
| Tbc1d10c | 1.45601 | Ldb3 | 1.3509 | Atf7ip2 | 1.28363 |
| Prkd2 | 1.45336 | Gpr173 | 1.34981 | Amacr | 1.2823 |
| Rbmx2 | 1.45103 | Mroh6 | 1.34981 | Vegfb | 1.27558 |
| Arntl2 | 1.45055 | Plce1 | 1.3453 | Grip2 | 1.27432 |
| Sycp2 | 1.44763 | 8430419L09Rik | 1.34516 | Slfn5 | 1.27378 |
| Cdk5r1 | 1.44717 | Bcl2l12 | 1.34451 | Triqk | 1.27105 |
| Bag3 | 1.44633 | 4732491K20Rik | 1.33815 | Rpusd3 | 1.27038 |
| Galc | 1.44537 | Duox1 | 1.33762 | Ercc8 | 1.26377 |

TABLE 1-continued

List of heat shock-upregulated genes shown by RNA-seq analysis.
Column A: Heat shock-upregulated gene shown by RNA-seq analysis of NIH/3T3 cells.
Column B: Log2 fold-change of the gene in post-H/S cells relative to pre-H/S state.

| gene | log2(fold_change) | gene | log2(fold_change) | gene | log2(fold_change) |
|---|---|---|---|---|---|
| Bcas3os1 | 1.43319 | Ms4a6c | 1.33762 | Gm13826 | 1.26355 |
| Pnma1 | 1.42344 | Rtp4 | 1.33762 | Kctd13 | 1.26328 |
| BC051226 | 1.26309 | Sobp | 1.20643 | Synpo2 | 1.15111 |
| Podxl | 1.26292 | 4933408B17Rik | 1.20613 | Alkbh7 | 1.14711 |
| Slc35g3 | 1.26292 | C030037D09Rik | 1.20613 | Tnik | 1.14696 |
| Hmgn5 | 1.25808 | Tmem151a | 1.20613 | Slc16a6 | 1.1454 |
| Cdt1 | 1.25486 | Slc44a5 | 1.20547 | Sema6b | 1.14345 |
| Kcnrg | 1.25459 | Fam189b | 1.2043 | C130083M11Rik | 1.1432 |
| Pcdhga4 | 1.25453 | Gstp2 | 1.20335 | Ppfia4 | 1.1432 |
| Kcnma1 | 1.25351 | Kcnc3 | 1.20036 | Slc4a10 | 1.13882 |
| Wnt4 | 1.25076 | Rasl10a | 1.20033 | Pitpnm3 | 1.13748 |
| 9430091E24Rik | 1.24955 | C1qtnf3 | 1.20031 | Macrod2 | 1.13675 |
| Fam131a | 1.24944 | 9030624G23Rik | 1.2003 | 4930443O20Rik | 1.13415 |
| Kcnj15 | 1.24725 | AY512931 | 1.2003 | Khk | 1.13195 |
| Acyp2 | 1.24385 | Adora2a | 1.2003 | Actr6 | 1.13087 |
| Cenpv | 1.24385 | Cmya5 | 1.2003 | Cspg5 | 1.12465 |
| A930005H10Rik | 1.24095 | Gm16880 | 1.2003 | Klhl36 | 1.12433 |
| Abhd14a | 1.24046 | Gm8234 | 1.2003 | Msantd1 | 1.12287 |
| Naa30 | 1.23835 | Nefh | 1.2003 | Epb4.1l5 | 1.11995 |
| Zfp58 | 1.23825 | Zglp1 | 1.2003 | Grin3b | 1.11589 |
| Aamdc | 1.23695 | Slc25a14 | 1.1969 | 8430427H17Rik | 1.11299 |
| E330009J07Rik | 1.23602 | Ptgir | 1.19468 | Htr2b | 1.11195 |
| Lbp | 1.23602 | Map2k3 | 1.1943 | Chrnb2 | 1.11104 |
| Depdc7 | 1.23422 | Ccdc101 | 1.19405 | Al606473 | 1.11064 |
| Celsr3 | 1.23292 | Tinagl1 | 1.19082 | Prorsd1 | 1.10873 |
| Ociad2 | 1.23033 | Serf1 | 1.1847 | Slc26a6 | 1.10492 |
| Napb | 1.22772 | Poc5 | 1.18338 | Ufsp1 | 1.10078 |
| Slc25a35 | 1.22618 | Arid5a | 1.18139 | Kcnc1 | 1.10075 |
| Nup210 | 1.22573 | Col6a6 | 1.18093 | Oip5 | 1.10073 |
| Morn4 | 1.22452 | Grpr | 1.18014 | Dnaic2 | 1.10063 |
| Marveld3 | 1.22407 | Ccl25 | 1.17567 | Cdkn1c | 1.10046 |
| Zbtb3 | 1.21949 | Fam96a | 1.17447 | 2410004P03Rik | 1.10043 |
| Sphk1 | 1.21867 | Zfp811 | 1.17432 | Gngt2 | 1.10035 |
| Nrip2 | 1.21705 | Cdkl3 | 1.17415 | 1700020L24Rik | 1.10019 |
| Mapt | 1.21439 | Cecr2 | 1.17257 | BC006965 | 1.10019 |
| Acox2 | 1.2111 | Smco4 | 1.17098 | Dll1 | 1.10019 |
| Cys1 | 1.21106 | Pkp2 | 1.16547 | Gm15455 | 1.10019 |
| Actl10 | 1.211 | Arc | 1.16474 | Tex38 | 1.10019 |
| Ccdc40 | 1.211 | Pcp4l1 | 1.16148 | Lrriq3 | 1.10001 |
| Clcn1 | 1.211 | Cyp2d22 | 1.16078 | Gbp10 | 1.09991 |
| Mog | 1.211 | A230073K19Rik | 1.15896 | Grhl1 | 1.09522 |
| Scube2 | 1.211 | H2-T24 | 1.15681 | Rab2b | 1.09438 |
| H2-T9 | 1.20949 | Olfr543 | 1.15681 | D8Ertd82e | 1.09279 |
| Rhbdl1 | 1.20785 | Tmem40 | 1.15112 | Foxl1 | 1.09279 |
| Dedd2 | 1.09278 | 6030408B16Rik | 1.04192 | C1qtnf5 | 1.01755 |
| Mtss1 | 1.08997 | Arhgdig | 1.04192 | Gm10653 | 1.01638 |
| Gm14446 | 1.08714 | Cd74 | 1.04192 | Cth | 1.01507 |
| Ppp1r3fos | 1.08702 | Ces1d | 1.04192 | Nrxn2 | 1.01162 |
| Arl4d | 1.08605 | Gbx1 | 1.04192 | Eif2d | 1.01147 |
| Pcdhga8 | 1.08499 | Gm12522 | 1.04192 | Rdh1 | 1.01121 |
| Gm15645 | 1.08387 | Gm6559 | 1.04192 | Egr2 | 1.01105 |
| Gpr21 | 1.08387 | Gpbar1 | 1.04192 | Herc3 | 1.01037 |
| Tymp | 1.08242 | Gpr52 | 1.04192 | Tmem251 | 1.00643 |
| Cntn2 | 1.07872 | Ifi205 | 1.04192 | Angptl6 | 1.00496 |
| Npr1 | 1.07872 | L1cam | 1.04192 | Catspergl | 1.00496 |
| Oas1c | 1.07872 | Lix1 | 1.04192 | 4833417C18Rik | 1.00443 |
| Olfm2 | 1.07872 | Me3 | 1.04192 | Cln3 | 1.0025 |
| Zfp114 | 1.07872 | Naaladl1 | 1.04192 | Lingo2 | 0.997291 |
| Angpt2 | 1.07759 | Nap1l3 | 1.04192 | Cyp2u1 | 0.994908 |
| Gm5088 | 1.07699 | Nlrp2 | 1.04192 | Fam57a | 0.994908 |
| Klhl15 | 1.07463 | Nmbr | 1.04192 | Trim7 | 0.994908 |
| Dnajc17 | 1.07353 | Npy1r | 1.04192 | Aipl1 | 0.993772 |
| Foxo6 | 1.07299 | Olfr267 | 1.04192 | Kif27 | 0.993772 |
| Prickle4 | 1.07299 | Pkp1 | 1.04192 | C130026I21Rik | 0.991507 |
| Setd4 | 1.07299 | Rsl1 | 1.04192 | Zscan29 | 0.987511 |
| Snora70 | 1.07254 | Serpinc1 | 1.04192 | Vwa5b2 | 0.987476 |
| Slc2a9 | 1.06974 | Slc35g2 | 1.04192 | Ldlrad4 | 0.98738 |
| Slc4a11 | 1.06881 | Sntb1 | 1.04192 | Polr2d | 0.985661 |
| Surf2 | 1.06676 | Tmem239 | 1.04192 | Asxl3 | 0.984939 |
| Mab21l3 | 1.0631 | Tspan1 | 1.04192 | Naip5 | 0.984869 |
| Chd5 | 1.06304 | Ccdc78 | 1.04189 | Plin5 | 0.984791 |
| 4930488L21Rik | 1.05868 | Gnb5 | 1.04179 | Cpeb2 | 0.98369 |
| Pdzd7 | 1.05763 | Cxx1b | 1.04109 | Gm1976 | 0.983577 |
| 1110008P14Rik | 1.05495 | Cd80 | 1.04098 | Ptpre | 0.983576 |

TABLE 1-continued

List of heat shock-upregulated genes shown by RNA-seq analysis.
Column A: Heat shock-upregulated gene shown by RNA-seq analysis of NIH/3T3 cells.
Column B: Log2 fold-change of the gene in post-H/S cells relative to pre-H/S state.

| gene | log2(fold_change) | gene | log2(fold_change) | gene | log2(fold_change) |
|---|---|---|---|---|---|
| Snord15a | 1.051 | Gmpr2 | 1.03962 | Pemt | 0.983353 |
| AI450353 | 1.05089 | Snhg7 | 1.03798 | Exd1 | 0.980189 |
| Kdf1 | 1.04853 | 2310061I04Rik | 1.03454 | Vkorc1 | 0.978895 |
| Msh5 | 1.04707 | Gpt | 1.03454 | Tdg | 0.978404 |
| Tmem88 | 1.04701 | Extl1 | 1.03012 | Ecm2 | 0.978362 |
| Atp6v0e2 | 1.04611 | Nabp1 | 1.02862 | Fuom | 0.97786 |
| Tgfb1 | 1.04536 | Cd200 | 1.02751 | Rnu12 | 0.977477 |
| Nr4a2 | 1.04375 | 2810408I11Rik | 1.02441 | Zc2hc1c | 0.976971 |
| Snph | 1.0423 | Mapk10 | 1.02441 | Unc119 | 0.976375 |
| 1700012D01Rik | 1.04192 | Gm7102 | 1.02141 | Gm8801 | 0.975702 |
| 3632451O06Rik | 1.04192 | Gpr63 | 1.01962 | Pdgfa | 0.975251 |
| 4933406J10Rik | 1.04192 | Mcmdc2 | 1.01962 | C2cd4c | 0.973608 |
| Tmem191c | 0.972035 | Ccdc73 | 0.917792 | Rdh5 | 0.880761 |
| Proser1 | 0.969728 | Taf9b | 0.917074 | 9130023H24Rik | 0.88045 |
| Ppapdc1b | 0.969129 | Prkaa2 | 0.917028 | Cklf | 0.880209 |
| 5730422E09Rik | 0.968698 | 1110054M08Rik | 0.917012 | Apobec4 | 0.878874 |
| Acyp1 | 0.966964 | Zfp959 | 0.917012 | Bai1 | 0.878874 |
| Gprc5a | 0.966757 | Zfp595 | 0.916656 | Ces1a | 0.878874 |
| Zfpm2 | 0.96574 | C530005A16Rik | 0.915701 | Dusp23 | 0.878874 |
| Ptprj | 0.962058 | Gm4432 | 0.915701 | Gm20594 | 0.878874 |
| Cpxm1 | 0.96165 | Tnnt1 | 0.914369 | Hal | 0.878874 |
| Slc25a16 | 0.958634 | Cgref1 | 0.913576 | LOC102634401 | 0.878874 |
| 9530027J09Rik | 0.958632 | Dancr | 0.912835 | Ppef2 | 0.878874 |
| P2rx3 | 0.958372 | Fastkd3 | 0.912483 | Sycp3 | 0.878874 |
| Spon1 | 0.957466 | Slc8b1 | 0.911925 | Ttc30a2 | 0.878874 |
| Arntl | 0.952404 | Ttc39a | 0.911876 | Zfp459 | 0.878874 |
| Bloc1s4 | 0.951861 | Zbtb26 | 0.910565 | Cdc25c | 0.872104 |
| Nfkbil1 | 0.951789 | Osbpl10 | 0.907185 | Akr1b3 | 0.871897 |
| Tpcn1 | 0.95107 | Adck3 | 0.907067 | Notch3 | 0.871894 |
| Camsap3 | 0.950006 | Gm10578 | 0.906363 | Tmem150b | 0.871884 |
| Gpm6b | 0.948516 | Itfg2 | 0.906018 | Pde2a | 0.87053 |
| 1700056E22Rik | 0.948305 | Megf11 | 0.905916 | Ddx59 | 0.869902 |
| Gabrb2 | 0.948305 | Apol6 | 0.905812 | Ggn | 0.869005 |
| Serac1 | 0.94768 | 3110040N11Rik | 0.904664 | Tysnd1 | 0.868374 |
| Nckap5 | 0.946966 | Dnaja4 | 0.903673 | B930003M22Rik | 0.867501 |
| Fgd3 | 0.945867 | Zmym1 | 0.903268 | Cdcp1 | 0.867501 |
| Rnd2 | 0.944931 | Fahd2a | 0.902592 | Chst3 | 0.867501 |
| Cyp4f13 | 0.943695 | Plekhh1 | 0.902592 | Rps6kl1 | 0.867501 |
| Gramd1b | 0.943094 | Cdk20 | 0.900992 | Zfp160 | 0.865721 |
| Adam22 | 0.941898 | Sbspon | 0.899119 | Pdf | 0.865008 |
| Tekt2 | 0.941898 | Snord17 | 0.898693 | Gm10845 | 0.864807 |
| Scoc | 0.941402 | 4930507D05Rik | 0.898355 | 9330020H09Rik | 0.864482 |
| Slc39a6 | 0.939491 | Zfp688 | 0.896366 | Btbd6 | 0.86434 |
| Ybey | 0.938154 | Sh2d4a | 0.896038 | Spef1 | 0.863728 |
| Mtpap | 0.936922 | Slc7a11 | 0.893529 | Dock8 | 0.862569 |
| 5730408K05Rik | 0.934471 | Pkn3 | 0.892733 | Bdkrb1 | 0.86228 |
| Xkr8 | 0.933427 | D030028A08Rik | 0.892603 | Yy2 | 0.86228 |
| Mtm1 | 0.933134 | AI506816 | 0.892334 | Hap1 | 0.860601 |
| Porcn | 0.932296 | Tmem64 | 0.890878 | Rmad1 | 0.859938 |
| Ugt1a6a | 0.932118 | Phyhd1 | 0.888334 | Arl15 | 0.859273 |
| 1700094D03Rik | 0.930346 | Tpk1 | 0.887405 | Pgap2 | 0.858987 |
| Acsl6 | 0.927489 | Nkiras1 | 0.884175 | Cd302 | 0.857087 |
| Agt | 0.925678 | Snora23 | 0.884144 | Magohb | 0.856945 |
| Aurkaip1 | 0.922869 | Lyrm2 | 0.8823 | Thsd1 | 0.854136 |
| Abcc6 | 0.853329 | 4933400F21Rik | 0.846084 | Mcts2 | 0.815087 |
| Nnat | 0.852521 | Stau1 | 0.84469 | Pim1 | 0.814866 |
| Rps6ka1 | 0.848375 | 9030025P20Rik | 0.844502 | Gm12338 | 0.81463 |
| Pex5l | 0.848217 | Lzic | 0.84265 | Mmachc | 0.814113 |
| Pla2g4c | 0.848196 | Paip1 | 0.842563 | Endod1 | 0.814107 |
| 1700034I23Rik | 0.848195 | Fam213a | 0.842291 | Grebl1 | 0.813839 |
| 2510049J12Rik | 0.848195 | Gkap1 | 0.840528 | Pam16 | 0.8135 |
| 6330418K02Rik | 0.848195 | Slc35b2 | 0.839747 | Ncor2 | 0.812126 |
| Adam1b | 0.848195 | 4931440P22Rik | 0.836634 | Ap4e1 | 0.80971 |
| Adrb3 | 0.848195 | B630019K06Rik | 0.835283 | Nyap1 | 0.808223 |
| Aldh3b2 | 0.848195 | Prtg | 0.832862 | Mccc1os | 0.805974 |
| B130034C11Rik | 0.848195 | Pcdhga3 | 0.830016 | Fam210b | 0.805673 |
| Bdkrb2 | 0.848195 | Atxn3 | 0.829792 | 4933411K16Rik | 0.805371 |
| Cacna2d2 | 0.848195 | Pms1 | 0.828572 | Stab2 | 0.805371 |
| Cacnb2 | 0.848195 | Vamp1 | 0.828083 | Tmem14c | 0.805168 |
| Ccdc170 | 0.848195 | Dlg2 | 0.827534 | Gfm2 | 0.80513 |
| Cux2 | 0.848195 | Nipal3 | 0.82751 | Spaca6 | 0.80475 |
| D730005E14Rik | 0.848195 | Ccrn4l | 0.827023 | Retn | 0.803861 |
| Ect2l | 0.848195 | Gm1943 | 0.826803 | Nanos1 | 0.803319 |
| Epsti1 | 0.848195 | Mfsd8 | 0.826239 | Dhrs13 | 0.802263 |

TABLE 1-continued

List of heat shock-upregulated genes shown by RNA-seq analysis.
Column A: Heat shock-upregulated gene shown by RNA-seq analysis of NIH/3T3 cells.
Column B: Log2 fold-change of the gene in post-H/S cells relative to pre-H/S state.

| gene | log2(fold_change) | gene | log2(fold_change) | gene | log2(fold_change) |
|---|---|---|---|---|---|
| Fscn3 | 0.848195 | Pfkp | 0.825156 | Rab7l1 | 0.802263 |
| Ftcd | 0.848195 | Rprl3 | 0.824685 | Fancg | 0.801687 |
| Gbp2b | 0.848195 | Al662270 | 0.824329 | Jph3 | 0.799945 |
| Gm10556 | 0.848195 | Gpr151 | 0.824329 | Zfp428 | 0.799896 |
| Gm11149 | 0.848195 | Osbpl6 | 0.82422 | Uxt | 0.796525 |
| Gm11517 | 0.848195 | Inhba | 0.823205 | Harbi1 | 0.796215 |
| Gm15880 | 0.848195 | Atpaf1 | 0.822957 | Capns2 | 0.795969 |
| Gm17746 | 0.848195 | Cmc2 | 0.822775 | Pabpc4l | 0.795968 |
| Gm4984 | 0.848195 | Mrpl41 | 0.822763 | Slc25a47 | 0.7942 |
| Gpx3 | 0.848195 | Relt | 0.822405 | Apip | 0.793004 |
| Itga4 | 0.848195 | Sirt4 | 0.821295 | Dbt | 0.792254 |
| Nkd2 | 0.848195 | Snora81 | 0.82116 | Rpph1 | 0.791102 |
| Nupr1l | 0.848195 | Zfp846 | 0.820109 | Jade3 | 0.790246 |
| Olfr544 | 0.848195 | Cmc1 | 0.818789 | Alkbh2 | 0.789058 |
| Panx3 | 0.848195 | Kptn | 0.817543 | Cntd1 | 0.789058 |
| Pde8a | 0.848195 | Leprotl1 | 0.817308 | Fndc5 | 0.789058 |
| Ppp1r3e | 0.848195 | Gna14 | 0.817146 | Gm16982 | 0.789058 |
| Srd5a2 | 0.848195 | Fxyd1 | 0.81712 | Slc24a5 | 0.789058 |
| Wdfy4 | 0.848195 | Mrpl1 | 0.816356 | Tmem100 | 0.789058 |
| Zfp85os | 0.848195 | Mob3b | 0.815682 | Zfp354b | 0.789058 |
| AU021063 | 0.848194 | Commd4 | 0.815445 | Zfp474 | 0.789058 |
| Megf10 | 0.847764 | Rmdn1 | 0.81537 | Dpm2 | 0.789044 |
| Igip | 0.788349 | 6720416L17Rik | 0.752659 | Cbx7 | 0.739073 |
| Vangl2 | 0.788187 | Adcy5 | 0.752659 | Chst12 | 0.739009 |
| Mum1l1 | 0.787543 | B3gnt3 | 0.752659 | Alg13 | 0.738372 |
| Adat3 | 0.785414 | BC021767 | 0.752659 | Plscr1 | 0.738264 |
| 2410018L13Rik | 0.785263 | Ccdc144b | 0.752659 | Gareml | 0.737958 |
| Gpr155 | 0.784518 | Cldn15 | 0.752659 | Morn1 | 0.737958 |
| Mertk | 0.783692 | Ggt5 | 0.752659 | Rfesd | 0.736998 |
| Tom1l1 | 0.781902 | Gm10125 | 0.752659 | Ago4 | 0.73664 |
| Apbb1ip | 0.780693 | Gm10789 | 0.752659 | Surf1 | 0.736503 |
| Dennd1b | 0.780558 | Gm6251 | 0.752659 | Urod | 0.735173 |
| Bbs4 | 0.779385 | Kcnk3 | 0.752659 | Vps8 | 0.735138 |
| Fermt3 | 0.778882 | Mslnl | 0.752659 | Tyw5 | 0.734593 |
| Tmem161b | 0.778178 | Omp | 0.752659 | Trim34b | 0.732648 |
| Pex11a | 0.778129 | Rab26os | 0.752659 | Tssk6 | 0.732185 |
| Shf | 0.777706 | Rab33a | 0.752659 | Ndufs6 | 0.731844 |
| A130077B15Rik | 0.773746 | She | 0.752659 | Lrrc1 | 0.731533 |
| 4930455C13Rik | 0.773479 | Stmn1-rs1 | 0.752659 | Exosc6 | 0.7314 |
| Tmem128 | 0.771253 | Stpg1 | 0.752659 | Gpr4 | 0.731132 |
| Ncf1 | 0.771184 | Ttc25 | 0.752659 | Eif5a2 | 0.730385 |
| Flt3l | 0.770416 | Ccdc125 | 0.752641 | Rnasek | 0.72918 |
| Timm21 | 0.770403 | Nudt17 | 0.752439 | Slc41a3 | 0.728341 |
| Kif24 | 0.770009 | Fahd1 | 0.752245 | Hsp90aa1 | 0.727456 |
| Foxj1 | 0.769525 | Hvcn1 | 0.751942 | Zfp524 | 0.727194 |
| Trmt2b | 0.768958 | Tcp11l2 | 0.751931 | Pogk | 0.72698 |
| Zfp558 | 0.768924 | Cd320 | 0.74905 | LOC106740 | 0.726647 |
| C230091D08Rik | 0.767682 | Map3k13 | 0.749038 | Stard5 | 0.726492 |
| Trim59 | 0.764706 | Phyhipl | 0.747059 | Prkar2b | 0.726386 |
| Ak6 | 0.763367 | Dscc1 | 0.745278 | Ttll3 | 0.72431 |
| Lrrc61 | 0.761217 | Mss51 | 0.745003 | BC061194 | 0.724219 |
| Slc25a27 | 0.760096 | Camk2n2 | 0.744507 | Nipa2 | 0.723398 |
| Gm17762 | 0.759466 | Asb3 | 0.743641 | Zdhhc12 | 0.723354 |
| Polq | 0.75938 | Emx2os | 0.742987 | Gm20319 | 0.722999 |
| Apoo | 0.757916 | Depdc1a | 0.742283 | Gpcpd1 | 0.722965 |
| Mrpl50 | 0.756048 | Bok | 0.741219 | Col4a3bp | 0.722612 |
| Zfp874b | 0.755962 | Slc15a4 | 0.740891 | Gnal | 0.722065 |
| Zfp954 | 0.755957 | 2610044O15Rik | | Arl6ip1 | 0.721104 |
| Prss53 | 0.754948 | 8 | 0.740567 | Snupn | 0.72027 |
| Peli3 | 0.754578 | Mb21d2 | 0.740516 | Sprtn | 0.719836 |
| Lfng | 0.753516 | Homer1 | 0.740491 | Pnpo | 0.718019 |
| Pxdc1 | 0.753057 | Prrg1 | 0.740343 | Wdr8 | 0.71784 |
| Phospho1 | 0.752661 | Cnp | 0.74021 | Fbxo11 | 0.717345 |
| 4930539J05Rik | 0.752659 | Ramp2 | 0.740134 | Cpne8 | 0.716441 |
| Cpa4 | 0.716207 | Gpr135 | 0.694222 | Steap1 | 0.669469 |
| Kcnj14 | 0.716207 | Serpine1 | 0.692035 | Cln6 | 0.66829 |
| Ap3m2 | 0.714914 | Slc38a9 | 0.689846 | Tvp23b | 0.667508 |
| Bid | 0.714076 | Fcho2 | 0.689564 | Hexdc | 0.665967 |
| Kri1 | 0.713345 | Ints6 | 0.687629 | Nr4a1 | 0.66566 |
| Ankrd42 | 0.711881 | Immp1l | 0.687536 | Pvt1 | 0.664854 |
| Azin1 | 0.710642 | Atg4d | 0.687146 | Mrpl32 | 0.664084 |
| Pcdhac1 | 0.710402 | Angpt1 | 0.685654 | A230020J21Rik | 0.663918 |
| Ndufc1 | 0.709634 | Begain | 0.685588 | Apol8 | 0.663706 |
| Has3 | 0.709572 | Pqlc2 | 0.685415 | Gng8 | 0.663679 |

TABLE 1-continued

List of heat shock-upregulated genes shown by RNA-seq analysis.
Column A: Heat shock-upregulated gene shown by RNA-seq analysis of NIH/3T3 cells.
Column B: Log2 fold-change of the gene in post-H/S cells relative to pre-H/S state.

| gene | log2(fold_change) | gene | log2(fold_change) | gene | log2(fold_change) |
|---|---|---|---|---|---|
| Aldh3b1 | 0.70932 | Mfsd9 | 0.685326 | Sdsl | 0.663679 |
| Shroom1 | 0.709143 | 1700120K04Rik | 0.685153 | Tmem223 | 0.663679 |
| Awat2 | 0.707302 | Cd14 | 0.684869 | Clvs1 | 0.663678 |
| Eps8l1 | 0.707095 | Foxg1 | 0.683375 | Apex1 | 0.661955 |
| Smg9 | 0.706269 | Ostm1 | 0.683047 | Tmem192 | 0.661617 |
| Gm8615 | 0.706096 | Fbrs | 0.68116 | Siah1b | 0.660784 |
| Cgnl1 | 0.706094 | Pqlc3 | 0.681088 | Krcc1 | 0.65898 |
| Dhx58 | 0.705249 | Insig1 | 0.680904 | Zeb2os | 0.658912 |
| Gm7609 | 0.704485 | Lrch2 | 0.67938 | Ahsa2 | 0.658866 |
| Piga | 0.702853 | A230057D06Rik | 0.678457 | Aph1b | 0.657954 |
| Gpld1 | 0.702609 | Sumo3 | 0.678457 | Degs2 | 0.657643 |
| Calcrl | 0.701227 | Tmem38b | 0.678361 | Pcdhga10 | 0.657617 |
| Slc36a4 | 0.701085 | Runx1 | 0.676638 | Zfp329 | 0.657543 |
| Tmem170b | 0.700545 | Efhc1 | 0.676024 | 9430038I01Rik | 0.656592 |
| Slc2a4rg-ps | 0.70028 | Parn | 0.675847 | Mfsd7a | 0.656592 |
| Ccdc53 | 0.700114 | Fbxo41 | 0.675628 | Tmem154 | 0.656592 |
| Mns1 | 0.699875 | Gba2 | 0.675114 | Dtwd2 | 0.655861 |
| Pyroxd1 | 0.699604 | Ptrhd1 | 0.674611 | Sla2 | 0.654917 |
| Dcaf11 | 0.699481 | Gng7 | 0.674239 | Eef1e1 | 0.654614 |
| Lrrtm2 | 0.699116 | Mrpl15 | 0.67413 | Nmral1 | 0.652852 |
| Foxd2os | 0.699048 | Slc6a8 | 0.673973 | Abcb9 | 0.651804 |
| Tmem260 | 0.698446 | Lmln | 0.673293 | Osbp | 0.651032 |
| Etohd2 | 0.697577 | Ralgps2 | 0.673136 | A730098P11Rik | 0.650639 |
| Smim13 | 0.696617 | Rsph3b | 0.672982 | Pgbd5 | 0.648948 |
| Vbp1 | 0.696407 | Gm128 | 0.672774 | Gpsm1 | 0.648374 |
| Gm10033 | 0.696287 | N6amt2 | 0.672643 | Tbce | 0.646814 |
| Epha1 | 0.69572 | Glrx3 | 0.672054 | Mkl2 | 0.646378 |
| Cd93 | 0.695059 | Lyrm5 | 0.671061 | Cep44 | 0.645635 |
| Cradd | 0.694944 | Bckdhb | 0.670957 | Omd | 0.645421 |
| Zfyve19 | 0.694588 | Ubxn2b | 0.670957 | Styx | 0.643302 |
| Lrrc73 | 0.694306 | Tmem176b | 0.670325 | Klhl28 | 0.6429 |
| Mettl22 | 0.694306 | Strip2 | 0.670093 | Rnf38 | 0.642831 |
| Rad1 | 0.641986 | Zfp300 | 0.623066 | Nsg2 | 0.611039 |
| Plekho2 | 0.641774 | Adora2b | 0.622927 | Rab27b | 0.610999 |
| Rabl3 | 0.641702 | Mnda | 0.622737 | Tmem258 | 0.610448 |
| Pqlc1 | 0.640004 | Tmem39a | 0.622735 | Smek1 | 0.609214 |
| Katna1 | 0.639256 | Gfpt2 | 0.622152 | Olfm1 | 0.608263 |
| Letm2 | 0.639051 | Athl1 | 0.621666 | Gprasp1 | 0.608247 |
| Rpusd1 | 0.638148 | Jmjd8 | 0.621474 | Gm14005 | 0.608228 |
| Mepce | 0.637215 | Pisd-ps3 | 0.621433 | Isg15 | 0.606174 |
| Prkra | 0.636744 | Cyb5rl | 0.621432 | Irgm1 | 0.605639 |
| Zfp788 | 0.634809 | 2700046G09Rik | 0.621166 | Snhg4 | 0.605639 |
| Fem1b | 0.633894 | Aox3 | 0.621166 | Tst | 0.605195 |
| Ppm1h | 0.633878 | Gm2381 | 0.621166 | Slc35e2 | 0.60484 |
| Msl2 | 0.633096 | Mmp16 | 0.621166 | Ift20 | 0.604186 |
| Chchd5 | 0.632246 | Zfp273 | 0.621166 | Ttc7b | 0.603738 |
| Irak4 | 0.631371 | Fzd7 | 0.621147 | Sirt5 | 0.603131 |
| Slc43a2 | 0.631227 | Thumpd2 | 0.621053 | Dtymk | 0.602386 |
| Procr | 0.630555 | Phkg2 | 0.620933 | Pdxp | 0.601831 |
| Peg3os | 0.630487 | Tmem181b-ps | 0.620847 | Wrap53 | 0.600599 |
| Ece2 | 0.630018 | Acad10 | 0.620113 | Kdm4c | 0.60056 |
| Cdc42ep5 | 0.629752 | Cckbr | 0.61997 | D430020J02Rik | 0.599646 |
| 4933434E20Rik | 0.629419 | Fam151b | 0.61997 | Sft2d3 | 0.599477 |
| Mif4gd | 0.628942 | Hpse | 0.61997 | Rnf19a | 0.599175 |
| Rsph3a | 0.62888 | Ptgdr2 | 0.61997 | Zfp609 | 0.598705 |
| C1galt1c1 | 0.628447 | Lysmd2 | 0.619798 | Apobec1 | 0.597047 |
| Tmbim4 | 0.628297 | Gsap | 0.619637 | Heca | 0.597013 |
| Cenph | 0.628231 | Ankrd39 | 0.619008 | Sec61g | 0.596673 |
| Pecam1 | 0.627064 | Ptges3l | 0.618627 | Tmem19 | 0.595994 |
| BC028528 | 0.626879 | Cbx4 | 0.618374 | Psmg3 | 0.595282 |
| C1ql3 | 0.626879 | Lat2 | 0.617924 | Zfp385c | 0.594687 |
| Ceacam16 | 0.626879 | Ogfod3 | 0.617793 | Cnih4 | 0.594569 |
| Gm15408 | 0.626879 | Gchfr | 0.617511 | Mppe1 | 0.594067 |
| Fam198a | 0.626827 | Ube2q2 | 0.617001 | Ten1 | 0.59351 |
| Ift57 | 0.626357 | Tac4 | 0.616837 | Tmem200a | 0.593417 |
| Diexf | 0.626265 | Gm16023 | 0.616481 | 2010111I01Rik | 0.593026 |
| Lrrc39 | 0.626042 | Mpc1 | 0.616368 | Pisd-ps2 | 0.592919 |
| Rnase10 | 0.626017 | Tsg101 | 0.615968 | Snx24 | 0.592641 |
| Nlrp1b | 0.624538 | Wdr47 | 0.614698 | Nfkbie | 0.592566 |
| Arxes1 | 0.62417 | Pcnxl4 | 0.614302 | 5830415F09Rik | 0.592261 |
| Unc13b | 0.623961 | Klhl8 | 0.613586 | Dcun1d2 | 0.592249 |
| Hdac11 | 0.623461 | Chek1 | 0.613071 | Rgag4 | 0.591944 |
| E230016K23Rik | 0.623341 | Chkb | 0.612202 | Dyx1c1 | 0.591382 |
| Slc25a22 | 0.62327 | Tmem126b | 0.61188 | Dcaf17 | 0.591272 |

TABLE 1-continued

List of heat shock-upregulated genes shown by RNA-seq analysis.
Column A: Heat shock-upregulated gene shown by RNA-seq analysis of NIH/3T3 cells.
Column B: Log2 fold-change of the gene in post-H/S cells relative to pre-H/S state.

| gene | log2(fold_change) | gene | log2(fold_change) | gene | log2(fold_change) |
|---|---|---|---|---|---|
| Ciart | 0.590954 | Gtf2h4 | 0.574845 | Tmem25 | 0.560892 |
| Ramp3 | 0.590861 | Ugt1a5 | 0.574447 | Myo19 | 0.560238 |
| Znrf2 | 0.589795 | Lrrc8d | 0.573823 | Aifl1 | 0.559823 |
| Mb21d1 | 0.58888 | Zfp963 | 0.573677 | Ppp2r5e | 0.559413 |
| Prkab2 | 0.58887 | Prox2 | 0.573599 | Scnm1 | 0.5593 |
| Pla2g7 | 0.588629 | Hoxd4 | 0.572448 | Nomo1 | 0.558574 |
| Efcab7 | 0.58861 | Lig4 | 0.572442 | Oma1 | 0.557833 |
| B330016D10Rik | 0.587808 | Il17d | 0.57166 | Helq | 0.557714 |
| Kcnj13 | 0.587808 | Ttpal | 0.571422 | Bivm | 0.557124 |
| A330009N23Rik | 0.587798 | Fam227a | 0.57119 | Caap1 | 0.556957 |
| AK129341 | 0.58761 | Tsc22d3 | 0.570947 | Tgm4 | 0.556805 |
| Agpat4 | 0.587377 | Rnf111 | 0.570455 | Mira | 0.556405 |
| Tafl1 | 0.586982 | Ube2m | 0.57044 | P2rx6 | 0.556297 |
| Fst | 0.58662 | Abcd3 | 0.570293 | Ap3s2 | 0.555981 |
| Slc35f6 | 0.586565 | Gab2 | 0.569957 | Mettl10 | 0.555565 |
| Cep70 | 0.585426 | Casq1 | 0.568093 | Perm1 | 0.555081 |
| 1110008F13Rik | 0.583769 | Gpr89 | 0.567585 | Cdh18 | 0.554378 |
| Acp6 | 0.582501 | Dimt1 | 0.567419 | 3110002H16Rik | 0.553881 |
| Gtdc1 | 0.580918 | Sccpdh | 0.567194 | Smpd5 | 0.55366 |
| Klra2 | 0.57994 | Ankrd9 | 0.566665 | Pcdha10 | 0.553628 |
| 4833418N02Rik | 0.57987 | Polr2g | 0.566507 | Pms2 | 0.553541 |
| AI848285 | 0.57987 | Ap3m1 | 0.566406 | Cyb5d2 | 0.553112 |
| B130006D01Rik | 0.57987 | 1500015A07Rik | 0.566239 | Exosc8 | 0.552342 |
| C920025E04Rik | 0.57987 | 5730508B09Rik | 0.566151 | Casz1 | 0.55191 |
| Dusp3 | 0.579592 | Chrm4 | 0.566151 | Tmem107 | 0.551467 |
| D930016D06Rik | 0.578811 | Plekhj1 | 0.565282 | Chn1 | 0.551282 |
| Ccdc84 | 0.578616 | 3110052M02Rik | 0.564375 | Dnal1 | 0.550887 |
| A230103J11Rik | 0.57856 | Pkp3 | 0.564178 | Ntn5 | 0.550711 |
| Wdr89 | 0.578542 | Arhgef39 | 0.564018 | Rnd1 | 0.550337 |
| Nav2 | 0.578471 | Map3k8 | 0.563651 | E530011L22Rik | 0.550039 |
| Dnah11 | 0.578348 | Serinc4 | 0.56365 | Slc9a3r2 | 0.549408 |
| Ankle1 | 0.578103 | Zfp345 | 0.563641 | Gtf3c3 | 0.547369 |
| Zkscan7 | 0.577966 | Spopl | 0.563258 | Armc7 | 0.547319 |
| Stx12 | 0.577634 | Cdh24 | 0.563141 | Tgfb3 | 0.547257 |
| Cited1 | 0.577184 | Ndfip2 | 0.562232 | Tmem229b | 0.546946 |
| Wdr5b | 0.576386 | Pithd1 | 0.562121 | Rgs16 | 0.545969 |
| Mmadhc | 0.576184 | Osbp2 | 0.561933 | Rfx3 | 0.545748 |
| Sycp1 | 0.575501 | Kin | 0.561629 | Dusp19 | 0.545573 |
| Klf10 | 0.575321 | Csnk2a2 | 0.561161 | Cisd2 | 0.544746 |
| A430078G23Rik | 0.575229 | Ccr9 | 0.561072 | Gm20199 | 0.544746 |
| Mdk | 0.575135 | Tmem184a | 0.560921 | Mfrp | 0.544483 |
| Pde4d | 0.574991 | Emid1 | 0.560892 | 3110062M04Rik | 0.544427 |
| Zfp446 | 0.544344 | Col18a1 | 0.530327 | Tmem183a | 0.515984 |
| Rnf13 | 0.544193 | Aox1 | 0.529754 | A830082K12Rik | 0.515819 |
| Styk1 | 0.543974 | Camk1d | 0.528434 | Orai3 | 0.515617 |
| Tyms | 0.543539 | Mrpl23 | 0.527912 | Csmd3 | 0.515432 |
| Npff | 0.543132 | Dph6 | 0.527526 | Egf | 0.515432 |
| Trik1 | 0.542397 | Cacng7 | 0.527458 | Tmtc4 | 0.515432 |
| Zdhhc4 | 0.542264 | Zfp14 | 0.527404 | Pcdhga6 | 0.514804 |
| E030030I06Rik | 0.541443 | Cdc42se2 | 0.527181 | Gm17066 | 0.514713 |
| Fam228a | 0.541443 | 2610002J02Rik | 0.526737 | Smim19 | 0.513809 |
| Gm6583 | 0.541443 | Hyls1 | 0.526574 | Hist1h4i | 0.513443 |
| Zfp385a | 0.540252 | Tnni1 | 0.526432 | Zfp935 | 0.513136 |
| H2-K1 | 0.540178 | Errfi1 | 0.526361 | Gas5 | 0.513087 |
| Stk19 | 0.540108 | 4930545L23Rik | 0.526358 | Serinc3 | 0.512927 |
| Wdr55 | 0.539619 | Clca1 | 0.526358 | Trmt13 | 0.512829 |
| 1110001J03Rik | 0.539364 | Fscn2 | 0.526358 | Mcts1 | 0.512614 |
| Spred3 | 0.539216 | Gm14379 | 0.526358 | Zfp362 | 0.511695 |
| Dpm3 | 0.53858 | Mroh7 | 0.526358 | Galnt13 | 0.511562 |
| Tmem238 | 0.538559 | Phf7 | 0.526358 | Rce1 | 0.511331 |
| Msrb1 | 0.538183 | Zfp931 | 0.526358 | Zufsp | 0.511331 |
| Psmd10 | 0.538183 | Srpx2 | 0.526211 | Ciita | 0.511154 |
| Tada3 | 0.538181 | 4833420G17Rik | 0.526076 | 4921524J17Rik | 0.510351 |
| 3110021N24Rik | 0.537005 | Creb3l1 | 0.525956 | Fam92a | 0.510289 |
| Zfp174 | 0.536428 | Rrp36 | 0.525482 | Fam193b | 0.509569 |
| Zfp579 | 0.535497 | Atg4b | 0.524675 | Adck5 | 0.509469 |
| Atp6v1g2 | 0.534769 | Hat1 | 0.524476 | 4930579G24Rik | 0.509424 |
| Icosl | 0.534769 | Cbfb | 0.524265 | Paqr3 | 0.509403 |
| Tmem47 | 0.534065 | Iba57 | 0.524034 | Myom1 | 0.508284 |
| Ube2b | 0.533897 | Pld1 | 0.523875 | Tmem29 | 0.508004 |
| Hscb | 0.533385 | Ehd4 | 0.523701 | Dbhos | 0.506884 |
| Rb1 | 0.533144 | Dram1 | 0.523638 | Ntn1 | 0.506518 |
| Slc45a3 | 0.533138 | Mrps14 | 0.522991 | Ap4s1 | 0.506184 |
| Lamtor4 | 0.532759 | Gp1ba | 0.52285 | Adprm | 0.505908 |

TABLE 1-continued

List of heat shock-upregulated genes shown by RNA-seq analysis.
Column A: Heat shock-upregulated gene shown by RNA-seq analysis of NIH/3T3 cells.
Column B: Log2 fold-change of the gene in post-H/S cells relative to pre-H/S state.

| gene | log2(fold_change) | gene | log2(fold_change) | gene | log2(fold_change) |
|---|---|---|---|---|---|
| Psmg1 | 0.532611 | Fgfr3 | 0.522807 | Vamp8 | 0.505153 |
| Pigp | 0.532384 | Zfp1 | 0.521457 | Ddt | 0.504355 |
| Gcnt7 | 0.532189 | Sez6l2 | 0.52067 | Stil | 0.50419 |
| Isg20 | 0.531979 | Setd6 | 0.518642 | Crtc3 | 0.503525 |
| Grcc10 | 0.531928 | Tnfsf12 | 0.517882 | Pla2g12a | 0.503497 |
| Pi16 | 0.53156 | Bbs10 | 0.517871 | Naa38 | 0.503395 |
| Usb1 | 0.53152 | 2700094K13Rik | 0.517218 | Nutf2-ps1 | 0.502546 |
| 2610301B20Rik | 0.531452 | Parpbp | 0.5172 | Polr1e | 0.502282 |
| Sh2d3c | 0.530616 | Qrsl1 | 0.516473 | Slc52a2 | 0.501981 |
| Tnr | 0.530556 | Acrbp | 0.516059 | Pcdhb22 | 0.50183 |
| Gpatch3 | 0.501768 | 1700030J22Rik | 0.500664 | Serpina3g | 0.500664 |
| 1700066M21Rik | 0.501414 | 4930503E14Rik | 0.500664 | Slc40a1 | 0.500664 |
| Bend6 | 0.501342 | Alpk3 | 0.500664 | Tmem204 | 0.500664 |
| Ell2 | 0.501311 | Gm13251 | 0.500664 | Stox2 | 0.500652 |
| Rbm7 | 0.50092 | Gm6654 | 0.500664 | Hoxa3 | 0.500622 |
| Gulp1 | 0.500836 | Ltc4s | 0.500664 | | |
| 0610010B08Rik, | 0.500664 | Piwil2 | 0.500664 | | |
| Gm4724 | | Rrad | 0.500664 | | |

TABLE 2

List of heat shock-downregulated genes shown by RNA-seq analysis.
Column A: Heat shock-downregulated gene shown by RNA-seq analysis of NIH/3T3 cells.
Column B: Log2 fold-change of the gene in post-H/S cells relative to pre-H/S state.

| gene | log2(fold_change) | gene | log2(fold_change) | gene | log2(fold_change) |
|---|---|---|---|---|---|
| Ing4 | −0.50031 | Hs1bp3 | −0.506507 | Mpv17l | −0.513925 |
| Pcdhb2 | −0.500595 | Hist1h3c | −0.506662 | Zcchc3 | −0.514007 |
| Hist2h4 | −0.500665 | Zfp961 | −0.507012 | Mrpl22 | −0.514214 |
| Mef2c | −0.501333 | Ptpn6 | −0.507148 | Xist | −0.514273 |
| Bcdin3d | −0.501479 | Rdh13 | −0.507474 | Fam46b | −0.514899 |
| Hist3h2a | −0.501508 | Papolg | −0.507547 | Hist1h2ad | −0.51514 |
| Rnf32 | −0.501903 | Cpox | −0.507785 | Elavl2 | −0.515613 |
| Camkmt | −0.502123 | Nif3l1 | −0.508042 | Ino80c | −0.515678 |
| Mafg | −0.502237 | Dek | −0.508221 | Ccdc23 | −0.516314 |
| Leng1 | −0.502735 | Cmtm7 | −0.509003 | Eme1 | −0.516865 |
| Crnde | −0.502792 | Gm11974 | −0.509778 | Slc19a1 | −0.517189 |
| Scly | −0.503023 | Cyp4f16 | −0.51008 | Fam60a | −0.517502 |
| Enthd2 | −0.503484 | 2210018M11Rik | −0.510129 | Zbtb24 | −0.517857 |
| Secisbp2 | −0.503669 | Jun | −0.510715 | Hemk1 | −0.51791 |
| Rbm20 | −0.503733 | Prr7 | −0.510734 | Glmn | −0.518255 |
| Creld2 | −0.503796 | Mllt6 | −0.511174 | 2610020H08Rik | −0.518407 |
| Lcorl | −0.503854 | Shq1 | −0.511474 | Pcsk7 | −0.518662 |
| Rhpn1 | −0.504378 | 4930577N17Rik | −0.511662 | Abtb1 | −0.518668 |
| A430005L14Rik | −0.504389 | Dna2 | −0.511662 | Ankrd6 | −0.518812 |
| Lace1 | −0.504576 | Tmem218 | −0.512172 | Rfxank | −0.518862 |
| Tmem208 | −0.504576 | Ppwd1 | −0.512219 | Zfp27 | −0.518912 |
| Fam50a | −0.506063 | Dbp | −0.512643 | Hist1h4b | −0.518934 |
| Irak3 | −0.506246 | Ip6k2 | −0.513135 | Naif1 | −0.519346 |
| Mamdc4 | −0.506246 | Prob1 | −0.513266 | Rab39b | −0.519346 |
| Mirg | −0.51971 | Pcca | −0.533789 | Siva1 | −0.547497 |
| Obscn | −0.519902 | Dnttip1 | −0.533998 | Zfp637 | −0.547733 |
| Slc4a1ap | −0.519928 | Birc2 | −0.534003 | Cry2 | −0.548168 |
| Pacsin3 | −0.520093 | Papd5 | −0.534515 | Bin3 | −0.548322 |
| Amn1 | −0.520166 | Prep | −0.534706 | 0610009O20Rik | −0.548329 |
| Lrrc14b | −0.520856 | Gorasp1 | −0.535042 | 3830408C21Rik | −0.548597 |
| Exosc4 | −0.520914 | Hist2h2ac | −0.536325 | Stk36 | −0.549294 |
| Mis18bp1 | −0.521761 | Ier2 | −0.537189 | Alkbh6 | −0.549329 |
| Hist1h2bf | −0.522018 | Nol12 | −0.5375 | Madd | −0.54934 |
| Jarid2 | −0.522317 | Mettl1 | −0.537775 | Tnfaip3 | −0.549519 |
| Ctgf | −0.522406 | Fgd6 | −0.538283 | Fbxl12 | −0.549547 |
| Zfp120 | −0.522641 | Ccne1 | −0.538454 | Thumpd1 | −0.54967 |
| Jph1 | −0.524609 | Mrpl42 | −0.538658 | Clcn6 | −0.550539 |
| Zfp93 | −0.525308 | Vmp1 | −0.538673 | 4933411K20Rik | −0.550935 |
| Far2 | −0.525753 | 2810021J22Rik | −0.539498 | Tmem129 | −0.551641 |
| Slc37a2 | −0.525982 | Tmem143 | −0.539673 | C330013E15Rik | −0.552251 |
| Slc7a7 | −0.526089 | Zkscan14 | −0.539712 | Zfp422 | −0.552646 |
| Coq7 | −0.526739 | Cdkn2d | −0.539849 | Dchs1 | −0.553193 |
| Epc1 | −0.527036 | Efcab11 | −0.539849 | Echdc1 | −0.553488 |
| Dhps | −0.527047 | A930013F10Rik | −0.540539 | Zfp775 | −0.553516 |

TABLE 2-continued

List of heat shock-downregulated genes shown by RNA-seq analysis.
Column A: Heat shock-downregulated gene shown by RNA-seq analysis of NIH/3T3 cells.
Column B: Log2 fold-change of the gene in post-H/S cells relative to pre-H/S state.

| gene | log2(fold_change) | gene | log2(fold_change) | gene | log2(fold_change) |
|---|---|---|---|---|---|
| Cbx8 | −0.527184 | Kif9 | −0.540604 | Scrn2 | −0.553607 |
| Hist1h2bn | −0.527204 | Uchl5 | −0.540704 | Rtkn2 | −0.553639 |
| N6amt1 | −0.527226 | Bmper | −0.541647 | Zfp90 | −0.554355 |
| Dguok | −0.527277 | AU040972 | −0.543 | Faim | −0.554597 |
| Nsun4 | −0.527444 | 4930478L05Rik | −0.543017 | Slc25a29 | −0.554769 |
| Mob2 | −0.527774 | Agap3 | −0.543024 | Taf4b | −0.555292 |
| Ttc30b | −0.528068 | B230217C12Rik | −0.543046 | Psmc3ip | −0.555487 |
| Dpm1 | −0.528659 | Clca2 | −0.543046 | Ecsit | −0.555716 |
| Cd160 | −0.528948 | Efcab2 | −0.543046 | Cdk18 | −0.555878 |
| A130010J15Rik | −0.529464 | Fli1 | −0.543046 | Gm13212 | −0.556088 |
| Tex261 | −0.529497 | Adam33 | −0.543153 | Zfp809 | −0.556774 |
| Zrsr1 | −0.529582 | Zfp692 | −0.543211 | Slc27a6 | −0.556931 |
| Ezh2 | −0.529736 | Tmem37 | −0.54398 | Pagr1a | −0.557216 |
| Spns1 | −0.529766 | Exoc6 | −0.543982 | Ankrd61 | −0.557364 |
| Rad52 | −0.530504 | Nab1 | −0.544948 | 2310061J03Rik | −0.557451 |
| A430105I19Rik | −0.530628 | Osgepl1 | −0.545206 | Atp5s | −0.557451 |
| D8Ertd738e | −0.530884 | Tdrp | −0.54622 | Taf6 | −0.557831 |
| Mettl23 | −0.530933 | Lzts1 | −0.546333 | BC005624 | −0.558161 |
| Hsdl2 | −0.531341 | Dtd1 | −0.546666 | Rpia | −0.558475 |
| Hmcn1 | −0.532021 | Sec23b | −0.546755 | Zfp110 | −0.558722 |
| C330018D20Rik | −0.533362 | Smg8 | −0.54728 | BC002163 | −0.559052 |
| Gzf1 | −0.560191 | B830017H08Rik | −0.573752 | Pnkp | −0.587455 |
| Ppp1r11 | −0.560436 | Cd55 | −0.573752 | Rgs4 | −0.58759 |
| Camta1 | −0.560626 | Cplx1 | −0.573752 | Ndufb2 | −0.588812 |
| Dennd6b | −0.560699 | D7Ertd715e | −0.573752 | Znrd1 | −0.58887 |
| Zfp958 | −0.561342 | E030018B13Rik | −0.573752 | Wdr76 | −0.589025 |
| Cog7 | −0.561344 | Frmd5 | −0.573752 | Tgif1 | −0.589098 |
| Slc35e4 | −0.561346 | Gm19466 | −0.573752 | Hist1h2bh | −0.589503 |
| Orc5 | −0.562315 | Itgb2 | −0.573752 | Srm | −0.589822 |
| Fam132b | −0.562321 | Mri1 | −0.575174 | 1700037C18Rik | −0.59005 |
| Infrsf1b | −0.562394 | Terc | −0.575417 | Hmga2-ps1 | −0.59005 |
| Zfp551 | −0.562656 | Tacc2 | −0.575468 | Otud1 | −0.590053 |
| Zfp703 | −0.563343 | Gpr146 | −0.575474 | Klhl11 | −0.590337 |
| Tor4a | −0.564252 | Lgals6 | −0.57582 | Zfp606 | −0.591307 |
| Kcnk2 | −0.564836 | Ptpmt1 | −0.576346 | Il2rb | −0.591498 |
| Kctd19 | −0.565341 | Ngf | −0.57681 | Fam174a | −0.592183 |
| Zfp398 | −0.565357 | Mutyh | −0.577625 | Pacrgl | −0.592657 |
| Ift43 | −0.565539 | Wdr31 | −0.577626 | Gucd1 | −0.593612 |
| Arid3a | −0.565912 | Hinfp | −0.577643 | Zfp442 | −0.594297 |
| Klf11 | −0.566662 | Ppp1r13b | −0.578079 | Utp3 | −0.595259 |
| Ints5 | −0.566901 | Rgs19 | −0.578324 | Cdkn3 | −0.595313 |
| Ppapdc2 | −0.567622 | Jade2 | −0.579041 | Apcdd1 | −0.595463 |
| Tmed8 | −0.567747 | Hist1h1c | −0.579818 | Ccdc173 | −0.595772 |
| Spry2 | −0.56794 | Vsig10l | −0.580002 | Fam43a | −0.596216 |
| 3830406C13Rik | −0.568015 | Sp110 | −0.5801 | Cir1 | −0.596439 |
| Dyrk2 | −0.568265 | Tcea2 | −0.580364 | Smn1 | −0.596571 |
| Cyp2j9 | −0.569269 | Tnfsf10 | −0.580765 | Ifi27l2a | −0.596679 |
| Ccdc55 | −0.569922 | Nt5m | −0.581035 | Siah1a | −0.59683 |
| Nat6 | −0.570533 | Mrps18b | −0.581333 | A330021E22Rik | −0.597171 |
| Haus4 | −0.57081 | Fgf18 | −0.581553 | Ppm1d | −0.597613 |
| Tmx2 | −0.571123 | Arhgap26 | −0.582712 | Zbtb39 | −0.598211 |
| Magee1 | −0.571345 | Brdt | −0.582829 | Fancf | −0.598231 |
| Urm1 | −0.571663 | Zfp169 | −0.582877 | Camk2b | −0.59927 |
| Zfp512 | −0.571718 | Egr3 | −0.583242 | Oard1 | −0.599343 |
| AU022252 | −0.572398 | Gatsl3 | −0.583612 | Cldn1 | −0.599465 |
| Zpr1 | −0.572764 | Tbc1d9 | −0.584085 | Npas2 | −0.599465 |
| Fam26e | −0.572969 | Magea8 | −0.585681 | Srp54b | −0.599643 |
| Tgds | −0.57346 | Tshz1 | −0.58579 | Zfp930 | −0.6002 |
| Hist1h2af | −0.573751 | Eed | −0.586174 | Rufy1 | −0.601076 |
| 4930465K10Rik | −0.573752 | Prdm11 | −0.586508 | Mrpl54 | −0.602695 |
| 4931431C16Rik | −0.573752 | Gm10336 | −0.587345 | Stx11 | −0.602949 |
| AA388235 | −0.573752 | Echdc3 | −0.587408 | Dusp6 | −0.603491 |
| Dnase1l1 | −0.60358 | Dda1 | −0.623173 | Ttc12 | −0.636575 |
| Gdnf | −0.603686 | Gcc1 | −0.623266 | Ypel4 | −0.636706 |
| Ldlrap1 | −0.604216 | Gdf5 | −0.623313 | Onecut2 | −0.637626 |
| B230319C09Rik | −0.604244 | Ap5b1 | −0.623908 | Polb | −0.637657 |
| Neu2 | −0.60437 | Ajuba | −0.624013 | Rhno1 | −0.637914 |
| Zfp839 | −0.605325 | Nek3 | −0.624323 | Eapp | −0.640406 |
| Apobr | −0.605604 | 1700052N19Rik | −0.624351 | Gm20748 | −0.64078 |
| Gins3 | −0.60594 | Zc3h12b | −0.624532 | Mphosph10 | −0.64086 |
| H2afj | −0.606179 | Frg1 | −0.624631 | Zc3h3 | −0.641326 |
| Metap1d | −0.606241 | Sh3bp1 | −0.62497 | Abcd4 | −0.641495 |
| Rpap3 | −0.606281 | Ssscal1 | −0.625186 | Stk35 | −0.641874 |
| Fbxo48 | −0.607001 | Arhgef19 | −0.625299 | Ccdc74a | −0.643065 |

TABLE 2-continued

List of heat shock-downregulated genes shown by RNA-seq analysis.
Column A: Heat shock-downregulated gene shown by RNA-seq analysis of NIH/3T3 cells.
Column B: Log2 fold-change of the gene in post-H/S cells relative to pre-H/S state.

| gene | log2(fold_change) | gene | log2(fold_change) | gene | log2(fold_change) |
| --- | --- | --- | --- | --- | --- |
| Scrn1 | −0.607001 | 2610035D17Rik | −0.625422 | Pfkfb1 | −0.643065 |
| Zbtb8os | −0.607287 | Hps6 | −0.626004 | Ctbs | −0.643279 |
| Tgif2 | −0.607855 | C030039L03Rik | −0.626041 | Zfp84 | −0.643772 |
| Gstm4 | −0.6093 | Tstd3 | −0.626207 | Abt1 | −0.64509 |
| Tcn2 | −0.609315 | Zfyve21 | −0.62677 | Lpar6 | −0.645267 |
| Vps18 | −0.609317 | 2810032G03Rik | −0.627497 | Mrpl44 | −0.645493 |
| Hist1h2bp | −0.609375 | Nfrkb | −0.628125 | Mapk1ip1 | −0.645745 |
| Oscp1 | −0.610464 | BC053749 | −0.628174 | Rfx5 | −0.645847 |
| Chst11 | −0.610524 | Fam161b | −0.628174 | Bsn | −0.645863 |
| Efna4 | −0.610525 | Dctd | −0.628978 | Chst1 | −0.645863 |
| Gm5069 | −0.610917 | Commd6 | −0.629479 | Mgst2 | −0.645863 |
| Kif3c | −0.612129 | Zfp59 | −0.629547 | Gm15401 | −0.645877 |
| Uap1l1 | −0.612707 | Edc3 | −0.629571 | Ptdss2 | −0.64628 |
| Slc16a2 | −0.613014 | Cecr5 | −0.629599 | Tmed1 | −0.647055 |
| Zfp960 | −0.613692 | Tprn | −0.630454 | Zbtb34 | −0.648021 |
| Hist1h3d | −0.613986 | Ccdc104 | −0.630718 | 4930556M19Rik | −0.648099 |
| Itpk1 | −0.614283 | Ddx55 | −0.631254 | Ccdc174 | −0.649049 |
| Cdk6 | −0.614877 | Plod2 | −0.632111 | Krt10 | −0.649049 |
| Pex11g | −0.614939 | Fignl1 | −0.632171 | 2810047C21Rik1 | −0.649356 |
| Arrdc4 | −0.617362 | Myo7a | −0.633202 | Dis3l2 | −0.650614 |
| Trp53rk | −0.618256 | 2810408M09Rik | −0.633783 | Gpr75 | −0.651521 |
| 2410004B18Rik | −0.618544 | Rad17 | −0.634016 | Necab3 | −0.651521 |
| Gins1 | −0.619211 | Rnf138 | −0.634935 | Dyrk3 | −0.651559 |
| Zfp532 | −0.620083 | Trim12c | −0.635249 | Snx11 | −0.651727 |
| Wnt10b | −0.620199 | Mettl15 | −0.636089 | Mid1ip1 | −0.652493 |
| Mr1 | −0.620456 | Hfe | −0.636366 | Rgs17 | −0.652537 |
| Zfp658 | −0.620595 | Fdxacb1 | −0.636473 | Zfp668 | −0.654208 |
| Ears2 | −0.622258 | Mrps28 | −0.636473 | Spock2 | −0.693274 |
| Loh12cr1 | −0.622411 | Fbxo32 | −0.670724 | Ttll11 | −0.693274 |
| Uhmk1 | −0.654745 | Cit | −0.671092 | 5730507C01Rik | −0.693346 |
| Polr3a | −0.655476 | Slc16a9 | −0.671699 | Pibf1 | −0.693752 |
| Inca1 | −0.655784 | Snai2 | −0.672634 | Gm16596 | −0.693878 |
| Coq4 | −0.655808 | Zfp382 | −0.672674 | Lpin3 | −0.694452 |
| Ccnf | −0.657503 | Ifit1 | −0.672916 | Zfp341 | −0.695049 |
| 4921513I03Rik | −0.657561 | Kcnj6 | −0.673846 | Trhde | −0.697817 |
| Fjx1 | −0.657561 | B4galt7 | −0.674757 | Haghl | −0.69896 |
| Gsg1l | −0.657561 | Il6ra | −0.675251 | Scx | −0.699475 |
| 5830418K08Rik | −0.657611 | Lrrc48 | −0.675405 | Ankrd23 | −0.699539 |
| Tada2a | −0.657686 | Zc3hc1 | −0.676349 | Dok4 | −0.699539 |
| Zfp599 | −0.658249 | Trim21 | −0.676785 | Zfp759 | −0.699539 |
| A630066F11Rik | −0.658756 | Il34 | −0.678002 | Osr1 | −0.700978 |
| 2210408I21Rik | −0.659112 | Zkscan5 | −0.678454 | Cxcl1 | −0.701207 |
| Rcan2 | −0.659781 | Fndc4 | −0.679377 | Capn5 | −0.702153 |
| Zfp248 | −0.660258 | Etohi1 | −0.680126 | Ftsj2 | −0.702185 |
| Nipsnap3b | −0.661068 | Nup210l | −0.68017 | Cbll1 | −0.702813 |
| Zfp947 | −0.661354 | Smim8 | −0.68017 | Trex1 | −0.703789 |
| Spryd7 | −0.661689 | Sharpin | −0.680316 | Terf1 | −0.704221 |
| 1810043G02Rik | −0.662097 | Ddx27 | −0.681203 | Rsad1 | −0.704583 |
| 4930453N24Rik | −0.662222 | Kctd21 | −0.682037 | Gla | −0.705089 |
| Armc8 | −0.662384 | Ifi44 | −0.682371 | Ccdc77 | −0.705819 |
| Tsen2 | −0.66291 | B4galt6 | −0.682375 | Eme2 | −0.705906 |
| Nhsl1 | −0.663326 | Pknox2 | −0.683044 | Tcf23 | −0.70598 |
| Dnmt3b | −0.664391 | Acy1 | −0.683377 | P2ry13 | −0.706026 |
| Hist1h2ai | −0.664475 | Dtnbp1 | −0.683623 | 4933402D24Rik | −0.706088 |
| Apitd1 | −0.664838 | 4931428F04Rik | −0.685205 | 9530026P05Rik | −0.706088 |
| Itpkc | −0.665082 | Sema5a | −0.685834 | A330032B11Rik | −0.706088 |
| Foxf2 | −0.665223 | Mlycd | −0.686426 | AI854703 | −0.706088 |
| Plekha5 | −0.666248 | Bnc1 | −0.686956 | Aknad1 | −0.706088 |
| 3110056K07Rik | −0.666493 | Hexim2 | −0.687181 | Apon | −0.706088 |
| Ftsj1 | −0.666502 | D330050I16Rik | −0.688364 | Aqp7 | −0.706088 |
| Slc39a8 | −0.666549 | Gltscr1 | −0.688913 | Cacna2d4 | −0.706088 |
| Primpol | −0.66774 | Lmf1 | −0.689297 | Dock3 | −0.706088 |
| 2700069I18Rik | −0.667935 | Ubl3 | −0.689301 | Dusp15 | −0.706088 |
| Dffb | −0.667935 | Rnf220 | −0.689847 | Efcab8 | −0.706088 |
| Sgcd | −0.667951 | 0610037L13Rik | −0.690647 | Fbxo47 | −0.706088 |
| Gm5512 | −0.667976 | Atl1 | −0.691053 | Gjb5 | −0.706088 |
| Mttp | −0.668287 | Tpgs1 | −0.691596 | Gm5779 | −0.706088 |
| Crebzf | −0.669662 | Sh3bp5 | −0.692301 | Gm6086 | −0.706088 |
| Pdik1l | −0.670509 | Csk | −0.692673 | Zbtb5 | −0.728635 |
| A430033K04Rik | −0.670721 | Gm20362 | −0.708245 | Mrps12 | −0.729756 |
| Gm9047 | −0.706088 | 9230105E05Rik | −0.709777 | Deb1 | −0.730002 |
| Gpr84 | −0.706088 | Ikzf2 | −0.710537 | Pop7 | −0.731847 |
| Gstm7 | −0.706088 | Mxd3 | −0.710562 | Hoxa6 | −0.732263 |
| Hs3st6 | −0.706088 | Dlx1 | −0.712027 | Rnf113a2 | −0.732286 |

TABLE 2-continued

List of heat shock-downregulated genes shown by RNA-seq analysis.
Column A: Heat shock-downregulated gene shown by RNA-seq analysis of NIH/3T3 cells.
Column B: Log2 fold-change of the gene in post-H/S cells relative to pre-H/S state.

| gene | log2(fold_change) | gene | log2(fold_change) | gene | log2(fold_change) |
|---|---|---|---|---|---|
| Hsd17b14 | −0.706088 | Zfp873 | −0.71301 | A630072M18Rik | −0.732412 |
| Kif26a | −0.706088 | B9d1 | −0.714355 | Mocs3 | −0.734491 |
| Krt16 | −0.706088 | Esyt3 | −0.71549 | 3830403N18Rik | −0.736767 |
| Pate2 | −0.706088 | Trit1 | −0.716494 | Cdrt4 | −0.736767 |
| Phyhip | −0.706088 | 1810043H04Rik | −0.718317 | Hes3 | −0.736767 |
| Pld4 | −0.706088 | Hist1h2an | −0.718552 | Mmp28 | −0.73698 |
| Prss38 | −0.706088 | Lipt2 | −0.718794 | Pou5f2 | −0.737044 |
| Rag1 | −0.706088 | Gsdmd | −0.719585 | Card10 | −0.737078 |
| Rasgrp2 | −0.706088 | 4921531C22Rik | −0.720481 | Lin37 | −0.737085 |
| Rbm3os | −0.706088 | Asic3 | −0.720481 | 2010002M12Rik | −0.737199 |
| Rimbp3 | −0.706088 | Fkbpl | −0.720481 | Abhd15 | −0.737199 |
| Rnf183 | −0.706088 | Galr2 | −0.720481 | Gps2 | −0.737236 |
| Ryr3 | −0.706088 | Klf5 | −0.720481 | Hmga1 | −0.738621 |
| Slc17a9 | −0.706088 | Psmb9 | −0.720481 | Prpf38b | −0.739789 |
| Snora69 | −0.706088 | Tert | −0.720481 | Rfng | −0.740839 |
| Snord23 | −0.706088 | Rbm38 | −0.720904 | Il10rb | −0.742049 |
| Srpk3 | −0.706088 | Pot1b | −0.72219 | Dtd2 | −0.742336 |
| Tmem140 | −0.706088 | Lcmt1 | −0.72227 | Hsd3b7 | −0.744176 |
| Ttc24 | −0.706088 | Gtf3c6 | −0.722322 | Klc3 | −0.745417 |
| Tubg2 | −0.706088 | Cyb5d1 | −0.723168 | Pcdh10 | −0.746236 |
| Uchl4 | −0.706088 | Alkbh4 | −0.723575 | Mfap3l | −0.751303 |
| Unc45b | −0.706088 | Tmem205 | −0.723904 | Dnm3os | −0.751652 |
| Usp17la | −0.706088 | Foxc2 | −0.724419 | Pex7 | −0.752295 |
| Xkrx | −0.706088 | Slc2a8 | −0.725225 | Pgap3 | −0.752692 |
| Zfp389 | −0.706088 | Rin1 | −0.725263 | Phf11d | −0.753085 |
| Zim1 | −0.706088 | B4galnt2 | −0.725681 | Zfp189 | −0.753931 |
| 2610203C22Rik | −0.706095 | Camk1g | −0.725681 | Smim1 | −0.754017 |
| Amy1 | −0.706183 | Ropn1l | −0.725681 | Adamts15 | −0.754746 |
| D630029K05Rik | −0.706215 | Zfp455 | −0.725681 | Mpp7 | −0.755586 |
| Crhr2 | −0.706229 | Fam83h | −0.725929 | Atg10 | −0.75615 |
| Tsen15 | −0.706252 | Sh3yl1 | −0.7263 | Nespas | −0.75615 |
| Tspan32 | −0.706259 | Lyrm1 | −0.726373 | Pctp | −0.756909 |
| 5730420D15Rik | −0.706377 | Taf1c | −0.727469 | Pdlim1 | −0.757538 |
| Gcnt1 | −0.706807 | Irx1 | −0.72786 | Napepld | −0.813393 |
| Cntfr | −0.706823 | AW209491 | −0.728344 | Fbxw17 | −0.81384 |
| Fam206a | −0.707078 | Fbxo31 | −0.72861 | Ndufs5 | −0.818532 |
| Strada | −0.707297 | Slc8a2 | −0.785323 | Cyb561d1 | −0.818996 |
| Nanp | −0.757989 | Col11a2 | −0.78544 | Tlcd1 | −0.819144 |
| Zfp280b | −0.759093 | 5930430L01Rik | −0.786193 | Plscr4 | −0.819756 |
| BC003965 | −0.759857 | Ganc | −0.789766 | Ndufaf1 | −0.820008 |
| Aaed1 | −0.761054 | Nxt2 | −0.79019 | 1700029J07Rik | −0.82059 |
| Mrps9 | −0.761167 | Nfatc1 | −0.790938 | Abca8a | −0.82059 |
| Cenpn | −0.761181 | Mrps10 | −0.791794 | G6b | −0.821414 |
| Zfp748 | −0.761254 | Amt | −0.795068 | Oxsm | −0.824032 |
| Pcdhb19 | −0.761436 | Gm5577 | −0.795068 | Romo1 | −0.824315 |
| Plagl2 | −0.762635 | Zfp580 | −0.795068 | Tagap1 | −0.824643 |
| Stradb | −0.76333 | Det1 | −0.795134 | Ubac1 | −0.826065 |
| Tfap2a | −0.763974 | Ezh1 | −0.795417 | Stra13 | −0.826126 |
| Ugt1a6b | −0.765062 | 2610305D13Rik | −0.79557 | Iqcd | −0.826795 |
| Rcor2 | −0.765091 | Ddx19a | −0.795726 | Unc5a | −0.826795 |
| Lactb | −0.765161 | Fam217b | −0.795905 | Nbn | −0.830417 |
| Emx2 | −0.765782 | Map3k5 | −0.796144 | Unc13a | −0.831698 |
| Haus1 | −0.766594 | Id1 | −0.796365 | Arhgap20os | −0.832304 |
| Gli2 | −0.767552 | Itgb4 | −0.797031 | Fam46c | −0.832304 |
| 4930562F07Rik | −0.76921 | Irak1bp1 | −0.798121 | Gm4890 | −0.83292 |
| Kifc2 | −0.76939 | Hkdc1 | −0.7997 | Eno3 | −0.833402 |
| Gm6548 | −0.770704 | Pbld2 | −0.7997 | 9630033F20Rik | −0.833713 |
| Gemin2 | −0.770972 | Zik1 | −0.800245 | Dpyd | −0.834529 |
| Plscr2 | −0.771217 | Mettl8 | −0.802344 | Fance | −0.835103 |
| Zfp418 | −0.772085 | Rab10os | −0.803345 | Gpr149 | −0.8367 |
| Pex12 | −0.7726 | Pias4 | −0.804324 | Kcnip2 | −0.837577 |
| Ankrd37 | −0.773332 | Fam188b | −0.804752 | BC039966 | −0.837581 |
| Ppargc1b | −0.773872 | Dnajb14 | −0.80512 | Fastkd1 | −0.837581 |
| Hes6 | −0.775006 | AW554918 | −0.805369 | Krt13 | −0.837581 |
| Vav3 | −0.77609 | Tigd3 | −0.805577 | Msl3l2 | −0.837581 |
| Mcur1 | −0.778208 | Rpl30 | −0.807526 | Neurl2 | −0.837581 |
| Fam216a | −0.778209 | Trappc5 | −0.808742 | Rarres2 | −0.837581 |
| Rhebl1 | −0.779977 | Rad9b | −0.810325 | Tdrd9 | −0.837581 |
| Snhg6 | −0.780158 | Gm3716 | −0.810571 | Zscan2 | −0.837609 |
| Zfp738 | −0.780195 | Shpk | −0.810652 | S100a13 | −0.838208 |
| Med27 | −0.780297 | Fam20a | −0.810681 | Cdca5 | −0.840608 |
| Gja1 | −0.780555 | Uqcc1 | −0.81206 | Ict1 | −0.840648 |
| Cstf1 | −0.781231 | Gm14139 | −0.812224 | Ggact | −0.841342 |
| Cxxc4 | −0.781643 | Gpr19 | −0.812392 | 4930570G19Rik | −0.841586 |

TABLE 2-continued

List of heat shock-downregulated genes shown by RNA-seq analysis.
Column A: Heat shock-downregulated gene shown by RNA-seq analysis of NIH/3T3 cells.
Column B: Log2 fold-change of the gene in post-H/S cells relative to pre-H/S state.

| gene | log2(fold_change) | gene | log2(fold_change) | gene | log2(fold_change) |
|---|---|---|---|---|---|
| Mtus2 | −0.782687 | 1600014C10Rik | −0.812875 | Kcnn1 | −0.918356 |
| Kiss1r | −0.782897 | Alg3 | −0.812992 | Rnpepl1 | −0.918389 |
| Saysd1 | −0.784631 | Atp10d | −0.813057 | Trmt5 | −0.919185 |
| Dusp2 | −0.785323 | Zfp764 | −0.894501 | Cryl1 | −0.92023 |
| Fignl2 | −0.841642 | Wdr44 | −0.894865 | Egfl6 | −0.921283 |
| E130307A14Rik | −0.841942 | Med26 | −0.895078 | Gm6402 | −0.921283 |
| Trim34a | −0.842282 | Zfp763 | −0.896189 | Hotair | −0.921283 |
| Pank1 | −0.843037 | Pusl1 | −0.896236 | Zfp708 | −0.921564 |
| Zfp191 | −0.843053 | Dgka | −0.89726 | Txnrd3 | −0.923589 |
| 6430550D23Rik | −0.84395 | Yae1d1 | −0.898458 | Zan | −0.936897 |
| Syce2 | −0.846123 | 2410076I21Rik | −0.89981 | Fam65b | −0.936953 |
| Nudt22 | −0.846437 | 4930521E06Rik | −0.89981 | Parvb | −0.937209 |
| Rbm47 | −0.847476 | A330040F15Rik | −0.89981 | Pigw | −0.940902 |
| Irgm2 | −0.847656 | E130018N17Rik | −0.89981 | Lysmd4 | −0.941065 |
| Rft1 | −0.849209 | E430016F16Rik | −0.89981 | Zfp37 | −0.941341 |
| A330074K22Rik | −0.849443 | Fam184b | −0.89981 | Lekr1 | −0.943815 |
| 1700029H14Rik | −0.85006 | Kctd4 | −0.89981 | Galnt9 | −0.947365 |
| Atp5sl | −0.851423 | Nipal2 | −0.89981 | Zfp943 | −0.953224 |
| Tmem14a | −0.852202 | Plekha7 | −0.89981 | Zfp87 | −0.957457 |
| As3mt | −0.852315 | Rims2 | −0.89981 | Gm12669 | −0.958069 |
| Mycn | −0.852315 | Soat2 | −0.89981 | 1600029I14Rik | −0.958083 |
| Poli | −0.85266 | Hhatl | −0.899876 | 2810405F15Rik | −0.958083 |
| Slc18a2 | −0.854831 | 9230110C19Rik | −0.902176 | Aldh1l1 | −0.958083 |
| Rwdd2b | −0.86081 | Kbtbd4 | −0.902319 | Ap1g2 | −0.958083 |
| Rnase4 | −0.865073 | Tmem8 | −0.902472 | Bmp8b | −0.958083 |
| Epha7 | −0.865657 | Palb2 | −0.903171 | Camk2n1 | −0.958083 |
| Aqp11 | −0.866944 | Pard6a | −0.904017 | Ccdc87 | −0.958083 |
| Rep15 | −0.866944 | Nme3 | −0.907648 | Cd46 | −0.958083 |
| Grin2d | −0.867395 | C1qtnf1 | −0.908103 | Cml5 | −0.958083 |
| Gpr162 | −0.868317 | Frs3 | −0.90817 | Fxyd7 | −0.958083 |
| Dcbld1 | −0.869465 | Zmat1 | −0.908467 | Gm14057 | −0.958083 |
| Zfp597 | −0.877144 | Ap5s1 | −0.910458 | Gm6642 | −0.958083 |
| 6330549D23Rik | −0.877973 | Zfp39 | −0.910573 | Kdm4d | −0.958083 |
| Gm10658 | −0.878877 | Zfp454 | −0.911083 | Tsacc | −0.958083 |
| Spata5l1 | −0.878877 | Gm10532 | −0.912189 | Uroc1 | −0.958083 |
| Arrb1 | −0.87975 | Dhx35 | −0.912651 | 1810019D21Rik | −0.958128 |
| Acsf2 | −0.882695 | Hist1h1d | −0.913021 | Frs3os | −0.958337 |
| Hic2 | −0.886541 | Fosb | −0.913754 | Syt8 | −0.959358 |
| Nova2 | −0.890182 | Lrfn3 | −0.913776 | Kbtbd7 | −0.961542 |
| Gm7334 | −0.890376 | Zfp593 | −0.914014 | Rpusd2 | −0.962275 |
| Neat1 | −0.890741 | Lins | −0.914152 | Brms1 | −0.962914 |
| Mgmt | −0.890925 | Irx5 | −0.915824 | Eif1b | −1.07147 |
| Ankrd35 | −0.891538 | 4930451G09Rik | −0.916876 | Mpp6 | −1.07444 |
| 1700019G17Rik | −0.892095 | Klf2 | −0.917442 | Catip | −1.07765 |
| Atp6v0c-ps2 | −0.893895 | Tnfsf9 | −1.02444 | Drp2 | −1.07888 |
| Fam120aos | −0.963613 | Abhd1 | −1.0251 | Pcdhb8 | −1.08078 |
| Pfkfb4 | −0.963796 | Ccdc51 | −1.02514 | Bhlha15 | −1.08206 |
| Sv2a | −0.963796 | Srd5a1 | −1.02627 | Bricd5 | −1.08206 |
| Tmem185b | −0.963796 | Wdr53 | −1.03014 | Car15 | −1.08206 |
| 1700086O06Rik | −0.964385 | Card14 | −1.0313 | Gm15612 | −1.08206 |
| Mitd1 | −0.964645 | Gm15446 | −1.0313 | Hspb9 | −1.08206 |
| Smco3 | −0.964993 | Gm6225 | −1.0313 | Rarb | −1.08206 |
| Col9a3 | −0.965064 | Krt80 | −1.0313 | Slc29a2 | −1.08206 |
| Tacr2 | −0.968807 | Sgpp2 | −1.0313 | Srcrb4d | −1.08206 |
| Tmem80 | −0.973976 | Trim36 | −1.0313 | Tubb4a | −1.08206 |
| Mcf2l | −0.974236 | Dolpp1 | −1.03212 | Gsto2 | −1.08209 |
| C4a | −0.976222 | Tmem220 | −1.03226 | Gmpr | −1.08297 |
| Zfp109 | −0.980712 | Gramd3 | −1.0325 | Zcchc5 | −1.0843 |
| Fam53b | −0.981167 | Plekha2 | −1.03449 | Pcdhgb8 | −1.08517 |
| 4632427E13Rik | −0.983515 | Zfp108 | −1.03621 | Gm10509 | −1.08634 |
| Gm13157 | −0.985491 | Irf7 | −1.03938 | Gm17769 | −1.08673 |
| Akap5 | −0.988789 | 1700021F05Rik | −1.03988 | Dbndd1 | −1.08763 |
| Gjb3 | −0.988966 | Map9 | −1.04035 | Katnal2 | −1.0887 |
| Pgbd1 | −0.994904 | B230217O12Rik | −1.04191 | Pip4k2a | −1.08881 |
| Fgfbp3 | −0.996304 | Col4a4 | −1.04191 | Mthfs | −1.08891 |
| Gm12070 | −0.999898 | Prr5l | −1.04327 | Casp4 | −1.08983 |
| Mir22hg | −1.00059 | Lrch4 | −1.04389 | 9130019O22Rik | −1.09251 |
| Msi1 | −1.0006 | Snx32 | −1.04743 | Enpp3 | −1.09271 |
| 3110009E18Rik | −1.00099 | Bcar3 | −1.04746 | 8430431K14Rik | −1.0935 |
| Il15ra | −1.00477 | Commd9 | −1.05007 | Gm16712 | −1.0935 |
| 9330151L19Rik | −1.00508 | Depdc1b | −1.05105 | Nugcc | −1.0935 |
| Adrb2 | −1.00509 | Pcdhga9 | −1.05114 | Dmkn | −1.09763 |
| Arhgef6 | −1.00509 | Zfp354a | −1.05515 | Bambi | −1.09927 |
| St6galnac2 | −1.00509 | Adhfe1 | −1.0558 | B4galnt4 | −1.09955 |

TABLE 2-continued

List of heat shock-downregulated genes shown by RNA-seq analysis.
Column A: Heat shock-downregulated gene shown by RNA-seq analysis of NIH/3T3 cells.
Column B: Log2 fold-change of the gene in post-H/S cells relative to pre-H/S state.

| gene | log2(fold_change) | gene | log2(fold_change) | gene | log2(fold_change) |
|---|---|---|---|---|---|
| A730017C20Rik | −1.0051 | Lcat | −1.0586 | Zfp677 | −1.10137 |
| Usp17le | −1.00834 | Pcdh12 | −1.0586 | Zfp870 | −1.10137 |
| Gan | −1.01104 | Slc44a3 | −1.0586 | Cmtr2 | −1.10287 |
| Ppdpf | −1.01151 | Rpp21 | −1.06131 | Mfsd6 | −1.10351 |
| Rassf7 | −1.02042 | Adamts13 | −1.06243 | Zfp408 | −1.10399 |
| Alyref2 | −1.02132 | Nafl | −1.06434 | Mtap7d3 | −1.10456 |
| A630001G21Rik | −1.0214 | Clhc1 | −1.06681 | Nudt6 | −1.11254 |
| Zbtb49 | −1.02217 | Dhrs3 | −1.06694 | Larp6 | −1.11285 |
| Taf7 | −1.02255 | Trnau1ap | −1.06825 | Acn9 | −1.29475 |
| Ppm1e | −1.02353 | Ccdc64 | −1.06964 | Hist2h2ab | −1.30242 |
| Zfp30 | −1.02424 | Cdnf | −1.06964 | Cep41 | −1.3043 |
| Hist1h3g | −1.02433 | Gm10814 | −1.18443 | Pcdha12 | −1.30484 |
| Gpr85 | −1.11496 | Ccnj | −1.18669 | Cml1 | −1.30544 |
| 9430018G01Rik | −1.11501 | Orai1 | −1.18774 | Zscan18 | −1.31459 |
| Gm14378 | −1.11501 | Cabyr | −1.19303 | Gpat2 | −1.31476 |
| Nmnat1 | −1.11501 | Sh3d21 | −1.19876 | Pkd2l2 | −1.31833 |
| Calml4 | −1.1162 | C030034I22Rik | −1.19914 | Nov | −1.3192 |
| Cyb561d2 | −1.11762 | Gm16740 | −1.20283 | Slc46a3 | −1.32016 |
| Hspa11 | −1.12163 | Crispld1 | −1.20403 | Rgs9bp | −1.32674 |
| Nupr1 | −1.12472 | Rap1gap | −1.20765 | Ap1s2 | −1.33649 |
| Zfp825 | −1.13017 | Nhej1 | −1.21038 | Mybl1 | −1.33714 |
| Rpp40 | −1.13045 | Apol9a | −1.21719 | Tusc1 | −1.33963 |
| Slc26a11 | −1.1325 | Kbtbd3 | −1.22009 | Mzf1 | −1.34088 |
| Trim65 | −1.1325 | Slc25a23 | −1.22118 | Zscan20 | −1.34132 |
| Ppargc1a | −1.13279 | Fbxl8 | −1.22878 | Tirap | −1.34754 |
| Tmem86a | −1.13369 | Hoxa1 | −1.22939 | Marveld2 | −1.37816 |
| Nudt16 | −1.13415 | Nat2 | −1.23305 | Akr1b10 | −1.37926 |
| Zfp202 | −1.13696 | Ndufaf6 | −1.23343 | Tulp2 | −1.37931 |
| Gdpgp1 | −1.13954 | Nlrc3 | −1.23968 | Omg | −1.38002 |
| Ccdc92 | −1.14011 | 4931414P19Rik | −1.24722 | 2300009A05Rik | −1.38003 |
| Pcdhgb4 | −1.14036 | Slc9a9 | −1.24734 | 4933427E11Rik | −1.38003 |
| Thtpa | −1.14065 | Repin1 | −1.24919 | 6230400D17Rik | −1.38003 |
| Tmtc1 | −1.15184 | Tspan2 | −1.25039 | Ankrd53 | −1.38003 |
| Mettl3 | −1.15326 | Btc | −1.25262 | Car5b | −1.38003 |
| Rab3a | −1.15447 | Spa17 | −1.25262 | Ccl9 | −1.38003 |
| C330006A16Rik | −1.15655 | Ccdc176 | −1.25346 | Cd247 | −1.38003 |
| Acvrl1 | −1.15764 | Raver1 | −1.26039 | E130102H24Rik | −1.38003 |
| Fancb | −1.15797 | 2310068J16Rik | −1.26102 | Efcab5 | −1.38003 |
| Morn2 | −1.15879 | Dusp8 | −1.26364 | Epha10 | −1.38003 |
| Dusp14 | −1.15914 | Piddl | −1.26865 | Fam154b | −1.38003 |
| Naip6 | −1.15914 | Pgp | −1.26976 | Fer1l5 | −1.38003 |
| 2010320M18Rik | −1.16332 | LOC100505025 | −1.27565 | Gm14634 | −1.38003 |
| 4932416H05Rik | −1.16416 | Agpat2 | −1.27578 | Gm16523 | −1.38003 |
| Spdya | −1.16524 | Fpr1 | −1.27578 | Gm773 | −1.38003 |
| Srcin1 | −1.16714 | Gm20753 | −1.27578 | Igfbp2 | −1.38003 |
| Dlec1 | −1.16812 | F630042J09Rik | −1.27804 | Igf1r1 | −1.38003 |
| Clcn2 | −1.17179 | Fam117a | −1.28065 | Lama5 | −1.38003 |
| Fam212a | −1.17501 | Ube2t | −1.28523 | Lect1 | −1.38003 |
| Myo1a | −1.17567 | A530032D15Rik | −1.29105 | Lenep | −1.38003 |
| Tubd1 | −1.18154 | Gm10791 | −1.29105 | 2310009A05Rik | −1.62251 |
| Fam19a5 | −1.18349 | Gm6034 | −1.29105 | Gm15787 | −1.62324 |
| Acy3 | −1.18443 | Poln | −1.29352 | Ntf5 | −1.62331 |
| Lhx4 | −1.38003 | Cst6 | −1.50625 | Trpc2 | −1.62464 |
| Lrrc15 | −1.38003 | Ydjc | −1.5258 | Gm3435 | −1.62687 |
| Mroh8 | −1.38003 | Gm14124 | −1.52882 | Slc35d2 | −1.6337 |
| Nrg4 | −1.38003 | Zfp78 | −1.53624 | 0610039K10Rik | −1.64586 |
| Rab20 | −1.38003 | Cideb | −1.54305 | Mettl20 | −1.65482 |
| Sag | −1.38003 | Col4a3 | −1.54305 | Pde3a | −1.65756 |
| Serpina3i | −1.38003 | E130012A19Rik | −1.54305 | Ccdc177 | −1.6754 |
| Spata20 | −1.38003 | E230008N13Rik | −1.54305 | Mterf1b | −1.6754 |
| Tmem144 | −1.38003 | Gm3604 | −1.54305 | Gm19557 | −1.68489 |
| Trcg1 | −1.38003 | Gpc3 | −1.54305 | Pde1a | −1.68652 |
| Zbtb32 | −1.38003 | Lrp2 | −1.54305 | Ccr7 | −1.69782 |
| Zfp750 | −1.38003 | Sh3tc1 | −1.54305 | Cdh22 | −1.70609 |
| 2610027K06Rik | −1.3801 | Tex26 | −1.54305 | E230025N22Rik | −1.70609 |
| Cct6b | −1.38046 | Wnt8b | −1.54305 | Lypd1 | −1.70609 |
| Slx1b | −1.39993 | Emilin3 | −1.54332 | Olfr1417 | −1.70609 |
| Aph1c | −1.4049 | Abat | −1.54336 | Otoa | −1.70609 |
| Mapk11 | −1.40895 | Impg2 | −1.54919 | Pard3b | −1.70609 |
| Rnaset2a, Rnaset2b | −1.40933 | Kcnh1 | −1.54936 | Ppm1j | −1.70609 |
| | | Gimap6 | −1.55225 | Siglec15 | −1.70609 |
| Grk4 | −1.42973 | Il20rb | −1.55225 | St8sia1 | −1.70609 |
| 4430402I18Rik | −1.43644 | Wdr93 | −1.55225 | Vmn2r-ps54 | −1.70609 |
| Foxd2 | −1.44034 | Gfi1 | −1.55229 | Col2a1 | −1.70638 |

TABLE 2-continued

List of heat shock-downregulated genes shown by RNA-seq analysis.
Column A: Heat shock-downregulated gene shown by RNA-seq analysis of NIH/3T3 cells.
Column B: Log2 fold-change of the gene in post-H/S cells relative to pre-H/S state.

| gene | log2(fold_change) | gene | log2(fold_change) | gene | log2(fold_change) |
|---|---|---|---|---|---|
| Mnd1 | −1.44746 | Tnfsf12Tnfsf13 | −1.55406 | Fam73a | −1.70643 |
| Phxr4 | −1.45029 | Lcmt2 | −1.55828 | Plekhg1 | −1.70665 |
| Hoxd3 | −1.45722 | Lsr | −1.55834 | Plb1 | −1.70728 |
| Spata24 | −1.45823 | 1190005I06Rik | −1.56266 | Tenm2 | −1.70774 |
| Treml1 | −1.46198 | Gls2 | −1.56293 | Mis18a | −1.71264 |
| Gdap1l1 | −1.46266 | 8430408G22Rik | −1.5646 | Pcbd2 | −1.71272 |
| Cpt1b | −1.46299 | Ppp1r3c | −1.57178 | Bbs5 | −1.72048 |
| Elovl4 | −1.46384 | 3000002C10Rik | −1.57375 | Jph2 | −1.73714 |
| Ggct | −1.46384 | 4930552P12Rik | −1.57375 | Cfp | −1.7401 |
| Tbx6 | −1.46384 | 4931430N09Rik | −1.57375 | 1700019L03Rik | −1.74597 |
| Zfp647 | −1.46627 | Prss12 | −1.57375 | Ushbp1 | −1.74597 |
| 2410016O06Rik | −1.46954 | Gm2897 | −1.57379 | Dlgap1 | −1.74779 |
| Rpl14-ps1 | −1.48126 | Pcdhga2 | −1.57681 | Cobl | −1.75624 |
| G630090E17Rik | −1.48442 | Vash1 | −1.58534 | Siglec1 | −1.76063 |
| Svop | −1.48477 | Samd5 | −1.58875 | Cdh17 | −1.76544 |
| Tmem235 | −1.48477 | Fhl4 | −1.59947 | 4930528A17Rik | −1.77333 |
| Ifitm1 | −1.4849 | 2810008D09Rik | −1.60233 | Usp27x | −2.19883 |
| Leng9 | −1.49253 | Dand5 | −1.60242 | Ubald2 | −2.22255 |
| Slc25a2 | −1.4971 | Dnajc12 | −1.61231 | 2310009B15Rik | −2.25952 |
| Gbp6 | −1.77333 | Gm10432 | −1.95808 | Stc2 | −2.28001 |
| 2810410L24Rik | −1.78516 | Vmn1r43 | −1.95808 | Ppp1r1b | −2.28554 |
| Chrnb1 | −1.78516 | Scnn1a | −1.96311 | 4930519F09Rik | −2.29105 |
| Kcnip3 | −1.7866 | Abhd3 | −1.9638 | Chn1os3 | −2.29105 |
| Cstad | −1.80581 | Gpr137c | −1.96499 | E130309D14Rik | −2.29105 |
| Rab27a | −1.80581 | Mapk12 | −1.96499 | Gsdmcl-ps | −2.29105 |
| Edaradd | −1.82059 | Itgae | −1.96724 | Zfp946 | −2.31977 |
| 2700097O09Rik | −1.82068 | Zfp784 | −1.99119 | Frat1 | −2.32787 |
| Plp1 | −1.8211 | Fam195a | −2.00996 | Scd4 | −2.32787 |
| 1810034E14Rik | −1.83758 | Plxdc1 | −2.02214 | Tex30 | −2.32948 |
| 4933430I17Rik | −1.83758 | Rnasel | −2.04804 | Lincrna-cox2 | −2.33623 |
| Angptl7 | −1.83758 | Dtwd1 | −2.05688 | E2f2 | −2.35593 |
| BC039771 | −1.83758 | LOC100861615 | −2.06437 | Fam169b | −2.38003 |
| Ccdc38 | −1.83758 | 3300002I08Rik | −2.08206 | Gm16062 | −2.38003 |
| Ccr10 | −1.83758 | Atg9b | −2.08206 | Nod2 | −2.38003 |
| Fam110c | −1.83758 | B3galt1 | −2.08206 | Usp13 | −2.38003 |
| Gata3 | −1.83758 | Ccdc17 | −2.08206 | 12-Sep | −2.42791 |
| Glipr1 | −1.83758 | Foxq1 | −2.08206 | Ino80dos | −2.44136 |
| Npm2 | −1.83758 | Gnat2 | −2.08206 | Slc3a1 | −2.46402 |
| Rgag1 | −1.83758 | Krt83 | −2.08206 | 1110019D14Rik | −2.55225 |
| Serpind1 | −1.83758 | Prlr | −2.08206 | B3gnt4 | −2.55225 |
| Gm16853 | −1.83759 | Zfp786 | −2.08206 | Ces4a | −2.55225 |
| Trim43c | −1.8376 | Gm19897 | −2.08215 | Dll4 | −2.55225 |
| Spns2 | −1.83764 | Aatk | −2.08227 | Usp18 | −2.57375 |
| 4930506M07Rik | −1.83767 | 9330159M07Rik | −2.11376 | C230029M16 | −2.58557 |
| Crmp1 | −1.83774 | 1500011K16Rik | −2.11501 | Snrnp35 | −2.59005 |
| Fyb | −1.83785 | Mettl18 | −2.1325 | Edn1 | −2.62687 |
| Frem1 | −1.87112 | 0610009L18Rik | −2.13415 | Luzp4 | −2.62687 |
| Grb14 | −1.87888 | 2810002D19Rik | −2.13415 | Tssk2 | −2.62687 |
| Hspbap1 | −1.8899 | Anxa8 | −2.15117 | Mme | −2.62733 |
| Gm15987 | −1.89981 | Fsbp | −2.15649 | A530016L24Rik | −2.65376 |
| Lpcat2b | −1.89981 | 1700024P16Rik | −2.1728 | Optc | −2.65956 |
| Neb | −1.89981 | Axin2 | −2.18443 | Cage1 | −2.6754 |
| Timp4 | −1.89981 | Ptprv | −2.18443 | Hpx | −2.70609 |
| Gm9855 | −1.90588 | Samd15 | −2.18443 | Armc2 | −2.77333 |
| Paqr7 | −1.90629 | Tmem252 | −2.18443 | Gm20257 | −2.77333 |
| Tmc3 | −1.90629 | 1600020E01Rik | −2.18457 | Lmcd1 | −2.77333 |
| Tnfrsf14 | −1.91198 | Gm2373 | −2.18509 | Adcy3 | −2.78028 |
| Lhx6 | −1.92398 | Hdhd3 | −2.1864 | Pisd-ps1 | −5.24468 |
| Btbd8 | −1.93985 | Zfp472 | −2.18696 | Amd1, Amd2 | −5.80573 |
| Ttc30a1 | −2.81623 | Endog | −3.0214 | Raet1d | −5.8346 |
| Ccdc151 | −2.82116 | Itga10 | −3.13415 | Zfp91Cntf | −7.85445 |
| Ankdd1b | −2.83758 | Emc9 | −3.18443 | Gm20604 | −11.0583 |
| Atp8b4 | −2.83758 | D6Ertd527e | −3.23872 | Rsc1a1 | −12.2259 |
| Zfp712 | −2.83758 | Dmrta2 | −3.28554 | | |
| Mterf1a | −2.87286 | Gm14827 | −3.33089 | | |
| Sec1 | −2.90629 | Lrrc51 | −3.86552 | | |
| Tmem169 | −2.96499 | Jmjd7-pla2g4b | −4.26272 | | |

REFERENCES

Afgan, E., Baker, D., van den Beek, M., Blankenberg, D., Bouvier, D., Cech, M., Chilton, J., Clements, D., Coraor, N., Eberhard, C., et al. (2016). The Galaxy platform for accessible, reproducible and collaborative biomedical analyses: 2016 update. Nucleic Acids Res.

Allen, T. A., Von Kaenel, S., Goodrich, J. A., and Kugel, J. F. (2004). The SINE-encoded mouse B2 RNA represses mRNA transcription in response to heat shock. Nat Struct Mol Biol 11, 816-821.

Bachvarova, R. (1988). Small B2 RNAs in mouse oocytes, embryos, and somatic tissues. Developmental biology 130, 513-523.

Basenko, E. Y., Sasaki, T., Ji, L., Prybol, C. J., Burckhardt, R. M., Schmitz, R. J., and Lewis, Z. A. (2015). Genome-wide redistribution of H3K27me3 is linked to genotoxic stress and defective growth. Proc Natl Acad Sci USA 112, E6339-6348.

Bourque, G., Leong, B., Vega, V. B., Chen, X., Lee, Y. L., Srinivasan, K. G., Chew, J. L., Ruan, Y., Wei, C. L., Ng, H. H., et al. (2008). Evolution of the mammalian transcription factor binding repertoire via transposable elements. Genome Res 18, 1752-1762.

Brown, S. A., Imbalzano, A. N., and Kingston, R. E. (1996). Activator-dependent regulation of transcriptional pausing on nucleosomal templates. Genes Dev 10, 1479-1490.

Chircop, M., and Speidel, D. (2014). Cellular stress responses in cancer and cancer therapy. Frontiers in oncology 4, 304.

Cifuentes-Rojas, C., Hernandez, A. J., Sarma, K., and Lee, J. T. (2014). Regulatory interactions between RNA and polycomb repressive complex 2. Mol Cell 55, 171-185.

Consortium, E. P., Birney, E., Stamatoyannopoulos, J. A., Dutta, A., Guigo, R., Gingeras, T. R., Margulies, E. H., Weng, Z., Snyder, M., Dermitzakis, E. T., et al. (2007). Identification and analysis of functional elements in 1% of the human genome by the ENCODE pilot project. Nature 447, 799-816.

Daniels, G. R., and Deininger, P. L. (1985). Repeat sequence families derived from mammalian tRNA genes. Nature 317, 819-822.

Davidovich, C., Wang, X., Cifuentes-Rojas, C., Goodrich, K. J., Gooding, A. R., Lee, J. T., and Cech, T. R. (2015). Toward a consensus on the binding specificity and promiscuity of PRC2 for RNA. Mol Cell 57, 552-558.

Davidovich, C., Zheng, L., Goodrich, K. J., and Cech, T. R. (2013). Promiscuous RNA binding by Polycomb repressive complex 2. Nat Struct Mol Biol 20, 1250-1257.

de Koning, A. P., Gu, W., Castoe, T. A., Batzer, M. A., and Pollock, D. D. (2011). Repetitive elements may comprise over two-thirds of the human genome. PLoS Genet 7, e1002384.

de Nadal, E., Ammerer, G., and Posas, F. (2011). Controlling gene expression in response to stress. Nature reviews Genetics 12, 833-845.

Down, T. A., and Hubbard, T. J. (2002). Computational detection and location of transcription start sites in mammalian genomic DNA. Genome Res 12, 458-461.

Espinoza, C. A., Allen, T. A., Hieb, A. R., Kugel, J. F., and Goodrich, J. A. (2004). B2 RNA binds directly to RNA polymerase II to repress transcript synthesis. Nat Struct Mol Biol 11, 822-829.

Espinoza, C. A., Goodrich, J. A., and Kugel, J. F. (2007). Characterization of the structure, function, and mechanism of B2 RNA, an ncRNA repressor of RNA polymerase II transcription. RNA 13, 583-596.

Ferrigno, O., Virolle, T., Djabari, Z., Ortonne, J. P., White, R. J., and Aberdam, D. (2001). Transposable B2 SINE elements can provide mobile RNA polymerase II promoters. Nature genetics 28, 77-81.

Fornace, A. J., Jr., and Mitchell, J. B. (1986). Induction of B2 RNA polymerase III transcription by heat shock: enrichment for heat shock induced sequences in rodent cells by hybridization subtraction. Nucleic Acids Res 14, 5793-5811.

Gall, J. G. (1981). Chromosome structure and the C-value paradox. J Cell Biol 91, 3s-14s.

Hasties, N. (1989). Highly repeated DNA families in the genome of *Mus musculus*. In Genetic Variants and Strains of the Laboratory Mouse (Oxford: Oxford University Press).

Huang, W., Loganantharaj, R., Schroeder, B., Fargo, D., and Li, L. (2013). PAVIS: a tool for Peak Annotation and Visualization. Bioinformatics 29, 3097-3099.

Kaczkowski, B., Tanaka, Y., Kawaji, H., Sandelin, A., Andersson, R., Itoh, M., Lassmann, T., Hayashizaki, Y., Carninci, P., Forrest, A. R., et al. (2016). Transcriptome Analysis of Recurrently Deregulated Genes across Multiple Cancers Identifies New Pan-Cancer Biomarkers. Cancer research 76, 216-226.

Kaneko, H., Dridi, S., Tarallo, V., Gelfand, B. D., Fowler, B. J., Cho, W. G., Kleinman, M. E., Ponicsan, S. L., Hauswirth, W. W., Chiodo, V. A., et al. (2011). DICER1 deficit induces Alu RNA toxicity in age-related macular degeneration. Nature 471, 325-330.

Kaneko, S., Son, J., Shen, S. S., Reinberg, D., and Bonasio, R. (2013). PRC2 binds active promoters and contacts nascent RNAs in embryonic stem cells. Nat Struct Mol Biol 20, 1258-1264.

Kapranov, P., Willingham, A. T., and Gingeras, T. R. (2007). Genome-wide transcription and the implications for genomic organization. Nature reviews Genetics 8, 413-423.

Kleinmanns, J. A., and Schubert, D. (2014). Polycomb and Trithorax group protein-mediated control of stress responses in plants. Biological chemistry 395, 1291-1300.

Kramerov, D. A., Lekakh, I. V., Samarina, O. P., and Ryskov, A. P. (1982). The sequences homologous to major interspersed repeats B1 and B2 of mouse genome are present in mRNA and small cytoplasmic poly(A)+RNA. Nucleic Acids Res 10, 7477-7491.

Kramerov, D. A., and Vassetzky, N. S. (2011). SINEs. Wiley Interdiscip Rev RNA 2, 772-786.

Krayev, A. S., Markusheva, T. V., Kramerov, D. A., Ryskov, A. P., Skryabin, K. G., Bayev, A. A., and Georgiev, G. P. (1982). Ubiquitous transposon-like repeats B1 and B2 of the mouse genome: B2 sequencing. Nucleic Acids Res 10, 7461-7475.

Kung, J. T., Kesner, B., An, J. Y., Ahn, J. Y., Cifuentes-Rojas, C., Colognori, D., Jeon, Y., Szanto, A., del Rosario, B. C., Pinter, S. F., et al. (2015). Locus-specific targeting to the X chromosome revealed by the RNA interactome of CTCF. Mol Cell 57, 361-375.

Kwak, H., Fuda, N.J., Core, L. J., and Lis, J. T. (2013). Precise maps of RNA polymerase reveal how promoters direct initiation and pausing. Science 339, 950-953.

Lawrence, C. B., McDonnell, D. P., and Ramsey, W. J. (1985). Analysis of repetitive sequence elements containing tRNA-like sequences. Nucleic Acids Res 13, 4239-4252.

Lee, J. T., and Bartolomei, M. S. (2013). X-Inactivation, Imprinting, and Long Noncoding RNAs in Health and Disease. Cell 152, 1308-1323.

Li, H., and Durbin, R. (2010). Fast and accurate long-read alignment with Burrows-Wheeler transform. Bioinformatics 26, 589-595.

Li, T., Spearow, J., Rubin, C. M., and Schmid, C. W. (1999). Physiological stresses increase mouse short interspersed element (SINE) RNA expression in vivo. Gene 239, 367-372.

Li, W., Notani, D., and Rosenfeld, M. G. (2016). Enhancers as non-coding RNA transcription units: recent insights and future perspectives. Nature reviews Genetics 17, 207-223.

Lowe, C. B., and Haussler, D. (2012). 29 mammalian genomes reveal novel exaptations of mobile elements for likely regulatory functions in the human genome. PLoS One 7, e43128.

Lunyak, V. V., Prefontaine, G. G., Nunez, E., Cramer, T., Ju, B. G., Ohgi, K. A., Hutt, K., Roy, R., Garcia-Diaz, A., Zhu, X., et al. (2007). Developmentally regulated activation of a SINE B2 repeat as a domain boundary in organogenesis. Science 317, 248-251.

Margueron, R., and Reinberg, D. (2011). The Polycomb complex PRC2 and its mark in life. Nature 469, 343-349.

Mirsky, A. E., Ris H. (1951). The desoxyribonucleic acid content of animal cells and its evolutionary significance. J Gen Physiol 34, 451-462.

Moolhuijzen, P., Kulski, J. K., Dunn, D. S., Schibeci, D., Barrero, R., Gojobori, T., and Bellgard, M. (2010). The transcript repeat element: the human Alu sequence as a component of gene networks influencing cancer. Functional & integrative genomics 10, 307-319.

Pandey, R. R., Mondal, T., Mohammad, F., Enroth, S., Redrup, L., Komorowski, J., Nagano, T., Mancini-DiNardo, D., and Kanduri, C. (2008). Kcnq1ot1 Antisense Noncoding RNA Mediates Lineage-Specific Transcriptional Silencing through Chromatin-Level Regulation. Molecular cell 32, 232-246.

Ponicsan, S. L., Kugel, J. F., and Goodrich, J. A. (2010). Genomic gems: SINE RNAs regulate mRNA production. Curr Opin Genet Dev 20, 149-155.

Ponicsan, S. L., Kugel, J. F., and Goodrich, J. A. (2015). Repression of RNA Polymerase II Transcription by B2 RNA Depends on a Specific Pattern of Structural Regions in the RNA. Noncoding RNA 1, 4-16.

Quinlan, A. R., and Hall, I. M. (2010). BEDTools: a flexible suite of utilities for comparing genomic features. Bioinformatics 26, 841-842.

Rinn, J. L., and Chang, H. Y. (2012). Genome regulation by long noncoding RNAs. Annu Rev Biochem 81, 145-166.

Robinson, J. T., Thorvaldsdottir, H., Winckler, W., Guttman, M., Lander, E. S., Getz, G., and Mesirov, J. P. (2011). Integrative genomics viewer. Nat Biotechnol 29, 24-26.

Siebold, A. P., Banerjee, R., Tie, F., Kiss, D. L., Moskowitz, J., and Harte, P. J. (2010). Polycomb Repressive Complex 2 and Trithorax modulate *Drosophila* longevity and stress resistance. Proc Natl Acad Sci USA 107, 169-174.

Simon, M. D. (2013). Capture hybridization analysis of RNA targets (CHART). Current protocols in molecular biology/edited by Frederick M Ausubel [et al] Chapter 21, Unit 21 25.

Simon, M. D., Pinter, S. F., Fang, R., Sarma, K., Rutenberg-Schoenberg, M., Bowman, S. K., Kesner, B. A., Maier, V. K., Kingston, R. E., and Lee, J. T. (2013). High-resolution Xist binding maps reveal two-step spreading during X-chromosome inactivation. Nature 504, 465-469.

Singh, K., Carey, M., Saragosti, S., and Botchan, M. (1985). Expression of enhanced levels of small RNA polymerase III transcripts encoded by the B2 repeats in simian virus 40-transformed mouse cells. Nature 314, 553-556.

Tarallo, V., Hirano, Y., Gelfand, B. D., Dridi, S., Kerur, N., Kim, Y., Cho, W. G., Kaneko, H., Fowler, B. J., Bogdanovich, S., et al. (2012). DICER1 loss and Alu RNA induce age-related macular degeneration via the NLRP3 inflammasome and MyD88. Cell 149, 847-859.

Tay, Y., Rinn, J., and Pandolfi, P. P. (2014). The multilayered complexity of ceRNA crosstalk and competition. Nature 505, 344-352.

Thomas, C. A. (1971). The genetic organization of chromosomes. Annu Rev Genet 5, 237-256.

Trapnell, C., Pachter, L., and Salzberg, S. L. (2009). TopHat: discovering splice junctions with RNA-Seq. Bioinformatics 25, 1105-1111.

Treangen, T. J., and Salzberg, S. L. (2012). Repetitive DNA and next-generation sequencing: computational challenges and solutions. Nature reviews Genetics 13, 36-46.

Xu, S., Grullon, S., Ge, K., and Peng, W. (2014). Spatial clustering for identification of ChIP-enriched regions (SICER) to map regions of histone methylation patterns in embryonic stem cells. Methods Mol Biol 1150, 97-111.

Yakovchuk, P., Goodrich, J. A., and Kugel, J. F. (2009). B2 RNA and Alu RNA repress transcription by disrupting contacts between RNA polymerase II and promoter DNA within assembled complexes. Proc Natl Acad Sci USA 106, 5569-5574.

Zhao, J., Ohsumi, T. K., Kung, J. T., Ogawa, Y., Grau, D. J., Sarma, K., Song, J. J., Kingston, R. E., Borowsky, M., and Lee, J. T. (2010). Genome-wide identification of polycomb-associated RNAs by RIP-seq. Mol Cell 40, 939-953.

Zhao, J., Sun, B. K., Erwin, J. A., Song, J. J., and Lee, J. T. (2008). Polycomb proteins targeted by a short repeat RNA to the mouse X chromosome. Science 322, 750-756.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of enhancing health or viability of a cell, the method comprising contacting the cell with an antisense oligonucleotide (ASO) comprising at least one locked nucleotide that binds to an Alu RNA and promotes cleavage of the Alu RNA, wherein the ASO targets a cut region of the Alu RNA.

2. The method of claim 1, wherein the ASO is a gapmer or mixmer.

3. The method of claim 1, wherein the cell is in a subject who suffers from an environmental stress.

4. The method of claim 3, wherein the environmental stress is any one of infection, thermal, heat, cold, radiation, hypoxic stress, or chemical exposure.

5. The method of claim 1, wherein the cell is in a subject who suffers from an inflammatory or autoimmune disorder affecting the cell.

6. The method of claim 1, wherein the cell is in a subject who suffers from a degenerative disorder affecting the cell.

7. The method of claim 6, wherein the degenerative disorder is macular degeneration.

8. The method of claim 1, wherein the cut region of the Alu RNA comprises nucleotides within the position range 49-52 from the start of the Alu.

9. A method of enhancing health or viability of a cell, the method comprising contacting the cell with an antisense oligonucleotide (ASO) comprising at least one locked nucleotide that binds to an Alu or B2 RNA and promotes cleavage of the Alu or B2 RNA, wherein the ASO targets a cut site of the Alu or B2 RNA.

10. The method of claim 9, wherein the ASO is a gapmer or mixmer.

11. The method of claim 9, wherein the cell is in a subject who suffers from an environmental stress.

12. The method of claim 11, wherein the environmental stress is any one of infection, thermal, heat, cold, radiation, hypoxic stress, or chemical exposure.

13. The method of claim 9, wherein the cell is in a subject who suffers from an inflammatory or autoimmune disorder affecting the cell.

14. The method of claim 9, wherein the cell is in a subject who suffers from a degenerative disorder affecting the cell.

15. The method of claim 14, wherein the degenerative disorder is macular degeneration.

16. The method of claim 9, wherein the cut site of the Alu RNA comprises a nucleotide at position 49-52 from the start of the Alu.

17. The method of claim 9, wherein the cut site of the B2 RNA comprises a nucleotide at position 33, 77, or 98 from the start of the B2.

18. The method of claim 9, wherein the cut site of the B2 RNA comprises a nucleotide at position 33 from the start of the B2.

19. The method of claim 9, wherein the cut site of the B2 RNA comprises a nucleotide at position 77 from the start of the B2.

20. The method of claim 9, wherein the cut site of the B2 RNA comprises a nucleotide at position 98 from the start of the B2.

* * * * *

SEQUENCE LISTING

<160> NUMBER OF SEQ ID NOS: 72

<210> SEQ ID NO 1
<211> LENGTH: 290
<212> TYPE: DNA
<213> ORGANISM: homo sapiens

<400> SEQUENCE: 1

```
ggccgggcgc ggtggctcac gcctgtaatc ccagcacttt gggaggccga ggcgggcgga      60
tcacgaggtc aggagatcga gaccatcctg gccaacacgg tgaaacccg tctctactaa      120 aaatacaaaa attagccggg cgtggtggcg ggcgcctgta gtcccagcta ctcgggaggc     180
tgaggcagga gaatggcgtg aacccgggag gcggagcttg cagtgagccg agatcgcgcc    240
actgcactcc agcctgggcg acagagcgag actccgtctc aaaaaaaaaa                290

<210> SEQ ID NO 2
<211> LENGTH: 312
<212> TYPE: DNA
<213> ORGANISM: homo sapiens

<400> SEQUENCE: 2
ggccgggcgc ggtggctcac gcctgtaatc ccagcacttt gggaggccga ggcgggagga     60
ttgcttgagc ccaggagttc gagaccagcc tgggcaacat agcgagaccc cgtctctaca   120
aaaaatacaa aaattagccg gcgtggtgg cgcgcgcctg tagtcccagc tactcgggag    180
gctgaggcag gaggatcgct tgagcccagg agttcgaggc tgcagtgagc tatgatcgcg   240
ccactgcact ccagcctggg cgacagagcg agaccctgtc tcaaaaaaaa aaaaaaaaaa   300
aaaaaaaaaa aa                                                        312

<210> SEQ ID NO 3
<211> LENGTH: 290
<212> TYPE: DNA
<213> ORGANISM: homo sapiens
<220> FEATURE:
<221> NAME/KEY: misc_feature
<222> LOCATION: (259)..(259)
<223> OTHER INFORMATION: n is a, c, g, or t

<400> SEQUENCE: 3
gccgggcgcg gtggctcacg cctgtaatcc cagcactgtg ggaggctgag gcgggaggat     60
tgctcgagct caggagttcg aggctcgtct gagcgagagt gagaccccga ctcatggaaa   120
aaaatggaaa aacccagccg ggcgccgcgg cgagcgcctg taatcccagc ggcttcggag   180
gctgaggcag caggatgccc acaagccgga gtctgaggtt gcagtgagct acgacgccac   240
tgcactctgc tcagggcana gggtagaact ctgtctcgac aaaaaaaaaa                290

<210> SEQ ID NO 4
<211> LENGTH: 299
<212> TYPE: DNA
<213> ORGANISM: homo sapiens

<400> SEQUENCE: 4
agccgggctc ggtggctcag cctgtaatcc cagcactttg ggaggctgag gtgagtggat     60
tgcctgagcc cgcgggttcg agaccgcct gggcaacttg gcgagacctc atctctacaa    120
taaatcaaaa aattagccgg gcgtggtagc gcgcgcctgt agttccagct acttggaagg   180
ctgaggcgga aggatcgccg gagcccagca ggtcgaggct gcggtggccg ggagcggcca   240
ctgcactcca gtctgggcga cagagtgaga ctccaactca aaaaaaaaaa aaaaaaaaa    299

<210> SEQ ID NO 5
<211> LENGTH: 237
<212> TYPE: DNA
<213> ORGANISM: homo sapiens

<400> SEQUENCE: 5
```

```
ggccgggcgc ggtggctcac gcctgtaatc ctagcactct ggaggccga ggcgggtgga      60 ttgcttgagc tcacgagttc gagaccagcc tgagcaaaag cgagacccg tctctactaa    120 aaatagaaaa actgaggcaa gaggatcgct tgagcccaag agttggaggt tgctgtgagc   180
tatgacgcca cggcactcta cccagggcga cagcttgaga ctctgtctca aaaaaaa      237

<210> SEQ ID NO 6
<211> LENGTH: 298
<212> TYPE: DNA
<213> ORGANISM: homo sapiens

<400> SEQUENCE: 6
ggccgggcgc ggtggctcac gcctgtaatc ccagcacttt gggaggccga ggcgggagga    60
ttgcttgagc ccaggagttc gagaccagcc tgggcaacat agcgagacct cgtctctaca   120
aaaaattaaa aaattagccg ggcgtggtgg cgcgcgcctg tagtcccagc tactcgggag   180
gctgaggcgg gaggatcgcc tgagcccagg aggtcgaggc tgcggtgagc cgtgatcgtg   240
ccactgcact ccagcctggg cgacagagtg agaccccgac tcaaaaaaaa aaaaaaaa    298

<210> SEQ ID NO 7
<211> LENGTH: 298
<212> TYPE: DNA
<213> ORGANISM: homo sapiens
<220> FEATURE:
<221> NAME/KEY: misc_feature
<222> LOCATION: (262)..(262)
<223> OTHER INFORMATION: n is a, c, g, or t

<400> SEQUENCE: 7
ggccgggcgc agtggctcag cctgtaatcc cagcactttg ggaggccgag gcgagaggat    60
tgcctgagcc cggggttcg agaccagcct gggcaacttg gtgagacctt gtctctacaa   120
taaataaaaa attagccagg cgtggtagcg cgcgcctgta gttccagcta cttggaaggc   180
tgaggcggaa ggatcgcctg ggcccagcag gttgggctg cggtggccgt gagcatgcca   240
ctgcactacg gcatgggggg angagactcc aaatcttaaa aaagtctgaa aggaaga     298

<210> SEQ ID NO 8
<211> LENGTH: 283
<212> TYPE: DNA
<213> ORGANISM: homo sapiens

<400> SEQUENCE: 8
ggccgggcgc ggtggctcac gcctgtaatc ccagcacttt gggaggccga ggcgggagga    60
tcacttgagc ccaggagttc gagaccagcc tgggcaacat ggtgaaaccc cgtctctaca   120
aaaaatacaa aaattagccg ggcgtggtgg cgcgcgcctg tagtcccagc tactcgggag   180
gctgaggcag gaggatcgct tgagcccggg aggtcgaggc tgcagtgagc cgtgatcgcg   240
ccactgcact ccagcctggg cgacagagcg agaccctgtc tca                     283

<210> SEQ ID NO 9
<211> LENGTH: 283
<212> TYPE: DNA
<213> ORGANISM: homo sapiens

<400> SEQUENCE: 9
ggccgggcgc ggtggctcac gcctgtaatc ccagcacttt gggaggccga ggcgggagga    60
ttgcttgagc ccaggagttc gagaccagcc tgggcaacat agcgagaccc cgtctctaca   120
aaaaatacaa aaattagccg ggcgtggtgg cgcgcgcctg tagtcccagc tactcgggag   180
```

```
gctgaggcag gaggatcgct tgagcccagg agttcgaggc tgcagtgagc tatgatcgcg    240
ccactgcact ccagcctggg cgacagagcg agaccctgtc tca                      283

<210> SEQ ID NO 10
<211> LENGTH: 312
<212> TYPE: DNA
<213> ORGANISM: homo sapiens

<400> SEQUENCE: 10 ggcccgggcgc ggtggctcac gcctgtaatc ccagcacttt gggaggccga ggcgggagga    60
tcgcttgagg ccaggagttc gagaccagcc tgggcaacat agcgagaccc cgtctctaca   120
aaaaatataa aaattagccg ggcgtggtgg cgcgcgcctg tagtcccagc tactcgggag   180
gctgaggcgg gaggatcgct tgagcccagg agttcgaggc tgcagtgagc tatgatcgcg   240
ccactgcact ccagcctggg cgacagagcg agaccctgtc tcaaaaaaaa aaaaaaaaaa   300
aaaaaaaaaa aa                                                       312

<210> SEQ ID NO 11
<211> LENGTH: 312
<212> TYPE: DNA
<213> ORGANISM: homo sapiens
<220> FEATURE:
<221> NAME/KEY: misc_feature
<222> LOCATION: (127)..(127)
<223> OTHER INFORMATION: n is a, c, g, or t

<400> SEQUENCE: 11 ggcccgggcgc ggtggctcac gcctgtaatc ccagcacttt gggaggccga ggcgggagga    60
tcgcttgagg ccaggagttc gagaccagcc tgggcaacat agcgagaccc cgtctctaca   120
aaaaatntaa aaattagccg ggcgtggtgg cgcgcgcctg tagtcctagc tactcgggag   180
gctgaggcag gaggatcgct tgagcccagg agttcgaggt tacagtgagc tatgatcgcg   240
ccactgcact ccagcctggg cgacagagcg agaccctgtc tcaaaaaaaa aaaaaaaaaa   300
aaaaaaaaaa aa                                                       312

<210> SEQ ID NO 12
<211> LENGTH: 329
<212> TYPE: DNA
<213> ORGANISM: homo sapiens

<400> SEQUENCE: 12 ggcccgggcgc ggtggctcac gcctgtaatc ctagcactct gggaggccga ggcgggagga    60
tcgctcgagg tcaggagttc gaaaccagcc tgagcaagag cgagacccccg tctctactaa   120 aaatagaaag aaattaattg gccaactaaa aatatataga aaaaattagc cgggcatggt   180
ggcgcatgcc tgtagtccca gctactcggg aggctgaggc aggaggatcg cttgagccca   240
ggagtttgag gttgctgtga gctaggctga cgccacggca ctctagcccg ggcaacagag   300
tgagactctg tctcaaaaaa aaaaaaaaa                                      329

<210> SEQ ID NO 13
<211> LENGTH: 310
<212> TYPE: DNA
<213> ORGANISM: homo sapiens

<400> SEQUENCE: 13 ggcccgggcgc ggtggctcaa gcctgtaatc ccagcacttt gggaggccga gacgggcgga    60
```

```
tcacgaggtc aggagatcga gaccatcctg gctaacacgg tgaaacccccg tctctactaa    120 aaaatacaaa aaactagccg ggcgaggtgg cgggcgcctg tagtcccagc tactcgggag    180
gctgaggcag gagaatggcg tgaacccggg aggcggagct tgcagtgagc tgagatccgg    240
ccactgcact ccagcctggg cgacagagcg agactccgtc tcaaaaaaaa aaaaaaaaaa    300
aaaaaaaaaa                                                           310
```

<210> SEQ ID NO 14
<211> LENGTH: 297
<212> TYPE: DNA
<213> ORGANISM: homo sapiens

<400> SEQUENCE: 14

```
ggccgggcgc ggtggctcac gcctgtaatc ccagcacttt gggaggccga ggcgggcgga     60
tcacaaggtc aggagatcga gaccacgtg aaacccccgtc tctactaaaa atacaaaaaa    120
ttagccgggc gcggttgtgg gcgcctgtag tcccagctac tcgggaggct gaggcaggag    180
aatggcgtga acccgggagg cggagcttgc agtgagccga gatcgcgcca ctgcactcca    240
gcctgggcga cagagcgaga ctccgtctca aaaaaaaaaa aaaaaaaaaa aaaaaaa      297
```

<210> SEQ ID NO 15
<211> LENGTH: 297
<212> TYPE: DNA
<213> ORGANISM: homo sapiens

<400> SEQUENCE: 15

```
ggccgggcgc ggtggctcaa gcctgtaatc ccagcacttt gggaggccga ggcgggcgga     60
tcacaaggtc aggagatcga gaccacagtg aaacccccgtc tctactaaaa atacaaaaaa   120
ttagccgggc gcggtggcgg gcgcctgtag tcccagctac tcaggaggct gaggcaggag    180
aatggcggga acccgggagg cggagcttgc agtgagccga gatcgcgcca ctgcactcca    240
gcctgggcaa cagcgtgaga ctccgtctca aaaaaaaaaa aaaaaaaaaa aaaaaaa      297
```

<210> SEQ ID NO 16
<211> LENGTH: 280
<212> TYPE: DNA
<213> ORGANISM: homo sapiens

<400> SEQUENCE: 16

```
ggccgggcgc ggtggctcac gcctgtaatc ccagcacttt gggaggccga ggcgggcgga     60
tcacgaggtc aagagatcga gaccatcctg gccaacatgg tgaaacccccg tctctactaa   120 aaatacaaaa attagctggg cgtggtggcg cgcgcctgta gtcccagcta ctcgggaggc    180
tgaggcagga gaatcgcttg aacccgggag gcggaggttg cagtgagccg agatcgcgcc    240
actgcactcc agcctggcga cagagcgaga ctccgtctca                         280
```

<210> SEQ ID NO 17
<211> LENGTH: 312
<212> TYPE: DNA
<213> ORGANISM: homo sapiens

<400> SEQUENCE: 17

```
ggccgggcgc ggtggctcac gcctgtaatc ccagcacttt gggaggccga ggcgggcgga     60
tcacgaggtc aggagatcga gaccatcctg gccaacatgg tgaaacccccg tctctactaa   120 aaatacaaaa attagctggg cgtggtggcg cgtgcctgta atcccagcta ctcgggaggc    180
tgaggcagga gaatcgcttg aaccagggag tcggaggttg cagtgagccg agatcgcgcc    240
```

```
actgcactcc agcctggcga cagagcgaga ctccgtctca aaaaaaaaaa aaaaaaaaaa    300
aaaaaaaaaa aa                                                       312

<210> SEQ ID NO 18
<211> LENGTH: 312
<212> TYPE: DNA
<213> ORGANISM: homo sapiens

<400> SEQUENCE: 18
ggccgggcgc ggtggctcac gcctgtaatc ccagcacttt gggaggccga ggcgggcgga    60
tcacgaggtc aggagatcga gaccatcctg gctaacacgg tgaaacccccg tctctactaa   120 aaatacaaaa aattagccgg gcgtggtggc acgcgcctgt agtcccagct actcgggagg   180
ctgaggcagg agaatcgctt gaacccggga ggcggaggtt gcagtgagcc gagatcgcgc   240
cactgcactc cagcctgggc gacagagcga gactccgtct caaaaaaaaa aaaaaaaaaa   300
aaaaaaaaaa aa                                                       312

<210> SEQ ID NO 19
<211> LENGTH: 281
<212> TYPE: DNA
<213> ORGANISM: homo sapiens

<400> SEQUENCE: 19
ggccgggcgc ggtggctcac gcctgtaatc ccagcacttt gggaggccga ggcgggcgga    60
tcacgaggtc aggagttcga gaccagcctg gccaacatgg tgaaacccccg tctctactaa   120 aaatacaaaa attagccggg cgtggtggcg cgcgcctgta atcccagcta ctcgggaggc   180
tgaggcagga gaatcgcttg aacccgggag gcggaggttg cagtgagccg agatcgcgcc   240
actgcactcc agcctgggcg acagagcgag actccgtctc a                       281

<210> SEQ ID NO 20
<211> LENGTH: 280
<212> TYPE: DNA
<213> ORGANISM: homo sapiens

<400> SEQUENCE: 20
rgccgggcgc ggtggctcac gcctgtaatc ccagcacttt gggaggccga ggcgggcgga    60
tcacgaggtc aggagttcga gaccagcctg gccaagatgg tgaaacccccg tctctactaa   120 aaatacaaaa attagccggg cgtggtggcg cgggcctgta atcccagcta ctcgggaggc   180
tgaggcagag aatcgcttga acccgggagg cggaggttgc agtgagccga gatcgcgcca   240
ctgcactcca gcctgggcga cagagcgaga ctccgtctca                         280

<210> SEQ ID NO 21
<211> LENGTH: 312
<212> TYPE: DNA
<213> ORGANISM: homo sapiens

<400> SEQUENCE: 21
ggccgggcgc ggtggctcac gcctgtaatc ccagcacttt gggaggccga ggcgggtgga    60
tcacgaggtc aggagttcga gaccagcctg gccaagatgg tgaaacccccg tctctactaa   120 aaatacaaaa attagccggg cgcggtggcg ggcgcctgta atcccagcta ctcgggaggc   180
tgaggcagga gaatcgcttg aacccgggag gcggaggttg cagtgagccg agatcgcgcc   240
actgcactcc agcctgggcg acagagcgag actccgtctc aaaaaaaaaa aaaaaaaaaa   300
```
aaaaaaaaaa aa                                                                  312

<210> SEQ ID NO 22
<211> LENGTH: 312
<212> TYPE: DNA
<213> ORGANISM: homo sapiens

<400> SEQUENCE: 22
ggccgggcgc ggtggctcac gcctgtaatc ccagcacttt gggaggccga ggcgggtgga      60
tcacgaggtc aggagttcaa gaccagcctg gccaagatgg tgaaaccccg tctctactaa     120
aaatacaaaa attagccggg cgtggtggcg ggcgcctgta atcccagcta ctcgggaggc     180
tgaggcagag aattgcttga acccggggagg cggaggttgc agtgagccga gatcgcgcca    240
ctgcactcca gcctgggcga cagagcgaga ctccgtctca aaaaaaaaaa aaaaaaaaa     300 aaaaaaaaaa aa                                                                  312

<210> SEQ ID NO 23
<211> LENGTH: 284
<212> TYPE: DNA
<213> ORGANISM: homo sapiens

<400> SEQUENCE: 23
ggccgggcgc ggtggctcac gcctgtaatc ccagcacttt gggaggccga ggcgggcgga      60
tcacctgagg tcgggagttc gagaccagcc tgaccaacat ggagaaaccc cgtctctact     120
aaaaatacaa aaattagccg ggcgtggtgg cgcatgcctg taatcccagc tactcgggag     180
gctgaggcag agaatcgct tgaacccggg aggcggaggt tgcggtgagc cgagatcgcg     240
ccattgcact ccagcctggg caacaagagc gaaactccgt ctca                          284

<210> SEQ ID NO 24
<211> LENGTH: 284
<212> TYPE: DNA
<213> ORGANISM: homo sapiens

<400> SEQUENCE: 24
ggccgggcgc ggtggctcac gcctgtaatc ccagcacttt gggaggccga ggcgggtgga      60
tcacctgagg tcaggagttc gagaccagcc tggccaacat ggtgaaaccc cgtctctact     120
aaaaatacaa aaattagccg ggcgtggtgg cgggcgcctg taatcccagc tactcgggag     180
gctgaggcag gagaatcgct tgaacccggg aggcggaggt tgcagtgagc cgagatcgcg    240
ccactgcact ccagcctggg caacaagagc gaaactccgt ctca                          284

<210> SEQ ID NO 25
<211> LENGTH: 312
<212> TYPE: DNA
<213> ORGANISM: homo sapiens

<400> SEQUENCE: 25
ggccgggcgc ggtggctcac gcctgtaatc ccagcacttt gggaggccga ggcgggtgga      60
tcacctgagg tcaggagttc tagaccagcc tggccaacat ggtgaaaccc cgtctctact     120
aaaaatacaa aaattagccg ggcgtggtgg caggcgcctg taatcccagc tactcggggg    180
gccgaggcag gagaatcgct tgaacccggg aggcggaggt tgcagtgagc cgagatcgcg    240
ccatcgcact ccagcctggg ggacaagagc gagacttcgt ctcaaaaaaa aaaaaaaaaa    300
aaaaaaaaaa aa                                                                  312

```
<210> SEQ ID NO 26
<211> LENGTH: 312
<212> TYPE: DNA
<213> ORGANISM: homo sapiens

<400> SEQUENCE: 26
ggccgggcgc ggtggctcac gcctgtaatc ccagcacttt gggaggccga ggcgggcgga      60
tcacctgagg tcaggagttc gagaccagcc tggccaacat ggtgaaaccc cgtctctact     120
aaaaatacaa aaattagccg gcgtggtgg cgggcgcctg taatcccagc tactcgggag      180
gctgaggcag gagaatcgct tgaacccggg aggcggaggt tgcagtgagc cgagatcgcg     240
ccattgcact ccagcctggg cgacaagagc gaaactccgt ctcaaaaaaa aaaaaaaaa     300 aaaaaaaaaa aa                                                         312

<210> SEQ ID NO 27
<211> LENGTH: 312
<212> TYPE: DNA
<213> ORGANISM: homo sapiens

<400> SEQUENCE: 27
ggccgggcgc ggtggctcac gcctgtaatc ccagcacttt gggaggccga ggcgggcgga      60
tcactgaggt caggagttcg agaccagcct ggccaacatg gtgaaacccc gtctctacta     120
aaaatacaaa aattagccgg gcgtggtggc gggcgcctgt aatcccagct actcgggagg     180
ctgaggcagg agaatcgctt gaaaccggaa ggcggaggtt gcagtgagcc gagatcgcgc     240
cactgcactc cagcctgggc aacaagagcg aaactccgtc tcaaaaaaaa aaaaaaaaaa     300
aaaaaaaaaa aa                                                         312

<210> SEQ ID NO 28
<211> LENGTH: 283
<212> TYPE: DNA
<213> ORGANISM: homo sapiens

<400> SEQUENCE: 28
ggccgggcgc ggtggctcac gcctgtaatc ccagcacttt gggaggccga ggcgggcgga      60
tcacctgagg tcaggagttc gagaccagcc tggccaacat ggtgaaaccc cgtctctact     120
aaaaatacaa aaattagccg gcgtggtgg cgcgcgcctg taatcccagc tactcgggag      180
gctgaggcag gagaatcgct tgaacccggg aggcggaggt tgcagtgagc cgagatcgcg     240
ccactgcact ccagcctggg cgacagagcg agactccgtc tca                       283

<210> SEQ ID NO 29
<211> LENGTH: 312
<212> TYPE: DNA
<213> ORGANISM: homo sapiens

<400> SEQUENCE: 29
ggccgggcgc ggtggctcac gcctgtaatc ccagcacttt gggaggccga ggcgggcgga      60
tcacctgagg tcaggagttc gagaccagcc tggccaacat ggtgaaaccc cgtctctact     120
aaaaatacaa aaattagccg gcgtggtgg cgggcgcctg taatcccagc tactcgggag      180
gctgaggcag gagaatcgct tgaacccggg aggcggaggt tgcagtgagc cgagatcgcg     240
ccactgcact ccagcctggg cgacagagcg agactccgtc tcaaaaaaaa aaaaaaaaaa     300
aaaaaaaaaa aa                                                         312

<210> SEQ ID NO 30
```

<211> LENGTH: 312
<212> TYPE: DNA
<213> ORGANISM: homo sapiens

<400> SEQUENCE: 30

```
ggccgggcgc ggtggctcac gcctgtaatc ccagcacttt gggaggccga ggcgggcgga      60
tcacgaggtc aggagttcga ccagcctg gccaacatgg tgaaacccg tctctactaa        120
aaatacaaaa aattagccgg gcgtggtggc gcgcgcctgt agtcccagct actcgggagg    180
ctgaggcagg agaatcgctt gaacccggga ggcggaggtt gcagtgagcc gagatcgcgc    240
cactgcactc cagcctgggc gacagagcga gactccgtct caaaaaaaaa aaaaaaaaaa    300
aaaaaaaaaa aa                                                        312
```

<210> SEQ ID NO 31
<211> LENGTH: 312
<212> TYPE: DNA
<213> ORGANISM: homo sapiens

<400> SEQUENCE: 31

```
ggccgggcgc ggtggctcac gcctgtaatc ccagcacttt gggaggccga ggcgggcgga      60
tcactgaggt caggagttcg agaccagcct ggccaatatg gtgaaacccc gtctctacta    120
aaaatacaaa aattagccgg gcgtggtggc gcgcgcctgt agtcccagct actcgggagg    180
ctgaggcaga agaatcgctt gaacccggga ggcggaggtt gcagtgagcc gagatcgcgc    240
cactgcactc cagcctgggc gacagagcga gactccgtct caaaaaaaaa aaaaaaaaaa    300
aaaaaaaaaa aa                                                        312
```

<210> SEQ ID NO 32
<211> LENGTH: 283
<212> TYPE: DNA
<213> ORGANISM: homo sapiens

<400> SEQUENCE: 32

```
ggcgggcgc ggtggctcac gcctgtaatc ccagcacttt gggaggccga ggcgggcgga       60
tcacttgagg tcaggagttc gagaccagcc tggccaacat ggtgaaaccc cgtctctact    120
aaaaatacaa aaattagccg ggcgtggtgg cgcgcgcctg taatcccagc tactcgggag    180
gctgaggcag gagaatcgct tgaacccggg aggcggaggt tgcagtgagc cgagatcgcg    240
ccactgcact ccagcctggg cgacagagcg agactccgtc tca                      283
```

<210> SEQ ID NO 33
<211> LENGTH: 312
<212> TYPE: DNA
<213> ORGANISM: homo sapiens

<400> SEQUENCE: 33

```
ggccgggcgc ggtggctcac gcctgtaatc ccagcacttt gggaggccga ggcgggcgga      60
tcacttgagg ccaggagttc gagaccagcc tggccaacat ggcaaaaccc cgtctctact    120
aaaaatacaa aaattagccg ggcgtggtgg cgcgcgcctg taatcccagc tactcgggag    180
gctgaggcac gagaatcgct tgaacccggg aggcggaggt tgcagtgagc cgagatcgcg    240
ccactgcact ccagcctggg cgacagagcg agactctgtc tcaaaaaaaa aaaaaaaaaa    300
aaaaaaaaaa aa                                                        312
```

<210> SEQ ID NO 34
<211> LENGTH: 282

```
<212> TYPE: DNA
<213> ORGANISM: homo sapiens

<400> SEQUENCE: 34
ggccgggcgc ggtggctcac gcctgtaatc ccagcacttt gggaggccga ggcgggcgga      60
tcacgaggtc aggagatcga gaccatcctg gctaacacgg tgaaacccccg tctctactaa    120
aaatacaaaa aattagccgg gcgtggtggc gggcgcctgt agtcccagct actcgggagg    180
ctgaggcagg agaatggcgt gaacccggga ggcggagctt gcagtgagcc gagatcgcgc    240
cactgcactc cagcctgggc gacagagcga gactccgtct ca                        282

<210> SEQ ID NO 35
<211> LENGTH: 282
<212> TYPE: DNA
<213> ORGANISM: homo sapiens

<400> SEQUENCE: 35
ggccgggcgc ggtggctcac gcctgtaatc ccagcacttt gggaggccga ggcgggcgga      60
tcacgaggtc aggagatcga gaccatcctg gctaacacgg tgaaacccccg tctctactaa    120
aaatacaaaa aattagccgg gcgtggtggc gggcgcctgt agtcccagct actcgggagg    180
ctgaggcagg agaatggcgt gaacccggga ggcggagctt gcagtgagcc gagatcccgc    240
cactgcactc cagcctgggc gacagagcga gactccgtct ca                        282

<210> SEQ ID NO 36
<211> LENGTH: 282
<212> TYPE: DNA
<213> ORGANISM: homo sapiens

<400> SEQUENCE: 36
ggccgggcgc ggtggctcac gcctgtaatc ccagcacttt gggaggccga ggcgggcgga      60
tcacgaggtc aggagatcga gaccatcccg gctaaaacgg tgaaacccccg tctctactaa    120
aaatacaaaa aattagccgg gcgtagtggc gggcgcctgt agtcccagct acttgggagg    180
ctgaggcagg agaatggcgt gaacccggga ggcggagctt gcagtgagcc gagatcgcgc    240
cactgcactc cagcctgggc gacagagcga gactccgtct ca                        282

<210> SEQ ID NO 37
<211> LENGTH: 282
<212> TYPE: DNA
<213> ORGANISM: homo sapiens

<400> SEQUENCE: 37
ggccgggcgc ggtggctcac gcctgtaatc ccagcacttt gggaggccga ggcgggcgga      60
tcacgaggtc aggagatcga gaccatcccg gctaaaacgg tgaaacccccg tctctactaa    120
aaatacaaaa aattagccgg gcgtagtggc gggcgcctgt agtcccagct acttgggagg    180
ctgaggcagg agaatggcgt gaacccggga ggcggagctt gcagtgagcc gagatcccgc    240
cactgcactc cagcctgggc gacagagcga gactccgtct ca                        282

<210> SEQ ID NO 38
<211> LENGTH: 281
<212> TYPE: DNA
<213> ORGANISM: homo sapiens

<400> SEQUENCE: 38
ggccgggcgc ggtggctcac gcctgtaatc ccagcacttt gggaggccga ggcgggcgga      60
```

```
tcacgaggtc aggagatcga gaccatcccg gctaaaacgg tgaaacccg tctctactaa    120 aactacaaaa aatagccggg cgtagtggcg ggcgcctgta gtcctagcta cttgggaggc    180
tgaggcagga gaatggcgtg aacccgggag gcggagcttg cagtgagccg agatcccgcc    240
actgcactcc agcctgggcg acagagcgag actccgtctc a                        281

<210> SEQ ID NO 39
<211> LENGTH: 282
<212> TYPE: DNA
<213> ORGANISM: homo sapiens

<400> SEQUENCE: 39
ggccgggcgc ggtggctcac gcctgtaatc ccagcacttt gggaggccga ggcgggtgga    60
tcacgaggtc aggagatcga gaccatcctg gctaacacgg tgaaacccg tctctactaa     120 aaatacaaaa aattagccgg gcgtggtggc gggcgcctgt agtcccagct actcgggagg    180
ctgaggcagg agaatggcgt gaacccggga ggcggagctt gcagtgagcc gagattgcgc    240
cactgcagtc cagcctgggc gacagagcga gactccgtct ca                       282

<210> SEQ ID NO 40
<211> LENGTH: 282
<212> TYPE: DNA
<213> ORGANISM: homo sapiens

<400> SEQUENCE: 40
ggccgggcgc ggtggctcac gcctgtaatc ccagcacttt gggaggccga ggcgggcgga    60
tcacgaggtc aggagatcga gaccatcctg gctaacacgg tgaaacccg tctctactaa     120 aaatacaaaa aattagccgg gcgcggtggc gggcgcctgt agtcccagct actcggagg     180 ctgaggcagg agaatggcgt gaacccggga ggcggagctt gcagtgagcc gagatagcgc    240
cactgcagtc cggcctgggc gaaagagcga gactccgtct ca                       282

<210> SEQ ID NO 41
<211> LENGTH: 289
<212> TYPE: DNA
<213> ORGANISM: homo sapiens

<400> SEQUENCE: 41
ggccgggcgc ggtggctcac gcctgtaatc ccagcacttt gggaggccga ggcgggtgga    60
tcatgaggtc aggagatcga gaccatcctg gctaacaagg tgaaacccg tctctactaa     120 aaatacaaaa aattagccgg gcgcggtggc gggcgcctgt agtcccagct actcgggagg    180
ctgaggcagg agaatggcgt gaacccggga agcggagctt gcagtgagcc gagattgcgc    240
cactgcagtc cgcagtccgg cctgggcgac agagcgagac tccgtctca                289

<210> SEQ ID NO 42
<211> LENGTH: 289
<212> TYPE: DNA
<213> ORGANISM: homo sapiens

<400> SEQUENCE: 42
ggccgggcgc ggtggctcac gcctgtaatc ccagcacttt gggaggccga ggcgggtgga    60
tcatgaggtc aggagatcga gaccatcctg gctaacaagg tgaaacccg tctctactaa     120 aaatacaaaa aattagccgg gcgcggtggc gggcgcctgt agtcccagct actggggagg    180
ctgaggcagg agaatggcgt gaacccggga agcggagctt gcagtgagcc gagattgcgc    240
cactgcagtc cgcagtccgg cctgggcgac agagcgagac tccgtctca                289
```

<210> SEQ ID NO 43
<211> LENGTH: 283
<212> TYPE: DNA
<213> ORGANISM: homo sapiens

<400> SEQUENCE: 43
ggccgggcgc ggtggctcac gcctgtaatc ccagcacttt gggaggccga ggcgggcgga    60
tcacgaggtc aggagatcga gaccatcctg gctaacacgg tgaaaccccg tctctactaa   120
aaatacaaaa aaattagccg ggcgtggtag cgggcgcctg tagtcccagc tactcgggag   180
gctgaggcag gagaatggcg tgaacccggg aggcggagct tgcagtgagc caagatagcg   240
ccactgcagt ccagcctggg cgaaagagcg agactccgtc tca                     283

<210> SEQ ID NO 44
<211> LENGTH: 282
<212> TYPE: DNA
<213> ORGANISM: homo sapiens

<400> SEQUENCE: 44
ggccgggcgc ggtggctcac gcctgtaatc ccagcacttt gggaggccga ggcgggcgga    60
tcacgaggtc aggagatcga gaccatcctg gctaacacgg tgaaaccccg tctctactaa   120
aaatacaaaa aattagccgg gcgtggtagc gggcgcctgt agtcccagct actcgggagg   180
ctgaggcagg agaatggcgt gaacccggga ggcggagctt gcagtgagcc gagatcgcgc   240
cactgcactc cagcctgggc gacagagcga gactccgtct ca                     282

<210> SEQ ID NO 45
<211> LENGTH: 282
<212> TYPE: DNA
<213> ORGANISM: homo sapiens

<400> SEQUENCE: 45
ggccgggcgc ggtggctcac gcctgtaatc ccagcacttt gggaggccga ggcgggcgga    60
tcacgaggtc aggagatcga gaccatcctg gctaacaagg tgaaaccccg tctctactaa   120
aaatacaaaa aattagccgg gcgtggtagc gggcgcctgt agtcccagct actcgggagg   180
ctgaggcagg agaatggcgt gaacccggga ggcggagctt gcagtgagcc gagatcgcgc   240
cactgcactc cagcctgggc gacagagcga gactccgtct ca                     282

<210> SEQ ID NO 46
<211> LENGTH: 299
<212> TYPE: DNA
<213> ORGANISM: homo sapiens

<400> SEQUENCE: 46
rgccgggcgc ggtggctcac gcctgtaatc ccagcacttt gggaggccga ggcgggcgga    60
tcacgaggtc aggagatcga gaccacggtg aaacccgtc tctactaaaa atacaaaaaa    120
ttagccgggc gcagtggcgg gcgcctgtag tcccagctac tcggaggct gaggcaggag    180 aatggcgtga acccggaagg cggagcttgc agtgagcgga gatcgcgcca cagcactccc   240
gcctgggcga cagagcgaga ctccgtctca aaaaaaaaaa aaaaaaaaa aaaaaaaa      299

<210> SEQ ID NO 47
<211> LENGTH: 270
<212> TYPE: DNA
<213> ORGANISM: homo sapiens

```
<400> SEQUENCE: 47
ggccgggcgc ggtggctcac gcctgtaatc ccagcacttt gggaggccga ggcgggcgga      60
tcacgaggtc aggagatcga gccacggtg aaaccccgtc tctactaaaa atacaaaaaa     120
ttagccgggc gcggtggcgg gcgcctgtag tcccagctac tcgggaggct gaggcaggag    180
aatggcgtga acccgggagg cggagcttgc agtgagccga gatcgcgcca ctgcactcca    240
gcctgggcga cagagcgaga ctccgtctca                                      270

<210> SEQ ID NO 48
<211> LENGTH: 270
<212> TYPE: DNA
<213> ORGANISM: homo sapiens

<400> SEQUENCE: 48
ggccgggcgc ggtggctcac gcttgtaatc ccagcacttt gggaggccga ggcgggcgga      60
tcacgaggtc aggagatcga gaccacggtg aaaccccgtc tctactaaaa atacaaaaaa    120
ttagccgggc gcggtggcgg gcgcctgtag tcccagctac tcgggaggct gaggcaggag    180
aatggcgtga acccgggagg cggagcttgc agtgagccga gatcgcgcca ctgcactcca    240
gcctgggcga cagagcgaga ctccgtctca                                      270

<210> SEQ ID NO 49
<211> LENGTH: 271
<212> TYPE: DNA
<213> ORGANISM: homo sapiens

<400> SEQUENCE: 49
ggccgggcgc ggtggctcac gcttgtaatc ccagcacttt gggaggccga ggcgggcgga      60
tcacgaggtc aggagatcga gaccacggtg aaaccccgtc tctactaaaa atacaaaaaa    120
ttagccgggc gcggtggcgg gcgcctgtag tcccagctac tcggagaggc tgaggcagga    180
gaatggcgtg aacccgggag gcggagcttg cagtgagccg agatcgcgcc actgcactcc    240
agcctgggcg acagagcgag actccgtctc a                                    271

<210> SEQ ID NO 50
<211> LENGTH: 272
<212> TYPE: DNA
<213> ORGANISM: homo sapiens

<400> SEQUENCE: 50
ggccgggcgc ggtggctcac gcttgtaatc ccagcacttt gggaggccga ggcgggcgga      60
tcacgaggtc aggagatcga gaccacggtg aaaccccgtc tctactaaaa atacaaaaaa    120
attagccggg cgtggtggcg ggcgcctgta gtcccagcta ctcggagagg ctgaggcagg    180
agaatggcgt gaacccggga ggcggagctt gcagtgagcc gagattgcgc cactgcactc    240
cagcctgggc gacagagcga gactccgtct ca                                   272

<210> SEQ ID NO 51
<211> LENGTH: 270
<212> TYPE: DNA
<213> ORGANISM: homo sapiens

<400> SEQUENCE: 51
ggccgggcgc ggtggctcac gcctgtaatc ccagcacttt gggaggccga ggcgggcgga      60
tcacgaggtc aggagatcga gaccacggtg aaaccccgtc tctactaaaa atacaaaaaa    120
ttagccgggc gcagtggcgg gcgcctgtag tcccagctac tcggaggct gaggcaggag     180
```
aatggcgtga acccggaagg cggagcttgc agtgagcgga gatcgcgcca cagcactccc    240
gcctgggcga cagaacgaga ctccgtctca    270

<210> SEQ ID NO 52
<211> LENGTH: 280
<212> TYPE: DNA
<213> ORGANISM: homo sapiens

<400> SEQUENCE: 52
ggccgggcgc ggtggctcac gcctgtaatc ccagcacttt gggaggccga ggcgggcgga    60
tcacgaggtc aggagatcga gaccatcctg gctaacacgg tgaaacccg tctctactaa    120 aaatacaaaa aattagccgg gcgaggtggc gggcgcctgt agtcccagct actcgggagg    180
ctgaggcagg agaatggcgt gaacccggga ggcggagctt gcagtgagcc gagatcgcgc    240
cactgcactc cagcctgggc gacagcgaga ctccgtctca    280

<210> SEQ ID NO 53
<211> LENGTH: 281
<212> TYPE: DNA
<213> ORGANISM: homo sapiens

<400> SEQUENCE: 53
ggccgggcgc ggtggctcac gcctgtaatc ccagcacttt gggaggccga ggcgggcgga    60
tcacgaggtc aggagatcga gaccatcctg gctaacacgg tgaaacccg tctctactaa    120 aaatacaaaa aattagccgg gcgaggtggc gggcgcctgt agtcccagct actcgggagg    180
ctgaggcagg agaatggcgt gaacccggg ggcggagcc tgcagtgagc cgagatcgcg    240
ccactgcact ccagcctggg cgacagcgag actccgtctc a    281

<210> SEQ ID NO 54
<211> LENGTH: 282
<212> TYPE: DNA
<213> ORGANISM: homo sapiens

<400> SEQUENCE: 54
ggccgggcgc ggtggctcac gcctgtaatc ccagcacttt gggaggccga ggcgggcgga    60
tcacgaggtc aggagatcga gaccatcctg gctaacacgg tgaaacccg tctctactaa    120 aaatacaaaa aattagccgg gcgtggtggc gggcgcctgt agtcccagct acgcgggagg    180
ctgaggcagg agaatggcgt gaacccggga ggcggagctt gcagtgagcc gagatcgcgc    240
cactgcactc cagcctgggc gacagagcga gactccgtct ca    282

<210> SEQ ID NO 55
<211> LENGTH: 284
<212> TYPE: DNA
<213> ORGANISM: homo sapiens

<400> SEQUENCE: 55
ggccgggcgc ggtggctcac gcctgtaatc ccagcacttt gggaggccga ggcgggcgga    60
tcacgaggtc aggagatcga gaccatcctg gctaacacag tgaaacccg tctctactaa    120 aaacacaaa aaattagcc gggcgtggtg gcgggcgcct gtagtcccag ctacgcggga    180
ggctgaggca ggagaatggc gtgaacccgg gaggcggagc ttgcagtgag ccgagatcgc    240
gccactgcac tccagcctgg gcgacagagc gagactccgt ctca    284

<210> SEQ ID NO 56

```
<211> LENGTH: 312
<212> TYPE: DNA
<213> ORGANISM: homo sapiens

<400> SEQUENCE: 56
ggccgggcgc ggtggctcac gcctgtaatc ccagcacttt gggaggccga ggcgggcgga      60
tcacgaggtc aggagatcga gaccatcctg gctaacacgg tgaaacccccg tctctactaa    120 aaatacaaaa aattagccgg gcgaggtggc gggcgcctgt agtcccagct acgcgggagg     180
ctgaggcagg agaatggcgt gaaccccggg gggcggagcc tgcagtgagc cgagatcgcg    240
ccactgcact ccagcctggg cgacagcgag actccgtctc aaaaaaaaaa aaaaaaaaa     300 aaaaaaaaaa aa                                                         312

<210> SEQ ID NO 57
<211> LENGTH: 282
<212> TYPE: DNA
<213> ORGANISM: homo sapiens

<400> SEQUENCE: 57
ggccgggcgc ggtggctcac gcctgtaatc ccagcacttt gggaggccga gacgggcgga     60
tcacgaggtc aggagatcga gaccatcctg gctaacacgg tgaaacccccg tctctactaa    120 aaatacaaaa aattagccgg gcatggtggc gcgcgcctgt agtcccagct acacgggagg    180
ctgaggcagg agaatggcgt gaacccggga ggcggagctt gcagtgagtc gagatcgcgc    240
cactgcactc cagcctgggc gacagagcga aactccgtct ca                       282

<210> SEQ ID NO 58
<211> LENGTH: 282
<212> TYPE: DNA
<213> ORGANISM: homo sapiens

<400> SEQUENCE: 58
ggccgggcgc ggtggctcac gcctgtaatc ccagcacttt gggaggcaga ggcgggcgga     60
tcatgaggtc aggagatcga gaccatcctg gctaacgcgg tgaaacccccg cctctactaa    120 aaatacaaaa aattagccgg gcgtggtggc gggcgcctgt ggtcccggct actcgggagg    180
ctgaggcagg agaatggcgt gaacccggga ggcggagctt gcagtgagct gaggtcgcgc    240
cactgcaccc cagcctgggc gacagagcga gactccgtct ca                       282

<210> SEQ ID NO 59
<211> LENGTH: 283
<212> TYPE: DNA
<213> ORGANISM: homo sapiens

<400> SEQUENCE: 59
ggccgggcgc ggtggctcac gcttgtaatc ccagcacttt gggaggccga ggcgggcgga     60
tcacgaggtc aggagatcga gaccatcctg gctaacacgg tgaaacccccg tctctactaa    120 aaatacaaaa aaattagccg ggcgtgatgg cgggcgcctg tagtcccagc tactcggagg    180
gctgaggcag gagaatggcg tgaacccggg aggcggagct tgcagtgagc cgagattgcg    240
ccactgcact cccgcctggg ccacagagcg agactccgtc tca                      283

<210> SEQ ID NO 60
<211> LENGTH: 312
<212> TYPE: DNA
<213> ORGANISM: homo sapiens

<400> SEQUENCE: 60
```

```
ggctgggcgc ggtggctcac gcctgtaatc ccagcacttt gggaggccga ggcgggcgga    60
tcacaaggtc aggagatcga gaccatcttg gctaacacgg tgaaacccsg tctctactaa   120
aaatacaaaa aattagccgg gcgcggtggc gggcgcctgt agtcccagct actcgggagg   180
ctgaggcagg agaatggcgt gaacctggga ggcggagctt gcagtgagcc gagattgcgc   240
cactgcaatc cggcctgggc taagagcgg gactccgtct caaaaaaaaa aaaaaaaaaa    300
aaaaaaaaaa aa                                                      312

<210> SEQ ID NO 61
<211> LENGTH: 312
<212> TYPE: DNA
<213> ORGANISM: homo sapiens

<400> SEQUENCE: 61
ggccgggcgc ggtggctcac gcctgtaatc ccagcacttt gggaggccga ggcgggcgga    60
tcacgaggtc aggagatcga gaccatcctg gctaacacgg tgaaacccsg tctctactaa   120
aaatacaaaa aattagccgg gcgtggtggt gggcgcctgt aatcccagct actcgggagg   180
ctgaggcagg agaatggcat gaacccaaga ggcggagctt gcagtgagcc gggatagcgc   240
cactgcagtc cagcttgggc gaaagagtga gactccgtct caaaaaaaaa aaaaaaaaaa   300
aaaaaaaaaa aa                                                      312

<210> SEQ ID NO 62
<211> LENGTH: 269
<212> TYPE: DNA
<213> ORGANISM: homo sapiens

<400> SEQUENCE: 62
ggccgggcgt ggtggctcac gcctgtaatc ccagcacttt gggaggccga ggcgggtgga    60
tcatgaggtc aggagatcga gaccatcctg gctaacacag tgaaacccsg tctctactaa   120
aaatacaaaa aattagccgg gagcggtggc gggctcctgt agtcccagct acttgagagg   180
ctgaggcagg agaatggcgt gaacccagga ggcggagctt gcagtgagcc gagatcgcgc   240
cactgcactc cagcctgggc gacagagcc                                     269

<210> SEQ ID NO 63
<211> LENGTH: 16
<212> TYPE: DNA
<213> ORGANISM: artificial
<220> FEATURE:
<223> OTHER INFORMATION: synthetic antisense oligonucleotide

<400> SEQUENCE: 63
gttacggatg gttgtg                                                   16

<210> SEQ ID NO 64
<211> LENGTH: 15
<212> TYPE: DNA
<213> ORGANISM: artificial
<220> FEATURE:
<223> OTHER INFORMATION: synthetic antisense oligonucleotide targeting
      B2

<400> SEQUENCE: 64
tgtagctgtc ttcag                                                    15

<210> SEQ ID NO 65
<211> LENGTH: 154
```

```
<212> TYPE: DNA
<213> ORGANISM: Mus musculus
<220> FEATURE:
<221> NAME/KEY: misc_feature
<222> LOCATION: (36)..(36)
<223> OTHER INFORMATION: n = t or g
<220> FEATURE:
<221> NAME/KEY: misc_feature
<222> LOCATION: (46)..(46)
<223> OTHER INFORMATION: n = g or c

<400> SEQUENCE: 65
ggggctggag agatggctca gcggttaaga gcactngctg ctcttncaga ggacccgggt      60
tcggttccca gcacccacat ggcggctcac aaccgtctgt aactccagtt ccagggatc     120 cgacgccctc ttctggcctc cgcgggcacc gcat                                154

<210> SEQ ID NO 66
<211> LENGTH: 142
<212> TYPE: DNA
<213> ORGANISM: Mus musculus

<400> SEQUENCE: 66
ggggctggtg agatggctca gtgggtaaga gcacccgact gctcttccga aggtccggag      60
ttcaaatccc agcaaccaca tgtggctca caaccatccg taacgagatc tgactccctc     120
ttctggagtg tctgaagaca gc                                             142

<210> SEQ ID NO 67
<211> LENGTH: 141
<212> TYPE: DNA
<213> ORGANISM: Mus musculus

<400> SEQUENCE: 67
gggctggtga gatggctcag tgggtaagag cacccgactg ctcttccgaa ggtccggagt      60
tcaaatccca gcaaccacat ggtggctcac aaccatccgt aacgagatct gacgccctct     120
tctggtgtgt ctgaagacag c                                              141

<210> SEQ ID NO 68
<211> LENGTH: 141
<212> TYPE: DNA
<213> ORGANISM: Mus musculus

<400> SEQUENCE: 68
ggggctggag agatggctca gcggttaaga gcactgactg ctcttccaga ggtcctgagt      60
tcaattccca gcaaccacat ggtggctcac aaccatctgt aatgggatct gatgccctct     120
tctggtgtgt ctgaagacag c                                              141

<210> SEQ ID NO 69
<211> LENGTH: 16
<212> TYPE: DNA
<213> ORGANISM: Artificial Sequence
<220> FEATURE:
<223> OTHER INFORMATION: antisense oligo

<400> SEQUENCE: 69
gttacggatg gttgtg                                                     16

<210> SEQ ID NO 70
<211> LENGTH: 15
<212> TYPE: DNA
<213> ORGANISM: Artificial Sequence
<220> FEATURE:
```

```
<223> OTHER INFORMATION: antisense oligo

<400> SEQUENCE: 70
tgtagctgtc ttcag                                                    15

<210> SEQ ID NO 71
<211> LENGTH: 15
<212> TYPE: DNA
<213> ORGANISM: Artificial Sequence
<220> FEATURE:
<223> OTHER INFORMATION: antisense oligo

<400> SEQUENCE: 71
ggccgaggcg ggcgg                                                    15

<210> SEQ ID NO 72
<211> LENGTH: 15
<212> TYPE: DNA
<213> ORGANISM: Artificial Sequence
<220> FEATURE:
<223> OTHER INFORMATION: antisense oligo

<400> SEQUENCE: 72
tttgggaggc cgagg                                                    15
```